United States Patent
Dugas et al.

(10) Patent No.: US 11,661,461 B2
(45) Date of Patent: May 30, 2023

(54) PHOSPHO-RAB ANTIBODIES, ASSAYS AND METHODS OF USE THEREOF

(71) Applicant: Denali Therapeutics Inc., South San Francisco, CA (US)

(72) Inventors: Jason C. Dugas, South San Francisco, CA (US); Anastasia Henry, South San Francisco, CA (US); Sarah Huntwork-Rodriguez, South San Francisco, CA (US); Michael T. Maloney, South San Francisco, CA (US); Nathan Moerke, South San Francisco, CA (US); Ella Negrou, South San Francisco, CA (US); Xiang Wang, South San Francisco, CA (US)

(73) Assignee: Denali Therapeutics Inc., South San Francisco, CA (US)

( * ) Notice: Subject to any disclaimer, the term of this patent is extended or adjusted under 35 U.S.C. 154(b) by 0 days.

(21) Appl. No.: 16/621,928

(22) PCT Filed: Jun. 15, 2018

(86) PCT No.: PCT/US2018/037809
§ 371 (c)(1),
(2) Date: Dec. 12, 2019

(87) PCT Pub. No.: WO2018/232278
PCT Pub. Date: Dec. 20, 2018

(65) Prior Publication Data
US 2021/0147573 A1 May 20, 2021

Related U.S. Application Data

(60) Provisional application No. 62/667,281, filed on May 4, 2018, provisional application No. 62/638,622, filed
(Continued)

(51) Int. Cl.
*C07K 16/40* (2006.01)
*G01N 33/573* (2006.01)
*G01N 33/68* (2006.01)

(52) U.S. Cl.
CPC .......... *C07K 16/40* (2013.01); *G01N 33/573* (2013.01); *G01N 33/6896* (2013.01);
(Continued)

(58) Field of Classification Search
None
See application file for complete search history.

(56) References Cited

U.S. PATENT DOCUMENTS 5,843,717 A 12/1998 Hillman et al.
6,300,472 B1 10/2001 Hillman et al.
(Continued)

FOREIGN PATENT DOCUMENTS

CN 1249345 A 4/2000
WO 2000/58464 A2 10/2000
(Continued)

OTHER PUBLICATIONS

Kussie et al., A single engineered amino acid substitution changes antibody fine specificity. J Immunol. Jan. 1, 1994;152(1):146-52. (Year: 1994).*
(Continued)

*Primary Examiner* — Aurora M Fontainhas
(74) *Attorney, Agent, or Firm* — McCarter & English, LLP; Steven G. Davis; Xin Zhang

(57) ABSTRACT

In one aspect, antibodies that specifically bind to a phosphorylated Rab protein are provided. In some embodiments, the antibody is a monoclonal antibody that specifically binds to a phosphorylated human Rab10 protein and recognizes an epitope within or comprising the sequence AGQERFH(pT)ITTSYYR (SEQ ID NO:123). In some embodiments, the
(Continued)

antibody is a monoclonal antibody that specifically binds to a phosphorylated human Rab8a protein and recognizes an epitope within or comprising the sequence QERFR(pT)ITTAY (SEQ ID NO:125). Methods and materials for detecting LRRK2 and Rab protein are also provided.

13 Claims, 7 Drawing Sheets

Specification includes a Sequence Listing.

Related U.S. Application Data on Mar. 5, 2018, provisional application No. 62/521,300, filed on Jun. 16, 2017.

(52) U.S. Cl.
CPC ...... *C07K 2317/21* (2013.01); *C07K 2317/24* (2013.01); *C07K 2317/33* (2013.01); *C07K 2317/34* (2013.01); *C07K 2317/56* (2013.01); *C07K 2317/565* (2013.01); *G01N 2440/14* (2013.01); *G01N 2800/2835* (2013.01); *G01N 2800/52* (2013.01)

(56) References Cited

U.S. PATENT DOCUMENTS

| | | |
|---|---|---|
| 6,867,019 B2 | 3/2005 | Shao et al. |
| 7,799,538 B2 | 9/2010 | Lienhard et al. |
| 9,572,820 B2 | 2/2017 | Deretic et al. |
| 2016/0312194 A1 | 10/2016 | Nichols et al. |

FOREIGN PATENT DOCUMENTS

| | | |
|---|---|---|
| WO | 2014/132191 A2 | 9/2014 |
| WO | 2016/025602 A1 | 2/2016 |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Chen et al., Enhancement and destruction of antibody function by somatic mutation: unequal occurrence is controlled by V gene combinatorial associations. EMBO J. Jun. 15, 1995;14(12):2784-94. (Year: 1995).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; https://doi.org/10.1073/pnas.1613231114 (Year: 2017).*

International Search Report dated Jan. 3, 2019 for International Application No. PCT/US2018/037809, 5 pages.

"#8127: Rab10 (D36C4) XP® Rabbit mAb," Cell Signaling Technology, 2016, 1 page.

Delbroek et al. "Development of an enzyme-linked immunosorbent assay for detection of cellular and in vivo LRRK2 S935 phosphorylation," Journal of Pharmaceutical and Biomedical Analysis, 2013, vol. 76, 49-58.

Fan et al. "Interrogating Parkinson's disease LRRK2 kinase pathway activity by assessing Rab10 phosphorylation in human neutrophils," Biochemical Journal, 2018, vol. 475, 23-44.

Fell et al. "MLi-2, a Potent, Selective, and Centrally Active Compound for Exploring the Therapeutic Potential and Safety of LRRK2 Kinase Inhibition," Journal of Pharmacology and Experimental Therapeutics, 2015, vol. 355, 397-409.

Fuji et al. "Effect of selective LRRK2 kinase inhibition on nonhuman primate lung," Science Translational Medicine, 2015, vol. 7, 273ra15-273ra15, 13 pgs.

Fujimoto et al. "Parkinson's disease-associated mutant LRRK2 phosphorylates Rab7L1 and modifies trans-Golgi morphology," Biochemical and Biophysical Research Communications, 2017, vol. 495, 1-8. Retrieved from the Internet: https://doi.org/10.1016/j.bbrc.2017.12.024.

Fujimoto et al. "Parkinson's disease-associated mutant LRRK2 phosphorylates Rab7L1 and modifies trans-Golgi morphology," Biochemical and Biophysical Research Communications, 2018, vol. 495, 1708-1715.

Ito et al. "Phos-tag analysis of Rab10 phosphorylation by LRRK2: a powerful assay for assessing kinase function and inhibitors," Biochemical Journal, 2016, vol. 473, 2671-2685.

"MC-028: Anti-Proteinase Inhibitor 9 mAb, clone PI9-17," Kamiya Biomedical Company, 2017, 1 page.

Lai et al. "Phosphoproteomic screening identifies Rab GTPases as novel downstream targets of PINK1," The EMBO Journal, 2015, vol. 34, 2840-2861.

Lis et al. "Development of phospho-specific Rab protein antibodies to monitor in vivo activity of the LRRK2 Parkinson's disease kinase," Biochemical Journal, 2018, vol. 475, 1-22.

Liu et al. "LRRK2 phosphorylates membrane-bound Rabs and is activated by GTP-bound Rab7L1 to promote recruitment to the trans-Golgi network," Human Molecular Genetics, 2017, vol. 27, 385-395.

Lobbestael et al. "Pharmacological LRRK2 kinase inhibition induces LRRK2 protein destabilization and proteasomal degradation," Scientific Reports, 2016, vol. 6:33897, 1-9.

Perera et al. "Inhibitor treatment of peripheral mononuclear cells from Parkinson's disease patients further validates LRRK2 dephosphorylation as a pharmacodynamic biomarker," Scientific Reports, 2016, vol. 6:31391, 1-8.

Purlyte et al. "Rab29 activation of the Parkinson's disease-associated LRRK2 kinase," The EMBO Journal, 2018, vol. 37, 1-18.

Steger et al. "Systematic proteomic analysis of LRRK2-mediated Rab GTPase phosphorylation establishes a connection to ciliogenesis," eLife, 2017, vol. 6:e31012, 1-22.

Steger et al. "Phosphoproteomics reveals that Parkinson's disease kinase LRRK2 regulates a subset of Rab GTPases," eLife, 2016, vol. 5:e12813, 1-28.

Thirstrup et al. "Selective LRRK2 kinase inhibition reduces phosphorylation of endogenous Rab10 and Rab12 in human peripheral mononuclear blood cells," Scientific Reports, 2017, vol. 7:10300, 1-18.

* cited by examiner

SEQUENCE LISTING

<160> NUMBER OF SEQ ID NOS: 150

<210> SEQ ID NO 1
<211> LENGTH: 136
<212> TYPE: PRT
<213> ORGANISM: Artificial Sequence
<220> FEATURE:
<223> OTHER INFORMATION: Synthetic construct

<400> SEQUENCE: 1

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Ala Met Val Trp Val Arg Gln Ala Pro Gly Lys Gly Leu Glu
    50                  55                  60

Tyr Ile Gly Leu Ile Ser Arg Ser Gly Val Thr Tyr Tyr Ala Thr Trp
65                  70                  75                  80

-continued

```
Ala Lys Gly Arg Phe Thr Ile Ser Lys Ala Ser Thr Val Asp Leu
            85                  90                  95

Lys Ile Ala Ser Pro Thr Thr Gly Asp Thr Ala Thr Tyr Phe Cys Val
            100                 105                 110

Arg Asp Tyr Asp Ile Asn Gly Trp Ser Gly Phe Thr Ile Trp Gly Pro
        115                 120                 125

Gly Thr Leu Val Thr Val Ser Ala
    130                 135

<210> SEQ ID NO 2
<211> LENGTH: 10
<212> TYPE: PRT
<213> ORGANISM: Artificial Sequence
<220> FEATURE:
<223> OTHER INFORMATION: Synthetic construct

<400> SEQUENCE: 2

Gly Phe Ser Leu Ser Ser Tyr Ala Met Val
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Synthetic construct

<400> SEQUENCE: 3

Leu Ile Ser Arg Ser Gly Val Thr Tyr Tyr Ala Thr Trp Ala Lys Gly
1               5                   10                  15

<210> SEQ ID NO 4
<211> LENGTH: 14
<212> TYPE: PRT
<213> ORGANISM: Artificial Sequence
<220> FEATURE:
<223> OTHER INFORMATION: Synthetic construct

<400> SEQUENCE: 4

Val Arg Asp Tyr Asp Ile Asn Gly Trp Ser Gly Phe Thr Ile
1               5                   10

<210> SEQ ID NO 5
<211> LENGTH: 130
<212> TYPE: PRT
<213> ORGANISM: Artificial Sequence
<220> FEATURE:
<223> OTHER INFORMATION: Synthetic construct

<400> SEQUENCE: 5

Met Asp Thr Arg Ala Pro Thr Gln Leu Leu Gly Leu Leu Leu Trp Leu
1               5                   10                  15

Pro Gly Ala Ile Cys Asp Pro Val Met Thr Gln Thr Pro Ser Ser Thr
            20                  25                  30

Ser Ala Ala Val Gly Gly Thr Val Thr Ile Asn Cys Gln Ser Ser Gln
        35                  40                  45

Ser Val Tyr Gly Asn Asn Tyr Phe Ser Trp Tyr Gln Gln Lys Pro Gly
    50                  55                  60

Gln Pro Pro Lys Leu Leu Ile Tyr Lys Ala Ser Thr Leu Ala Ser Gly
65                  70                  75                  80

Val Pro Ser Arg Phe Lys Gly Ser Gly Ser Gly Thr Gln Phe Thr Leu
                85                  90                  95
```

Thr Ile Ser Asp Leu Glu Cys Asp Asp Ala Ala Thr Tyr Tyr Cys Ala
            100                 105                 110

Gly Ala Ala Ser Asp Thr Arg Phe Phe Gly Gly Gly Thr Glu Leu Val
        115                 120                 125

Val Asn
    130

<210> SEQ ID NO 6
<211> LENGTH: 13
<212> TYPE: PRT
<213> ORGANISM: Artificial Sequence
<220> FEATURE:
<223> OTHER INFORMATION: Synthetic construct

<400> SEQUENCE: 6

Gln Ser Ser Gln Ser Val Tyr Gly Asn Asn Tyr Phe Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic construct

<400> SEQUENCE: 7

Lys Ala Ser Thr Leu Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic construct

<400> SEQUENCE: 8

Ala Gly Ala Ala Ser Asp Thr Arg Phe
1               5

<210> SEQ ID NO 9
<211> LENGTH: 408
<212> TYPE: DNA
<213> ORGANISM: Artificial Sequence
<220> FEATURE:
<223> OTHER INFORMATION: Synthetic construct

<400> SEQUENCE: 9
atggagactg ggctgcgctg cttctcctg gtcgctgtgc tcaaaggtgt ccagtgtcag     60
tcggtggagg agtccggggg tcgcctggtc acgcctggga cacccctgac actcacctgc    120
accgtctctg gattctcccct cagtagctat gcaatggtct gggtccgcca ggctccaggg   180
aaggggctgg aatacatcgg actcattagt aggagtggtg tgacatacta cgcgacctgg   240
gcgaaaggcc gattcaccat ctccaaagcc tcgaccacag tggatctgaa aatcgccagt   300
ccgacaaccg gggacacggc cacctatttt tgtgtcagag attacgatat taatggctgg   360
agtgggttta ccatctgggg cccaggcacc ctggtcaccg tctccgca                408

<210> SEQ ID NO 10
<211> LENGTH: 390
<212> TYPE: DNA
<213> ORGANISM: Artificial Sequence
<220> FEATURE:

<223> OTHER INFORMATION: Synthetic construct

<400> SEQUENCE: 10

```
atggacacga gggcccccac tcagctgctg gggctcctgc tctggctccc aggtgccata    60
tgtgaccctg tgatgaccca gactccatct tccacgtctg cggctgtggg aggcacagtc   120
accatcaact gccagtccag tcagagtgtt tatggtaaca actactttc ctggtatcag   180
cagaaaccag gcagcctcc caagctcctg atctacaagg cttccactct ggcatctggg   240
gtcccatcgc gattcaaagg cagtggatct gggacacagt tcactctcac catcagcgac   300
ctggagtgtg acgatgctgc cacttactac tgtgcaggcg ctgctagtga tactagattt   360
ttcggcggag ggaccgaact ggtggtcaat                                    390
```

<210> SEQ ID NO 11
<211> LENGTH: 136
<212> TYPE: PRT
<213> ORGANISM: Artificial Sequence
<220> FEATURE:
<223> OTHER INFORMATION: Synthetic construct

<400> SEQUENCE: 11

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Ala Met Val Trp Val Arg Gln Ala Pro Gly Lys Gly Leu Glu
    50                  55                  60

Tyr Ile Gly Leu Ile Ser Arg Ser Gly Val Thr Tyr Tyr Ala Thr Trp
65                  70                  75                  80

Ala Lys Gly Arg Phe Thr Ile Ser Lys Ala Ser Thr Thr Val Asp Leu
                85                  90                  95

Lys Ile Ala Ser Pro Thr Thr Gly Asp Thr Ala Thr Tyr Phe Cys Val
            100                 105                 110

Arg Asp Tyr Asp Ser Ala Gly Trp Ser Gly Phe Thr Ile Trp Gly Pro
        115                 120                 125

Gly Thr Leu Val Thr Val Ser Ala
    130                 135
```

<210> SEQ ID NO 12
<211> LENGTH: 14
<212> TYPE: PRT
<213> ORGANISM: Artificial Sequence
<220> FEATURE:
<223> OTHER INFORMATION: Synthetic construct

<400> SEQUENCE: 12

```
Val Arg Asp Tyr Asp Ser Ala Gly Trp Ser Gly Phe Thr Ile
1               5                   10
```

<210> SEQ ID NO 13
<211> LENGTH: 131
<212> TYPE: PRT
<213> ORGANISM: Artificial Sequence
<220> FEATURE:
<223> OTHER INFORMATION: Synthetic construct

<400> SEQUENCE: 13

Met Asp Thr Arg Ala Pro Thr Gln Leu Leu Gly Leu Leu Leu Leu Trp

```
                1               5                  10                  15
Leu Pro Gly Ala Ile Cys Asp Pro Val Met Thr Gln Thr Pro Ser Ser
            20                  25                  30

Thr Ser Ala Ala Val Gly Gly Thr Val Thr Ile Asn Cys Gln Ser Ser
            35                  40                  45

Gln Ser Val Tyr Gly Asn Asn Tyr Leu Ser Trp Tyr Gln Gln Lys Pro
    50                  55                  60

Gly Gln Pro Pro Lys Leu Leu Ile Tyr Lys Ala Ser Thr Leu Ala Ser
65                  70                  75                  80

Gly Val Pro Ser Arg Ser Val Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Ala Gly Ala Ala Ser Asp Thr Arg Phe Phe Gly Gly Gly Thr Glu Leu
            115                 120                 125

Val Val Asn
    130
```

<210> SEQ ID NO 14
<211> LENGTH: 13
<212> TYPE: PRT
<213> ORGANISM: Artificial Sequence
<220> FEATURE:
<223> OTHER INFORMATION: Synthetic construct

<400> SEQUENCE: 14

```
Gln Ser Ser Gln Ser Val Tyr Gly Asn Asn Tyr Leu Ser
1               5                   10
```

<210> SEQ ID NO 15
<211> LENGTH: 408
<212> TYPE: DNA
<213> ORGANISM: Artificial Sequence
<220> FEATURE:
<223> OTHER INFORMATION: Synthetic construct

<400> SEQUENCE: 15

| | | | | | |
|---|---|---|---|---|---|
| atggagactg | ggctgcgctg | gcttctcctg | gtcgctgtgc | tcaaaggtgt | ccagtgtcag | 60 |
| tcggtggagg | agtccggggg | tcgcctggtc | acgcctggga | cacccctgac | actcacctgc | 120 |
| accgtctctg | gattctccct | cagtagctat | gcaatggtct | gggtccgcca | ggctccaggg | 180 |
| aaggggctgg | aatacatcgg | actcattagt | aggagtggtg | tgacatacta | cgcgacctgg | 240 |
| gcgaaaggcc | gattcaccat | ctccaaagcc | tcgaccacag | tggatctgaa | aatcgccagt | 300 |
| ccgacaaccg | ggacacggc  | cacctatttt | tgtgtcagag | attacgatag | tgctggctgg | 360 |
| agtgggttta | ccatctgggg | cccaggcacc | ctggtcaccg | tctccgca   |            | 408 |

<210> SEQ ID NO 16
<211> LENGTH: 393
<212> TYPE: DNA
<213> ORGANISM: Artificial Sequence
<220> FEATURE:
<223> OTHER INFORMATION: Synthetic construct

<400> SEQUENCE: 16

| | | | | | |
|---|---|---|---|---|---|
| atggacacga | gggcccccac | tcagctgctg | ggctcctgc  | tgctctggct | cccaggtgcc | 60 |
| atatgtgacc | ctgtgatgac | ccagactcca | tcttccacgt | ctgcggctgt | gggaggcaca | 120 |
| gtcaccatca | actgccagtc | cagtcagagt | gtttatggta | caaactactt | gtcctggtat | 180 |

```
cagcagaaac cagggcagcc tcccaagctc ctgatctaca aggcttccac tctggcatct    240
ggggtcccat cgcggtccgt aggcagtgga tctgggacac agttcactct caccatcagc    300
gacctggagt gtgacgatgc tgccacttac tactgtgcag gcgctgctag tgatactaga    360
tttttcggcg gagggaccga actggtggtc aat                                 393
```

```
<210> SEQ ID NO 17
<211> LENGTH: 136
<212> TYPE: PRT
<213> ORGANISM: Artificial Sequence
<220> FEATURE:
<223> OTHER INFORMATION: Synthetic construct

<400> SEQUENCE: 17

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Ala Met Val Trp Val Arg Gln Ala Pro Gly Lys Gly Leu Glu
    50                  55                  60

Tyr Ile Gly Leu Ile Ser Arg Ser Gly Val Thr Tyr Tyr Ala Thr Trp
65                  70                  75                  80

Ala Lys Gly Arg Phe Thr Ile Ser Lys Ala Ser Thr Thr Val Asp Leu
                85                  90                  95

Lys Ile Ala Ser Pro Thr Thr Gly Asp Thr Ala Thr Tyr Phe Cys Val
            100                 105                 110

Arg Asp Tyr Asp Ser Ala Gly Trp Ser Gly Phe Thr Ile Trp Gly Pro
        115                 120                 125

Gly Thr Leu Val Thr Val Ser Ala
    130                 135

<210> SEQ ID NO 18
<211> LENGTH: 131
<212> TYPE: PRT
<213> ORGANISM: Artificial Sequence
<220> FEATURE:
<223> OTHER INFORMATION: Synthetic construct

<400> SEQUENCE: 18

Met Asp Thr Arg Ala Pro Thr Gln Leu Leu Gly Leu Leu Leu Leu Trp
1               5                   10                  15

Leu Pro Gly Ala Ile Cys Asp Pro Val Met Thr Gln Thr Pro Ser Ser
            20                  25                  30

Thr Ser Ala Ala Val Gly Gly Thr Val Thr Ile Asn Cys Gln Ser Ser
        35                  40                  45

Gln Ser Val Tyr Gly Asn Asn Tyr Leu Ser Trp Tyr Gln Gln Lys Pro
    50                  55                  60

Gly Gln Pro Pro Lys Leu Leu Ile Tyr Lys Ala Ser Thr Leu Ala Ser
65                  70                  75                  80

Gly Val Pro Ser Arg Phe Val Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Ala Gly Ala Ala Ser Asp Thr Arg Phe Phe Gly Gly Gly Thr Glu Leu
        115                 120                 125
```

Val Val Asn
    130

<210> SEQ ID NO 19
<211> LENGTH: 408
<212> TYPE: DNA
<213> ORGANISM: Artificial Sequence
<220> FEATURE:
<223> OTHER INFORMATION: Synthetic construct

<400> SEQUENCE: 19

```
atggagactg ggctgcgctg gcttctcctg gtcgctgtgc tcaaaggtgt ccagtgtcag      60
tcggtggagg agtccggggg tcgcctggtc acgcctggga cccccctgac actcacctgc     120
accgtctctg ggttctcccct cagtagctat gcaatggtct gggtccgcca ggctccaggg    180
aaggggctgg aatacatcgg actcattagt aggagtggtg tgacatacta cgcgacctgg    240
gcgaaaggcc gattcaccat ctccaaagcc tcgaccacag tggatctgaa aatcgccagt    300
ccgacaaccg gggacacggc cacctatttt tgtgtcagag attacgatag tgctggctgg    360
agtgggttta ccatctgggg cccaggcacc ctggtcaccg tctccgca                  408
```

<210> SEQ ID NO 20
<211> LENGTH: 393
<212> TYPE: DNA
<213> ORGANISM: Artificial Sequence
<220> FEATURE:
<223> OTHER INFORMATION: Synthetic construct

<400> SEQUENCE: 20

```
atggacacga gggcccccac tcagctgctg gggctcctgc tgctctggct cccaggtgcc      60
atatgtgacc ctgtgatgac ccagactcca tcttccacgt ctgcggctgt ggaggcaca     120
gtcaccatca actgccagtc cagtcagagt gtttatggta caactactt gtcctggtat     180
cagcagaaac cagggcagcc tcccaagctc ctgatctaca aggcttccac tctggcatct    240
ggggtcccat cgcggttcgt aggcagtgga tctgggacac agttcactct caccatcagc    300
gacctggagt gtgacgatgc tgccacttac tactgtgcag cgctgctag tgatactaga    360
tttttcggcg agggaccga actggtggtc aat                                   393
```

<210> SEQ ID NO 21
<211> LENGTH: 136
<212> TYPE: PRT
<213> ORGANISM: Artificial Sequence
<220> FEATURE:
<223> OTHER INFORMATION: Synthetic construct

<400> SEQUENCE: 21

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Ala Met Ser Trp Val Arg Gln Ala Pro Gly Lys Gly Leu Glu
    50                  55                  60

Tyr Ile Gly Leu Phe Asn Asp Val Gly Ile Ala Tyr Tyr Ala Asn Trp
65                  70                  75                  80

Ala Lys Gly Arg Phe Thr Phe Ser Lys Thr Ser Thr Thr Val Asp Leu
                85                  90                  95

```
Lys Ile Thr Ser Pro Thr Thr Glu Asp Thr Ala Thr Tyr Phe Cys Ala
                100                 105                 110

Arg Val Gly Gly Thr Thr Arg Val Tyr Gly Met Asp Leu Trp Gly Pro
        115                 120                 125

Gly Thr Leu Val Thr Val Ser Ser
    130                 135

<210> SEQ ID NO 22
<211> LENGTH: 10
<212> TYPE: PRT
<213> ORGANISM: Artificial Sequence
<220> FEATURE:
<223> OTHER INFORMATION: Synthetic construct

<400> SEQUENCE: 22

Gly Phe Ser Leu Ser Ser Tyr Ala Met Ser
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Synthetic construct

<400> SEQUENCE: 23

Leu Phe Asn Asp Val Gly Ile Ala Tyr Tyr Ala Asn Trp Ala Lys Gly
1               5                   10                  15

<210> SEQ ID NO 24
<211> LENGTH: 14
<212> TYPE: PRT
<213> ORGANISM: Artificial Sequence
<220> FEATURE:
<223> OTHER INFORMATION: Synthetic construct

<400> SEQUENCE: 24

Ala Arg Val Gly Gly Thr Thr Arg Val Tyr Gly Met Asp Leu
1               5                   10

<210> SEQ ID NO 25
<211> LENGTH: 133
<212> TYPE: PRT
<213> ORGANISM: Artificial Sequence
<220> FEATURE:
<223> OTHER INFORMATION: Synthetic construct

<400> SEQUENCE: 25

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Ser Ile Ser Cys Gln Ser Ser
        35                  40                  45

Lys Ser Val Arg His Asn Asn Tyr Leu Ser Trp Tyr Gln Gln Lys Pro
    50                  55                  60

Gly Gln Arg Pro Lys Leu Leu Ile Tyr Gly Ala Ser Thr Leu Ala Ser
65                  70                  75                  80

Gly Val Pro Ser Arg Phe Ser Gly Ser Gly Ser Gly Thr Glu Phe Thr
                85                  90                  95

Leu Thr Ile Ser Asp Val Gln Cys Asp Asp Ala Ala Thr Tyr Tyr Cys
                100                 105                 110
```

Ala Gly Gly Tyr Ser Gly Gly Gly Asp Asp Ala Phe Gly Gly Gly Thr
        115                 120                 125

Glu Val Val Val Glu
    130

<210> SEQ ID NO 26
<211> LENGTH: 13
<212> TYPE: PRT
<213> ORGANISM: Artificial Sequence
<220> FEATURE:
<223> OTHER INFORMATION: Synthetic construct

<400> SEQUENCE: 26

Gln Ser Ser Lys Ser Val Arg His Asn Asn Tyr Leu Ser
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic construct

<400> SEQUENCE: 27

Gly Ala Ser Thr Leu Ala Ser
1               5

<210> SEQ ID NO 28
<211> LENGTH: 11
<212> TYPE: PRT
<213> ORGANISM: Artificial Sequence
<220> FEATURE:
<223> OTHER INFORMATION: Synthetic construct

<400> SEQUENCE: 28

Ala Gly Gly Tyr Ser Gly Gly Gly Asp Asp Ala
1               5                   10

<210> SEQ ID NO 29
<211> LENGTH: 408
<212> TYPE: DNA
<213> ORGANISM: Artificial Sequence
<220> FEATURE:
<223> OTHER INFORMATION: Synthetic construct

<400> SEQUENCE: 29
atggagactg ggctgcgctg gcttctcctg gtcgctgtgc tcaaaggtgt ccagtgtcag    60
tcggtggagg agtccggggg tcgcctggtc acgcctggga cacccctgac actcacctgc   120
acagtctctg gattctcccct cagtagttat gcaatgagct gggtccgcca ggctccaggg   180
aaggggctgg aatacatcgg attatttaat gatgttggta tcgcatacta cgcgaactgg   240
gcgaaaggcc gattcacctt ctccaaaacc tcgaccacgg tggatctgaa aatcaccagt   300
ccgacaaccg aggacacggc cacctatttc tgtgccagag tggtggtac tactcgtgtc   360 tacggcatgg acctctgggg cccagggacc ctcgtcaccg tctcttca              408

<210> SEQ ID NO 30
<211> LENGTH: 399
<212> TYPE: DNA
<213> ORGANISM: Artificial Sequence
<220> FEATURE:
<223> OTHER INFORMATION: Synthetic construct

<400> SEQUENCE: 30

```
atggacacga gggcccccac tcagctgctg gggctcctgc tgctctggct cccaggtgcc    60
acatttgccg ccgtgctgac ccagactcca tctcccgtgt ctgcagctgt gggaggcaca   120
gtcagcatca gttgccagtc cagtaagagt gttaggcata caactactt atcctggtat   180 cagcagaaac cagggcagcg tcccaagctc ctgatctatg gtgcatccac tctggcatct   240
ggggtcccat cgcggttcag cggcagtgga tctgggacag agttcactct caccatcagc   300
gacgtgcagt gtgacgatgc tgccacttac tactgtgcag gcggttatag tggtggtggt   360
gacgatgcgt tcggcggagg gaccgaggtg gtggtcgaa                          399
```

```
<210> SEQ ID NO 31
<211> LENGTH: 140
<212> TYPE: PRT
<213> ORGANISM: Artificial Sequence
<220> FEATURE:
<223> OTHER INFORMATION: Synthetic construct

<400> SEQUENCE: 31

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Lys Ala Ser Gly Phe Asp Leu
        35                  40                  45

Ser Ser His Tyr Tyr Met Cys Trp Val Arg Gln Ala Pro Gly Lys Gly
    50                  55                  60

Leu Glu Trp Ile Val Cys Ile Ser Asn Gly Ser Gly Asn Thr Tyr Tyr
65                  70                  75                  80

Ala Ser Trp Ala Lys Gly Arg Phe Thr Ile Ser Lys Thr Ser Ser Thr
                85                  90                  95

Thr Val Thr Leu His Met Thr Ser Leu Thr Val Ala Asp Thr Ala Thr
            100                 105                 110

Tyr Phe Cys Ala Arg Asn Phe Gly Ser Asn Tyr Gly Asp Ala Phe Asp
        115                 120                 125

Pro Trp Gly Pro Gly Thr Leu Val Thr Val Ser Ser
    130                 135                 140

<210> SEQ ID NO 32
<211> LENGTH: 11
<212> TYPE: PRT
<213> ORGANISM: Artificial Sequence
<220> FEATURE:
<223> OTHER INFORMATION: Synthetic construct

<400> SEQUENCE: 32

Gly Phe Asp Leu Ser Ser His Tyr Tyr Met Cys
1               5                   10

<210> SEQ ID NO 33
<211> LENGTH: 17
<212> TYPE: PRT
<213> ORGANISM: Artificial Sequence
<220> FEATURE:
<223> OTHER INFORMATION: Synthetic construct

<400> SEQUENCE: 33

Cys Ile Ser Asn Gly Ser Gly Asn Thr Tyr Tyr Ala Ser Trp Ala Lys
1               5                   10                  15

Gly
```

<210> SEQ ID NO 34
<211> LENGTH: 14
<212> TYPE: PRT
<213> ORGANISM: Artificial Sequence
<220> FEATURE:
<223> OTHER INFORMATION: Synthetic construct

<400> SEQUENCE: 34

```
Ala Arg Asn Phe Gly Ser Asn Tyr Gly Asp Ala Phe Asp Pro
1               5                   10
```

<210> SEQ ID NO 35
<211> LENGTH: 134
<212> TYPE: PRT
<213> ORGANISM: Artificial Sequence
<220> FEATURE:
<223> OTHER INFORMATION: Synthetic construct

<400> SEQUENCE: 35

```
Met Asp Thr Arg Ala Pro Thr Gln Leu Leu Gly Leu Leu Leu Trp
1               5                   10                  15

Leu Pro Gly Ala Thr Phe Ala Gln Val Leu Thr Gln Thr Pro Ser Pro
                20                  25                  30

Val Ser Ala Ala Val Gly Gly Thr Val Thr Ile Ser Cys Gln Ser Ser
            35                  40                  45

Lys Ser Val Tyr Ser Asn Asn Tyr Leu Ser Trp Tyr Gln Gln Lys Pro
    50                  55                  60

Gly Gln Pro Pro Lys Leu Leu Ile Tyr Ser Ala Ser Ile Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Gln Gly Ser Tyr Ala Gly Ser Gly Trp Tyr Ile Gly Phe Gly Gly Gly
        115                 120                 125

Thr Glu Val Val Val Lys
    130
```

<210> SEQ ID NO 36
<211> LENGTH: 13
<212> TYPE: PRT
<213> ORGANISM: Artificial Sequence
<220> FEATURE:
<223> OTHER INFORMATION: Synthetic construct

<400> SEQUENCE: 36

```
Gln Ser Ser Lys Ser Val Tyr Ser Asn Asn Tyr Leu Ser
1               5                   10
```

<210> SEQ ID NO 37
<211> LENGTH: 7
<212> TYPE: PRT
<213> ORGANISM: Artificial Sequence
<220> FEATURE:
<223> OTHER INFORMATION: Synthetic construct

<400> SEQUENCE: 37

```
Ser Ala Ser Ile Leu Ala Ser
1               5
```

<210> SEQ ID NO 38
<211> LENGTH: 12

```
<212> TYPE: PRT
<213> ORGANISM: Artificial Sequence
<220> FEATURE:
<223> OTHER INFORMATION: Synthetic construct

<400> SEQUENCE: 38

Gln Gly Ser Tyr Ala Gly Ser Gly Trp Tyr Ile Gly
1               5                   10

<210> SEQ ID NO 39
<211> LENGTH: 133
<212> TYPE: PRT
<213> ORGANISM: Artificial Sequence
<220> FEATURE:
<223> OTHER INFORMATION: Synthetic construct

<400> SEQUENCE: 39

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Thr Tyr Tyr Met Ser Trp Val Arg Gln Ala Pro Gly Lys Gly Leu Glu
    50                  55                  60

Trp Ile Gly Ile Ile Asn Thr Gly Gly Ile Val His Tyr Ala Asn Trp
65                  70                  75                  80

Val Arg Gly Arg Phe Thr Ile Ser Lys Thr Ser Thr Thr Val Asp Leu
                85                  90                  95

Arg Ile Thr Ser Pro Thr Ala Glu Asp Thr Ala Thr Tyr Phe Cys Ala
            100                 105                 110

Arg Ala Tyr Ser Ala Asp Arg Leu Asp Leu Trp Gly Gln Gly Thr Leu
        115                 120                 125

Val Thr Val Ser Ser
    130

<210> SEQ ID NO 40
<211> LENGTH: 10
<212> TYPE: PRT
<213> ORGANISM: Artificial Sequence
<220> FEATURE:
<223> OTHER INFORMATION: Synthetic construct

<400> SEQUENCE: 40

Gly Phe Ser Leu Ser Thr Tyr Tyr Met Ser
1               5                   10

<210> SEQ ID NO 41
<211> LENGTH: 16
<212> TYPE: PRT
<213> ORGANISM: Artificial Sequence
<220> FEATURE:
<223> OTHER INFORMATION: Synthetic construct

<400> SEQUENCE: 41

Ile Ile Asn Thr Gly Gly Ile Val His Tyr Ala Asn Trp Val Arg Gly
1               5                   10                  15

<210> SEQ ID NO 42
<211> LENGTH: 11
<212> TYPE: PRT
<213> ORGANISM: Artificial Sequence
<220> FEATURE:
```

<223> OTHER INFORMATION: Synthetic construct

<400> SEQUENCE: 42

Ala Arg Ala Tyr Ser Ala Asp Arg Leu Asp Leu
1               5                   10

<210> SEQ ID NO 43
<211> LENGTH: 133
<212> TYPE: PRT
<213> ORGANISM: Artificial Sequence
<220> FEATURE:
<223> OTHER INFORMATION: Synthetic construct

<400> SEQUENCE: 43

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Thr Ile Ser Cys Gln Ser Ser
        35                  40                  45

Glu Ser Val Tyr Gly Asn Asn Arg Leu Ser Trp Tyr Gln Gln Lys Pro
    50                  55                  60

Gly Gln Pro Pro Lys Leu Leu Met Tyr Tyr Ala Ser Thr Leu Ala Ser
65                  70                  75                  80

Gly Val Pro Ser Arg Phe Arg Gly Ser Gly Ser Gly Thr Gln Phe Thr
                85                  90                  95

Leu Thr Ile Ser Asp Val Gln Cys Asp Asp Ala Ala Ser Tyr Tyr Cys
            100                 105                 110

Leu Gly Gly Tyr Lys Arg Asp Ser Asn Asn Ala Phe Gly Gly Gly Thr
        115                 120                 125

Glu Val Val Val Lys
    130

<210> SEQ ID NO 44
<211> LENGTH: 13
<212> TYPE: PRT
<213> ORGANISM: Artificial Sequence
<220> FEATURE:
<223> OTHER INFORMATION: Synthetic construct

<400> SEQUENCE: 44

Gln Ser Ser Glu Ser Val Tyr Gly Asn Asn Arg Leu Ser
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Synthetic construct

<400> SEQUENCE: 45

Tyr Ala Ser Thr Leu Ala Ser
1               5

<210> SEQ ID NO 46
<211> LENGTH: 11
<212> TYPE: PRT
<213> ORGANISM: Artificial Sequence
<220> FEATURE:
<223> OTHER INFORMATION: Synthetic construct

<400> SEQUENCE: 46

```
Leu Gly Gly Tyr Lys Arg Asp Ser Asn Asn Ala
1               5                   10

<210> SEQ ID NO 47
<211> LENGTH: 136
<212> TYPE: PRT
<213> ORGANISM: Artificial Sequence
<220> FEATURE:
<223> OTHER INFORMATION: Synthetic construct

<400> SEQUENCE: 47

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Ala Met Gly Trp Val Arg Gln Ala Pro Gly Lys Gly Leu Glu
    50                  55                  60

Tyr Ile Gly Ile Ile Ser Arg Ser Gly Ile Thr Tyr Tyr Ala Thr Trp
65                  70                  75                  80

Ala Lys Gly Arg Phe Thr Ile Ser Lys Ala Ser Thr Thr Val Asp Leu
                85                  90                  95

Arg Ile Ala Ser Pro Thr Thr Glu Asp Thr Ala Thr Phe Phe Cys Val
            100                 105                 110

Arg Asp Tyr Asp Ser Ser Gly Trp Ser Gly Phe Asn Ile Trp Gly Pro
        115                 120                 125

Gly Thr Leu Val Thr Val Ser Leu
        130                 135

<210> SEQ ID NO 48
<211> LENGTH: 10
<212> TYPE: PRT
<213> ORGANISM: Artificial Sequence
<220> FEATURE:
<223> OTHER INFORMATION: Synthetic construct

<400> SEQUENCE: 48

Gly Phe Ser Leu Ser Ser Tyr Ala Met Gly
1               5                   10

<210> SEQ ID NO 49
<211> LENGTH: 16
<212> TYPE: PRT
<213> ORGANISM: Artificial Sequence
<220> FEATURE:
<223> OTHER INFORMATION: Synthetic construct

<400> SEQUENCE: 49

Ile Ile Ser Arg Ser Gly Ile Thr Tyr Tyr Ala Thr Trp Ala Lys Gly
1               5                   10                  15

<210> SEQ ID NO 50
<211> LENGTH: 14
<212> TYPE: PRT
<213> ORGANISM: Artificial Sequence
<220> FEATURE:
<223> OTHER INFORMATION: Synthetic construct

<400> SEQUENCE: 50

Val Arg Asp Tyr Asp Ser Ser Gly Trp Ser Gly Phe Asn Ile
1               5                   10
```

<210> SEQ ID NO 51
<211> LENGTH: 131
<212> TYPE: PRT
<213> ORGANISM: Artificial Sequence
<220> FEATURE:
<223> OTHER INFORMATION: Synthetic construct

<400> SEQUENCE: 51

```
Met Asp Thr Arg Ala Pro Thr Gln Leu Leu Gly Leu Leu Leu Leu Trp
1               5                   10                  15

Leu Pro Gly Ala Ile Cys Asp Pro Val Met Thr Gln Thr Pro Ser Ser
            20                  25                  30

Thr Ser Ala Ala Val Gly Gly Thr Val Thr Ile Asn Cys Gln Ser Ser
        35                  40                  45

Gln Ser Val Tyr Gly Asn Asn Tyr Leu Ser Trp Phe Gln Gln Lys Pro
    50                  55                  60

Gly Gln Pro Pro Lys Leu Leu Ile Tyr Lys Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Ala Gly Ala Tyr Ser Asp Asn Arg Val Phe Gly Gly Gly Thr Glu Val
        115                 120                 125

Val Val Lys
    130
```

<210> SEQ ID NO 52
<211> LENGTH: 9
<212> TYPE: PRT
<213> ORGANISM: Artificial Sequence
<220> FEATURE:
<223> OTHER INFORMATION: Synthetic construct

<400> SEQUENCE: 52

```
Ala Gly Ala Tyr Ser Asp Asn Arg Val
1               5
```

<210> SEQ ID NO 53
<211> LENGTH: 136
<212> TYPE: PRT
<213> ORGANISM: Artificial Sequence
<220> FEATURE:
<223> OTHER INFORMATION: Synthetic construct

<400> SEQUENCE: 53

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Asn Tyr Ala Met Val Trp Val Arg Gln Ala Pro Gly Lys Gly Leu Glu
    50                  55                  60

Tyr Ile Gly Leu Ile Ser Arg Ser Gly Val Thr Tyr Tyr Ala Thr Trp
65                  70                  75                  80

Ala Lys Gly Arg Phe Thr Ile Ser Lys Ala Ser Thr Thr Val Asp Leu
                85                  90                  95
```

```
Lys Ile Ala Ser Pro Thr Thr Gly Asp Thr Ala Thr Tyr Phe Cys Val
            100                 105                 110

Arg Asp Tyr Asp Ala Asn Gly Trp Ser Gly Phe Thr Ile Trp Gly Pro
        115                 120                 125

Gly Thr Leu Val Thr Val Ser Ala
        130             135

<210> SEQ ID NO 54
<211> LENGTH: 10
<212> TYPE: PRT
<213> ORGANISM: Artificial Sequence
<220> FEATURE:
<223> OTHER INFORMATION: Synthetic construct

<400> SEQUENCE: 54

Gly Phe Ser Leu Ser Asn Tyr Ala Met Val
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Synthetic construct

<400> SEQUENCE: 55

Val Arg Asp Tyr Asp Ala Asn Gly Trp Ser Gly Phe Thr Ile
1               5                   10

<210> SEQ ID NO 56
<211> LENGTH: 131
<212> TYPE: PRT
<213> ORGANISM: Artificial Sequence
<220> FEATURE:
<223> OTHER INFORMATION: Synthetic construct

<400> SEQUENCE: 56

Met Asp Thr Arg Ala Pro Thr Gln Leu Leu Gly Leu Leu Leu Leu Trp
1               5                   10                  15

Leu Pro Gly Ala Ile Cys Asp Pro Val Met Thr Gln Thr Pro Ser Ser
            20                  25                  30

Thr Ser Ala Ala Val Gly Gly Thr Val Thr Ile Asn Cys Gln Ser Ser
        35                  40                  45

Gln Ser Val Tyr Gly Asn Asn Tyr Leu Ser Trp Tyr Gln Gln Lys Pro
    50                  55                  60

Gly Gln Pro Pro Lys Leu Leu Ile Tyr Lys Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Asp Cys Asp Asp Ala Ala Thr Tyr Tyr Cys
            100                 105                 110

Ala Gly Ala Ala Ser Asp Thr Arg Phe Phe Gly Gly Gly Thr Glu Val
        115                 120                 125

Val Val Lys
        130

<210> SEQ ID NO 57
<211> LENGTH: 10
<212> TYPE: PRT
<213> ORGANISM: Unknown
<220> FEATURE:
<223> OTHER INFORMATION: Consensus sequence
```

```
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 57

Gly Phe Ser Leu Ser Xaa Tyr Xaa Met Xaa
1               5                   10

<210> SEQ ID NO 58
<211> LENGTH: 16
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 58

Xaa Xaa Xaa Xaa Xaa Gly Xaa Xaa Tyr Tyr Ala Xaa Trp Ala Lys Gly
1               5                   10                  15

<210> SEQ ID NO 59
<211> LENGTH: 14
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 59

Val Arg Asp Tyr Asp Xaa Xaa Gly Trp Ser Gly Phe Xaa Ile
1               5                   10

<210> SEQ ID NO 60
<211> LENGTH: 13
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
```

```
<220> FEATURE:
<221> NAME/KEY: misc_feature
<222> LOCATION: (11)..(12)
<223> OTHER INFORMATION: Xaa can be any naturally occurring amino acid

<400> SEQUENCE: 60

Gln Ser Ser Xaa Ser Val Xaa Xaa Asn Asn Xaa Xaa Ser
1               5                   10

<210> SEQ ID NO 61
<211> LENGTH: 7
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 61

Xaa Ala Ser Xaa Leu Ala Ser
1               5

<210> SEQ ID NO 62
<211> LENGTH: 9
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 62

Ala Gly Ala Xaa Ser Asp Xaa Arg Xaa
1               5

<210> SEQ ID NO 63
<211> LENGTH: 136
<212> TYPE: PRT
<213> ORGANISM: Artificial Sequence
<220> FEATURE:
<223> OTHER INFORMATION: Synthetic construct

<400> SEQUENCE: 63

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Ala Met Gly Trp Val Arg Gln Ala Pro Gly Glu Gly Leu Glu
    50                  55                  60

Tyr Phe Gly Ile Ile Asn Thr Gly Gly Ser Ala Tyr Tyr Thr Asn Trp
```

```
                65                  70                  75                  80
Ala Lys Gly Arg Phe Thr Ile Ser Arg Thr Ser Thr Val His Leu
                    85                  90                  95
Lys Ile Thr Ser Pro Thr Thr Glu Asp Thr Ala Thr Tyr Phe Cys Ala
                100                 105                 110
Arg Ile Ala Gly Asp Thr Arg Tyr Tyr Gly Met Asp Pro Trp Gly Pro
                115                 120                 125
Gly Thr Leu Val Thr Val Ser Ser
                130                 135

<210> SEQ ID NO 64
<211> LENGTH: 16
<212> TYPE: PRT
<213> ORGANISM: Artificial Sequence
<220> FEATURE:
<223> OTHER INFORMATION: Synthetic construct

<400> SEQUENCE: 64

Ile Ile Asn Thr Gly Gly Ser Ala Tyr Tyr Thr Asn Trp Ala Lys Gly
1               5                   10                  15

<210> SEQ ID NO 65
<211> LENGTH: 14
<212> TYPE: PRT
<213> ORGANISM: Artificial Sequence
<220> FEATURE:
<223> OTHER INFORMATION: Synthetic construct

<400> SEQUENCE: 65

Ala Arg Ile Ala Gly Asp Thr Arg Tyr Tyr Gly Met Asp Pro
1               5                   10

<210> SEQ ID NO 66
<211> LENGTH: 133
<212> TYPE: PRT
<213> ORGANISM: Artificial Sequence
<220> FEATURE:
<223> OTHER INFORMATION: Synthetic construct

<400> SEQUENCE: 66

Met Asp Thr Arg Ala Pro Thr Gln Leu Leu Gly Leu Leu Leu Leu Trp
1               5                   10                  15
Leu Pro Gly Ala Thr Phe Ala Ala Val Leu Thr Gln Thr Pro Ser Pro
                20                  25                  30
Val Ser Ala Ala Val Gly Gly Thr Val Ser Ile Ser Cys Gln Ser Ser
                35                  40                  45
Lys Ser Val Arg Asn Asn Asn Tyr Leu Ala Trp Tyr Gln Gln Lys Pro
            50                  55                  60
Gly Gln Pro Pro Lys Leu Leu Ile Tyr Gly Ala Ser Thr Leu Ala Ser
65                  70                  75                  80
Gly Val Pro Ser Arg Phe Lys Gly Ser Gly Ser Gly Thr Gln Phe Thr
                    85                  90                  95
Leu Thr Ile Ser Asp Val Gln Cys Asp Asp Ala Ala Thr Tyr Tyr Cys
                100                 105                 110
Ala Gly Gly Tyr Asp Gly Gly Ser Asp Asp Ala Phe Gly Gly Gly Thr
                115                 120                 125
Glu Val Val Val Lys
    130

<210> SEQ ID NO 67
```

<211> LENGTH: 13
<212> TYPE: PRT
<213> ORGANISM: Artificial Sequence
<220> FEATURE:
<223> OTHER INFORMATION: Synthetic construct

<400> SEQUENCE: 67

Gln Ser Ser Lys Ser Val Arg Asn Asn Asn Tyr Leu Ala
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic construct

<400> SEQUENCE: 68

Ala Gly Gly Tyr Asp Gly Gly Ser Asp Asp Ala
1               5                   10

<210> SEQ ID NO 69
<211> LENGTH: 408
<212> TYPE: DNA
<213> ORGANISM: Artificial Sequence
<220> FEATURE:
<223> OTHER INFORMATION: Synthetic construct

<400> SEQUENCE: 69
atggagactg ggctgcgctg gcttctcctg gtcgctgtgc tcaagggtgt ccagtgtcag      60
tcggtggagg agtccggggg tcgcctggtc acgcctggga cacccctgac actcacctgc     120
acagtctctg gattctcccc cagtagctat gcaatgggct gggtccgcca ggctccaggg     180
gaggggctgg aatacttcgg aatcattaat actggtggta gcgcatacta cacgaactgg    240
gcaaaaggcc gattcaccat ctccagaacc tcgaccacgg tgcatctgaa aatcaccagt    300
ccgacaaccg aggacacggc cacctatttc tgtgccagga ttgctggtga tactagatac    360
tacggcatgg acccctgggg cccagggacc ctcgtcaccg tctcttca                 408

<210> SEQ ID NO 70
<211> LENGTH: 399
<212> TYPE: DNA
<213> ORGANISM: Artificial Sequence
<220> FEATURE:
<223> OTHER INFORMATION: Synthetic construct

<400> SEQUENCE: 70
atggacacga gggcccccac tcagctgctg gggctcctgc tgctctggct cccaggtgcc      60
acatttgccg ccgtgctgac ccagactcca tctcccgtgt ctgcagctgt gggaggcaca    120
gtcagcatca gttgccagtc cagtaagagt gttcgtaata caactactt agcctggtat     180
cagcagaaac tgggcagcc tcccaaactc ctgatctatg gtgcatccac tctggcatct    240
ggggtcccat cgcggttcaa aggcagtgga tctgggacac agttcactct caccatcagc    300
gacgtgcagt gtgacgatgc tgccacttac tactgtgcag gcggttatga tggtggtagt    360
gatgatgctt cggcggagg gaccgaggtg gtggtcaaa                           399

<210> SEQ ID NO 71
<211> LENGTH: 133
<212> TYPE: PRT
<213> ORGANISM: Artificial Sequence
<220> FEATURE:
<223> OTHER INFORMATION: Synthetic construct

<400> SEQUENCE: 71

```
Met Glu Thr Gly Leu Arg Trp Leu Leu Leu Val Ala Val Leu Lys Gly
1               5                  10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Asn
        35                  40                  45

Val Tyr Tyr Met Thr Trp Val Arg Gln Ala Pro Gly Lys Gly Leu Asp
    50                  55                  60

Trp Ile Gly Ile Ile Asn Thr Asp Ile Thr Val His Tyr Ala Asn Trp
65                  70                  75                  80

Ala Arg Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Ala Arg Asn Ser Ala Trp Met Asp Ile Trp Gly Pro Gly Thr Leu
        115                 120                 125

Val Thr Val Ser Leu
    130
```

<210> SEQ ID NO 72
<211> LENGTH: 10
<212> TYPE: PRT
<213> ORGANISM: Artificial Sequence
<220> FEATURE:
<223> OTHER INFORMATION: Synthetic construct

<400> SEQUENCE: 72

```
Gly Phe Ser Leu Asn Val Tyr Tyr Met Thr
1               5                  10
```

<210> SEQ ID NO 73
<211> LENGTH: 16
<212> TYPE: PRT
<213> ORGANISM: Artificial Sequence
<220> FEATURE:
<223> OTHER INFORMATION: Synthetic construct

<400> SEQUENCE: 73

```
Ile Ile Asn Thr Asp Ile Thr Val His Tyr Ala Asn Trp Ala Arg Gly
1               5                  10                  15
```

<210> SEQ ID NO 74
<211> LENGTH: 11
<212> TYPE: PRT
<213> ORGANISM: Artificial Sequence
<220> FEATURE:
<223> OTHER INFORMATION: Synthetic construct

<400> SEQUENCE: 74

```
Ala Arg Ala Arg Asn Ser Ala Trp Met Asp Ile
1               5                  10
```

<210> SEQ ID NO 75
<211> LENGTH: 132
<212> TYPE: PRT
<213> ORGANISM: Artificial Sequence
<220> FEATURE:
<223> OTHER INFORMATION: Synthetic construct

<400> SEQUENCE: 75

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Thr Ile Asn Cys Gln Ser Asp
        35                  40                  45

Trp Ser Val Tyr Asn Asn Asn Leu Ala Trp Tyr Gln His Lys Pro Gly
    50                  55                  60

Gln Pro Pro Lys Leu Leu Ile Tyr Lys Thr Ser Thr Leu Ala Ser Gly
65                  70                  75                  80

Val Pro Ser Arg Phe Arg Gly Ser Gly Ser Gly Thr Gln Phe Thr Leu
            85                  90                  95

Thr Ile Ser Asp Val Gln Cys Asp Asp Thr Ala Thr Tyr Tyr Cys Ala
            100                 105                 110

Gly Gly Tyr Tyr Arg Asp Ser Asp Thr Ala Phe Gly Gly Gly Thr Glu
            115                 120                 125

Val Val Val Lys
        130

<210> SEQ ID NO 76
<211> LENGTH: 12
<212> TYPE: PRT
<213> ORGANISM: Artificial Sequence
<220> FEATURE:
<223> OTHER INFORMATION: Synthetic construct

<400> SEQUENCE: 76

Gln Ser Asp Trp Ser Val Tyr Asn Asn Asn Leu Ala
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Synthetic construct

<400> SEQUENCE: 77

Lys Thr Ser Thr Leu Ala Ser
1               5

<210> SEQ ID NO 78
<211> LENGTH: 11
<212> TYPE: PRT
<213> ORGANISM: Artificial Sequence
<220> FEATURE:
<223> OTHER INFORMATION: Synthetic construct

<400> SEQUENCE: 78

Ala Gly Gly Tyr Tyr Arg Asp Ser Asp Thr Ala
1               5                   10

<210> SEQ ID NO 79
<211> LENGTH: 399
<212> TYPE: DNA
<213> ORGANISM: Artificial Sequence
<220> FEATURE:
<223> OTHER INFORMATION: Synthetic construct

<400> SEQUENCE: 79
atggagactg ggctgcgctg gcttctcctg gtcgctgtgc tcaaaggtgt ccagtgtcag      60
tcagtggagg agtccggggg tcgcctggtc acgcctggga cacccctgac actcacctgc    120
```

```
acagcctctg gattctccct caatgtctac tacatgacct gggtccgcca ggctccaggg    180
aaggggctgg attggatcgg aatcattaat acagatatta ccgtgcacta cgcgaactgg    240
gcgagaggcc gattcaccat ctccaaaacc tcgaccacgg tggatctgaa aatcaccagt    300
ccgacaaccg aggacacggc cacctatttc tgtgccagag ctcgtaatag tgcttggatg    360
gacatctggg gcccaggcac cctggtcacc gtctcgttg                            399

<210> SEQ ID NO 80
<211> LENGTH: 396
<212> TYPE: DNA
<213> ORGANISM: Artificial Sequence
<220> FEATURE:
<223> OTHER INFORMATION: Synthetic construct

<400> SEQUENCE: 80
atggacacga gggcccccac tcagctgctg ggctcctgc tgctctggct cccaggtgcc      60
acatttgccg ccgtgctgac ccagactcca tcccccgtgt ctgcagctgt gggaggcaca    120
gtcaccatca attgccagtc cgattggagt gtttataata caacttagc ctggtatcag    180 cacaagccag gcagcctcc caagctcctg atctacaaga cttccactct ggcatctggg    240
gtcccatcgc ggttcagagg cagtggatct gggacacagt tcactctcac catcagcgac    300
gttcagtgtg acgatactgc cacttattac tgtgcaggcg ttattatcg cgacagtgat    360 acggctttcg gcggagggac cgaggtggtg gtcaaa                              396

<210> SEQ ID NO 81
<211> LENGTH: 133
<212> TYPE: PRT
<213> ORGANISM: Artificial Sequence
<220> FEATURE:
<223> OTHER INFORMATION: Synthetic construct

<400> SEQUENCE: 81

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Tyr Ile Thr Trp Val Arg Gln Ala Pro Gly Lys Gly Leu Glu
    50                  55                  60

Trp Leu Gly Ile Met Asn Ala Gly Thr Thr Val His Tyr Ala Asn Trp
65                  70                  75                  80

Val Lys Gly Arg Phe Ala Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Ala Arg Asn Ser Val Trp Met Asp Ile Trp Gly Pro Gly Thr Leu
        115                 120                 125

Val Thr Val Ser Leu
    130

<210> SEQ ID NO 82
<211> LENGTH: 10
<212> TYPE: PRT
<213> ORGANISM: Artificial Sequence
<220> FEATURE:
<223> OTHER INFORMATION: Synthetic construct
```

<400> SEQUENCE: 82

Gly Phe Ser Leu Ser Ser Tyr Tyr Ile Thr
1               5                   10

<210> SEQ ID NO 83
<211> LENGTH: 16
<212> TYPE: PRT
<213> ORGANISM: Artificial Sequence
<220> FEATURE:
<223> OTHER INFORMATION: Synthetic construct

<400> SEQUENCE: 83

Ile Met Asn Ala Gly Thr Thr Val His Tyr Ala Asn Trp Val Lys Gly
1               5                   10                  15

<210> SEQ ID NO 84
<211> LENGTH: 11
<212> TYPE: PRT
<213> ORGANISM: Artificial Sequence
<220> FEATURE:
<223> OTHER INFORMATION: Synthetic construct

<400> SEQUENCE: 84

Ala Arg Ala Arg Asn Ser Val Trp Met Asp Ile
1               5                   10

<210> SEQ ID NO 85
<211> LENGTH: 132
<212> TYPE: PRT
<213> ORGANISM: Artificial Sequence
<220> FEATURE:
<223> OTHER INFORMATION: Synthetic construct

<400> SEQUENCE: 85

Met Asp Thr Arg Ala Pro Thr Gln Leu Leu Gly Leu Leu Leu Leu Trp
1               5                   10                  15

Leu Pro Gly Ala Thr Leu Ala Ala Val Leu Thr Gln Thr Pro Ser Pro
                20                  25                  30

Val Ser Gly Ala Val Gly Gly Ser Val Thr Val Asn Cys Gln Ser Asp
            35                  40                  45

Lys Ser Val Tyr Arg Asp Asn Leu Ala Trp Tyr Gln Gln Lys Pro Gly
        50                  55                  60

Gln Pro Pro Lys Leu Leu Ile Tyr Lys Ala Ser Thr Leu Ala Ser Gly
65                  70                  75                  80

Val Pro Ser Arg Phe Arg Gly Ser Gly Ala Gly Thr Gln Phe Thr Leu
                85                  90                  95

Thr Ile Ser Asp Val Gln Cys Asp Asp Ala Ala Thr Tyr Phe Cys Ala
            100                 105                 110

Gly Gly Tyr Ser Ser Asp Ser Asp Thr Ala Phe Gly Gly Gly Thr Glu
        115                 120                 125

Val Val Val Lys
        130

<210> SEQ ID NO 86
<211> LENGTH: 12
<212> TYPE: PRT
<213> ORGANISM: Artificial Sequence
<220> FEATURE:
<223> OTHER INFORMATION: Synthetic construct

<400> SEQUENCE: 86

Gln Ser Asp Lys Ser Val Tyr Arg Asp Asn Leu Ala
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic construct

<400> SEQUENCE: 87

Ala Gly Gly Tyr Ser Ser Asp Ser Asp Thr Ala
1               5                   10

<210> SEQ ID NO 88
<211> LENGTH: 399
<212> TYPE: DNA
<213> ORGANISM: Artificial Sequence
<220> FEATURE:
<223> OTHER INFORMATION: Synthetic construct

<400> SEQUENCE: 88
atggagactg ggctgcgctg gcttctcctg gtcgctgtgc tcaaaggtgt ccagtgtcag    60
tcggtggagg agtccggggg tcgcctggtc acgcctggga caccctgac actcacctgc   120 acagtctctg gattctcct cagtagctac tacataacct gggtccgcca ggctccaggg    180
aaggggctgg agtggctcgg aatcatgaat gctggtacta ccgtacatta tgcgaactgg    240
gtgaaaggcc gattcgccat ctccaaaacc tcgaccacgg tggatctgaa aatcaccagt    300
ccgacaaccg aggacacggc cacctatttc tgtgccagag ctcgtaatag tgtttggatg    360
gacatctggg gcccaggcac cctggtcacc gtctcctta                         399

<210> SEQ ID NO 89
<211> LENGTH: 396
<212> TYPE: DNA
<213> ORGANISM: Artificial Sequence
<220> FEATURE:
<223> OTHER INFORMATION: Synthetic construct

<400> SEQUENCE: 89
atggacacga gggcccccac tcagctgctg ggctcctgc tgctctggct cccaggtgcc    60
acgcttgccg ccgttctgac ccagactcca tccccgtgt ctggagctgt gggaggctca    120
gtcaccgtca attgccagtc cgataagagt gtttataggg acaacttagc ctggtatcag    180
cagaaaccag ggcagcctcc caagctcctg atctacaagg cttccactct ggcatctggg    240
gtcccatcgc gtttcagagg cagtggagct gggacacagt tcactctcac catcagcgac    300
gtgcagtgtg acgatgctgc cacttacttc tgtgcaggcg gttatagtag cgacagtgat    360
acggctttcg gcggagggac cgaggtggtg gtcaaa                            396

<210> SEQ ID NO 90
<211> LENGTH: 133
<212> TYPE: PRT
<213> ORGANISM: Artificial Sequence
<220> FEATURE:
<223> OTHER INFORMATION: Synthetic construct

<400> SEQUENCE: 90

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

-continued

Gly Thr Pro Leu Thr Leu Thr Cys Thr Val Ser Gly Phe Ser Leu Ser
            35                  40                  45

Ser Tyr Tyr Ile Thr Trp Val Arg Gln Ala Pro Gly Lys Gly Arg Glu
        50                  55                  60

Trp Leu Gly Ile Met Asn Ala Gly Thr Thr Val His Tyr Ala Asn Trp
 65                  70                  75                  80

Val Lys Gly Arg Phe Ala Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Ala Arg Asn Ser Val Trp Met Asp Ile Trp Gly Pro Gly Thr Leu
            115                 120                 125

Val Thr Val Ser Leu
        130

<210> SEQ ID NO 91
<211> LENGTH: 137
<212> TYPE: PRT
<213> ORGANISM: Artificial Sequence
<220> FEATURE:
<223> OTHER INFORMATION: Synthetic construct

<400> SEQUENCE: 91

Met Glu Thr Gly Leu Arg Trp Leu Leu Leu Val Ala Val Leu Lys Gly
 1               5                  10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Ser
            35                  40                  45

Thr Tyr Val Met Ser Trp Val Arg Gln Ala Pro Gly Lys Gly Leu Glu
        50                  55                  60

Trp Ile Gly Val Leu Ser Ser Gly Arg Thr Asp Tyr Ala Ser Trp
 65                  70                  75                  80

Ala Lys Gly Arg Phe Ala Ile Ser Lys Thr Ser Thr Thr Val Asp Leu
                85                  90                  95

Arg Ile Thr Ser Pro Thr Thr Glu Asp Thr Ala Thr Tyr Phe Cys Val
            100                 105                 110

Arg Ala Pro Ile Tyr Ser Asn Gly Gly Tyr Tyr Leu Asp Ile Trp Gly
            115                 120                 125

Pro Gly Thr Leu Val Thr Val Ser Leu
        130                 135

<210> SEQ ID NO 92
<211> LENGTH: 10
<212> TYPE: PRT
<213> ORGANISM: Artificial Sequence
<220> FEATURE:
<223> OTHER INFORMATION: Synthetic construct

<400> SEQUENCE: 92

Gly Phe Ser Leu Ser Thr Tyr Val Met Ser
 1               5                  10

<210> SEQ ID NO 93
<211> LENGTH: 16
<212> TYPE: PRT
<213> ORGANISM: Artificial Sequence
<220> FEATURE:
<223> OTHER INFORMATION: Synthetic construct

<400> SEQUENCE: 93

Val Leu Ser Ser Gly Arg Thr Asp Tyr Ala Ser Trp Ala Lys Gly
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic construct

<400> SEQUENCE: 94

Val Arg Ala Pro Ile Tyr Ser Asn Gly Gly Tyr Tyr Leu Asp Ile
1               5                   10                  15

<210> SEQ ID NO 95
<211> LENGTH: 135
<212> TYPE: PRT
<213> ORGANISM: Artificial Sequence
<220> FEATURE:
<223> OTHER INFORMATION: Synthetic construct

<400> SEQUENCE: 95

Met Asp Thr Arg Ala Pro Thr Gln Leu Leu Gly Leu Leu Leu Leu Trp
1               5                   10                  15

Leu Pro Gly Ala Arg Cys Ala Val Val Met Thr Gln Thr Ala Ser Pro
            20                  25                  30

Val Ser Ala Ala Val Gly Gly Thr Val Thr Ile Asn Cys Gln Ala Ser
        35                  40                  45

Arg Ser Leu Leu Ser Leu Thr Tyr Leu Ser Trp Tyr Gln Gln Lys Pro
    50                  55                  60

Gly Gln Pro Pro Lys Leu Leu Ile Tyr Arg Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Glu Cys Ala Asp Ala Ala Thr Tyr Tyr Cys
            100                 105                 110

Leu Tyr Gly Tyr Tyr Ser Arg Gly Ser Gly Asp Thr Ala Phe Gly Gly
        115                 120                 125

Gly Thr Glu Val Val Val Lys
    130                 135

<210> SEQ ID NO 96
<211> LENGTH: 13
<212> TYPE: PRT
<213> ORGANISM: Artificial Sequence
<220> FEATURE:
<223> OTHER INFORMATION: Synthetic construct

<400> SEQUENCE: 96

Gln Ala Ser Arg Ser Leu Leu Ser Leu Thr Tyr Leu Ser
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Synthetic construct

<400> SEQUENCE: 97

Arg Ala Ser Thr Leu Ala Ser
1               5

<210> SEQ ID NO 98
<211> LENGTH: 13
<212> TYPE: PRT
<213> ORGANISM: Artificial Sequence
<220> FEATURE:
<223> OTHER INFORMATION: Synthetic construct

<400> SEQUENCE: 98

Leu Tyr Gly Tyr Tyr Ser Arg Gly Ser Gly Asp Thr Ala
1               5                   10

<210> SEQ ID NO 99
<211> LENGTH: 140
<212> TYPE: PRT
<213> ORGANISM: Artificial Sequence
<220> FEATURE:
<223> OTHER INFORMATION: Synthetic construct

<400> SEQUENCE: 99

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Glu Gly Ser Pro Thr Leu Thr Cys Thr Ala Ser Gly Phe Ser Phe Ser
        35                  40                  45

Ser Ser Tyr Trp Ile Cys Trp Val Arg Gln Ala Pro Gly Lys Gly Leu
    50                  55                  60

Glu Trp Ile Ala Cys Ile Tyr Gly Gly Ser Ser Gly Thr Ile Tyr Tyr
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Arg Arg Ala Ala Gly Gly Tyr Gly Gly Arg Leu Asp
        115                 120                 125

Leu Trp Gly Gln Gly Thr Leu Val Thr Val Ser Ser
    130                 135                 140

<210> SEQ ID NO 100
<211> LENGTH: 11
<212> TYPE: PRT
<213> ORGANISM: Artificial Sequence
<220> FEATURE:
<223> OTHER INFORMATION: Synthetic construct

<400> SEQUENCE: 100

Gly Phe Ser Phe Ser Ser Ser Tyr Trp Ile Cys
1               5                   10

<210> SEQ ID NO 101
<211> LENGTH: 18
<212> TYPE: PRT
<213> ORGANISM: Artificial Sequence
<220> FEATURE:
<223> OTHER INFORMATION: Synthetic construct

<400> SEQUENCE: 101

Cys Ile Tyr Gly Gly Ser Ser Gly Thr Ile Tyr Tyr Ala Ser Trp Ala
1               5                   10                  15

Lys Gly

<210> SEQ ID NO 102
<211> LENGTH: 14
<212> TYPE: PRT
<213> ORGANISM: Artificial Sequence
<220> FEATURE:
<223> OTHER INFORMATION: Synthetic construct

<400> SEQUENCE: 102

Ala Arg Arg Ala Ala Gly Gly Tyr Gly Gly Arg Leu Asp Leu
1               5                   10

<210> SEQ ID NO 103
<211> LENGTH: 134
<212> TYPE: PRT
<213> ORGANISM: Artificial Sequence
<220> FEATURE:
<223> OTHER INFORMATION: Synthetic construct

<400> SEQUENCE: 103

Met Asp Thr Arg Ala Pro Thr Gln Leu Leu Gly Leu Leu Leu Leu Trp
1               5                   10                  15

Leu Pro Gly Ala Thr Phe Ala Gln Val Met Thr Gln Thr Pro Ala Ser
                20                  25                  30

Val Ser Ala Ala Val Gly Gly Thr Val Thr Ile Asn Cys Gln Ser Ser
            35                  40                  45

Glu Ser Val Leu Asn Asn Asn Tyr Leu Ala Trp Tyr Gln Gln Lys Ser
        50                  55                  60

Gly Gln Pro Pro Lys Leu Leu Ile Trp Thr Ala Ser Ser Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Ala Gly Gly Tyr Tyr Ile Gly Ser Asp Ile Phe Ala Phe Gly Gly Gly
        115                 120                 125

Thr Glu Val Val Val Arg
    130

<210> SEQ ID NO 104
<211> LENGTH: 13
<212> TYPE: PRT
<213> ORGANISM: Artificial Sequence
<220> FEATURE:
<223> OTHER INFORMATION: Synthetic construct

<400> SEQUENCE: 104

Gln Ser Ser Glu Ser Val Leu Asn Asn Asn Tyr Leu Ala
1               5                   10

<210> SEQ ID NO 105
<211> LENGTH: 7
<212> TYPE: PRT
<213> ORGANISM: Artificial Sequence
<220> FEATURE:
<223> OTHER INFORMATION: Synthetic construct

<400> SEQUENCE: 105

Thr Ala Ser Ser Leu Ala Ser
1               5

<210> SEQ ID NO 106
<211> LENGTH: 12
<212> TYPE: PRT
<213> ORGANISM: Artificial Sequence
<220> FEATURE:
<223> OTHER INFORMATION: Synthetic construct

<400> SEQUENCE: 106

```
Ala Gly Gly Tyr Tyr Ile Gly Ser Asp Ile Phe Ala
1               5                   10
```

<210> SEQ ID NO 107
<211> LENGTH: 141
<212> TYPE: PRT
<213> ORGANISM: Artificial Sequence
<220> FEATURE:
<223> OTHER INFORMATION: Synthetic construct

<400> SEQUENCE: 107

```
Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Asp Leu Val Lys
            20                  25                  30

Pro Glu Gly Ser Pro Thr Leu Thr Cys Thr Ala Ser Gly Phe Ser Phe
        35                  40                  45

Ser Ser Ser Tyr Gly Ile Cys Trp Val Arg Gln Ala Pro Gly Lys Gly
    50                  55                  60

Arg Glu Trp Ile Ala Cys Ile Tyr Gly Gly Ser Ser Gly Thr Ile Tyr
65                  70                  75                  80

Tyr Ala Ser Trp Ala Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Arg Ala Ala Gly Gly Tyr Gly Gly Arg Leu
        115                 120                 125

Asp Leu Trp Gly Gln Gly Thr Leu Val Thr Val Ser Ser
    130                 135                 140
```

<210> SEQ ID NO 108
<211> LENGTH: 11
<212> TYPE: PRT
<213> ORGANISM: Artificial Sequence
<220> FEATURE:
<223> OTHER INFORMATION: Synthetic construct

<400> SEQUENCE: 108

```
Gly Phe Ser Phe Ser Ser Ser Tyr Gly Ile Cys
1               5                   10
```

<210> SEQ ID NO 109
<211> LENGTH: 133
<212> TYPE: PRT
<213> ORGANISM: Artificial Sequence
<220> FEATURE:
<223> OTHER INFORMATION: Synthetic construct

<400> SEQUENCE: 109

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Ser
```

```
                35                  40                  45
Ser Tyr Tyr Met Thr Trp Val Arg Gln Ala Pro Gly Lys Gly Leu Glu
 50                  55                  60

Trp Ile Gly Ile Ile Asn Thr Gly Val Thr Val His Tyr Ala Asn Trp
 65                  70                  75                  80

Ala Arg Gly Arg Phe Thr Ile Ser Lys Ser Thr Thr Val Asp Leu
                 85                  90                  95

Arg Ile Thr Ser Pro Thr Thr Glu Asp Thr Ala Thr Tyr Phe Cys Ala
                100                 105                 110

Arg Ala Arg Asn Ser Ala Trp Met Asp Leu Trp Gly Pro Gly Thr Leu
            115                 120                 125

Val Thr Val Ser Leu
        130

<210> SEQ ID NO 110
<211> LENGTH: 10
<212> TYPE: PRT
<213> ORGANISM: Artificial Sequence
<220> FEATURE:
<223> OTHER INFORMATION: Synthetic construct

<400> SEQUENCE: 110

Gly Phe Ser Leu Ser Ser Tyr Tyr Met Thr
 1               5                  10

<210> SEQ ID NO 111
<211> LENGTH: 16
<212> TYPE: PRT
<213> ORGANISM: Artificial Sequence
<220> FEATURE:
<223> OTHER INFORMATION: Synthetic construct

<400> SEQUENCE: 111

Ile Ile Asn Thr Gly Val Thr Val His Tyr Ala Asn Trp Ala Arg Gly
 1               5                  10                  15

<210> SEQ ID NO 112
<211> LENGTH: 11
<212> TYPE: PRT
<213> ORGANISM: Artificial Sequence
<220> FEATURE:
<223> OTHER INFORMATION: Synthetic construct

<400> SEQUENCE: 112

Ala Arg Ala Arg Asn Ser Ala Trp Met Asp Leu
 1               5                  10

<210> SEQ ID NO 113
<211> LENGTH: 132
<212> TYPE: PRT
<213> ORGANISM: Artificial Sequence
<220> FEATURE:
<223> OTHER INFORMATION: Synthetic construct

<400> SEQUENCE: 113

Met Asp Thr Arg Ala Pro Thr Gln Leu Leu Gly Leu Leu Leu Leu Trp
 1               5                  10                  15

Leu Pro Gly Ala Thr Phe Ala Ala Val Leu Thr Gln Thr Pro Ser Ser
            20                  25                  30

Val Ser Ala Ala Val Gly Gly Thr Val Thr Ile Asn Cys Gln Ser Asp
        35                  40                  45

Trp Ser Val Val Asn Asn Asn Leu Ala Trp Tyr Gln Gln Lys Pro Gly
```

```
                    50                  55                  60

Gln Pro Pro Lys Leu Leu Ile Tyr Lys Thr Ser Ser Leu Pro Ser Gly
 65                  70                  75                  80

Val Pro Ser Arg Phe Arg Gly Ser Gly Ser Gly Thr Gln Phe Thr Leu
                 85                  90                  95

Thr Ile Ser Asp Val Gln Cys Asp Asp Ala Ala Thr Tyr Tyr Cys Ala
                100                 105                 110

Gly Gly Tyr Ser Ser Asp Ser Asp Thr Ala Phe Gly Gly Gly Thr Glu
            115                 120                 125

Val Val Val Lys
        130

<210> SEQ ID NO 114
<211> LENGTH: 12
<212> TYPE: PRT
<213> ORGANISM: Artificial Sequence
<220> FEATURE:
<223> OTHER INFORMATION: Synthetic construct

<400> SEQUENCE: 114

Gln Ser Asp Trp Ser Val Val Asn Asn Asn Leu Ala
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Synthetic construct

<400> SEQUENCE: 115

Lys Thr Ser Ser Leu Pro Ser
1               5

<210> SEQ ID NO 116
<211> LENGTH: 10
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid

<400> SEQUENCE: 116

Gly Phe Ser Leu Xaa Xaa Tyr Xaa Xaa Xaa
1               5                   10

<210> SEQ ID NO 117
<211> LENGTH: 16
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(9)
<223> OTHER INFORMATION: Xaa can be any naturally occurring amino acid
```

```
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 117

Ile Xaa Asn Xaa Xaa Xaa Xaa Xaa Tyr Xaa Asn Trp Xaa Xaa Gly
1               5                   10                  15

<210> SEQ ID NO 118
<211> LENGTH: 11
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 118

Ala Arg Ala Arg Asn Ser Xaa Trp Met Asp Xaa
1               5                   10

<210> SEQ ID NO 119
<211> LENGTH: 13
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 119

Gln Ser Xaa Xaa Ser Val Xaa Xaa Xaa Asn Xaa Leu Ala
1               5                   10

<210> SEQ ID NO 120
<211> LENGTH: 7
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
```

<400> SEQUENCE: 120

Xaa Xaa Ser Xaa Leu Xaa Ser
1               5

<210> SEQ ID NO 121
<211> LENGTH: 12
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 121

Ala Gly Gly Tyr Xaa Xaa Xaa Ser Asp Xaa Xaa Ala
1               5                   10

<210> SEQ ID NO 122
<211> LENGTH: 200
<212> TYPE: PRT
<213> ORGANISM: Homo sapiens

<400> SEQUENCE: 122

Met Ala Lys Lys Thr Tyr Asp Leu Leu Phe Lys Leu Leu Ile Gly
1               5                   10                  15

Asp Ser Gly Val Gly Lys Thr Cys Val Leu Phe Arg Phe Ser Asp Asp
                20                  25                  30

Ala Phe Asn Thr Thr Phe Ile Ser Thr Ile Gly Ile Asp Phe Lys Ile
            35                  40                  45

Lys Thr Val Glu Leu Gln Gly Lys Lys Ile Lys Leu Gln Ile Trp Asp
        50                  55                  60

Thr Ala Gly Gln Glu Arg Phe His Thr Ile Thr Thr Ser Tyr Tyr Arg
65                  70                  75                  80

Gly Ala Met Gly Ile Met Leu Val Tyr Asp Ile Thr Asn Gly Lys Ser
                85                  90                  95

Phe Glu Asn Ile Ser Lys Trp Leu Arg Asn Ile Asp Glu His Ala Asn
            100                 105                 110

Glu Asp Val Glu Arg Met Leu Leu Gly Asn Lys Cys Asp Met Asp Asp
        115                 120                 125

Lys Arg Val Val Pro Lys Gly Lys Gly Glu Gln Ile Ala Arg Glu His
    130                 135                 140

Gly Ile Arg Phe Phe Glu Thr Ser Ala Lys Ala Asn Ile Asn Ile Glu
145                 150                 155                 160

Lys Ala Phe Leu Thr Leu Ala Glu Asp Ile Leu Arg Lys Thr Pro Val
                165                 170                 175

Lys Glu Pro Asn Ser Glu Asn Val Asp Ile Ser Ser Gly Gly Gly Val
            180                 185                 190

Thr Gly Trp Lys Ser Lys Cys Cys
        195                 200

<210> SEQ ID NO 123
<211> LENGTH: 15
<212> TYPE: PRT
<213> ORGANISM: Artificial Sequence

```
<220> FEATURE:
<223> OTHER INFORMATION: Synthetic construct
<220> FEATURE:
<221> NAME/KEY: MOD_RES
<222> LOCATION: (8)..(8)
<223> OTHER INFORMATION: PHOSPHORYLATION

<400> SEQUENCE: 123

Ala Gly Gln Glu Arg Phe His Thr Ile Thr Thr Ser Tyr Tyr Arg
1               5                   10                  15

<210> SEQ ID NO 124
<211> LENGTH: 207
<212> TYPE: PRT
<213> ORGANISM: Homo sapiens

<400> SEQUENCE: 124

Met Ala Lys Thr Tyr Asp Tyr Leu Phe Lys Leu Leu Leu Ile Gly Asp
1               5                   10                  15

Ser Gly Val Gly Lys Thr Cys Val Leu Phe Arg Phe Ser Glu Asp Ala
            20                  25                  30

Phe Asn Ser Thr Phe Ile Ser Thr Ile Gly Ile Asp Phe Lys Ile Arg
        35                  40                  45

Thr Ile Glu Leu Asp Gly Lys Arg Ile Lys Leu Gln Ile Trp Asp Thr
    50                  55                  60

Ala Gly Gln Glu Arg Phe Arg Thr Ile Thr Thr Ala Tyr Tyr Arg Gly
65                  70                  75                  80

Ala Met Gly Ile Met Leu Val Tyr Asp Ile Thr Asn Glu Lys Ser Phe
                85                  90                  95

Asp Asn Ile Arg Asn Trp Ile Arg Asn Ile Glu Glu His Ala Ser Ala
            100                 105                 110

Asp Val Glu Lys Met Ile Leu Gly Asn Lys Cys Asp Val Asn Asp Lys
        115                 120                 125

Arg Gln Val Ser Lys Glu Arg Gly Glu Lys Leu Ala Leu Asp Tyr Gly
    130                 135                 140

Ile Lys Phe Met Glu Thr Ser Ala Lys Ala Asn Ile Asn Val Glu Asn
145                 150                 155                 160

Ala Phe Phe Thr Leu Ala Arg Asp Ile Lys Ala Lys Met Asp Lys Lys
                165                 170                 175

Leu Glu Gly Asn Ser Pro Gln Gly Ser Asn Gln Gly Val Lys Ile Thr
            180                 185                 190

Pro Asp Gln Gln Lys Arg Ser Ser Phe Phe Arg Cys Val Leu Leu
        195                 200                 205

<210> SEQ ID NO 125
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (6)..(6)
<223> OTHER INFORMATION: PHOSPHORYLATION

<400> SEQUENCE: 125

Gln Glu Arg Phe Arg Thr Ile Thr Thr Ala Tyr
1               5                   10

<210> SEQ ID NO 126
<211> LENGTH: 15
```

```
<212> TYPE: PRT
<213> ORGANISM: Homo sapiens

<400> SEQUENCE: 126

Ala Gly Gln Glu Arg Phe His Thr Ile Thr Thr Ser Tyr Tyr Arg
1               5                   10                  15

<210> SEQ ID NO 127
<211> LENGTH: 11
<212> TYPE: PRT
<213> ORGANISM: Homo sapiens

<400> SEQUENCE: 127

Gln Glu Arg Phe Arg Thr Ile Thr Thr Ala Tyr
1               5                   10

<210> SEQ ID NO 128
<211> LENGTH: 15
<212> TYPE: PRT
<213> ORGANISM: Homo sapiens

<400> SEQUENCE: 128

Ala Gly Gln Glu Arg Phe Arg Thr Ile Thr Thr Ala Tyr Tyr Arg
1               5                   10                  15

<210> SEQ ID NO 129
<211> LENGTH: 22
<212> TYPE: PRT
<213> ORGANISM: Homo sapiens

<400> SEQUENCE: 129

Pro Val Lys Glu Pro Asn Ser Glu Asn Val Asp Ile Ser Ser Gly Gly
1               5                   10                  15

Gly Val Thr Gly Trp Lys
            20

<210> SEQ ID NO 130
<211> LENGTH: 15
<212> TYPE: PRT
<213> ORGANISM: Homo sapiens

<400> SEQUENCE: 130

Asp Lys Arg Val Val Pro Lys Gly Lys Gly Glu Gln Ile Ala Arg
1               5                   10                  15

<210> SEQ ID NO 131
<211> LENGTH: 136
<212> TYPE: PRT
<213> ORGANISM: Artificial Sequence
<220> FEATURE:
<223> OTHER INFORMATION: Synthetic construct

<400> SEQUENCE: 131

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Ser Tyr Tyr Met Asn Trp Val Arg Gln Ala Pro Gly Lys Gly Leu Glu
    50                  55                  60

Trp Ile Gly Phe Ile Ser Ser Gly Gly Arg Thr Tyr Tyr Ala Asn Trp
65                  70                  75                  80
```

```
Ala Lys Gly Arg Phe Thr Ile Ser Lys Thr Ser Thr Thr Val Asp Leu
                85                  90                  95

Lys Ile Thr Ser Pro Thr Thr Glu Asp Met Ala Thr Tyr Phe Cys Ala
            100                 105                 110

Arg Ala Ile Tyr Ser Ser Gly Asn Ser Ala Met Ala Ile Trp Gly Pro
        115                 120                 125

Gly Thr Leu Val Thr Val Ser Leu
    130                 135

<210> SEQ ID NO 132
<211> LENGTH: 10
<212> TYPE: PRT
<213> ORGANISM: Artificial Sequence
<220> FEATURE:
<223> OTHER INFORMATION: Synthetic construct

<400> SEQUENCE: 132

Gly Phe Ser Leu Ser Ser Tyr Tyr Met Asn
1               5                   10

<210> SEQ ID NO 133
<211> LENGTH: 16
<212> TYPE: PRT
<213> ORGANISM: Artificial Sequence
<220> FEATURE:
<223> OTHER INFORMATION: Synthetic construct

<400> SEQUENCE: 133

Phe Ile Ser Ser Gly Gly Arg Thr Tyr Tyr Ala Asn Trp Ala Lys Gly
1               5                   10                  15

<210> SEQ ID NO 134
<211> LENGTH: 14
<212> TYPE: PRT
<213> ORGANISM: Artificial Sequence
<220> FEATURE:
<223> OTHER INFORMATION: Synthetic construct

<400> SEQUENCE: 134

Ala Arg Ala Ile Tyr Ser Ser Gly Asn Ser Ala Met Ala Ile
1               5                   10

<210> SEQ ID NO 135
<211> LENGTH: 135
<212> TYPE: PRT
<213> ORGANISM: Artificial Sequence
<220> FEATURE:
<223> OTHER INFORMATION: Synthetic construct

<400> SEQUENCE: 135

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Val Thr Ile Ser Cys Gln Ala Ser
        35                  40                  45

Gln Ser Val Tyr Asp Asn Ser Asn Leu Ala Trp Tyr Gln Gln Lys Pro
    50                  55                  60

Gly Gln Pro Pro Glu Leu Leu Ile Tyr Tyr Thr Ser Thr Leu Ala Ser
65                  70                  75                  80

Gly Val Pro Ser Arg Phe Ser Gly Ser Gly Ser Gly Thr Gln Phe Thr
                85                  90                  95
```

```
Leu Thr Ile Ser Gly Val Gln Cys Asp Asp Ala Ala Ile Tyr Tyr Cys
                100                 105                 110

Leu Gly Ala Phe Thr Cys Ser Ser Gly Asp Cys Asn Val Phe Gly Gly
        115                 120                 125

Gly Thr Glu Val Val Val Lys
    130                 135

<210> SEQ ID NO 136
<211> LENGTH: 13
<212> TYPE: PRT
<213> ORGANISM: Artificial Sequence
<220> FEATURE:
<223> OTHER INFORMATION: Synthetic construct

<400> SEQUENCE: 136

Gln Ala Ser Gln Ser Val Tyr Asp Asn Ser Asn Leu Ala
1               5                   10

<210> SEQ ID NO 137
<211> LENGTH: 7
<212> TYPE: PRT
<213> ORGANISM: Artificial Sequence
<220> FEATURE:
<223> OTHER INFORMATION: Synthetic construct

<400> SEQUENCE: 137

Tyr Thr Ser Thr Leu Ala Ser
1               5

<210> SEQ ID NO 138
<211> LENGTH: 10
<212> TYPE: PRT
<213> ORGANISM: Artificial Sequence
<220> FEATURE:
<223> OTHER INFORMATION: Synthetic construct

<400> SEQUENCE: 138

Leu Gly Ala Phe Thr Cys Ser Ser Gly Asp
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa = Asn, Ser, or Thr
<220> FEATURE:
<221> NAME/KEY: MISC_FEATURE
<222> LOCATION: (8)..(8)
<223> OTHER INFORMATION: Xaa = Ala or Tyr
<220> FEATURE:
<221> NAME/KEY: MISC_FEATURE
<222> LOCATION: (10)..(10)
<223> OTHER INFORMATION: Xaa = Ser or Val

<400> SEQUENCE: 139

Gly Phe Ser Leu Ser Xaa Tyr Xaa Met Xaa
1               5                   10

<210> SEQ ID NO 140
<211> LENGTH: 16
<212> TYPE: PRT
<213> ORGANISM: Artificial Sequence
```

```
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Ile or Leu
<220> FEATURE:
<221> NAME/KEY: MISC_FEATURE
<222> LOCATION: (2)..(2)
<223> OTHER INFORMATION: Xaa = Phe or Ile
<220> FEATURE:
<221> NAME/KEY: MISC_FEATURE
<222> LOCATION: (3)..(3)
<223> OTHER INFORMATION: Xaa = Asn or Ser
<220> FEATURE:
<221> NAME/KEY: MISC_FEATURE
<222> LOCATION: (4)..(4)
<223> OTHER INFORMATION: Xaa = Asp or Arg
<220> FEATURE:
<221> NAME/KEY: MISC_FEATURE
<222> LOCATION: (5)..(5)
<223> OTHER INFORMATION: Xaa = Ser or Val
<220> FEATURE:
<221> NAME/KEY: MISC_FEATURE
<222> LOCATION: (7)..(7)
<223> OTHER INFORMATION: Xaa = Ile or Val
<220> FEATURE:
<221> NAME/KEY: MISC_FEATURE
<222> LOCATION: (8)..(8)
<223> OTHER INFORMATION: Xaa = Ala or Thr
<220> FEATURE:
<221> NAME/KEY: MISC_FEATURE
<222> LOCATION: (12)..(12)
<223> OTHER INFORMATION: Xaa = Asn or Thr

<400> SEQUENCE: 140

Xaa Xaa Xaa Xaa Xaa Gly Xaa Xaa Tyr Tyr Ala Xaa Trp Ala Lys Gly
1               5                   10                  15

<210> SEQ ID NO 141
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa = Ala, Ile, or Ser
<220> FEATURE:
<221> NAME/KEY: MISC_FEATURE
<222> LOCATION: (7)..(7)
<223> OTHER INFORMATION: Xaa = Ala, Asn, or Ser
<220> FEATURE:
<221> NAME/KEY: MISC_FEATURE
<222> LOCATION: (13)..(13)
<223> OTHER INFORMATION: Xaa = Asn or Thr

<400> SEQUENCE: 141

Val Arg Asp Tyr Asp Xaa Xaa Gly Trp Ser Gly Phe Xaa Ile
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa = Glu, Lys, or Gln
<220> FEATURE:
<221> NAME/KEY: MISC_FEATURE
<222> LOCATION: (7)..(7)
```

```
<223> OTHER INFORMATION: Xaa = Arg or Tyr
<220> FEATURE:
<221> NAME/KEY: MISC_FEATURE
<222> LOCATION: (8)..(8)
<223> OTHER INFORMATION: Xaa = Gly, His, or Ser
<220> FEATURE:
<221> NAME/KEY: MISC_FEATURE
<222> LOCATION: (11)..(11)
<223> OTHER INFORMATION: Xaa = Arg or Tyr
<220> FEATURE:
<221> NAME/KEY: MISC_FEATURE
<222> LOCATION: (12)..(12)
<223> OTHER INFORMATION: Xaa = Phe or Leu

<400> SEQUENCE: 142

Gln Ser Ser Xaa Ser Val Xaa Xaa Asn Asn Xaa Xaa Ser
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Gly, Lys, Ser, or Tyr
<220> FEATURE:
<221> NAME/KEY: MISC_FEATURE
<222> LOCATION: (4)..(4)
<223> OTHER INFORMATION: Xaa = Ile or Thr

<400> SEQUENCE: 143

Xaa Ala Ser Xaa Leu Ala Ser
1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa = Ala or Tyr
<220> FEATURE:
<221> NAME/KEY: MISC_FEATURE
<222> LOCATION: (7)..(7)
<223> OTHER INFORMATION: Xaa = Asn or Thr
<220> FEATURE:
<221> NAME/KEY: MISC_FEATURE
<222> LOCATION: (9)..(9)
<223> OTHER INFORMATION: Xaa = Phe or Val

<400> SEQUENCE: 144

Ala Gly Ala Xaa Ser Asp Xaa Arg Xaa
1               5

<210> SEQ ID NO 145
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa = Asn or Ser
<220> FEATURE:
<221> NAME/KEY: MISC_FEATURE
<222> LOCATION: (6)..(6)
```

```
<223> OTHER INFORMATION: Xaa = Ser, Thr, or Val
<220> FEATURE:
<221> NAME/KEY: MISC_FEATURE
<222> LOCATION: (8)..(8)
<223> OTHER INFORMATION: Xaa = Ala, Val, or Tyr
<220> FEATURE:
<221> NAME/KEY: MISC_FEATURE
<222> LOCATION: (9)..(9)
<223> OTHER INFORMATION: Xaa = Ile or Met
<220> FEATURE:
<221> NAME/KEY: MISC_FEATURE
<222> LOCATION: (10)..(10)
<223> OTHER INFORMATION: Xaa = Gly, Ser, or Thr

<400> SEQUENCE: 145

Gly Phe Ser Leu Xaa Xaa Tyr Xaa Xaa Xaa
1               5                   10

<210> SEQ ID NO 146
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa = Ile or Met
<220> FEATURE:
<221> NAME/KEY: MISC_FEATURE
<222> LOCATION: (4)..(4)
<223> OTHER INFORMATION: Xaa = Ala or Thr
<220> FEATURE:
<221> NAME/KEY: MISC_FEATURE
<222> LOCATION: (5)..(5)
<223> OTHER INFORMATION: Xaa = Asp or Gly
<220> FEATURE:
<221> NAME/KEY: MISC_FEATURE
<222> LOCATION: (6)..(6)
<223> OTHER INFORMATION: Xaa = Gly, Ile, Thr, or Val
<220> FEATURE:
<221> NAME/KEY: MISC_FEATURE
<222> LOCATION: (7)..(7)
<223> OTHER INFORMATION: Xaa = Ser or Thr
<220> FEATURE:
<221> NAME/KEY: MISC_FEATURE
<222> LOCATION: (8)..(8)
<223> OTHER INFORMATION: Xaa = Ala or Val
<220> FEATURE:
<221> NAME/KEY: MISC_FEATURE
<222> LOCATION: (9)..(9)
<223> OTHER INFORMATION: Xaa = His or Tyr
<220> FEATURE:
<221> NAME/KEY: MISC_FEATURE
<222> LOCATION: (11)..(11)
<223> OTHER INFORMATION: Xaa = Ala or Thr
<220> FEATURE:
<221> NAME/KEY: MISC_FEATURE
<222> LOCATION: (14)..(14)
<223> OTHER INFORMATION: Xaa = Ala or Val
<220> FEATURE:
<221> NAME/KEY: MISC_FEATURE
<222> LOCATION: (15)..(15)
<223> OTHER INFORMATION: Xaa = Lys or Arg

<400> SEQUENCE: 146

Ile Xaa Asn Xaa Xaa Xaa Xaa Xaa Xaa Tyr Xaa Asn Trp Xaa Xaa Gly
1               5                   10                  15

<210> SEQ ID NO 147
<211> LENGTH: 11
<212> TYPE: PRT
<213> ORGANISM: Artificial Sequence
<220> FEATURE:
<223> OTHER INFORMATION: Synthetic construct
```

```
<220> FEATURE:
<221> NAME/KEY: MISC_FEATURE
<222> LOCATION: (7)..(7)
<223> OTHER INFORMATION: Xaa = Ala or Val
<220> FEATURE:
<221> NAME/KEY: MISC_FEATURE
<222> LOCATION: (11)..(11)
<223> OTHER INFORMATION: Xaa = Ile or Leu

<400> SEQUENCE: 147

Ala Arg Ala Arg Asn Ser Xaa Trp Met Asp Xaa
1               5                   10

<210> SEQ ID NO 148
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa = Asp or Ser
<220> FEATURE:
<221> NAME/KEY: MISC_FEATURE
<222> LOCATION: (4)..(4)
<223> OTHER INFORMATION: Xaa = Glu, Lys, or Trp
<220> FEATURE:
<221> NAME/KEY: MISC_FEATURE
<222> LOCATION: (7)..(7)
<223> OTHER INFORMATION: Xaa = Leu, Arg, Val, or Tyr
<220> FEATURE:
<221> NAME/KEY: MISC_FEATURE
<222> LOCATION: (8)..(8)
<223> OTHER INFORMATION: Xaa = Asn or Arg
<220> FEATURE:
<221> NAME/KEY: MISC_FEATURE
<222> LOCATION: (9)..(9)
<223> OTHER INFORMATION: Xaa = Asp or Asn
<220> FEATURE:
<221> NAME/KEY: MISC_FEATURE
<222> LOCATION: (11)..(11)
<223> OTHER INFORMATION: Xaa = Tyr, or is absent

<400> SEQUENCE: 148

Gln Ser Xaa Xaa Ser Val Xaa Xaa Asn Xaa Leu Ala
1               5                   10

<210> SEQ ID NO 149
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Gly, Lys, or Thr
<220> FEATURE:
<221> NAME/KEY: MISC_FEATURE
<222> LOCATION: (2)..(2)
<223> OTHER INFORMATION: Xaa = Ala or Thr
<220> FEATURE:
<221> NAME/KEY: MISC_FEATURE
<222> LOCATION: (4)..(4)
<223> OTHER INFORMATION: Xaa = Ser or Thr
<220> FEATURE:
<221> NAME/KEY: MISC_FEATURE
<222> LOCATION: (6)..(6)
<223> OTHER INFORMATION: Xaa = Ala or Pro

<400> SEQUENCE: 149

Xaa Xaa Ser Xaa Leu Xaa Ser
1               5
```

```
<210> SEQ ID NO 150
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa = Asp, Ser, or Tyr
<220> FEATURE:
<221> NAME/KEY: MISC_FEATURE
<222> LOCATION: (6)..(6)
<223> OTHER INFORMATION: Xaa = Gly, Ile, Arg, or Ser
<220> FEATURE:
<221> NAME/KEY: MISC_FEATURE
<222> LOCATION: (7)..(7)
<223> OTHER INFORMATION: Xaa = Asp or Gly
<220> FEATURE:
<221> NAME/KEY: MISC_FEATURE
<222> LOCATION: (10)..(10)
<223> OTHER INFORMATION: Xaa = Asp, Ile, or Thr
<220> FEATURE:
<221> NAME/KEY: MISC_FEATURE
<222> LOCATION: (11)..(11)
<223> OTHER INFORMATION: Xaa = Phe, or is absent

<400> SEQUENCE: 150

Ala Gly Gly Tyr Xaa Xaa Xaa Ser Asp Xaa Xaa Ala
1               5                   10
```

PHOSPHO-RAB ANTIBODIES, ASSAYS AND METHODS OF USE THEREOF

CROSS-REFERENCE TO RELATED APPLICATIONS

This application claims priority to U.S. Provisional Patent Application Nos. 62/521,300, filed Jun. 16, 2017, 62/638,622, filed Mar. 5, 2018, and 62/667,281, filed May 4, 2018, the content of each of which is incorporated by reference in its entirety.

REFERENCE TO SEQUENCE LISTING

The present application includes a Sequence Listing filed in electronic format. The material in the accompanying sequence listing is hereby incorporated by reference in its entirety into this application. The accompanying file, named 16621928_ST25.txt was created on Apr. 14, 2022 and is 83,274 bytes.

BACKGROUND OF THE INVENTION

Parkinson's disease is a neurodegenerative disease that affects the motor system. Although the exact causes of Parkinson's disease are unknown, it is believed that a combination of genetic and environmental factors contribute to the etiology of the disease. Among the genes that been implicated in Parkinson's disease is Park8, which encodes the leucine-rich repeat kinase 2 (LRRK2). Mutations in Park8 are found in both familial and non-familial (sporadic) forms of Parkinson's disease, and increased kinase activity of LRRK2 is implicated in the pathogenesis of Parkinson's disease.

LRRK2 inhibitors have been proposed for the treatment of Parkinson's disease. However, there remains a need for methods of identifying subjects who are suitable candidates for treatment with a LRRK2 inhibitor, as well as methods of monitoring the progression of treatment.

BRIEF SUMMARY OF THE INVENTION

In one aspect, isolated monoclonal antibodies (or antigen-binding portions thereof) that specifically bind to a Rab protein are provided. In one aspect, isolated monoclonal antibodies (or antigen-binding portions thereof) that specifically bind to a phosphorylated Rab protein are provided. In some embodiments, the monoclonal antibody is an antibody that specifically binds to a phosphorylated human Rab10 protein. In some embodiments, the monoclonal antibody is an antibody that specifically binds to a phosphorylated human Rab8a protein. In some embodiments, the antibody or antigen-binding portion thereof specifically binds to a phosphorylated Rab10 protein or to a phosphorylated Rab8a protein that is endogenously expressed in a human biological sample (e.g., in a sample comprising peripheral blood mononuclear cells). In one aspect, isolated monoclonal antibodies (or antigen-binding portions thereof) that specifically bind to phosphorylated and unphosphorylated Rab protein (e.g., phosphorylated and unphosphorylated Rab10 protein) are provided. In another aspect, methods and materials for detecting LRRK2 or Rab protein are provided.

In some embodiments, the monoclonal antibody is an antibody that specifically binds to a phosphorylated human Rab10 protein and recognizes an epitope within or comprising the sequence AGQERFH(pT)ITTSYYR (SEQ ID NO:123). In some embodiments, the antibody or antigen-binding portion exhibits cross-reactivity with one or more of a phosphorylated cynomolgus monkey Rab10 protein, a phosphorylated mouse Rab10 protein, and a phosphorylated rat Rab10 protein. In some embodiments, the antibody comprises one or more complementarity determining regions (CDRs) selected from the group consisting of:
  (a) a heavy chain CDR1 having at least 90% sequence identity to the amino acid sequence of any one of SEQ ID NOs:2, 22, 32, 40, 48, 54, or 57 or having up to two amino acid substitutions relative to the amino acid sequence of any one of SEQ ID NOs:2, 22, 32, 40, 48, 54, or 57;
  (b) a heavy chain CDR2 having at least 90% sequence identity to the amino acid sequence of any one of SEQ ID NOs:3, 23, 33, 41, 49, or 58 or having up to two amino acid substitutions relative to the amino acid sequence of any one of SEQ ID NOs:3, 23, 33, 41, 49, or 58;
  (c) a heavy chain CDR3 having at least 90% sequence identity to the amino acid sequence of any one of SEQ ID NOs:4, 12, 24, 34, 42, 50, 55, or 59 or having up to two amino acid substitutions relative to the amino acid sequence of any one of SEQ ID NOs:4, 12, 24, 34, 42, 50, 55, or 59;
  (d) a light chain CDR1 having at least 90% sequence identity to the amino acid sequence of any one of SEQ ID NOs:6, 14, 26, 36, 44, or 60 or having up to two amino acid substitutions relative to the amino acid sequence of any one of SEQ ID NOs:6, 14, 26,
  (e) a light chain CDR2 having at least 90% sequence identity to the amino acid sequence of any one of SEQ ID NOs:7, 27, 37, 45, or 61 or having up to two amino acid substitutions relative to the amino acid sequence of any one of SEQ ID NOs:7, 27, 37, 45, or 61; and
  (f) a light chain CDR3 having at least 90% sequence identity to the amino acid sequence of any one of SEQ ID NOs:8, 38, 46, 52, or 62 or having up to two amino acid substitutions relative to the amino acid sequence of any one of SEQ ID NOs:8, 38, 46, 52, or 62.

In some embodiments, the antibody comprises one or more CDRs selected from the group consisting of:
  (a) a heavy chain CDR1 comprising the amino acid sequence of any one of SEQ ID NOs:2, 22, 32, 40, 48, 54, or 57;
  (b) a heavy chain CDR2 comprising the amino acid sequence of any one of SEQ ID NOs:3, 23, 33, 41, 49, or 58;
  (c) a heavy chain CDR3 comprising the amino acid sequence of any one of SEQ ID NOs:4, 12, 24, 34, 42, 50, 55, or 59;
  (d) a light chain CDR1 comprising the amino acid sequence of any one of SEQ ID NOs:6, 14, 26, 36, 44, or 60;
  (e) a light chain CDR2 comprising the amino acid sequence of any one of SEQ ID NOs:7, 27, 37, 45, or 61; and
  (f) a light chain CDR3 comprising the amino acid sequence of any one of SEQ ID NOs:8, 38, 46, 52, or 62.

In some embodiments, the antibody comprises a heavy chain CDR1 comprising the amino acid sequence of SEQ ID NO:2, a heavy chain CDR2 comprising the amino acid sequence of SEQ ID NO:3, and a heavy chain CDR3 comprising the amino acid sequence of SEQ ID NO:4. In some embodiments, the antibody comprises a light chain CDR1 comprising the amino acid sequence of SEQ ID NO:6, a light chain CDR2 comprising the amino acid sequence of SEQ ID NO:7, and a light chain CDR3 comprising the amino acid sequence of SEQ ID NO:8. In some embodiments, the antibody comprises a heavy chain CDR1 comprising the amino acid sequence of SEQ ID NO:2, a heavy chain CDR2 comprising the amino acid sequence of SEQ ID NO:3, a heavy chain CDR3 comprising the amino acid sequence of SEQ ID NO:4, a light chain CDR1 comprising the amino acid sequence of SEQ ID NO:6, a light chain CDR2 comprising the amino acid sequence of SEQ ID NO:7, and a light chain CDR3 comprising the amino acid sequence of SEQ ID NO:8.

In some embodiments, the antibody comprises a heavy chain CDR1 comprising the amino acid sequence of SEQ ID NO:2, a heavy chain CDR2 comprising the amino acid sequence of SEQ ID NO:3, and a heavy chain CDR3 comprising the amino acid sequence of SEQ ID NO:12. In some embodiments, the antibody comprises a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:8. In some embodiments, the antibody comprises a heavy chain CDR1 comprising the amino acid sequence of SEQ ID NO:2, a heavy chain CDR2 comprising the amino acid sequence of SEQ ID NO:3, a heavy chain CDR3 comprising the amino acid sequence of SEQ ID NO:12, a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:8.

In some embodiments, the antibody comprises a heavy chain CDR1 comprising the amino acid sequence of SEQ ID NO:22, a heavy chain CDR2 comprising the amino acid sequence of SEQ ID NO:23, and a heavy chain CDR3 comprising the amino acid sequence of SEQ ID NO:24. In some embodiments, the antibody comprises a light chain CDR1 comprising the amino acid sequence of SEQ ID NO:26, a light chain CDR2 comprising the amino acid sequence of SEQ ID NO:27, and a light chain CDR3 comprising the amino acid sequence of SEQ ID NO:28. In some embodiments, the antibody comprises a heavy chain CDR1 comprising the amino acid sequence of SEQ ID NO:22, a heavy chain CDR2 comprising the amino acid sequence of SEQ ID NO:23, a heavy chain CDR3 comprising the amino acid sequence of SEQ ID NO:24, a light chain CDR1 comprising the amino acid sequence of SEQ ID NO:26, a light chain CDR2 comprising the amino acid sequence of SEQ ID NO:27, and a light chain CDR3 comprising the amino acid sequence of SEQ ID NO:28.

In some embodiments, the antibody comprises a heavy chain CDR1 comprising the amino acid sequence of SEQ ID NO:32, a heavy chain CDR2 comprising the amino acid sequence of SEQ ID NO:33, and a heavy chain CDR3 comprising the amino acid sequence of SEQ ID NO:34. In some embodiments, the antibody comprises a light chain CDR1 comprising the amino acid sequence of SEQ ID NO:36, a light chain CDR2 comprising the amino acid sequence of SEQ ID NO:37, and a light chain CDR3 comprising the amino acid sequence of SEQ ID NO:38. In some embodiments, the antibody comprises a heavy chain CDR1 comprising the amino acid sequence of SEQ ID NO:32, a heavy chain CDR2 comprising the amino acid sequence of SEQ ID NO:33, a heavy chain CDR3 comprising the amino acid sequence of SEQ ID NO:34, a light chain CDR1 comprising the amino acid sequence of SEQ ID NO:36, a light chain CDR2 comprising the amino acid sequence of SEQ ID NO:37, and a light chain CDR3 comprising the amino acid sequence of SEQ ID NO:38.

In some embodiments, the antibody comprises a heavy chain CDR1 comprising the amino acid sequence of SEQ ID NO:40, a heavy chain CDR2 comprising the amino acid sequence of SEQ ID NO:41, and a heavy chain CDR3 comprising the amino acid sequence of SEQ ID NO:42. In some embodiments, the antibody comprises a light chain CDR1 comprising the amino acid sequence of SEQ ID NO:44, a light chain CDR2 comprising the amino acid sequence of SEQ ID NO:45, and a light chain CDR3 comprising the amino acid sequence of SEQ ID NO:46. In some embodiments, the antibody comprises a heavy chain CDR1 comprising the amino acid sequence of SEQ ID NO:40, a heavy chain CDR2 comprising the amino acid sequence of SEQ ID NO:41, a heavy chain CDR3 comprising the amino acid sequence of SEQ ID NO:42, a light chain CDR1 comprising the amino acid sequence of SEQ ID NO:44, a light chain CDR2 comprising the amino acid sequence of SEQ ID NO:45, and a light chain CDR3 comprising the amino acid sequence of SEQ ID NO:46.

In some embodiments, the antibody comprises a heavy chain CDR1 comprising the amino acid sequence of SEQ ID NO:48, a heavy chain CDR2 comprising the amino acid sequence of SEQ ID NO:49, and a heavy chain CDR3 comprising the amino acid sequence of SEQ ID NO:50. In some embodiments, the antibody comprises a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:52. In some embodiments, the antibody comprises a heavy chain CDR1 comprising the amino acid sequence of SEQ ID NO:48, a heavy chain CDR2 comprising the amino acid sequence of SEQ ID NO:49, a heavy chain CDR3 comprising the amino acid sequence of SEQ ID NO:50, a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:52.

In some embodiments, the antibody comprises a heavy chain CDR1 comprising the amino acid sequence of SEQ ID NO:54, a heavy chain CDR2 comprising the amino acid sequence of SEQ ID NO:3, and a heavy chain CDR3 comprising the amino acid sequence of SEQ ID NO:55. In some embodiments, the antibody comprises a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:8. In some embodiments, the antibody comprises a heavy chain CDR1 comprising the amino acid sequence of SEQ ID NO:54, a heavy chain CDR2 comprising the amino acid sequence of SEQ ID NO:3, a heavy chain CDR3 comprising the amino acid sequence of SEQ ID NO:55, a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:8.

In some embodiments, the antibody comprises a heavy chain variable region comprising an amino acid sequence that has at least 90% sequence identity to any one of SEQ ID NOs:1, 11, 17, 21, 31, 39, 47, or 53. In some embodiments, the antibody comprises a light chain variable region comprising an amino acid sequence that has at least 90% sequence identity to any one of SEQ ID NOs:5, 13, 18, 25, 35, 43, 51, or 56. In some embodiments, the antibody comprises a heavy chain variable region comprising an amino acid sequence that has at least 90% sequence identity to any one of SEQ ID NOs:1, 11, 17, 21, 31, 39, 47, or 53 and a light chain variable region comprising an amino acid sequence that has at least 90% sequence identity to any one of SEQ ID NOs:5, 13, 18, 25, 35, 43, 51, or 56.

In some embodiments, the antibody comprises a heavy chain variable region comprising an amino acid sequence that has at least 90% sequence identity to SEQ ID NO:1 and a light chain variable region comprising an amino acid sequence that has at least 90% sequence identity to SEQ ID NO:5.

In some embodiments, the antibody comprises a heavy chain variable region comprising an amino acid sequence that has at least 90% sequence identity to SEQ ID NO:11 and a light chain variable region comprising an amino acid sequence that has at least 90% sequence identity to SEQ ID NO:13.

In some embodiments, the antibody comprises a heavy chain variable region comprising an amino acid sequence that has at least 90% sequence identity to SEQ ID NO:17 and a light chain variable region comprising an amino acid sequence that has at least 90% sequence identity to SEQ ID NO:18.

In some embodiments, the antibody comprises a heavy chain variable region comprising an amino acid sequence that has at least 90% sequence identity to SEQ ID NO:21 and a light chain variable region comprising an amino acid sequence that has at least 90% sequence identity to SEQ ID NO:25.

In some embodiments, the antibody comprises a heavy chain variable region comprising an amino acid sequence that has at least 90% sequence identity to SEQ ID NO:31 and a light chain variable region comprising an amino acid sequence that has at least 90% sequence identity to SEQ ID NO:35.

In some embodiments, the antibody comprises a heavy chain variable region comprising an amino acid sequence that has at least 90% sequence identity to SEQ ID NO:39 and a light chain variable region comprising an amino acid sequence that has at least 90% sequence identity to SEQ ID NO:43.

In some embodiments, the antibody comprises a heavy chain variable region comprising an amino acid sequence that has at least 90% sequence identity to SEQ ID NO:47 and a light chain variable region comprising an amino acid sequence that has at least 90% sequence identity to SEQ ID NO:51.

In some embodiments, the antibody comprises a heavy chain variable region comprising an amino acid sequence that has at least 90% sequence identity to SEQ ID NO:53 and a light chain variable region comprising an amino acid sequence that has at least 90% sequence identity to SEQ ID NO:56.

In some embodiments, the monoclonal antibody is an antibody that specifically binds to a phosphorylated human Rab8a protein and recognizes an epitope within or comprising the sequence QERFR(pT)ITTAY (SEQ ID NO:125). In some embodiments, the antibody or antigen-binding portion exhibits cross-reactivity with one or more of a phosphorylated cynomolgus monkey Rab8a protein, a phosphorylated mouse Rab8a protein, and a phosphorylated rat Rab8a protein. In some embodiments, the antibody comprises one or more complementarity determining regions (CDRs) selected from the group consisting of:

(a) a heavy chain CDR1 having at least 90% sequence identity to the amino acid sequence of any one of SEQ ID NOs:48, 72, 82, 92, 100, 108, 110, or 116 or having up to two amino acid substitutions relative to the amino acid sequence of any one of SEQ ID NOs:48, 72, 82, 92, 100, 108, 110, or 116;

(b) a heavy chain CDR2 having at least 90% sequence identity to the amino acid sequence of any one of SEQ ID NOs:64, 73, 83, 93, 101, 111, or 117 or having up to two amino acid substitutions relative to the amino acid sequence of any one of SEQ ID NOs:64, 73, 83, 93, 101, 111, or 117;

(c) a heavy chain CDR3 having at least 90% sequence identity to the amino acid sequence of any one of SEQ ID NOs:65, 74, 84, 94, 102, 112, or 118 or having up to two amino acid substitutions relative to the amino acid sequence of any one of SEQ ID NOs:65, 74, 84, 94, 102, 112, or 118;

(d) a light chain CDR1 having at least 90% sequence identity to the amino acid sequence of any one of SEQ ID NOs:67, 76, 86, 96, 104, 114, or 119 or having up to two amino acid substitutions relative to the amino acid sequence of any one of SEQ ID NOs:67, 76, 86, 96, 104, 114, or 119;

(e) a light chain CDR2 having at least 90% sequence identity to the amino acid sequence of any one of SEQ ID NOs:27, 77, 7, 97, 105, 115, or 120 or having up to two amino acid substitutions relative to the amino acid sequence of any one of SEQ ID NOs:27, 77, 7, 97, 105, 115, or 120; and (f) a light chain CDR3 having at least 90% sequence identity to the amino acid sequence of any one of SEQ ID NOs:68, 78, 87, 98, 106, or 121 or having up to two amino acid substitutions relative to the amino acid sequence of any one of SEQ ID NOs:68, 78, 87, 98, 106, or 121.

In some embodiments, the antibody comprises one or more CDRs selected from the group consisting of:

(a) a heavy chain CDR1 comprising the amino acid sequence of any one of SEQ ID NOs:48, 72, 82, 92, 100, 108, 110, or 116;

(b) a heavy chain CDR2 comprising the amino acid sequence of any one of SEQ ID NOs:64, 73, 83, 93, 101, 111, or 117;

(c) a heavy chain CDR3 comprising the amino acid sequence of any one of SEQ ID NOs:65, 74, 84, 94, 102, 112, or 118;

(d) a light chain CDR1 comprising the amino acid sequence of any one of SEQ ID NOs:67, 76, 86, 96, 104, 114, or 119;

(e) a light chain CDR2 comprising the amino acid sequence of any one of SEQ ID NOs:27, 77, 7, 97, 105, 115, or 120; and (f) a light chain CDR3 comprising the amino acid sequence of any one of SEQ ID NOs:68, 78, 87, 98, 106, or 121.

In some embodiments, the antibody comprises a heavy chain CDR1 comprising the amino acid sequence of SEQ ID NO:48, a heavy chain CDR2 comprising the amino acid sequence of SEQ ID NO:64, and a heavy chain CDR3 comprising the amino acid sequence of SEQ ID NO:65. In some embodiments, the antibody comprises a light chain CDR1 comprising the amino acid sequence of SEQ ID NO:67, a light chain CDR2 comprising the amino acid sequence of SEQ ID NO:27, and a light chain CDR3 comprising the amino acid sequence of SEQ ID NO:68. In some embodiments, the antibody comprises a heavy chain CDR1 comprising the amino acid sequence of SEQ ID NO:48, a heavy chain CDR2 comprising the amino acid sequence of SEQ ID NO:64, a heavy chain CDR3 comprising the amino acid sequence of SEQ ID NO:65, a light chain CDR1 comprising the amino acid sequence of SEQ ID NO:67, a light chain CDR2 comprising the amino acid sequence of SEQ ID NO:27, and a light chain CDR3 comprising the amino acid sequence of SEQ ID NO:68.

In some embodiments, the antibody comprises a heavy chain CDR1 comprising the amino acid sequence of SEQ ID NO:72, a heavy chain CDR2 comprising the amino acid sequence of SEQ ID NO:73, and a heavy chain CDR3 comprising the amino acid sequence of SEQ ID NO:74. In some embodiments, the antibody comprises a light chain CDR1 comprising the amino acid sequence of SEQ ID NO:76, a light chain CDR2 comprising the amino acid sequence of SEQ ID NO:77, and a light chain CDR3 comprising the amino acid sequence of SEQ ID NO:78. In some embodiments, the antibody comprises a heavy chain CDR1 comprising the amino acid sequence of SEQ ID NO:72, a heavy chain CDR2 comprising the amino acid sequence of SEQ ID NO:73, a heavy chain CDR3 comprising the amino acid sequence of SEQ ID NO:74, a light chain CDR1 comprising the amino acid sequence of SEQ ID NO:76, a light chain CDR2 comprising the amino acid sequence of SEQ ID NO:77, and a light chain CDR3 comprising the amino acid sequence of SEQ ID NO:78.

In some embodiments, the antibody comprises a heavy chain CDR1 comprising the amino acid sequence of SEQ ID NO:82, a heavy chain CDR2 comprising the amino acid sequence of SEQ ID NO:83, a heavy chain CDR3 comprising the amino acid sequence of SEQ ID NO:84. In some embodiments, the antibody comprises a light chain CDR1 comprising the amino acid sequence of SEQ ID NO:86, a light chain CDR2 comprising the amino acid sequence of SEQ ID NO:7, and a light chain CDR3 comprising the amino acid sequence of SEQ ID NO:87. In some embodiments, the antibody comprises a heavy chain CDR1 comprising the amino acid sequence of SEQ ID NO:82, a heavy chain CDR2 comprising the amino acid sequence of SEQ ID NO:83, a heavy chain CDR3 comprising the amino acid sequence of SEQ ID NO:84, a light chain CDR1 comprising the amino acid sequence of SEQ ID NO:86, a light chain CDR2 comprising the amino acid sequence of SEQ ID NO:7, and a light chain CDR3 comprising the amino acid sequence of SEQ ID NO:87.

In some embodiments, the antibody comprises a heavy chain CDR1 comprising the amino acid sequence of SEQ ID NO:92, a heavy chain CDR2 comprising the amino acid sequence of SEQ ID NO:93, and a heavy chain CDR3 comprising the amino acid sequence of SEQ ID NO:94. In some embodiments, the antibody comprises a light chain CDR1 comprising the amino acid sequence of SEQ ID NO:96, a light chain CDR2 comprising the amino acid sequence of SEQ ID NO:97, and a light chain CDR3 comprising the amino acid sequence of SEQ ID NO:98. In some embodiments, the antibody comprises a heavy chain CDR1 comprising the amino acid sequence of SEQ ID NO:92, a heavy chain CDR2 comprising the amino acid sequence of SEQ ID NO:93, a heavy chain CDR3 comprising the amino acid sequence of SEQ ID NO:94, a light chain CDR1 comprising the amino acid sequence of SEQ ID NO:96, a light chain CDR2 comprising the amino acid sequence of SEQ ID NO:97, and a light chain CDR3 comprising the amino acid sequence of SEQ ID NO:98.

In some embodiments, the antibody comprises a heavy chain CDR1 comprising the amino acid sequence of SEQ ID NO:100, a heavy chain CDR2 comprising the amino acid sequence of SEQ ID NO:101, and a heavy chain CDR3 comprising the amino acid sequence of SEQ ID NO:102. In some embodiments, the antibody comprises a light chain CDR1 comprising the amino acid sequence of SEQ ID NO:104, a light chain CDR2 comprising the amino acid sequence of SEQ ID NO:105, and a light chain CDR3 comprising the amino acid sequence of SEQ ID NO:106. In some embodiments, the antibody comprises a heavy chain CDR1 comprising the amino acid sequence of SEQ ID NO:100, a heavy chain CDR2 comprising the amino acid sequence of SEQ ID NO:101, a heavy chain CDR3 comprising the amino acid sequence of SEQ ID NO:102, a light chain CDR1 comprising the amino acid sequence of SEQ ID NO:104, a light chain CDR2 comprising the amino acid sequence of SEQ ID NO:105, and a light chain CDR3 comprising the amino acid sequence of SEQ ID NO:106.

In some embodiments, the antibody comprises a heavy chain CDR1 comprising the amino acid sequence of SEQ ID NO:108, a heavy chain CDR2 comprising the amino acid sequence of SEQ ID NO:101, and a heavy chain CDR3 comprising the amino acid sequence of SEQ ID NO:102. In some embodiments, the antibody comprises a light chain CDR1 comprising the amino acid sequence of SEQ ID NO:104, a light chain CDR2 comprising the amino acid sequence of SEQ ID NO:105, and a light chain CDR3 comprising the amino acid sequence of SEQ ID NO:106. In some embodiments, the antibody comprises a heavy chain CDR1 comprising the amino acid sequence of SEQ ID NO:100, a heavy chain CDR2 comprising the amino acid sequence of SEQ ID NO:101, a heavy chain CDR3 comprising the amino acid sequence of SEQ ID NO:102, a light chain CDR1 comprising the amino acid sequence of SEQ ID NO:104, a light chain CDR2 comprising the amino acid sequence of SEQ ID NO:105, and a light chain CDR3 comprising the amino acid sequence of SEQ ID NO:106.

In some embodiments, the antibody comprises a heavy chain CDR1 comprising the amino acid sequence of SEQ ID NO:110, a heavy chain CDR2 comprising the amino acid sequence of SEQ ID NO:111, and a heavy chain CDR3 comprising the amino acid sequence of SEQ ID NO:112. In some embodiments, the antibody comprises a light chain CDR1 comprising the amino acid sequence of SEQ ID NO:114, a light chain CDR2 comprising the amino acid sequence of SEQ ID NO:115, and a light chain CDR3 comprising the amino acid sequence of SEQ ID NO:87. In some embodiments, the antibody comprises a heavy chain CDR1 comprising the amino acid sequence of SEQ ID NO:110, a heavy chain CDR2 comprising the amino acid sequence of SEQ ID NO:111, a heavy chain CDR3 comprising the amino acid sequence of SEQ ID NO:112, a light chain CDR1 comprising the amino acid sequence of SEQ ID NO:114, a light chain CDR2 comprising the amino acid sequence of SEQ ID NO:115, and a light chain CDR3 comprising the amino acid sequence of SEQ ID NO:87.

In some embodiments, the antibody comprises a heavy chain variable region comprising an amino acid sequence that has at least 90% sequence identity to any one of SEQ ID NOs:63, 71, 81, 90, 91, 99, 107, or 109. In some embodiments, the antibody comprises a light chain variable region comprising an amino acid sequence that has at least 90% sequence identity to any one of SEQ ID NOs:66, 75, 85, 95, 103, or 113. In some embodiments, the antibody comprises a heavy chain variable region comprising an amino acid sequence that has at least 90% sequence identity to any one of SEQ ID NOs:63, 71, 81, 90, 91, 99, 107, or 109 and a light chain variable region comprising an amino acid sequence that has at least 90% sequence identity to any one of SEQ ID NOs:66, 75, 85, 95, 103, or 113.

In some embodiments, the antibody comprises a heavy chain variable region comprising an amino acid sequence that has at least 90% sequence identity to SEQ ID NO:63 and a light chain variable region comprising an amino acid sequence that has at least 90% sequence identity to SEQ ID NO:66.

In some embodiments, the antibody comprises a heavy chain variable region comprising an amino acid sequence that has at least 90% sequence identity to SEQ ID NO:71 and a light chain variable region comprising an amino acid sequence that has at least 90% sequence identity to SEQ ID NO:75.

In some embodiments, the antibody comprises a heavy chain variable region comprising an amino acid sequence that has at least 90% sequence identity to SEQ ID NO:81 and a light chain variable region comprising an amino acid sequence that has at least 90% sequence identity to SEQ ID NO:85.

In some embodiments, the antibody comprises a heavy chain variable region comprising an amino acid sequence that has at least 90% sequence identity to SEQ ID NO:90 and a light chain variable region comprising an amino acid sequence that has at least 90% sequence identity to SEQ ID NO:85.

In some embodiments, the antibody comprises a heavy chain variable region comprising an amino acid sequence that has at least 90% sequence identity to SEQ ID NO:91 and a light chain variable region comprising an amino acid sequence that has at least 90% sequence identity to SEQ ID NO:95.

In some embodiments, the antibody comprises a heavy chain variable region comprising an amino acid sequence that has at least 90% sequence identity to SEQ ID NO:99 and a light chain variable region comprising an amino acid sequence that has at least 90% sequence identity to SEQ ID NO:103.

In some embodiments, the antibody comprises a heavy chain variable region comprising an amino acid sequence that has at least 90% sequence identity to SEQ ID NO:107 and a light chain variable region comprising an amino acid sequence that has at least 90% sequence identity to SEQ ID NO:103.

In some embodiments, the antibody comprises a heavy chain variable region comprising an amino acid sequence that has at least 90% sequence identity to SEQ ID NO:109 and a light chain variable region comprising an amino acid sequence that has at least 90% sequence identity to SEQ ID NO:113.

In some embodiments, the antibody is an monoclonal antibody that specifically binds to phosphorylated and unphosphorylated human Rab10 protein. In some embodiments, the antibody comprises one or more CDRs selected from the group consisting of:
(a) a heavy chain CDR1 having at least 90% sequence identity to the amino acid sequence of SEQ ID NO:132 or having up to two amino acid substitutions relative to the amino acid sequence of SEQ ID NO:132;
(b) a heavy chain CDR2 having at least 90% sequence identity to the amino acid sequence of SEQ ID NO:133 or having up to two amino acid substitutions relative to the amino acid sequence of SEQ ID NO:133;
(c) a heavy chain CDR3 having at least 90% sequence identity to the amino acid sequence of SEQ ID NO:134 or having up to two amino acid substitutions relative to the amino acid sequence of SEQ ID NO:134;
(d) a light chain CDR1 having at least 90% sequence identity to the amino acid sequence of SEQ ID NO:136 or having up to two amino acid substitutions relative to the amino acid sequence of SEQ ID NO:136;
(e) a light chain CDR2 having at least 90% sequence identity to the amino acid sequence of SEQ ID NO:137 or having up to two amino acid substitutions relative to the amino acid sequence of SEQ ID NO:137; and
(f) a light chain CDR3 having at least 90% sequence identity to the amino acid sequence of SEQ ID NO:138 or having up to two amino acid substitutions relative to the amino acid sequence of SEQ ID NO:138.

In some embodiments, the antibody comprises one or more CDRs selected from the group consisting of:
(a) a heavy chain CDR1 comprising the amino acid sequence of SEQ ID NO:132;
(b) a heavy chain CDR2 comprising the amino acid sequence of SEQ ID
(c) a heavy chain CDR3 comprising the amino acid sequence of SEQ ID NO:134;
(d) a light chain CDR1 comprising the amino acid sequence of SEQ ID NO:136;
(e) a light chain CDR2 comprising the amino acid sequence of SEQ ID NO:137; and
(f) a light chain CDR3 comprising the amino acid sequence of SEQ ID NO:138.

In some embodiments, the antibody comprises a heavy chain CDR1 comprising the amino acid sequence of SEQ ID NO:132, a heavy chain CDR2 comprising the amino acid sequence of SEQ ID NO:133, and a heavy chain CDR3 comprising the amino acid sequence of SEQ ID NO:134. In some embodiments, the antibody comprises a light chain CDR1 comprising the amino acid sequence of SEQ ID NO:136, a light chain CDR2 comprising the amino acid sequence of SEQ ID NO:137, and a light chain CDR3 comprising the amino acid sequence of SEQ ID NO:138. In some embodiments, the antibody comprises a heavy chain CDR1 comprising the amino acid sequence of SEQ ID NO:132, a heavy chain CDR2 comprising the amino acid sequence of SEQ ID NO:133, a heavy chain CDR3 comprising the amino acid sequence of SEQ ID NO:134, a light chain CDR1 comprising the amino acid sequence of SEQ ID NO:136, a light chain CDR2 comprising the amino acid sequence of SEQ ID NO:137, and a light chain CDR3 comprising the amino acid sequence of SEQ ID NO:138.

In some embodiments, the antibody comprises a heavy chain variable region comprising an amino acid sequence that has at least 90% sequence identity to SEQ ID NO:131. In some embodiments, the antibody comprises a light chain variable region comprising an amino acid sequence that has at least 90% sequence identity to SEQ ID NO:135. In some embodiments, the antibody comprises a heavy chain variable region comprising an amino acid sequence that has at least 90% sequence identity to SEQ ID NO:131 and a light chain variable region comprising an amino acid sequence that has at least 90% sequence identity to SEQ ID NO:135.

In some embodiments, the antibody is a chimeric antibody. In some embodiments, the antibody is a humanized antibody. In some embodiments, the antibody is a fully human antibody. In some embodiments, the antigen-binding portion is a Fab, a F(ab')$_2$, a scFv, or a bivalent scFv.

In some embodiments, the antibody is labeled with a detectable label (e.g., a biotin/streptavidin label, nucleic acid label, chemically reactive label, fluorescent label, enzyme label, or radioactive label).

In another aspect, pharmaceutical compositions are provided. In some embodiments, the pharmaceutical composition comprises a monoclonal antibody that specifically binds to a phosphorylated human Rab10 protein or phosphorylated human Rab8a protein as described herein and further comprises one or more pharmaceutically acceptable excipients.

In another aspect, isolated polynucleotides are provided. In some embodiments, the isolated polynucleotide comprises a nucleotide sequence encoding an isolated monoclonal antibody that specifically binds to a phosphorylated human Rab10 protein or phosphorylated human Rab8a protein as described herein. In some embodiments, the isolated polynucleotide comprises a nucleotide sequence encoding an isolated monoclonal antibody that specifically binds to phosphorylated and unphosphorylated human Rab10 protein as described herein. In another aspect, vectors and host cells comprising such an isolated polynucleotide are provided.

In yet another aspect, antibodies are provided that compete with an anti-phosphorylated Rab10 monoclonal antibody or an anti-phosphorylated Rabb monoclonal antibody as described herein for specific binding to a phosphorylated human Rab10 or phosphorylated human Rab8a protein (e.g., a Rab10 protein that is phosphorylated at an amino acid residue corresponding to Thr73 or a Rab8a protein that is phosphorylated at an amino acid residue corresponding to Thr72). In another aspect, antibodies are provided that compete with an anti-total Rab10 monoclonal antibody as described herein for specific binding to phosphorylated and unphosphorylated human Rab10 protein.

In still another aspect, kits are provided for diagnostic, prognostic, or therapeutic use as described herein. In some embodiments, the kit comprises one or more of (a) a monoclonal antibody that specifically binds to a phosphorylated human Rab10 protein as described herein, (b) a monoclonal antibody that specifically binds to phosphorylated human Rab8a protein as described herein, or (c) a monoclonal antibody that specifically binds to phosphorylated and unphosphorylated human Rab10 protein as described herein, and further comprises instructions for diagnostic, prognostic, or therapeutic use.

In yet another aspect, methods are provided for determining the level of Rab protein or phosphorylated Rab protein in a subject, to identify whether the subject is a candidate for LRRK2 inhibitor treatment for treatment of Parkinson's disease (e.g, LRRK2-associated Parkinson's disease). In certain embodiments of the methods, the Rab protein is Rab5, Rab8a, Rab12 or Rab29. In certain embodiments, the Rab protein is Rab8a. In certain embodiments, the method further includes administering the LRRK2 inhibitor to the subject, in some embodiments including in an effective amount to treat the Parkinson's disease.

In yet another aspect, methods of diagnosing a subject as having Parkinson's disease (e.g., leucine-rich repeat kinase 2 (LRRK2)-associated Parkinson's disease) are provided. In some embodiments, methods are provided for determining the extent of inhibition of LRRK2 in a subject treated with a LRRK2 inhibitor. In some embodiments, the method comprises:
contacting a sample from the subject with an antibody that specifically binds to a phosphorylated human Rab protein as described herein, and measuring the amount of phosphorylated Rab in the sample from the subject;
wherein an amount of phosphorylated Rab protein in the sample from the subject that is at least as high as a control value identifies the subject as having Parkinson's disease (e.g., LRRK2-associated Parkinson's disease).

In some embodiments, an increased amount of phosphorylated Rab protein in the sample from the subject, as compared to the control value, identifies the subject as having Parkinson's disease (e.g., LRRK2-associated Parkinson's disease). In some embodiments, a comparison of an amount of phosphorylated Rab protein in the sample from the subject to a sample prior to administration determines the extent of inhibition of LRRK2. In some embodiments, an increased amount of phosphorylated Rab protein in the sample from the subject, as compared to the control value, identifies the subject as candidate for LRRK2 inhibitor treatment for treatment of Parkinson's disease (e.g, LRRK2-associated Parkinson's disease). In certain embodiments of the methods, the Rab protein is Rab5, Rab8a, Rab12 or Rab29. In certain embodiments, the Rab protein is Rab8a.

In yet another aspect, methods of diagnosing a subject as having Parkinson's disease (e.g., leucine-rich repeat kinase 2 (LRRK2)-associated Parkinson's disease) are provided. In some embodiments, methods are provided for determining the extent of inhibition of LRRK2 in a subject treated with a LRRK2 inhibitor. In some embodiments, the method comprises:
contacting a sample from the subject with a monoclonal antibody that specifically binds to a phosphorylated human Rab10 protein or phosphorylated Rab8a protein as described herein, and measuring the amount of phosphorylated Rab10 or phosphorylated Rab8a protein in the sample from the subject;
wherein an amount of phosphorylated Rab10 protein or phosphorylated Rab8a in the sample from the subject that is at least as high as a control value identifies the subject as having Parkinson's disease (e.g., LRRK2-associated Parkinson's disease). In some embodiments, an increased amount of phosphorylated Rab10 protein or phosphorylated human Rab8a protein in the sample from the subject, as compared to the control value, identifies the subject as having Parkinson's disease (e.g., LRRK2-associated Parkinson's disease). In some embodiments, a comparison of an amount of phosphorylated Rab10 protein or phosphorylated Rab8a in the sample from the subject to a sample prior to administration determines the extent of inhibition of LRRK2.

In another aspect, methods of identifying a subject having Parkinson's disease as a candidate for treatment with a LRRK2 inhibitor are provided. In some embodiments, the subject has been diagnosed as having an LRRK2-associated Parkinson's disease that is characterized by a I1122V, N1437H, R1441C/G/H, R1728H, R1628P, Y1699C, G2019S, I2020T, T2031S or G2385R mutation in LRRK2. In some embodiments, the method comprises:
contacting a sample from the subject with a monoclonal antibody that specifically binds to a phosphorylated human Rab10 protein or phosphorylated Rab8a protein as described herein, and measuring the amount of phosphorylated Rab10 or phosphorylated Rab8a protein in the sample from the subject;
wherein an amount of phosphorylated Rab10 protein or phosphorylated Rab8a in the sample from the subject that is at least as high as a control value identifies the subject as a candidate for treatment with a LRRK2 inhibitor. In some embodiments, an increased amount of or phosphorylated human Rab10 protein or phosphorylated Rab8a protein in the sample from the subject, as compared to the control value, identifies the subject as having LRRK2-associated Parkinson's disease.

For the methods described herein, in some embodiments, the sample comprises blood, plasma, serum, cerebrospinal fluid, or urine. In some embodiments, the detecting step comprises an ELISA. In some embodiments, the detecting step comprises the use of a capture antibody and a detection antibody. In some embodiments, an antibody against total Rab10 or total Rab8a protein is the capture antibody and a monoclonal antibody that specifically binds to a phosphorylated human Rab10 protein or phosphorylated human Rab8a protein as described herein is the detection antibody. In some embodiments, a monoclonal antibody that specifically binds to a phosphorylated human Rab10 protein or phosphorylated human Rab8a protein as described herein is the capture antibody and an antibody against total Rab10 or total Rab8a protein is the detection antibody. In some embodiments, the antibody against total Rab10 protein is a monoclonal anti-total Rab10 antibody as disclosed herein.

In some embodiments the sample is from an exosome. The exosome can be from blood, plasma, serum, cerebrospinal fluid, or urine. Exosomes can be lysed and the contents can be identified and measured using the methods described here, and can include total LRRK2, phosphorylated LRRK2, unphosphorylated LRRK2, total Rab10, phosphorylated Rab10 and/or unphosphorylated Rab10.

In some embodiments the exosome is from at least 10, 11, 12, 13, 14, or 15 mL of CSF, plasma, or urine. In some embodiments the exosome is from at least 10 mL of urine. In some embodiments the exosome is from at least 12 mL of CSF. In some embodiments the exosome is from CSF. In some embodiments the exosome is from urine. In some embodiments the sample is enriched in exosome by centrifugation.

In another aspect, monoclonal antibodies that specifically bind to a phosphorylated human Rab10 protein or phosphorylated human Rab8a protein as described herein for use in the diagnosis of Parkinson's disease (e.g., LRRK2-associated Parkinson's disease) are provided.

In another aspect, monoclonal antibodies that specifically bind to a phosphorylated human Rab10 protein or phosphorylated human Rab8a protein as described herein for use in the identification of a subject as a candidate for treatment with a LRRK2 inhibitor are provided. In some embodiments, the subject has been diagnosed with Parkinson's disease, e.g., an LRRK2-associated Parkinson's disease that is characterized by a I1122V, N1437H, R1441C/G/H, R1728H, R1628P, Y1699C, G2019S, I2020T, T2031S or G2385R mutation in LRRK2.

In another aspect, monoclonal antibodies that specifically bind to a phosphorylated human Rab10 protein or phosphorylated human Rab8a protein as described herein for use in the treatment of a neurodegenerative disease are provided. In some embodiments, the neurodegenerative disease is Parkinson's disease.

In another aspect, monoclonal antibodies that specifically bind to a phosphorylated human Rab8a protein as described herein for use in the treatment of a neurodegenerative disease are provided. In some embodiments, the neurodegenerative disease is Parkinson's disease.

In yet another aspect, monoclonal antibodies that specifically bind to a phosphorylated human Rab10 protein or phosphorylated human Rab8a protein as described herein are provided for use in determining a suitable dosage of a LRRK2 inhibitor to be administered to a subject, monitoring efficacy of treatment with a LRRK2 inhibitor, and/or adjusting a dosage of a LRRK2 inhibitor. In some embodiments, the subject being treated with the LRRK2 inhibitor has a neurodegenerative disease. In some embodiments, the neurodegenerative disease is Parkinson's disease.

In still another aspect, the use of a monoclonal antibody that specifically binds to a phosphorylated human Rab10 protein or phosphorylated human Rab8a protein as described herein (or an antigen-binding portion thereof or pharmaceutical composition as described herein) in the manufacture of a medicament for the treatment of a neurodegenerative disease (e.g., Parkinson's disease) is provided.

In still another aspect, assay kits are provided. In some embodiments, the assay kit is for electroluminescence detection of phospho-Serine 935-LRRK2 or total LRRK2. In some embodiments, the assay comprises:
(a) anti-phospho-Serine 935-LRRK2 (e.g., Abcam Catalog No. ab133450) or anti-LRRK2 clone 8G10; and
(b) an anti-LRRK2 antibody clone MC.028 covalently attached to an electrochemiluminescence label.

In some embodiments, the electrochemiluminescence label is a ruthenium-containing organometallic compound. In some embodiments, the assay kit further comprises a multi-well plate and an amine for reacting with the electrochemiluminescence label to generate light when stimulated by electricity, wherein the multi-well plate is covalently attached to the anti-phospho-Serine 935-LRRK2 (e.g., Abcam Catalog No. ab133450) or the anti-LRRK2 clone 8G10 by a biotin linker. In some embodiments, the amine is tripropylamine.

DETAILED DESCRIPTION OF THE INVENTION

I. Introduction

Figure 1B:
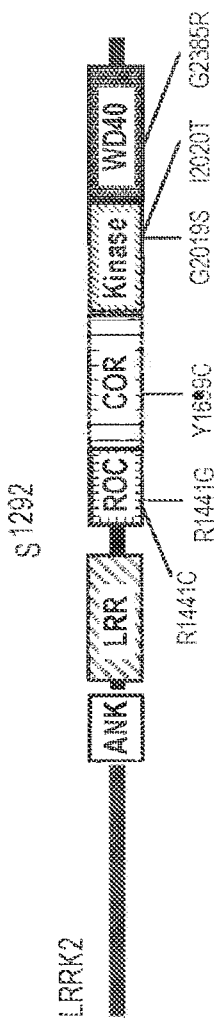
FIG. 1A-1D. Parkinson's-associated LRRK2 mutations increase phosphorylation of Rab10. (A) Rab proteins (e.g., Rab10 and Rab8a) are identified as direct substrates of LRRK2. Phosphorylation of a series of LRRK2 residues upstream of the LRR repeats (including S935) has shown dose-dependent dephosphorylation to LRRK2 inhibitors, but are not from LRRK2 autophosphorylation. S1292 has been identified as a LRRK2 autophosphorylation site in cells or mice overexpressing LRRK2, but phosphorylation of S1292 is undetectable with endogenous LRRK2 expression. (B) Schematic showing LRRK2 protein domain structure and the domains in which Parkinson's disease (PD)-associated LRRK2 variants R1441C, R1441G, Y1699C, G2019S, I2020T and G2385R occur. (C) Western blot analysis of total Rab10, phosphorylated T73-Rab10, total LRRK2 and phosphorylated S935-LRRK2 in HEK 293T cells overexpressing Rab10 and either wild-type LRRK2 or the PD-associated LRRK2 variant R1441C, R1441G, Y1699C, G2019S, I2020T, or G2385R. (D) PD-associated LRRK2 mutations in different domains cause an increase in phosphorylation of Rab10. Compared with wild-type LRRK2, all the mutations tested showed significantly increased phosphorylation of Rab10 (approximately 2- to 4-fold, depending on the mutation).

Mutations in the gene encoding leucine-rich repeat kinase 2 (LRRK2) are found in both familial and non-familial (sporadic) forms of Parkinson's disease (PD). Several different mutations have been identified as pathogenic mutations, including the mutations I1122V, N1437H, R1441C/G/H, R1728H, R1628P, Y1699C, G2019S, I2020T, T2031S, and G2385R, and other mutations in LRRK2 are associated with susceptibility to PD. At least some of the known pathogenic mutations in LRRK2 have been found to affect its kinase activity, and accordingly, LRRK2 inhibitors have been proposed as a treatment for PD.

Several proteins have been identified as possible physiological substrates of LRRK2, including Rab10 and Rab8a, which are members of the Rab GTPase family. As described herein in the Examples section, phosphorylation of the Rab protein is detected in human cells that overexpress LRRK2 and either Rab10 or Rab8a. Furthermore, increased phosphorylation of Rab10 or Rab8a is detected in different PD-linked LRRK2 mutants, relative to wild-type LRRK2. The enhanced phosphorylation of Rab10 and Rab8a in the presence of LRRK2 variants suggests that there is increased LRRK2 kinase activity in pathogenic variants in vivo. Thus, in some embodiments, phosphorylation of Rab10 or Rab8a represents a useful clinical marker for identifying patients having a pathogenic mutation in LRRK2, such as a I1122V, N1437H, R1441C/G/H, R1728H, R1628P, Y1699C, G2019S, I2020T, T2031S or G2385R mutation, and in another embodiment, a R1441C, R1441G, Y1699C, G2019S, or I2020T mutation.

As detailed in the Examples section below, monoclonal antibodies have been generated that specifically bind to phosphorylated Rab10 protein or phosphorylated Rab8a protein that is endogenously expressed in a human biological sample, such as human peripheral blood mononuclear cells. See, e.g., Example 2 and FIGS. 2A-2B. In contrast, known polyclonal antibodies against phosphorylated Rab10 or phosphorylated Rab8a do not exhibit a significant decrease in detectable phosphorylated Rab10 or phosphorylated Rab8a, respectively, in response to treatment with a LRRK2 inhibitor. See, FIGS. 2A-2B. Thus, in one aspect, the present disclosure provides monoclonal antibodies and antigen-binding fragments thereof that specifically bind to phosphorylated Rab10 or phosphorylated Rab8a protein. In another aspect, the present disclosure provides methods of diagnosing a subject as having LRRK2-associated PD using the anti-phosphorylated Rab10 and anti-phosphorylated Rab8a monoclonal antibodies to detect an increased amount of phosphorylated Rab10 or Rab8a protein in a sample from the subject.

It has also been found that the levels of phosphorylated Rab10 and phosphorylated Rab8a protein decrease in a dose-dependent manner in response to treatment with a LRRK2 inhibitor, as measured using an anti-phosphorylated Rab10 or anti-phosphorylated Rab8a monoclonal antibody as described herein. See, Example 2 and FIGS. 2A-2B. Thus, in another aspect, the present disclosure provides methods of determining a suitable dosage of a LRRK2 inhibitor or adjusting the dosage of a LRRK2 inhibitor that is administered to a subject (e.g., for the treatment of a neurodegenerative disease such as Parkinson's disease) as well as methods of monitoring efficacy of treatment with a LRRK2 inhibitor or predicting whether a subject will respond to treatment with a LRRK2 inhibitor.

II. Definitions

As used herein, the singular forms "a," "an" and "the" include plural referents unless the content clearly dictates otherwise. Thus, for example, reference to "an antibody" optionally includes a combination of two or more such molecules, and the like.

As used herein, the terms "about" and "approximately," when used to modify an amount specified in a numeric value or range indicate that the numeric value as well as reasonable deviations from the value known to the skilled person in the art, for example ±20%, ±10%, or ±5%, are within the intended meaning of the recited value.

"Alkyl" refers to an unbranched or branched saturated hydrocarbon chain, which may be optionally substituted as described herein. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., $-(CH_2)_3CH_3$), sec-butyl (i.e., $-CH(CH_3)CH_2CH_3$), isobutyl (i.e., $-CH_2CH(CH_3)_2$) and tert-butyl (i.e., $-C(CH_3)_3$); and "propyl" includes n-propyl (i.e., $-(CH_2)_2CH_3$) and isopropyl (i.e., $-CH(CH_3)_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively, which may be optionally substituted as described herein.

"Alkenyl" refers to an alkyl group containing at least one carbon-carbon double bond and having from 2 to 20 carbon atoms (i.e., $C_{2\text{-}20}$ alkenyl), 2 to 8 carbon atoms (i.e., $C_{2\text{-}8}$ alkenyl), 2 to 6 carbon atoms (i.e., $C_{2\text{-}6}$ alkenyl) or 2 to 4 carbon atoms (i.e., $C_{2\text{-}4}$ alkenyl), which may be optionally substituted as described herein. Examples of alkenyl groups include ethenyl, propenyl, and butadienyl (including 1,2-butadienyl and 1,3-butadienyl).

"Alkynyl" refers to an alkyl group containing at least one carbon-carbon triple bond and having from 2 to 20 carbon atoms (i.e., $C_{2\text{-}20}$ alkynyl), 2 to 8 carbon atoms (i.e., $C_{2\text{-}8}$ alkynyl), 2 to 6 carbon atoms (i.e., $C_{2\text{-}6}$ alkynyl) or 2 to 4 carbon atoms (i.e., $C_{2\text{-}4}$ alkynyl), which may be optionally substituted as described herein. The term "alkynyl" also includes those groups having one triple bond and one double bond.

"Alkoxy" refers to the group "alkyl-O—", which may be optionally substituted as described herein. Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Aryl" refers to an aromatic carbocyclic group having a single ring (e.g., monocyclic) or multiple rings (e.g., bicyclic or tricyclic) including fused systems, which may be optionally substituted as described herein. As used herein, aryl has 6 to 20 ring carbon atoms (i.e., $C_{6\text{-}20}$ aryl), 6 to 12 carbon ring atoms (i.e., $C_{6\text{-}12}$ aryl) or 6 to 10 carbon ring atoms (i.e., $C_{6\text{-}10}$ aryl). Examples of aryl groups include phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Cycloalkyl" refers to a saturated or partially unsaturated cyclic alkyl group having a single ring or multiple rings including fused, bridged and spiro ring systems, which may be optionally substituted as described herein. The term "cycloalkyl" includes cycloalkenyl groups (i.e., the cyclic group having at least one double bond). As used herein, cycloalkyl has from 3 to 20 ring carbon atoms (i.e., $C_{3\text{-}20}$ cycloalkyl), 3 to 12 ring carbon atoms (i.e., $C_{3\text{-}12}$ cycloalkyl), 3 to 10 ring carbon atoms (i.e., $C_{3\text{-}10}$ cycloalkyl), 3 to 8 ring carbon atoms (i.e., $C_{3\text{-}8}$ cycloalkyl) or 3 to 6 ring carbon atoms (i.e., $C_{3\text{-}6}$ cycloalkyl). Monocyclic radicals include, for example, cyclopropyl, cyclobutyl, cyclopentyl, cyclohexyl, cycloheptyl and cyclooctyl. Polycyclic radicals include, for example, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom.

"Halogen" or "halo" includes fluoro, chloro, bromo and iodo.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom, which may be optionally substituted as described herein. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where hydrogen, alkyl, alkenyl, alkynyl, cycloalkyl, heterocyclyl, aryl, heteroalkyl, or heteroaryl; each of which may be optionally substituted, as defined herein. Examples of heteroalkyl groups include —CH$_2$OCH$_3$, —CH$_2$SCH$_3$, and —CH$_2$NRCH$_3$, where R is hydrogen, alkyl, alkenyl, alkynyl, cycloalkyl, heterocyclyl, aryl, heteroalkyl, or heteroaryl; each of which may be optionally substituted, as defined herein. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen and sulfur, which may be optionally substituted as described herein. As used herein, heteroaryl includes 1 to 20 ring carbon atoms (i.e., $C_{1\text{-}20}$ heteroaryl), 3 to 12 ring carbon atoms (i.e., $C_{3\text{-}12}$ heteroaryl) or 3 to 8 carbon ring atoms (i.e., $C_{3\text{-}8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen and sulfur. Examples of heteroaryl groups include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo [4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl and thiophenyl (i.e., thienyl). Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" or "heterocycloalkyl" refers to a saturated or unsaturated cyclic alkyl group, with one or more ring heteroatoms independently selected from nitrogen, oxygen and sulfur, which may be optionally substituted as described herein. The term "heterocyclyl" includes heterocycloalkenyl groups (i.e. the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more oxo (C=O) or N-oxide (N—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl) or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom.

Examples of the spiro-heterocyclyl rings include bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Haloalkyl" refers to an unbranched or branched alkyl group as defined above, wherein one or more hydrogen atoms are replaced by a halogen, which may be optionally substituted as described herein. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Haloalkoxy" refers to an alkoxy group as defined above, wherein one or more hydrogen atoms are replaced by a halogen.

"Hydroxy" or "hydroxyl" refers to the group —OH.

"Oxo" refers to the group (=O) or (O).

Unless indicated explicitly otherwise, where combinations of groups are referred to herein as one moiety, e.g., arylalkyl or aralkyl, the last mentioned group contains the atom by which the moiety is attached to the rest of the molecule.

The terms "optional" or "optionally" means that the subsequently described event or circumstance may or may not occur and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one hydrogen atom is replaced by a bond to a non-hydrogen atom such as, but not limited to, alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si$(R^{100})_3$ wherein each $R^{100}$ is independently hydrogen, alkyl, alkenyl, alkynyl, heteroalkyl, cycloalkyl, aryl, heteroaryl or heterocyclyl.

In one embodiment, "substituted" includes any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) in which one or more hydrogen atoms are replaced with —NR$^g$R$^h$, —NR$^g$C(=O)R$^h$, —NR$^g$C(=O)NR$^g$R$^h$, —NR$^g$C(=O)OR$^h$, —NR$^g$SO$_2$R$^h$, —OC(=O)NR$^g$R$^h$, —OR$^g$, —SR$^g$, —SOR$^g$, —SO$_2$R$^g$, —OSO$_2$R$^g$, —SO$_2$OR$^g$, =NSO$_2$R$^g$, and —SO$_2$NR$^g$R$^h$. "Substituted" also means any of the above groups in which one or more hydrogen atoms are replaced with —C(=O)R$^g$, —C(=O)OR$^g$, —C(=O)NR$^g$R$^h$, —CH$_2$SO$_2$R$^g$, —CH$_2$SO$_2$NR$^g$R$^h$. In the foregoing, R$^g$ and R$^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl group. In addition, each of the foregoing substituents may also be optionally substituted with one or more of the above substituents.

Any compound or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I and $^{125}$I, respectively. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound when administered to a mammal, particularly a human. See, for example, Foster, "Deuterium Isotope Effects in Studies of Drug Metabolism," *Trends Pharmacol. Sci.* 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^{3}$H, or $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, stereoisomers and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., NH$_2$(alkyl)), dialkyl amines (i.e., HN(alkyl)$_2$), trialkyl amines (i.e., N(alkyl)$_3$), substituted alkyl amines (i.e., NH$_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$) or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

As used herein, the term "Rab protein" refers to a protein that is a Ras-like GTPase. Ras proteins have been identified in numerous organisms from yeast to humans, and to date there are at least 60 Rab family members that have been identified in humans. In some embodiments, a Rab protein is a native (i.e., wild-type) Rab protein from any vertebrate source, such as but not limited to human.

As used herein, the term "Rab10 protein" refers to a Rab GTPase protein that is encoded by the gene Rab10. As used herein, a "Rab10 protein" refers to a native (i.e., wild-type) Rab10 protein from any vertebrate source, such as but not limited to human (Human Rab10 Uniprot number: P61026), non-human primates (e.g., cynomolgus monkey), rodents (e.g., mice, rat), and other mammals. In some embodiments, a Rab10 protein is a human Rab10 protein having the amino acid sequence of SEQ ID NO:122.

As used herein, the term "phosphorylated Rab10 protein" refers to a Rab10 protein that is phosphorylated at the amino acid residue Thr73, as numbered with reference to SEQ ID NO:122.

As used herein, the terms "an antibody that specifically binds to a phosphorylated Rab10 protein" and "anti-phosphorylated Rab10 antibody" interchangeably refer to an antibody that specifically binds to a Rab10 protein that is phosphorylated at the amino acid residue Thr73, as numbered with reference to SEQ ID NO:122.

As used herein, the term "Rab8a protein" refers to a Rab GTPase protein that is encoded by the gene Rab8a. As used herein, a "Rab8a protein" refers to a native (i.e., wild-type) Rab8a protein from any vertebrate source, such as but not limited to human (human Rab8a Uniprot number: P61006), non-human primates (e.g., cynomolgus monkey), rodents (e.g., mice, rat), and other mammals. In some embodiments, a Rab8a protein is a human Rab8a protein having the amino acid sequence of SEQ ID NO:124.

As used herein, the term "phosphorylated Rab8a protein" refers to a Rab8a protein that is phosphorylated at one or more residues. In some embodiments, a phosphorylated Rab8a protein is phosphorylated at the amino acid residue Thr72, as numbered with reference to SEQ ID NO:124.

As used herein, the terms "an antibody that specifically binds to a phosphorylated Rab8a protein" and "anti-phosphorylated Rab8a antibody" interchangeably refer to an antibody that specifically binds to Rab8a protein that is phosphorylated at the amino acid residue Thr72, as numbered with reference to SEQ ID NO:124.

As used herein, the term "antibody" refers to a protein functionally defined as a binding protein and structurally defined as comprising an amino acid sequence that is recognized by one of skill as being derived from the framework region of an immunoglobulin encoding gene of an animal producing antibodies. The term "antibody," as used herein, also includes antibody fragments that retain binding specificity, including but not limited to Fab, F(ab')$_2$, Fv, and scFv. An antibody can consist of one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains, respectively.

The term "variable region" refers to a domain in an antibody heavy chain or light chain that gives an antibody its specificity for binding to an antigen. Typically, an antibody variable region comprises four conserved "framework" regions interspersed with three hypervariable "complementarity determining regions."

The term "complementarity determining region" or "CDR" refers to the three hypervariable regions in each chain that interrupt the four framework regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found.

The "framework regions" or "FRs" of different light or heavy chains are relatively conserved within a species. The framework region of an antibody, that is the combined framework regions of the constituent light and heavy chains, serves to position and align the CDRs in three-dimensional space. Framework sequences can be obtained from public DNA databases or published references that include germline antibody gene sequences. For example, germline DNA sequences for human heavy and light chain variable region genes can be found in the "VBASE2" germline variable gene sequence database for human and mouse sequences.

The amino acid sequences of the CDRs and framework regions can be determined using various well known definitions in the art, e.g., Kabat, Chothia, international ImMunoGeneTics database (IMGT), AbM, and observed antigen contacts ("Contact"). In some embodiments, CDRs are determined according to the Contact defintion. See, MacCallum et al., *J. Mol. Biol.*, 262:732-745 (1996). In some embodiments, CDRs are determined by a combination of Kabat, Chothia, and Contact CDR definitions.

The terms "antigen-binding portion" and "antigen-binding fragment" are used interchangeably herein and refer to one or more fragments of an antibody that retains the ability to specifically bind to an antigen (e.g., a phosphorylated Rab protein, e.g., phosphorylated Rab10 or phosphorylated Rab8a). Examples of antigen-binding fragments include, but are not limited to, a Fab fragment (a monovalent fragment consisting of the VL, VH, CL and CH1 domains), F(ab')$_2$ fragment (a bivalent fragment comprising two Fab fragments linked by a disulfide bridge at the hinge region), single chain Fv (scFv), disulfide-linked Fv (dsFv), complementarity determining regions (CDRs), VL (light chain variable region), VH (heavy chain variable region), nanobodies, diabodies and other formats as described in Spiess et al., Mol. Immun. 67 (2015) 95-106, which is incorporated herein by reference, and any combination of these or any other functional portion of an immunoglobulin peptide capable of binding to a target antigen.

The term "epitope" refers to the area or region of an antigen to which an antibody specifically binds and can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid.

In some cases, the epitope is a three-dimensional moiety. Thus, for example, where the target is a protein, the epitope can be comprised of consecutive amino acids (e.g., a linear epitope), or amino acids from different parts of the protein that are brought into proximity by protein folding (e.g., a discontinuous or conformational epitope). In some embodiments, the epitope is phosphorylated at one amino acid (e.g., at a serine or threonine residue).

As used herein, the phrase "recognizes an epitope," as used with reference to an anti-phosphorylated Rab10 antibody or an anti-phosphorylated Rab8a antibody, means that the antibody interacts with or specifically binds to the antigen (i.e., the phosphorylated Rab10 protein or the phosphorylated Rab8a protein, respectively) at that epitope or a portion thereof.

A "monoclonal antibody" refers to antibodies produced by a single clone of cells or a single cell line and consisting of or consisting essentially of antibody molecules that are identical in their primary amino acid sequence. In some embodiments, a monoclonal antibody preparation comprises a population of antibodies that are identical and bind to the same epitope of an antigen, except for mutations that arise during monoclonal antibody production.

A "polyclonal antibody" refers to a pool of antibodies obtained from a heterogeneous population of antibodies in which different antibodies in the population bind to different epitopes of an antigen.

A "chimeric antibody" refers to an antibody molecule in which the constant region, or a portion thereof, is altered, replaced or exchanged so that the antigen binding site (variable region, CDR, or portion thereof) is linked to a constant region of a different or altered class, effector function and/or species, or in which the variable region, or a portion thereof, is altered, replaced or exchanged with a variable region having a different or altered antigen specificity (e.g., CDR and framework regions from different species). In some embodiments, a chimeric antibody is a monoclonal antibody comprising a variable region from one source or species (e.g., mouse) and a constant region derived from a second source or species (e.g., human). Methods for producing chimeric antibodies are described in the art.

A "humanized antibody" is an antibody that retains the reactivity of a non-human antibody while being less immunogenic in humans. This can be achieved, for instance, by retaining the non-human CDR regions and replacing the remaining parts of the antibody with their human counterparts.

A "human antibody" or a "fully human antibody" is an antibody having human heavy chain and light chain sequences. In some embodiments, the antibody is produced by a human cell, by a non-human animal that utilizes human antibody repertoires (e.g., transgenic mice that are genetically engineered to express human antibody sequences), or by phage display platforms.

The term "specifically binds" refers to a molecule (e.g., an antibody or an antigen-binding fragment) that binds to an epitope or target with greater affinity, greater avidity, and/or greater duration to that epitope or target in a sample than it binds to another epitope or non-target compound (e.g., a structurally different antigen). In some embodiments, an antibody or antigen-binding portion thereof that specifically binds to an epitope or target is an antibody or antigen-binding portion that binds to the epitope or target with at least 5-fold greater affinity than other epitopes or non-target compounds, e.g., at least 6-fold, 7-fold, 8-fold, 9-fold, 10-fold, 20-fold, 25-fold, 50-fold, or 100-fold greater affinity. In some embodiments, an antibody that specifically binds to a phosphorylated Rab protein (e.g., phosphorylated Rab10 or phosphorylated Rab8a) binds to the phosphorylated Rab protein with at least a 5-fold greater affinity than to a protein other than phosphorylated Rab (e.g., at least 6-fold, at least 7-fold, at least 8-fold, at least 9-fold, or at least 10-fold greater affinity). It will be recognized by one of skill that an antibody that specifically binds to a target (e.g., a phosphorylated Rab10 protein or a phosphorylated Rab8a protein) from one species may also specifically bind to orthologs of that target.

The term "binding affinity" is used herein to refer to the strength of a non-covalent interaction between two molecules, e.g., an antibody (or an antigen-binding fragment thereof) and an antigen. Thus, for example, the term may refer to 1:1 interactions between an antibody (or an antigen-binding fragment thereof) and an antigen, unless otherwise indicated or clear from context. Binding affinity may be quantified by measuring an equilibrium dissociation constant ($K_D$), which refers to the dissociation rate constant ($k_d$, time$^{-1}$) divided by the association rate constant ($k_a$, time$^{-1}$ M$^{-1}$). $K_D$ can be determined by measurement of the kinetics of complex formation and dissociation, e.g., using Surface Plasmon Resonance (SPR) methods, e.g., a Biacore™ system; kinetic exclusion assays such as KinExA®; and Bio-Layer interferometry (e.g., using the ForteBio® Octet platform). As used herein, "binding affinity" includes not only formal binding affinities, such as those reflecting 1:1 interactions between an antibody (or an antigen-binding fragment thereof) and an antigen, but also apparent affinities for which $K_D$s are calculated that may reflect avid binding.

The term "cross-reacts," as used herein, refers to the ability of an antibody to bind to an antigen other than the antigen against which the antibody was raised. In some embodiments, cross-reactivity refers to the ability of an antibody to bind to an antigen from another species than the antigen against which the antibody was raised. As a non-limiting example, an anti-phosphorylated Rab (e.g., Rab10 or Rab8a) antibody as described herein that is raised against a human Rab peptide can exhibit cross-reactivity with a phosphorylated Rab (e.g., Rab10 or Rab8a) peptide or protein from a different species (e.g., monkey or mouse).

The term "isolated," as used with reference to a nucleic acid or protein (e.g., antibody), denotes that the nucleic acid or protein is essentially free of other cellular components with which it is associated in the natural state. It is preferably in a homogeneous state. Purity and homogeneity are typically determined using analytical chemistry techniques such as electrophoresis (e.g., polyacrylamide gel electrophoresis) or chromatography (e.g., high performance liquid chromatography). In some embodiments, an isolated nucleic acid or protein (e.g., antibody) is at least 85% pure, at least 90% pure, at least 95% pure, or at least 99% pure.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins, wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

An amino acid "corresponding to position [X] of [specific sequence]" refers to an amino acid in a polypeptide of interest that aligns with the equivalent amino acid of a specified sequence. In some embodiments, the amino acid corresponding to a position of a Rab protein (e.g., Rab10 or Rab8a) can be determined using an alignment algorithm such as BLAST. As a non-limiting example, "correspondence" of an amino acid position in Rab10 is determined by aligning to a region of the Rab10 protein of SEQ ID NO:122. When a Rab10 protein sequence differs from SEQ ID NO:122 (e.g., by changes in amino acids or addition or deletion of amino acids), it may be that a particular amino acid residue (e.g., a phosphorylation site in Rab10) will not be in the same position number as it is in SEQ ID NO:122.

The terms "polynucleotide" and "nucleic acid" interchangeably refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. Examples of polynucleotides contemplated herein include single- and double-stranded DNA, single- and double-stranded RNA, and hybrid molecules having mixtures of single- and double-stranded DNA and RNA.

The terms "subject," "individual," and "patient," as used interchangeably herein, refer to a mammal, including but not limited to humans, non-human primates, rodents (e.g., rats, mice, and guinea pigs), rabbits, cows, pigs, horses, and other mammalian species. In one embodiment, the subject, individual or patient is a human.

The terms "treat" and "treatment" refer to any indicia of success in the treatment or amelioration of an injury, disease, or condition, including any objective or subjective parameter such as abatement, remission, improvement in patient survival, increase in survival time or rate, diminishing of symptoms or making the injury, disease, or condition more tolerable to the patient, slowing in the rate of degeneration or decline, or improving a patient's physical or mental well-being. The treatment or amelioration of symptoms can be based on objective or subjective parameters. The effect of treatment can be compared to an individual or pool of individuals not receiving the treatment, or to the same patient prior to treatment or at a different time during treatment.

The term "pharmaceutically acceptable excipient" refers to a non-active pharmaceutical ingredient that is biologically or pharmacologically compatible for use in humans or animals, such as, but not limited to a buffer, carrier, or preservative.

As used herein, a "therapeutic amount" or "therapeutically effective amount" of an agent (e.g., an antibody or a LRRK2 inhibitor as described herein) is an amount of the agent that treats, ameliorates, abates, remits, improves patient survival, increases survival time or rate, diminishes symptoms, makes an injury, disease, or condition (e.g., Parkinson's disease) more tolerable, slows the rate of degeneration or decline, or improves a patient's physical or mental well-being. For example, for the given parameter, a therapeutically effective amount will show an increase or decrease of therapeutic effect at least 5%, 10%, 15%, 20%, 25%, 40%, 50%, 60%, 75%, 80%, 90%, or 100%. Therapeutic efficacy can also be expressed as "-fold" increase or decrease. For example, a therapeutically effective amount can have at least a 1.2-fold, 1.5-fold, 2-fold, 5-fold, or more effect over a control.

The term "administer" refers to a method of delivering agents, compounds, or compositions to the desired site of biological action. These methods include, but are not limited to, topical delivery, parenteral delivery, intravenous delivery, intradermal delivery, intramuscular delivery, colonic delivery, rectal delivery, or intraperitoneal delivery. In one embodiment, an antibody as described herein is administered intravenously.

III. Anti-Phosphorylated Rab Antibodies

In one aspect, antibodies and antigen-binding portions of antibodies that specifically bind to a phosphorylated Rab protein (e.g., Rab10 or Rab8a) are provided. In some embodiments, the antibody or antigen-binding portion thereof specifically binds to phosphorylated human protein (e.g., human Rab10 or human Rab8a). In some embodiments, the antibody that specifically binds to a phosphorylated Rab protein (e.g., Rab10 or Rab8a) is a monoclonal antibody.

In some embodiments, the antibody or antigen-binding portion thereof specifically binds to phosphorylated Rab10 protein. In some embodiments, a phosphorylated Rab10 protein includes 1, 2, 3, 4, 5, or more phosphorylated serine and/or threonine residues. In some embodiments, a phosphorylated Rab10 protein is phosphorylated at an amino acid residue corresponding to Thr73, as numbered with reference to the full-length human Rab10 protein of SEQ ID NO:122. In some embodiments, the antibody or antigen-binding portion thereof specifically binds to a Rab10 protein that is phosphorylated at an amino acid residue corresponding to Thr73, as numbered with reference to SEQ ID NO:122. In some embodiments, the antibody or antigen-binding portion thereof specifically binds to a phosphorylated human Rab10 protein having the amino acid sequence of SEQ ID NO:122 and having a phosphorylated Thr73 residue. In some embodiments, the antibody or antigen-binding portion thereof specifically binds to a phosphorylated Rab10 protein (e.g., a Rab10 protein that is phosphorylated at an amino acid residue corresponding to Thr73, as numbered with reference to SEQ ID NO:122) that is endogenously expressed in a human biological sample (e.g., in a sample comprising peripheral blood mononuclear cells).

In some embodiments, the antibody or antigen-binding portion thereof specifically binds to phosphorylated Rab8a protein. In some embodiments, a phosphorylated Rab8a protein includes 1, 2, 3, 4, 5, or more phosphorylated serine and/or threonine residues. In some embodiments, a phosphorylated Rab8a protein is phosphorylated at an amino acid residue corresponding to Thr72, as numbered with reference to the full-length human Rab8a protein of SEQ ID NO:124. In some embodiments, the antibody or antigen-binding portion thereof specifically binds to a Rab8a protein that is phosphorylated at an amino acid residue corresponding to Thr72, as numbered with reference to SEQ ID NO:124. In some embodiments, the antibody or antigen-binding portion thereof specifically binds to a phosphorylated human Rab8a protein having the amino acid sequence of SEQ ID NO:124 and having a phosphorylated Thr72 residue. In some embodiments, the antibody or antigen-binding portion thereof specifically binds to a phosphorylated Rab8a protein (e.g., a Rab8a protein that is phosphorylated at an amino acid residue corresponding to Thr72, as numbered with reference to SEQ ID NO:124) that is endogenously expressed in a human biological sample (e.g., in a sample comprising peripheral blood mononuclear cells).

In some embodiments, an antibody that specifically binds to phosphorylated human Rab protein (e.g., phosphorylated human Rab10 or phosphorylated human Rab8a) exhibits cross-reactivity with one or more phosphorylated Rab proteins of another species. In some embodiments, an antibody that specifically binds to a phosphorylated human Rab protein (e.g., phosphorylated human Rab10 or phosphorylated human Rab8a) exhibits cross-reactivity with a phosphorylated cynomolgus monkey ("cyno") Rab (e.g., cyno Rab10 or cyno Rab8a, respectively). In some embodiments, an antibody that specifically binds to a phosphorylated human Rab protein (e.g., phosphorylated human Rab10 or phosphorylated human Rab8a) exhibits cross-reactivity with a phosphorylated mouse Rab (e.g., mouse Rab10 or mouse Rab8a, respectively). In some embodiments, an antibody that specifically binds to a phosphorylated human Rab protein (e.g., phosphorylated human Rab10 or phosphorylated human Rab8a) exhibits cross-reactivity with a phosphorylated rat Rab (e.g., rat Rab10 or rat Rab8a, respectively). In some embodiments, an antibody that specifically binds to phosphorylated human Rab10 exhibits cross-reactivity with one, two, or all three of phosphorylated cyno Rab10, phosphorylated mouse Rab10, and phosphorylated rat Rab10. In some embodiments, an antibody that specifically binds to phosphorylated human Rab8a exhibits cross-reactivity with one, two, or all three of phosphorylated cyno Rab8a, phosphorylated mouse Rab8a, and phosphorylated rat Rab8a.

Methods for analyzing binding affinity, binding kinetics, and cross-reactivity are known in the art. These methods include, but are not limited to, solid-phase binding assays (e.g., ELISA assay), immunoprecipitation, surface plasmon resonance (e.g., Biacore™ (GE Healthcare, Piscataway, N.J.)), kinetic exclusion assays (e.g., KinExA®), flow cytometry, fluorescence-activated cell sorting (FACS), Bio-Layer interferometry (e.g., Octet™ (FortdBio, Inc., Menlo Park, Calif.)), and western blot analysis. In some embodiments, ELISA is used to determine binding affinity, binding kinetics, and/or cross-reactivity. Methods for performing ELISA assays are known in the art, and are also described in the Examples section below. In some embodiments, surface plasmon resonance (SPR) is used to determine binding affinity, binding kinetics, and/or cross-reactivity. In some embodiments, kinetic exclusion assays are used to determine binding affinity, binding kinetics, and/or cross-reactivity. In some embodiments, BioLayer interferometry assays are used to determine binding affinity, binding kinetics, and/or cross-reactivity.

Anti-Phosphorylated Rab10 Antibodies

In some embodiments, monoclonal antibodies or antigen-binding portions thereof that specifically bind to phosphorylated human Rab10 protein are provided. In some embodiments, the monoclonal antibody recognizes an epitope within or comprising the sequence AGQERFH(pT)ITTSYYR (SEQ ID NO:123). In some embodiments, an anti-phosphorylated Rab10 monoclonal antibody recognizes an epitope within or comprising the sequence AGQERFH(pT)ITTSYYR (SEQ ID NO:123). In some embodiments, an anti-phosphorylated Rab10 monoclonal antibody recognizes an epitope comprising at least 4, at least 5, at least 6, at least 7, at least 8, at least 9, or at least 10 amino acids within the sequence AGQERFH(pT)ITTSYYR (SEQ ID NO:123). In some embodiments, an anti-phosphorylated Rab10 monoclonal antibody recognizes an epitope comprising 4-12, 4-10, 4-8, 5-10, 5-8, 6-12, 6-10, 8-12, or 8-10 contiguous amino acids within the sequence AGQERFH(pT)ITTSYYR (SEQ ID NO:123). In some embodiments, an anti-phosphorylated Rab10 monoclonal antibody recognizes an epitope comprising the sequence AGQERFH(pT)ITTSYYR (SEQ ID NO:123). In some embodiments, an anti-phosphorylated Rab10 monoclonal antibody recognizes an epitope consisting of the sequence AGQERFH(pT)ITTSYYR (SEQ ID NO:123).

In some embodiments, an anti-phosphorylated Rab10 monoclonal antibody comprises one or more complementarity determining region (CDR), heavy chain variable region, and/or light chain variable region sequences as described herein (e.g., as described in Table 5 below). In some embodiments, an anti-phosphorylated Rab10 monoclonal antibody comprises one or more CDRs selected from the group consisting of:

(a) a heavy chain CDR1 having at least 90% sequence identity to the amino acid sequence of any one of SEQ ID NOs:2, 22, 32, 40, 48, 54, or 57 or having up to two amino acid substitutions relative to the amino acid sequence of any one of SEQ ID NOs:2, 22, 32, 40, 48, 54, or 57;

(b) a heavy chain CDR2 having at least 90% sequence identity to the amino acid sequence of any one of SEQ ID NOs:3, 23, 33, 41, 49, or 58 or having up to two amino acid substitutions relative to the amino acid sequence of any one of SEQ ID NOs:3, 23, 33, 41, 49, or 58;

(c) a heavy chain CDR3 having at least 90% sequence identity to the amino acid sequence of any one of SEQ ID NOs:4, 12, 24, 34, 42, 50, 55, or 59 or having up to two amino acid substitutions relative to the amino acid sequence of any one of SEQ ID NOs:4, 12, 24, 34, 42, 50, 55, or 59;

(d) a light chain CDR1 having at least 90% sequence identity to the amino acid sequence of any one of SEQ ID NOs:6, 14, 26, 36, 44, or 60 or having up to two amino acid substitutions relative to the amino acid sequence of any one of SEQ ID NOs:6, 14, 26, 36, 44, or 60;

(e) a light chain CDR2 having at least 90% sequence identity to the amino acid sequence of any one of SEQ ID NOs:7, 27, 37, 45, or 61 or having up to two amino acid substitutions relative to the amino acid sequence of any one of SEQ ID NOs:7, 27, 37, 45, or 61; and (f) a light chain CDR3 having at least 90% sequence identity to the amino acid sequence of any one of SEQ ID NOs:8, 38, 46, 52, or 62 or having up to two amino acid substitutions relative to the amino acid sequence of any one of SEQ ID NOs:8, 38, 46, 52, or 62.

In some embodiments, an anti-phosphorylated Rab10 monoclonal antibody comprises two, three, four, five, or all six of (a)-(f). In some embodiments, an anti-phosphorylated Rab10 monoclonal antibody comprises the heavy chain CDR1 of (a), the heavy chain CDR2 of (b), and the heavy chain CDR3 of (c). In some embodiments, an anti-phosphorylated Rab10 monoclonal antibody comprises the light chain CDR1 of (d), the light chain CDR2 of (e), and the light chain CDR3 of (f). In some embodiments, a CDR having up to two amino acid substitutions has one amino acid substitution relative to the reference sequence. In some embodiments, a CDR having up to two amino acid substitutions has two amino acid substitutions relative to the reference sequence. In some embodiments, the up to two amino acid substitutions are conservative substitutions.

In some embodiments, an anti-phosphorylated Rab10 monoclonal antibody comprises one or more CDRs selected from the group consisting of:

(a) a heavy chain CDR1 comprising the amino acid sequence of any one of SEQ ID NOs:2, 22, 32, 40, 48, 54, or 57;

(b) a heavy chain CDR2 comprising the amino acid sequence of any one of SEQ ID NOs:3, 23, 33, 41, 49, or 58;

(c) a heavy chain CDR3 comprising the amino acid sequence of any one of SEQ ID NOs:4, 12, 24, 34, 42, 50, 55, or 59;

(d) a light chain CDR1 comprising the amino acid sequence of any one of SEQ ID NOs:6, 14, 26, 36, 44, or 60;

(e) a light chain CDR2 comprising the amino acid sequence of any one of SEQ ID NOs:7, 27, 37, 45, or 61; and (f) a light chain CDR3 comprising the amino acid sequence of any one of SEQ ID NOs:8, 38, 46, 52, or 62.

In some embodiments, an anti-phosphorylated Rab10 monoclonal antibody comprises two, three, four, five, or all six of (a)-(f). In some embodiments, an anti-phosphorylated Rab10 monoclonal antibody comprises the heavy chain CDR1 of (a), the heavy chain CDR2 of (b), and the heavy chain CDR3 of (c). In some embodiments, an anti-phosphorylated Rab10 monoclonal antibody comprises the light chain CDR1 of (d), the light chain CDR2 of (e), and the light chain CDR3 of (f).

In some embodiments, an anti-phosphorylated Rab10 monoclonal antibody comprises one or more consensus sequences. Consensus sequences can be identified by aligning heavy chain or light chain sequences (e.g., CDRs) for antibodies that bind to the same or similar (e.g., overlapping) epitopes to determine conserved amino acids or motifs (i.e., where alteration in sequences may alter protein function) and regions where variation occurs in alignment of sequences (i.e., where variation of sequence is not likely to significantly affect protein function). In some embodiments, one or more consensus sequences can be identified for antibodies that recognize the epitope AGQERFH(pT)ITT-SYYR (SEQ ID NO:123). Exemplary consensus sequences include SEQ ID NOs:57-62. In the consensus sequences of SEQ ID NOs:57-62, the capitalized letter represents an amino acid residue that is absolutely conserved among the aligned sequences (e.g., aligned CDR sequences from two or more of Clone 5, Clone 19, Clone 19-4, Clone 81-11, Clone 133-2, Clone 153-2, Clone 247-8, and Clone 256-6), while "x" represents an amino acid residue that is not absolutely conserved among the aligned sequences. It will be appreciated that when selecting an amino acid to insert at a position marked by an "x" that in some embodiments, the amino acid is selected from those amino acids found at the corresponding position in the aligned sequences.

In some embodiments, the antibody comprises a heavy chain CDR1 sequence having the consensus sequence GFSLSxYxMx (SEQ ID NO:57). In some embodiments, the heavy chain CDR1 consensus sequence comprises the sequence GFSLS[N/S/T]Y[A/Y]M[S/V] (SEQ ID NO:139).

In some embodiments, the antibody comprises a heavy chain CDR2 sequence having the consensus sequence xxxxxGxxYYAxWAKG (SEQ ID NO:58). In some embodiments, the heavy chain CDR2 consensus sequence comprises the sequence [I/L][F/I][N/S][D/R][S/V]G[I/V][A/T]YYA[N/T]WAKG (SEQ ID NO:140).

In some embodiments, the antibody comprises a heavy chain CDR3 sequence having the consensus sequence VRDYDxxGWSGFxI (SEQ ID NO:59). In some embodiments, the heavy chain CDR3 consensus sequence comprises the sequence VRDYD[A/I/S][A/N/S]GWSGF[N/T]I (SEQ ID NO:141).

In some embodiments, the antibody comprises a light chain CDR1 sequence having the consensus sequence QSSxSVxxNNxxS (SEQ ID NO:60). In some embodiments, the light chain CDR1 consensus sequence comprises the sequence QSS[E/K/Q]SV[R/Y][G/H/S]NN[R/Y][F/L]S (SEQ ID NO:142).

In some embodiments, the antibody comprises a light chain CDR2 sequence having the consensus sequence xAS-xLAS (SEQ ID NO:61). In some embodiments, the light chain CDR2 consensus sequence comprises the sequence [G/K/S/Y]AS[I/T]LAS (SEQ ID NO:143).

In some embodiments, the antibody comprises a light chain CDR3 sequence having the consensus sequence AGAxSDxRx (SEQ ID NO:62). In some embodiments, the light chain CDR3 consensus sequence comprises the sequence AGA[A/Y]SD[N/T]R[F/V] (SEQ ID NO:144).

In some embodiments, a monoclonal antibody or antigen-binding portion thereof that specifically binds to phosphorylated human Rab10 protein comprises a light chain sequence, or a portion thereof, and/or a heavy chain sequence, or a portion thereof, derived from any of the following antibodies described herein: Clone 5, Clone 19, Clone 19-4, Clone 81-11, Clone 133-2, Clone 153-2, Clone 247-8, and Clone 256-6. The amino acid sequences of the light chain variable domain (VL) and heavy chain variable domain (VH) of the anti-phosphorylated Rab10 monoclonal antibodies Clone 5, Clone 19, Clone 19-4, Clone 81-11, Clone 133-2, Clone 153-2, Clone 247-8, and Clone 256-6 are set forth in Table 5 below.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to any one of SEQ ID NOs:1, 11, 17, 21, 31, 39, 47, or 53. In some embodiments, an anti-phosphorylated Rab10 monoclonal antibody comprises a heavy chain variable region comprising the amino acid sequence of any one of SEQ ID NOs:1, 11, 17, or 21. In some embodiments, a heavy chain variable region having at least 90% sequence identity to a reference sequence (e.g., SEQ ID NOs:1, 11, 17, 21, 31, 39, 47, or 53) contains one, two, three, four, five, six, seven, eight, nine, ten or more substitutions (e.g., conservative substitutions), insertions, or deletions relative to the reference sequence but retains the ability to specifically bind to a phosphorylated Rab10 protein and recognize an epitope as described herein. In some embodiments, a heavy chain variable region contains one, two, or three substitutions (e.g., conservative substitutions) in any one of SEQ ID NOs:1, 11, 17, 21, 31, 39, 47, or 53.

In some embodiments, an anti-phosphorylated Rab10 monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to any one of SEQ ID NOs:5, 13, 18, 25, 35, 43, 51, or 56. In some embodiments, an anti-phosphorylated Rab10 monoclonal antibody comprises a light chain variable region comprising the amino acid sequence of any one of SEQ ID NOs:5, 13, 18, 25, 35, 43, 51, or 56. In some embodiments, a light chain variable region having at least 90% sequence identity to a reference sequence (e.g., SEQ ID NOs:5, 13, 18, 25, 35, 43, 51, or 56) contains one, two, three, four, five, six, seven, eight, nine, ten or more substitutions (e.g., conservative substitutions), insertions, or deletions relative to the reference sequence but retains the ability to specifically bind to a phosphorylated Rab10 protein and recognize an epitope as described herein. In some embodiments, a light chain variable region contains one, two, or three substitutions (e.g., conservative substitutions) in any one of SEQ ID NOs:5, 13, 18, 25, 35, 43, 51, or 56.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to any one of SEQ ID NOs:1, 11, 17, 21, 31, 39, 47, or 53 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to any one of SEQ ID NOs:5, 13, 18, 25, 35, 43, 51, or 56. In some embodiments, an anti-phosphorylated Rab10 monoclonal antibody comprises a heavy chain variable region comprising the amino acid sequence of any one of SEQ ID NOs:1, 11, 17, 21, 31, 39, 47, or 53 and further comprises a light chain variable region comprising the amino acid sequence of any one of SEQ ID NOs:5, 13, 18, 25, 35, 43, 51, or 56.

Clone 5

In some embodiments, an anti-phosphorylated Rab10 monoclonal antibody comprises a heavy chain CDR1 comprising the amino acid sequence of SEQ ID NO:2, a heavy chain CDR2 comprising the amino acid sequence of SEQ ID NO:3, and a heavy chain CDR3 comprising the amino acid sequence of SEQ ID NO:4. In some embodiments, an anti-phosphorylated Rab10 monoclonal antibody comprises a light chain CDR1 comprising the amino acid sequence of SEQ ID NO:6, a light chain CDR2 comprising the amino acid sequence of SEQ ID NO:7, and a light chain CDR3 comprising the amino acid sequence of SEQ ID NO:8. In some embodiments, an anti-phosphorylated Rab10 monoclonal antibody comprises a heavy chain CDR1-3 and a light chain CDR1-3 comprising the amino acid sequences of SEQ ID NOs:2, 3, 4, 6, 7, and 8, respectively.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:1. In some embodiments, an anti-phosphorylated Rab10 monoclonal antibody comprises a heavy chain variable region comprising the amino acid sequence of SEQ ID NO:1.

In some embodiments, an anti-phosphorylated Rab10 monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:5. In some embodiments, an anti-phosphorylated Rab10 monoclonal antibody comprises a light chain variable region comprising the amino acid sequence of SEQ ID NO:5.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:1 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:5. In some embodiments, an anti-phosphorylated Rab10 monoclonal antibody comprises a heavy chain variable region comprising the amino acid sequence of SEQ ID NO:1 and further comprises a light chain variable region comprising the amino acid sequence of SEQ ID NO:5.

In some embodiments, an anti-phosphorylated Rab10 monoclonal antibody is an antibody that competes for binding with an antibody as described herein (e.g., an antibody comprising a heavy chain CDR1-3 and a light chain CDR1-3 comprising the amino acid sequences of SEQ ID NOs:2, 3, 4, 6, 7, and 8, respectively, or an antibody comprising a heavy chain variable region comprising the amino acid sequence of SEQ ID NO:1 and further comprising a light chain variable region comprising the amino acid sequence of SEQ ID NO:5).

Clone 19

In some embodiments, an anti-phosphorylated Rab10 monoclonal antibody comprises a heavy chain CDR1 comprising the amino acid sequence of SEQ ID NO:2, a heavy chain CDR2 comprising the amino acid sequence of SEQ ID NO:3, and a heavy chain CDR3 comprising the amino acid sequence of SEQ ID NO:12. In some embodiments, an anti-phosphorylated Rab10 monoclonal antibody comprises a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:8. In some embodiments, an anti-phosphorylated Rab10 monoclonal antibody comprises a heavy chain CDR1-3 and a light chain CDR1-3 comprising the amino acid sequences of SEQ ID NOs:2, 3, 12, 14, 7, and 8, respectively.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:11. In some embodiments, an anti-phosphorylated Rab10 monoclonal antibody comprises a heavy chain variable region comprising the amino acid sequence of SEQ ID NO:11.

In some embodiments, an anti-phosphorylated Rab10 monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:13. In some embodiments, an anti-phosphorylated Rab10 monoclonal antibody comprises a light chain variable region comprising the amino acid sequence of SEQ ID NO:13.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:11 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:13. In some embodiments, an anti-phosphorylated Rab10 monoclonal antibody comprises a heavy chain variable region comprising the amino acid sequence of SEQ ID NO:11 and further comprises a light chain variable region comprising the amino acid sequence of SEQ ID NO:13.

In some embodiments, an anti-phosphorylated Rab10 monoclonal antibody is an antibody that competes for binding with an antibody as described herein (e.g., an antibody comprising a heavy chain CDR1-3 and a light chain CDR1-3 comprising the amino acid sequences of SEQ ID NOs:2, 3, 12, 14, 7, and 8, respectively, or an antibody comprising a heavy chain variable region comprising the amino acid sequence of SEQ ID NO:11 and further comprising a light chain variable region comprising the amino acid sequence of SEQ ID NO:13).

Clone 19-4

In some embodiments, an anti-phosphorylated Rab10 monoclonal antibody comprises a heavy chain CDR1 comprising the amino acid sequence of SEQ ID NO:2, a heavy chain CDR2 comprising the amino acid sequence of SEQ ID NO:3, and a heavy chain CDR3 comprising the amino acid sequence of SEQ ID NO:12. In some embodiments, an anti-phosphorylated Rab10 monoclonal antibody comprises a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:8. In some embodiments, an anti-phosphorylated Rab10 monoclonal antibody comprises a heavy chain CDR1-3 and a light chain CDR1-3 comprising the amino acid sequences of SEQ ID NOs:2, 3, 12, 14, 7, and 8, respectively.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:17. In some embodiments, an anti-phosphorylated Rab10 monoclonal antibody comprises a heavy chain variable region comprising the amino acid sequence of SEQ ID NO:17.

In some embodiments, an anti-phosphorylated Rab10 monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:18. In some embodiments, an anti-phosphorylated Rab10 monoclonal antibody comprises a light chain variable region comprising the amino acid sequence of SEQ ID NO:18.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:17 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:18. In some embodiments, an anti-phosphorylated Rab10 monoclonal antibody comprises a heavy chain variable region comprising the amino acid sequence of SEQ ID NO:17 and further comprises a light chain variable region comprising the amino acid sequence of SEQ ID NO:18.

In some embodiments, an anti-phosphorylated Rab10 monoclonal antibody is an antibody that competes for binding with an antibody as described herein (e.g., an antibody comprising a heavy chain CDR1-3 and a light chain CDR1-3 comprising the amino acid sequences of SEQ ID NOs:2, 3, 12, 14, 7, and 8, respectively, or an antibody comprising a heavy chain variable region comprising the amino acid sequence of SEQ ID NO:17 and further comprising a light chain variable region comprising the amino acid sequence of SEQ ID NO:18).

Clone 81-11

In some embodiments, an anti-phosphorylated Rab10 monoclonal antibody comprises a heavy chain CDR1 comprising the amino acid sequence of SEQ ID NO:22, a heavy chain CDR2 comprising the amino acid sequence of SEQ ID NO:23, and a heavy chain CDR3 comprising the amino acid sequence of SEQ ID NO:24. In some embodiments, an anti-phosphorylated Rab10 monoclonal antibody comprises a light chain CDR1 comprising the amino acid sequence of SEQ ID NO:26, a light chain CDR2 comprising the amino acid sequence of SEQ ID NO:27, and a light chain CDR3 comprising the amino acid sequence of SEQ ID NO:28. In some embodiments, an anti-phosphorylated Rab10 monoclonal antibody comprises a heavy chain CDR1-3 and a light chain CDR1-3 comprising the amino acid sequences of SEQ ID NOs:22, 23, 24, 26, 27, and 28, respectively.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:21. In some embodiments, an anti-phosphorylated Rab10 monoclonal antibody comprises a heavy chain variable region comprising the amino acid sequence of SEQ ID NO:21.

In some embodiments, an anti-phosphorylated Rab10 monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:25. In some embodiments, an anti-phosphorylated Rab10 monoclonal antibody comprises a light chain variable region comprising the amino acid sequence of SEQ ID NO:25.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:21 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:25. In some embodiments, an anti-phosphorylated Rab10 monoclonal antibody comprises a heavy chain variable region comprising the amino acid sequence of SEQ ID NO:21 and further comprises a light chain variable region comprising the amino acid sequence of SEQ ID NO:25.

In some embodiments, an anti-phosphorylated Rab10 monoclonal antibody is an antibody that competes for binding with an antibody as described herein (e.g., an antibody comprising a heavy chain CDR1-3 and a light chain CDR1-3 comprising the amino acid sequences of SEQ ID NOs:22, 23, 24, 26, 27, and 28, respectively, or an antibody comprising a heavy chain variable region comprising the amino acid sequence of SEQ ID NO:21 and further comprising a light chain variable region comprising the amino acid sequence of SEQ ID NO:25).

Clone 133-2

In some embodiments, an anti-phosphorylated Rab10 monoclonal antibody comprises a heavy chain CDR1 comprising the amino acid sequence of SEQ ID NO:32, a heavy chain CDR2 comprising the amino acid sequence of SEQ ID NO:33, and a heavy chain CDR3 comprising the amino acid sequence of SEQ ID NO:34. In some embodiments, an anti-phosphorylated Rab10 monoclonal antibody comprises a light chain CDR1 comprising the amino acid sequence of SEQ ID NO:36, a light chain CDR2 comprising the amino acid sequence of SEQ ID NO:37, and a light chain CDR3 comprising the amino acid sequence of SEQ ID NO:38. In some embodiments, an anti-phosphorylated Rab10 monoclonal antibody comprises a heavy chain CDR1-3 and a light chain CDR1-3 comprising the amino acid sequences of SEQ ID NOs:32, 33, 34, 36, 37, and 38, respectively.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:31. In some embodiments, an anti-phosphorylated Rab10 monoclonal antibody comprises a heavy chain variable region comprising the amino acid sequence of SEQ ID NO:31.

In some embodiments, an anti-phosphorylated Rab10 monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:35. In some embodiments, an anti-phosphorylated Rab10 monoclonal antibody comprises a light chain variable region comprising the amino acid sequence of SEQ ID NO:35.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:31 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:35. In some embodiments, an anti-phosphorylated Rab10 monoclonal antibody comprises a heavy chain variable region comprising the amino acid sequence of SEQ ID NO:31 and further comprises a light chain variable region comprising the amino acid sequence of SEQ ID NO:35.

In some embodiments, an anti-phosphorylated Rab10 monoclonal antibody is an antibody that competes for binding with an antibody as described herein (e.g., an antibody comprising a heavy chain CDR1-3 and a light chain CDR1-3 comprising the amino acid sequences of SEQ ID NOs:32, 33, 34, 36, 37, and 38, respectively, or an antibody comprising a heavy chain variable region comprising the amino acid sequence of SEQ ID NO:31 and further comprising a light chain variable region comprising the amino acid sequence of SEQ ID NO:35).

Clone 153-2

In some embodiments, an anti-phosphorylated Rab10 monoclonal antibody comprises a heavy chain CDR1 comprising the amino acid sequence of SEQ ID NO:40, a heavy chain CDR2 comprising the amino acid sequence of SEQ ID NO:41, and a heavy chain CDR3 comprising the amino acid sequence of SEQ ID NO:42. In some embodiments, an anti-phosphorylated Rab10 monoclonal antibody comprises a light chain CDR1 comprising the amino acid sequence of SEQ ID NO:44, a light chain CDR2 comprising the amino acid sequence of SEQ ID NO:45, and a light chain CDR3 comprising the amino acid sequence of SEQ ID NO:46. In some embodiments, an anti-phosphorylated Rab10 monoclonal antibody comprises a heavy chain CDR1-3 and a light chain CDR1-3 comprising the amino acid sequences of SEQ ID NOs:40, 41, 42, 44, 45, and 46, respectively.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:39. In some embodiments, an anti-phosphorylated Rab10 monoclonal antibody comprises a heavy chain variable region comprising the amino acid sequence of SEQ ID NO:39.

In some embodiments, an anti-phosphorylated Rab10 monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:43. In some embodiments, an anti-phosphorylated Rab10 monoclonal antibody comprises a light chain variable region comprising the amino acid sequence of SEQ ID NO:43.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:39 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:43. In some embodiments, an anti-phosphorylated Rab10 monoclonal antibody comprises a heavy chain variable region comprising the amino acid sequence of SEQ ID NO:39 and further comprises a light chain variable region comprising the amino acid sequence of SEQ ID NO:43.

In some embodiments, an anti-phosphorylated Rab10 monoclonal antibody is an antibody that competes for binding with an antibody as described herein (e.g., an antibody comprising a heavy chain CDR1-3 and a light chain CDR1-3 comprising the amino acid sequences of SEQ ID NOs:40, 41, 42, 44, 45, and 46, respectively, or an antibody comprising a heavy chain variable region comprising the amino acid sequence of SEQ ID NO:39 and further comprising a light chain variable region comprising the amino acid sequence of SEQ ID NO:43).

Clone 247-8

In some embodiments, an anti-phosphorylated Rab10 monoclonal antibody comprises a heavy chain CDR1 comprising the amino acid sequence of SEQ ID NO:48, a heavy chain CDR2 comprising the amino acid sequence of SEQ ID NO:49, and a heavy chain CDR3 comprising the amino acid sequence of SEQ ID NO:50. In some embodiments, an anti-phosphorylated Rab10 monoclonal antibody comprises a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:52. In some embodiments, an anti-phosphorylated Rab10 monoclonal antibody comprises a heavy chain CDR1-3 and a light chain CDR1-3 comprising the amino acid sequences of SEQ ID NOs:48, 49, 50, 14, 7, and 52, respectively.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:47. In some embodiments, an anti-phosphorylated Rab10 monoclonal antibody comprises a heavy chain variable region comprising the amino acid sequence of SEQ ID NO:47.

In some embodiments, an anti-phosphorylated Rab10 monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:51. In some embodiments, an anti-phosphorylated Rab10 monoclonal antibody comprises a light chain variable region comprising the amino acid sequence of SEQ ID NO:51.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:47 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:51. In some embodiments, an anti-phosphorylated Rab10 monoclonal antibody comprises a heavy chain variable region comprising the amino acid sequence of SEQ ID NO:47 and further comprises a light chain variable region comprising the amino acid sequence of SEQ ID NO:51.

In some embodiments, an anti-phosphorylated Rab10 monoclonal antibody is an antibody that competes for binding with an antibody as described herein (e.g., an antibody comprising a heavy chain CDR1-3 and a light chain CDR1-3 comprising the amino acid sequences of SEQ ID NOs:48, 49, 50, 14, 7, and 52, respectively, or an antibody comprising a heavy chain variable region comprising the amino acid sequence of SEQ ID NO:47 and further comprising a light chain variable region comprising the amino acid sequence of SEQ ID NO:51).

Clone 256-6

In some embodiments, an anti-phosphorylated Rab10 monoclonal antibody comprises a heavy chain CDR1 comprising the amino acid sequence of SEQ ID NO:54, a heavy chain CDR2 comprising the amino acid sequence of SEQ ID NO:3, and a heavy chain CDR3 comprising the amino acid sequence of SEQ ID NO:55. In some embodiments, an anti-phosphorylated Rab10 monoclonal antibody comprises a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:8. In some embodiments, an anti-phosphorylated Rab10 monoclonal antibody comprises a heavy chain CDR1-3 and a light chain CDR1-3 comprising the amino acid sequences of SEQ ID NOs:54, 3, 55, 14, 7, and 8, respectively.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:53. In some embodiments, an anti-phosphorylated Rab10 monoclonal antibody comprises a heavy chain variable region comprising the amino acid sequence of SEQ ID NO:53.

In some embodiments, an anti-phosphorylated Rab10 monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:56. In some embodiments, an anti-phosphorylated Rab10 monoclonal antibody comprises a light chain variable region comprising the amino acid sequence of SEQ ID NO:56.

In some embodiments, an anti-phosphorylated Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:53 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:56. In some embodiments, an anti-phosphorylated Rab10 monoclonal antibody comprises a heavy chain variable region comprising the amino acid sequence of SEQ ID NO:53 and further comprises a light chain variable region comprising the amino acid sequence of SEQ ID NO:56.

In some embodiments, an anti-phosphorylated Rab10 monoclonal antibody is an antibody that competes for binding with an antibody as described herein (e.g., an antibody comprising a heavy chain CDR1-3 and a light chain CDR1-3 comprising the amino acid sequences of SEQ ID NOs:54, 3, 55, 14, 7, and 8, respectively, or an antibody comprising a heavy chain variable region comprising the amino acid sequence of SEQ ID NO:53 and further comprising a light chain variable region comprising the amino acid sequence of SEQ ID NO:56).

Anti-Phosphorylated Rab8a Antibodies

In some embodiments, monoclonal antibodies or antigen-binding portions thereof that specifically bind to phosphorylated human Rab8a protein are provided. In some embodiments, the monoclonal antibody recognizes an epitope within or comprising the sequence QERFR(pT)ITTAY (SEQ ID NO:125). In some embodiments, an anti-phosphorylated Rab8a monoclonal antibody recognizes an epitope within or comprising the sequence QERFR(pT)ITTAY (SEQ ID NO:125). In some embodiments, an anti-phosphorylated Rab8a monoclonal antibody recognizes an epitope comprising at least 4, at least 5, at least 6, at least 7, at least 8, at least 9, or at least 10 amino acids within the sequence QERFR(pT)ITTAY (SEQ ID NO:125). In some embodiments, an anti-phosphorylated Rab8a monoclonal antibody recognizes an epitope comprising 4-10, 4-8, 5-10, 5-8, 6-10, or 8-10 contiguous amino acids within the sequence QERFR(pT)ITTAY (SEQ ID NO:125). In some embodiments, an anti-phosphorylated Rab8a monoclonal antibody recognizes an epitope comprising the sequence QERFR(pT)ITTAY (SEQ ID NO:125). In some embodiments, an anti-phosphorylated Rab8a monoclonal antibody recognizes an epitope consisting of the sequence QERFR(pT)ITTAY (SEQ ID NO:125).

In some embodiments, an anti-phosphorylated Rab8a monoclonal antibody comprises one or more complementarity determining region (CDR), heavy chain variable region, and/or light chain variable region sequences as described herein (e.g., as described in Table 5 below). In some embodiments, an anti-phosphorylated Rab8a monoclonal antibody comprises one or more CDRs selected from the group consisting of:

(a) a heavy chain CDR1 having at least 90% sequence identity to the amino acid sequence of any one of SEQ ID NOs:48, 72, 82, 92, 100, 108, 110, or 116or having up to two amino acid substitutions relative to the amino acid sequence of any one of SEQ ID NOs:48, 72, 82, 92, 100, 108, 110, or 116;

(b) a heavy chain CDR2 having at least 90% sequence identity to the amino acid sequence of any one of SEQ ID NOs:64, 73, 83, 93, 101, 111, or 117 or having up to two amino acid substitutions relative to the amino acid sequence of any one of SEQ ID NOs:64, 73, 83, 93, 101, 111, or 117;

(c) a heavy chain CDR3 having at least 90% sequence identity to the amino acid sequence of any one of SEQ ID NOs:65, 74, 84, 94, 102, 112, or 118 or having up to two amino acid substitutions relative to the amino acid sequence of any one of SEQ ID NOs:65, 74, 84, 94, 102, 112, or 118;

(d) a light chain CDR1 having at least 90% sequence identity to the amino acid sequence of any one of SEQ ID NOs:67, 76, 86, 96, 104, 114, or 119 or having up to two amino acid substitutions relative to the amino acid sequence of any one of SEQ ID NOs:67, 76, 86, 96, 104, 114, or 119;

(e) a light chain CDR2 having at least 90% sequence identity to the amino acid sequence of any one of SEQ ID NOs:27, 77, 7, 97, 105, 115, or 120 or having up to two amino acid substitutions relative to the amino acid sequence of any one of SEQ ID NOs:27, 77, 7, 97, 105, 115, or 120; and (f) a light chain CDR3 having at least 90% sequence identity to the amino acid sequence of any one of SEQ ID NOs:68, 78, 87, 98, 106, or 121 or having up to two amino acid substitutions relative to the amino acid sequence of any one of SEQ ID NOs:68, 78, 87, 98, 106, or 121.

In some embodiments, an anti-phosphorylated Rab8a monoclonal antibody comprises two, three, four, five, or all six of (a)-(f). In some embodiments, an anti-phosphorylated Rab8a monoclonal antibody comprises the heavy chain CDR1 of (a), the heavy chain CDR2 of (b), and the heavy chain CDR3 of (c). In some embodiments, an anti-phosphorylated Rab8a monoclonal antibody comprises the light chain CDR1 of (d), the light chain CDR2 of (e), and the light chain CDR3 of (f). In some embodiments, a CDR having up to two amino acid substitutions has one amino acid substitution relative to the reference sequence. In some embodiments, a CDR having up to two amino acid substitutions has two amino acid substitutions relative to the reference sequence. In some embodiments, the up to two amino acid substitutions are conservative substitutions.

In some embodiments, an anti-phosphorylated Rab8a monoclonal antibody comprises one or more CDRs selected from the group consisting of:

(a) a heavy chain CDR1 comprising the amino acid sequence of any one of SEQ ID NOs:48, 72, 82, 92, 100, 108, 110, or 116;

(b) a heavy chain CDR2 comprising the amino acid sequence of any one of SEQ ID NOs:64, 73, 83, 93, 101, 111, or 117;

(c) a heavy chain CDR3 comprising the amino acid sequence of any one of SEQ ID NOs:65, 74, 84, 94, 102, 112, or 118;

(d) a light chain CDR1 comprising the amino acid sequence of any one of SEQ ID NOs:67, 76, 86, 96, 104, 114, or 119;

(e) a light chain CDR2 comprising the amino acid sequence of any one of SEQ ID NOs:27, 77, 7, 97, 105, 115, or 120; and (f) a light chain CDR3 comprising the amino acid sequence of any one of SEQ ID NOs:68, 78, 87, 98, 106, or 121.

In some embodiments, an anti-phosphorylated Rab8a monoclonal antibody comprises two, three, four, five, or all six of (a)-(f). In some embodiments, an anti-phosphorylated Rab8a monoclonal antibody comprises the heavy chain CDR1 of (a), the heavy chain CDR2 of (b), and the heavy chain CDR3 of (c). In some embodiments, an anti-phosphorylated Rab8a monoclonal antibody comprises the light chain CDR1 of (d), the light chain CDR2 of (e), and the light chain CDR3 of (f).

In some embodiments, an anti-phosphorylated Rab8a monoclonal antibody comprises one or more consensus sequences. Consensus sequences can be identified by aligning heavy chain or light chain sequences (e.g., CDRs) for antibodies that bind to the same or similar (e.g., overlapping) epitopes to determine conserved amino acids or motifs (i.e., where alteration in sequences may alter protein function) and regions where variation occurs in alignment of sequences (i.e., where variation of sequence is not likely to significantly affect protein function). In some embodiments, one or more consensus sequences can be identified for antibodies that recognize the epitope QERFR(pT)ITTAY (SEQ ID NO:125). Exemplary consensus sequences include SEQ ID NOs:116-121. In the consensus sequences of SEQ ID NOs:116-121, the capitalized letter represents an amino acid residue that is absolutely conserved among the aligned sequences (e.g., aligned CDR sequences from two or more of Clone 20, Clone 71-3, Clone 86-9, Clone 24-3, Clone 165-4, Clone 170-1, Clone 170-3, and Clone 184-1), while "x" represents an amino acid residue that is not absolutely conserved among the aligned sequences. It will be appreciated that when selecting an amino acid to insert at a position marked by an "x" that in some embodiments, the amino acid is selected from those amino acids found at the corresponding position in the aligned sequences.

In some embodiments, the antibody comprises a heavy chain CDR1 sequence having the consensus sequence GFSLxxYxxx (SEQ ID NO:116). In some embodiments, the heavy chain CDR1 consensus sequence comprises the sequence GFSL[N/S][S/T/V]Y[A/V/Y][I/M][G/S/T] (SEQ ID NO:145).

In some embodiments, the antibody comprises a heavy chain CDR2 sequence having the consensus sequence IxNxxxxxxYxNWxxG (SEQ ID NO:117). In some embodiments, the heavy chain CDR2 consensus sequence comprises the sequence I[I/M]N[A/T][D/G][G/I/T/V][S/T][A/V][H/Y]Y[A/T]NW[A/V][K/R]G (SEQ ID NO:146).

In some embodiments, the antibody comprises a heavy chain CDR3 sequence having the consensus sequence ARARNSxWMDx (SEQ ID NO:118). In some embodiments, the heavy chain CDR3 consensus sequence comprises the sequence ARARNS[A/V]WMD[I/L] (SEQ ID NO:147).

In some embodiments, the antibody comprises a light chain CDR1 sequence having the consensus sequence QSxxSVxxxNxLA (SEQ ID NO:119). In some embodiments, the light chain CDR1 consensus sequence comprises the sequence QS[D/S][E/K/W]SV[L/R/V/Y][N/R][D/N]N[Y/-]LA (SEQ ID NO:148).

In some embodiments, the antibody comprises a light chain CDR2 sequence having the consensus sequence xxSxLxS (SEQ ID NO:120). In some embodiments, the light chain CDR2 consensus sequence comprises the sequence [G/K/T][A/T]S[S/T]L[A/P]S (SEQ ID NO:149).

In some embodiments, the antibody comprises a light chain CDR3 sequence having the consensus sequence AGGYxxxSDxxA (SEQ ID NO:121). In some embodiments, the light chain CDR3 consensus sequence comprises the sequence AGGY[D/S/Y][G/I/R/S][D/G]SD[D/I/T][F/-]A (SEQ ID NO:150).

In some embodiments, a monoclonal antibody or antigen-binding portion thereof that specifically binds to phosphorylated human Rab8a protein comprises a light chain sequence, or a portion thereof, and/or a heavy chain sequence, or a portion thereof, derived from any of the following antibodies described herein: Clone 20, Clone 71-3, Clone 86-9, Clone 24-3, Clone 165-4, Clone 170-1, Clone 170-3, and Clone 184-1. The amino acid sequences of the light chain variable domain (VL) and heavy chain variable domain (VH) of the anti-phosphorylated Rab8a monoclonal antibodies Clone 20, Clone 71-3, Clone 86-9, Clone 24-3, Clone 165-4, Clone 170-1, Clone 170-3, and Clone 184-1 are set forth in Table 5 below.

In some embodiments, an anti-phosphorylated Rab8a monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to any one of SEQ ID NOs:63, 71, 81, 90, 91, 99, 107, or 109. In some embodiments, an anti-phosphorylated Rab8a monoclonal antibody comprises a heavy chain variable region comprising the amino acid sequence of any one of SEQ ID NOs:63, 71, 81, 90, 91, 99, 107, or 109. In some embodiments, a heavy chain variable region having at least 90% sequence identity to a reference sequence (e.g., SEQ ID NOs:63, 71, 81, 90, 91, 99, 107, or 109) contains one, two, three, four, five, six, seven, eight, nine, ten or more substitutions (e.g., conservative substitutions), insertions, or deletions relative to the reference sequence but retains the ability to specifically bind to a phosphorylated Rab8a protein and recognize an epitope as described herein. In some embodiments, a heavy chain variable region contains one, two, or three substitutions (e.g., conservative substitutions) in any one of SEQ ID NOs:63, 71, 81, 90, 91, 99, 107, or 109.

In some embodiments, an anti-phosphorylated Rab8a monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to any one of SEQ ID NOs:66, 75, 85, 95, 103, or 113. In some embodiments, an anti-phosphorylated Rab8a monoclonal antibody comprises a light chain variable region comprising the amino acid sequence of any one of SEQ ID NOs:66, 75, 85, 95, 103, or 113. In some embodiments, a light chain variable region having at least 90% sequence identity to a reference sequence (e.g., SEQ ID NOs:66, 75, 85, 95, 103, or 113) contains one, two, three, four, five, six, seven, eight, nine, ten or more substitutions (e.g., conservative substitutions), insertions, or deletions relative to the reference sequence but retains the ability to specifically bind to a phosphorylated Rab8a protein and recognize an epitope as described herein. In some embodiments, a light chain variable region contains one, two, or three substitutions (e.g., conservative substitutions) in any one of SEQ ID NOs:66, 75, 85, 95, 103, or 113.

In some embodiments, an anti-phosphorylated Rab8a monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to any one of SEQ ID NOs:63, 71, 81, 90, 91, 99, 107, or 109 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to any one of SEQ ID NOs:66, 75, 85, 95, 103, or 113. In some embodiments, an anti-phosphorylated Rab8a monoclonal antibody comprises a heavy chain variable region comprising the amino acid sequence of any one of SEQ ID NOs:63, 71, 81, 90, 91, 99, 107, or 109 and further comprises a light chain variable region comprising the amino acid sequence of any one of SEQ ID NOs:66, 75, 85, 95, 103, or 113.

Clone 20

In some embodiments, an anti-phosphorylated Rab8a monoclonal antibody comprises a heavy chain CDR1 comprising the amino acid sequence of SEQ ID NO:48, a heavy chain CDR2 comprising the amino acid sequence of SEQ ID NO:64, and a heavy chain CDR3 comprising the amino acid sequence of SEQ ID NO:65. In some embodiments, an anti-phosphorylated Rab8a monoclonal antibody comprises a light chain CDR1 comprising the amino acid sequence of SEQ ID NO:67, a light chain CDR2 comprising the amino acid sequence of SEQ ID NO:27, and a light chain CDR3 comprising the amino acid sequence of SEQ ID NO:68. In some embodiments, an anti-phosphorylated Rab8a monoclonal antibody comprises a heavy chain CDR1-3 and a light chain CDR1-3 comprising the amino acid sequences of SEQ ID NOs:48, 64, 65, 67, 27, and 68, respectively.

In some embodiments, an anti-phosphorylated Rab8a monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:63. In some embodiments, an anti-phosphorylated Rab8a monoclonal antibody comprises a heavy chain variable region comprising the amino acid sequence of SEQ ID NO:63.

In some embodiments, an anti-phosphorylated Rab8a monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:66. In some embodiments, an anti-phosphorylated Rab8a monoclonal antibody comprises a light chain variable region comprising the amino acid sequence of SEQ ID NO:66.

In some embodiments, an anti-phosphorylated Rab8a monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:63 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:66. In some embodiments, an anti-phosphorylated Rab8a monoclonal antibody comprises a heavy chain variable region comprising the amino acid sequence of SEQ ID NO:63 and further comprises a light chain variable region comprising the amino acid sequence of SEQ ID NO:66.

In some embodiments, an anti-phosphorylated Rab8a monoclonal antibody is an antibody that competes for binding with an antibody as described herein (e.g., an antibody comprising a heavy chain CDR1-3 and a light chain CDR1-3 comprising the amino acid sequences of SEQ ID NOs:48, 64, 65, 67, 27, and 68, respectively, or an antibody comprising a heavy chain variable region comprising the amino acid sequence of SEQ ID NO:63 and further comprising a light chain variable region comprising the amino acid sequence of SEQ ID NO:66).

Clone 71-3

In some embodiments, an anti-phosphorylated Rab8a monoclonal antibody comprises a heavy chain CDR1 comprising the amino acid sequence of SEQ ID NO:72, a heavy chain CDR2 comprising the amino acid sequence of SEQ ID NO:73, and a heavy chain CDR3 comprising the amino acid sequence of SEQ ID NO:74. In some embodiments, an anti-phosphorylated Rab8a monoclonal antibody comprises a light chain CDR1 comprising the amino acid sequence of SEQ ID NO:76, a light chain CDR2 comprising the amino acid sequence of SEQ ID NO:77, and a light chain CDR3 comprising the amino acid sequence of SEQ ID NO:78. In some embodiments, an anti-phosphorylated Rab8a monoclonal antibody comprises a heavy chain CDR1-3 and a light chain CDR1-3 comprising the amino acid sequences of SEQ ID NOs:72, 73, 74, 76, 77, and 78, respectively.

In some embodiments, an anti-phosphorylated Rab8a monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:71. In some embodiments, an anti-phosphorylated Rab8a monoclonal antibody comprises a heavy chain variable region comprising the amino acid sequence of SEQ ID NO:71.

In some embodiments, an anti-phosphorylated Rab8a monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:75. In some embodiments, an anti-phosphorylated Rab8a monoclonal antibody comprises a light chain variable region comprising the amino acid sequence of SEQ ID NO:75.

In some embodiments, an anti-phosphorylated Rab8a monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:71 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:75. In some embodiments, an anti-phosphorylated Rab8a monoclonal antibody comprises a heavy chain variable region comprising the amino acid sequence of SEQ ID NO:71 and further comprises a light chain variable region comprising the amino acid sequence of SEQ ID NO:75.

In some embodiments, an anti-phosphorylated Rab8a monoclonal antibody is an antibody that competes for binding with an antibody as described herein (e.g., an antibody comprising a heavy chain CDR1-3 and a light chain CDR1-3 comprising the amino acid sequences of SEQ ID NOs:72, 73, 74, 76, 77, and 78, respectively, or an antibody comprising a heavy chain variable region comprising the amino acid sequence of SEQ ID NO:71 and further comprising a light chain variable region comprising the amino acid sequence of SEQ ID NO:75).

Clone 86-9

In some embodiments, an anti-phosphorylated Rab8a monoclonal antibody comprises a heavy chain CDR1 comprising the amino acid sequence of SEQ ID NO:82, a heavy chain CDR2 comprising the amino acid sequence of SEQ ID NO:83, and a heavy chain CDR3 comprising the amino acid sequence of SEQ ID N084. In some embodiments, an anti-phosphorylated Rab8a monoclonal antibody comprises a light chain CDR1 comprising the amino acid sequence of SEQ ID NO:86, a light chain CDR2 comprising the amino acid sequence of SEQ ID NO:7, and a light chain CDR3 comprising the amino acid sequence of SEQ ID NO:87. In some embodiments, an anti-phosphorylated Rab8a monoclonal antibody comprises a heavy chain CDR1-3 and a light chain CDR1-3 comprising the amino acid sequences of SEQ ID NOs:82, 83, 84, 86, 7, and 87, respectively.

In some embodiments, an anti-phosphorylated Rab8 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:81. In some embodiments, an anti-phosphorylated Rab8 monoclonal antibody comprises a heavy chain variable region comprising the amino acid sequence of SEQ ID NO:81.

In some embodiments, an anti-phosphorylated Rab8a monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:85. In some embodiments, an anti-phosphorylated Rab8a monoclonal antibody comprises a light chain variable region comprising the amino acid sequence of SEQ ID NO:85.

In some embodiments, an anti-phosphorylated Rab8a monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:81 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:85. In some embodiments, an anti-phosphorylated Rab8a monoclonal antibody comprises a heavy chain variable region comprising the amino acid sequence of SEQ ID NO:81 and further comprises a light chain variable region comprising the amino acid sequence of SEQ ID NO:85.

In some embodiments, an anti-phosphorylated Rab8a monoclonal antibody is an antibody that competes for binding with an antibody as described herein (e.g., an antibody comprising a heavy chain CDR1-3 and a light chain CDR1-3 comprising the amino acid sequences of SEQ ID NOs:82, 83, 84, 86, 7, and 87, respectively, or an antibody comprising a heavy chain variable region comprising the amino acid sequence of SEQ ID NO:81 and further comprising a light chain variable region comprising the amino acid sequence of SEQ ID NO:85).

Clone 24-3

In some embodiments, an anti-phosphorylated Rab8a monoclonal antibody comprises a heavy chain CDR1 comprising the amino acid sequence of SEQ ID NO:82, a heavy chain CDR2 comprising the amino acid sequence of SEQ ID NO:83, and a heavy chain CDR3 comprising the amino acid sequence of SEQ ID N084. In some embodiments, an anti-phosphorylated Rab8a monoclonal antibody comprises a light chain CDR1 comprising the amino acid sequence of SEQ ID NO:86, a light chain CDR2 comprising the amino acid sequence of SEQ ID NO:7, and a light chain CDR3 comprising the amino acid sequence of SEQ ID NO:87. In some embodiments, an anti-phosphorylated Rab8a monoclonal antibody comprises a heavy chain CDR1-3 and a light chain CDR1-3 comprising the amino acid sequences of SEQ ID NOs:82, 83, 84, 86, 7, and 87, respectively.

In some embodiments, an anti-phosphorylated Rab8 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:90. In some embodiments, an anti-phosphorylated Rab8 monoclonal antibody comprises a heavy chain variable region comprising the amino acid sequence of SEQ ID NO:90.

In some embodiments, an anti-phosphorylated Rab8a monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:85. In some embodiments, an anti-phosphorylated Rab8a monoclonal antibody comprises a light chain variable region comprising the amino acid sequence of SEQ ID NO:85.

In some embodiments, an anti-phosphorylated Rab8a monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:90 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:85. In some embodiments, an anti-phosphorylated Rab8a monoclonal antibody comprises a heavy chain variable region comprising the amino acid sequence of SEQ ID NO:90 and further comprises a light chain variable region comprising the amino acid sequence of SEQ ID NO:85.

In some embodiments, an anti-phosphorylated Rab8a monoclonal antibody is an antibody that competes for binding with an antibody as described herein (e.g., an antibody comprising a heavy chain CDR1-3 and a light chain CDR1-3 comprising the amino acid sequences of SEQ ID NOs:82, 83, 84, 86, 7, and 87, respectively, or an antibody comprising a heavy chain variable region comprising the amino acid sequence of SEQ ID NO:90 and further comprising a light chain variable region comprising the amino acid sequence of SEQ ID NO:85).

Clone 165-4

In some embodiments, an anti-phosphorylated Rab8a monoclonal antibody comprises a heavy chain CDR1 comprising the amino acid sequence of SEQ ID NO:92, a heavy chain CDR2 comprising the amino acid sequence of SEQ ID NO:93, and a heavy chain CDR3 comprising the amino acid sequence of SEQ ID NO:94. In some embodiments, an anti-phosphorylated Rab8a monoclonal antibody comprises a light chain CDR1 comprising the amino acid sequence of SEQ ID NO:96, a light chain CDR2 comprising the amino acid sequence of SEQ ID NO:97, and a light chain CDR3 comprising the amino acid sequence of SEQ ID NO:98. In some embodiments, an anti-phosphorylated Rab8a monoclonal antibody comprises a heavy chain CDR1-3 and a light chain CDR1-3 comprising the amino acid sequences of SEQ ID NOs:92, 93, 94, 96, 97, and 98, respectively.

In some embodiments, an anti-phosphorylated Rab8 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:91. In some embodiments, an anti-phosphorylated Rab8 monoclonal antibody comprises a heavy chain variable region comprising the amino acid sequence of SEQ ID NO:91.

In some embodiments, an anti-phosphorylated Rab8a monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:95. In some embodiments, an anti-phosphorylated Rab8a monoclonal antibody comprises a light chain variable region comprising the amino acid sequence of SEQ ID NO:95.

In some embodiments, an anti-phosphorylated Rab8a monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:91 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:95. In some embodiments, an anti-phosphorylated Rab8a monoclonal antibody comprises a heavy chain variable region comprising the amino acid sequence of SEQ ID NO:91 and further comprises a light chain variable region comprising the amino acid sequence of SEQ ID NO:95.

In some embodiments, an anti-phosphorylated Rab8a monoclonal antibody is an antibody that competes for binding with an antibody as described herein (e.g., an antibody comprising a heavy chain CDR1-3 and a light chain CDR1-3 comprising the amino acid sequences of SEQ ID NOs:92, 93, 94, 96, 97, and 98, respectively, or an antibody comprising a heavy chain variable region comprising the amino acid sequence of SEQ ID NO:91 and further comprising a light chain variable region comprising the amino acid sequence of SEQ ID NO:95).

Clone 170-1

In some embodiments, an anti-phosphorylated Rab8a monoclonal antibody comprises a heavy chain CDR1 comprising the amino acid sequence of SEQ ID NO:100, a heavy chain CDR2 comprising the amino acid sequence of SEQ ID NO:101, and a heavy chain CDR3 comprising the amino acid sequence of SEQ ID NO:102. In some embodiments, an anti-phosphorylated Rab8a monoclonal antibody comprises a light chain CDR1 comprising the amino acid sequence of SEQ ID NO:104, a light chain CDR2 comprising the amino acid sequence of SEQ ID NO:105, and a light chain CDR3 comprising the amino acid sequence of SEQ ID NO:106. In some embodiments, an anti-phosphorylated Rab8a monoclonal antibody comprises a heavy chain CDR1-3 and a light chain CDR1-3 comprising the amino acid sequences of SEQ ID NOs:100, 101, 102, 104, 105, and 106, respectively.

In some embodiments, an anti-phosphorylated Rab8 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:99. In some embodiments, an anti-phosphorylated Rab8 monoclonal antibody comprises a heavy chain variable region comprising the amino acid sequence of SEQ ID NO:99.

In some embodiments, an anti-phosphorylated Rab8a monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:103. In some embodiments, an anti-phosphorylated Rab8a monoclonal antibody comprises a light chain variable region comprising the amino acid sequence of SEQ ID NO:103.

In some embodiments, an anti-phosphorylated Rab8a monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:99 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:103. In some embodiments, an anti-phosphorylated Rab8a monoclonal antibody comprises a heavy chain variable region comprising the amino acid sequence of SEQ ID NO:99 and further comprises a light chain variable region comprising the amino acid sequence of SEQ ID NO:103.

In some embodiments, an anti-phosphorylated Rab8a monoclonal antibody is an antibody that competes for binding with an antibody as described herein (e.g., an antibody comprising a heavy chain CDR1-3 and a light chain CDR1-3 comprising the amino acid sequences of SEQ ID NOs:100, 101, 102, 104, 105, and 106, respectively, or an antibody comprising a heavy chain variable region comprising the amino acid sequence of SEQ ID NO:99 and further comprising a light chain variable region comprising the amino acid sequence of SEQ ID NO:103).

Clone 170-3

In some embodiments, an anti-phosphorylated Rab8a monoclonal antibody comprises a heavy chain CDR1 comprising the amino acid sequence of SEQ ID NO:108, a heavy chain CDR2 comprising the amino acid sequence of SEQ ID NO:101, and a heavy chain CDR3 comprising the amino acid sequence of SEQ ID NO:102. In some embodiments, an anti-phosphorylated Rab8a monoclonal antibody comprises a light chain CDR1 comprising the amino acid sequence of SEQ ID NO:104, a light chain CDR2 comprising the amino acid sequence of SEQ ID NO:105, and a light chain CDR3 comprising the amino acid sequence of SEQ ID NO:106. In some embodiments, an anti-phosphorylated Rab8a monoclonal antibody comprises a heavy chain CDR1-3 and a light chain CDR1-3 comprising the amino acid sequences of SEQ ID NOs:108, 101, 102, 104, 105, and 106, respectively.

In some embodiments, an anti-phosphorylated Rab8 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:107. In some embodiments, an anti-phosphorylated Rab8 monoclonal antibody comprises a heavy chain variable region comprising the amino acid sequence of SEQ ID NO:107.

In some embodiments, an anti-phosphorylated Rab8a monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:103. In some embodiments, an anti-phosphorylated Rab8a monoclonal antibody comprises a light chain variable region comprising the amino acid sequence of SEQ ID NO:103.

In some embodiments, an anti-phosphorylated Rab8a monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:107 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:103. In some embodiments, an anti-phosphorylated Rab8a monoclonal antibody comprises a heavy chain variable region comprising the amino acid sequence of SEQ ID NO:107 and further comprises a light chain variable region comprising the amino acid sequence of SEQ ID NO:103.

In some embodiments, an anti-phosphorylated Rab8a monoclonal antibody is an antibody that competes for binding with an antibody as described herein (e.g., an antibody comprising a heavy chain CDR1-3 and a light chain CDR1-3 comprising the amino acid sequences of SEQ ID NOs:108, 101, 102, 104, 105, and 106, respectively, or an antibody comprising a heavy chain variable region comprising the amino acid sequence of SEQ ID NO:107 and further comprising a light chain variable region comprising the amino acid sequence of SEQ ID NO:103).

Clone 184-1

In some embodiments, an anti-phosphorylated Rab8a monoclonal antibody comprises a heavy chain CDR1 comprising the amino acid sequence of SEQ ID NO:110, a heavy chain CDR2 comprising the amino acid sequence of SEQ ID NO:111, and a heavy chain CDR3 comprising the amino acid sequence of SEQ ID NO:112. In some embodiments, an anti-phosphorylated Rab8a monoclonal antibody comprises a light chain CDR1 comprising the amino acid sequence of SEQ ID NO:114, a light chain CDR2 comprising the amino acid sequence of SEQ ID NO:115, and a light chain CDR3 comprising the amino acid sequence of SEQ ID NO:87. In some embodiments, an anti-phosphorylated Rab8a monoclonal antibody comprises a heavy chain CDR1-3 and a light chain CDR1-3 comprising the amino acid sequences of SEQ ID NOs:110, 111, 112, 114, 115, and 87, respectively.

In some embodiments, an anti-phosphorylated Rab8 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:109. In some embodiments, an anti-phosphorylated Rab8 monoclonal antibody comprises a heavy chain variable region comprising the amino acid sequence of SEQ ID NO:109.

In some embodiments, an anti-phosphorylated Rab8a monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:113. In some embodiments, an anti-phosphorylated Rab8a monoclonal antibody comprises a light chain variable region comprising the amino acid sequence of SEQ ID NO:113.

In some embodiments, an anti-phosphorylated Rab8a monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:109 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:113. In some embodiments, an anti-phosphorylated Rab8a monoclonal antibody comprises a heavy chain variable region comprising the amino acid sequence of SEQ ID NO:109 and further comprises a light chain variable region comprising the amino acid sequence of SEQ ID NO:113.

In some embodiments, an anti-phosphorylated Rab8a monoclonal antibody is an antibody that competes for binding with an antibody as described herein (e.g., an antibody comprising a heavy chain CDR1-3 and a light chain CDR1-3 comprising the amino acid sequences of SEQ ID NOs:110, 111, 112, 114, 115, and 87, respectively, or an antibody comprising a heavy chain variable region comprising the amino acid sequence of SEQ ID NO:109 and further comprising a light chain variable region comprising the amino acid sequence of SEQ ID NO:113).

Preparation of Antibodies

For preparing an anti-phosphorylated Rab (e.g., Rab10 or Rab8a) monoclonal antibody, many techniques known in the art can be used. In some embodiments, antibodies are prepared by immunizing an animal or animals (e.g., mice, rabbits, or rats) with an antigen or a mixture of antigens for the induction of an antibody response. In some embodiments, the antigen or mixture of antigens is administered in conjugation with an adjuvant (e.g., Freund's adjuvant). After an initial immunization, one or more subsequent booster injections of the antigen or antigens may be administered to improve antibody production. Following immunization, antigen-specific B cells are harvested, e.g., from the spleen and/or lymphoid tissue. For generating monoclonal antibodies, the B cells are fused with myeloma cells, which are subsequently screened for antigen specificity. Methods of preparing antibodies are also described in the Examples section below. In some embodiments, a method of preparing an anti-phosphorylated Rab (e.g., Rab10 or Rab8a) monoclonal antibody comprises immunizing an animal with a phosphorylated Rab peptide (e.g., the peptide of SEQ ID NO:123 or SEQ ID NO:125) that is coupled to a carrier protein. In some embodiments, the carrier protein is keyhole limpet hemocyanin (KLH), bovine serum albumin (BSA), or ovalbumin (OVA).

The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Alternatively, phage or yeast display technology can be used to identify antibodies and Fab fragments that specifically bind to selected antigens. Techniques for the production of single chain antibodies or recombinant antibodies can also be adapted to produce antibodies. Antibodies can also be made bispecific, i.e., able to recognize two different antigens. Antibodies can also be heteroconjugates, e.g., two covalently joined antibodies, or immunotoxins.

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a VH and VL region, the VH and VL regions may be expressed using a single vector, e.g., in a di-cistronic expression unit, or under the control of different promoters. In other embodiments, the VH and VL region may be expressed using separate vectors. A VH or VL region as described herein may optionally comprise a methionine at the N-terminus.

In some embodiments, the antibody is a chimeric antibody. Methods for making chimeric antibodies are known in the art. For example, chimeric antibodies can be made in which the antigen binding region (heavy chain variable region and light chain variable region) from one species, such as a mouse, is fused to the effector region (constant domain) of another species, such as a human. As another example, "class switched" chimeric antibodies can be made in which the effector region of an antibody is substituted with an effector region of a different immunoglobulin class or subclass.

In some embodiments, the antibody is a humanized antibody. Generally, a non-human antibody is humanized in order to reduce its immunogenicity. Humanized antibodies typically comprise one or more variable regions (e.g., CDRs) or portions thereof that are non-human (e.g., derived from a mouse variable region sequence), and possibly some framework regions or portions thereof that are non-human, and further comprise one or more constant regions that are derived from human antibody sequences. Methods for humanizing non-human antibodies are known in the art. Transgenic mice, or other organisms such as other mammals, can be used to express humanized or human antibodies. Other methods of humanizing antibodies include, for example, variable domain resurfacing, CDR grafting, grafting specificity-determining residues (SDR), guided selection, and framework shuffling.

In some embodiments, the antibody is a fully human antibody. As a non-limiting example, transgenic animals (e.g., mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. As another example, human antibodies can be produced by hybridoma-based methods, such as by using primary human B cells for generating cell lines producing human monoclonal antibodies.

Human antibodies can also be produced using phage display or yeast display technology. In phage display, repertoires of variable heavy chain and variable light chain genes are amplified and expressed in phage display vectors. In some embodiments, the antibody library is a natural repertoire amplified from a human source. In some embodiments, the antibody library is a synthetic library made by cloning heavy chain and light chain sequences and recombining to generate a large pool of antibodies with different antigenic specificity. Phage typically display antibody fragments (e.g., Fab fragments or scFv fragments), which are then screened for binding to an antigen of interest.

In some embodiments, antibody fragments (such as a Fab, a Fab', a F(ab')$_2$, a scFv, a $V_H$, a $V_{HH}$, or a diabody) are generated. Various techniques have been developed for the production of antibody fragments. Traditionally, these fragments were derived via proteolytic digestion of intact antibodies. However, these fragments can now be produced directly using recombinant host cells. For example, antibody fragments can be isolated from antibody phage libraries. Alternatively, Fab'-SH fragments can be directly recovered from *E. coli* cells and chemically coupled to form F(ab')$_2$ fragments. According to another approach, F(ab')$_2$ fragments can be isolated directly from recombinant host cell culture. Other techniques for the production of antibody fragments will be apparent to those skilled in the art.

In some embodiments, the antibody or an antibody fragment is conjugated to another molecule, e.g., polyethylene glycol (PEGylation) or serum albumin, to provide an extended half-life in vivo.

Nucleic Acids, Vectors, and Host Cells

In some embodiments, an anti-phosphorylated Rab (e.g., Rab10 or Rab8a) monoclonal antibody as described herein is preparing using recombinant methods. Thus, in some aspects, the present disclosure provides isolated nucleic acids comprising a polynucleotide sequence encoding any of the anti-phosphorylated Rab10 or anti-phosphorylated Rab8a antibodies as described herein (e.g., any one or more of the CDRs, heavy chain variable regions, and light chain variable regions described herein); vectors comprising such nucleic acids; and host cells into which the nucleic acids are introduced that are used to replicate the antibody-encoding nucleic acids and/or to express the antibodies.

In some embodiments, a polynucleotide (e.g., an isolated polynucleotide) comprises a nucleotide sequence encoding an antibody or antigen-binding portion thereof as described herein (e.g., as described in the Sections above entitled "Anti-Phosphorylated Rab10 Antibodies" or "Anti-Phosphorylated Rab8a Antibodies"). In some embodiments, the polynucleotide comprises a nucleotide sequence encoding one or more amino acid sequences (e.g., CDR, heavy chain, light chain, and/or framework regions) disclosed in Table 5 below. In some embodiments, the polynucleotide comprises a nucleotide sequence encoding an amino acid sequence having at least 85% sequence identity (e.g., at least 85%, at least 90%, at least 91%, at least 92%, at least 93%, at least 94%, at least 95%, at least 96%, at least 97%, at least 98%, or at least 99% sequence identity) to a sequence (e.g., a CDR, heavy chain, light chain, or framework region sequence) disclosed in Table 5 below. In some embodiments, the polynucleotide comprises a nucleotide sequence having at least 85% sequence identity (e.g., at least 85%, at least 90%, at least 91%, at least 92%, at least 93%, at least 94%, at least 95%, at least 96%, at least 97%, at least 98%, or at least 99% sequence identity) to a nucleic acid sequence of any one of SEQ ID NOs:9, 10, 15, 16, 19, 20, 29, 30, 69, 70, 79, 80, 88, or 89. In some embodiments, the polynucleotide comprises a nucleotide sequence comprising the nucleic acid sequence of any one of SEQ ID NOs:9, 10, 15, 16, 19, 20, 29, 30, 69, 70, 79, 80, 88, or 89. In some embodiments, a polynucleotide as described herein is operably linked to a heterologous nucleic acid, e.g., a heterologous promoter.

Suitable vectors containing polynucleotides encoding antibodies of the present disclosure, or fragments thereof, include cloning vectors and expression vectors. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicate in the host cells either as episomes or as an integral part of the chromosomal DNA. Suitable expression vectors include but are not limited to plasmids, viral vectors, including adenoviruses, adeno-associated viruses, retroviruses, and any other vector.

Suitable host cells for cloning or expressing a polynucleotide or vector as described herein include prokaryotic or eukaryotic cells. In some embodiments, the host cell is prokaryotic. In some embodiments, the host cell is eukaryotic, e.g., Chinese Hamster Ovary (CHO) cells or lymphoid cells. In some embodiments, the host cell is a human cell, e.g., a Human Embryonic Kidney (HEK) cell.

In another aspect, methods of making an anti-phosphorylated Rab (e.g., Rab10 or Rab8a) monoclonal antibody as described herein are provided. In some embodiments, the method comprises culturing a host cell as described herein (e.g., a host cell expressing a polynucleotide or vector as described herein) under conditions suitable for expression of the antibody. In some embodiments, the antibody is subsequently recovered from the host cell (or host cell culture medium).

IV. Anti-total RAB10 Antibodies

In another aspect, antibodies and antigen-binding portions of antibodies that specifically bind to total Rab protein (e.g., total Rab10 protein) are provided. As used herein, the term "total Rab protein" refers to both phosphorylated and unphosphorylated forms of a Rab protein. Thus, for example, "total Rab10 protein" refers to both phosphorylated and unphosphorylated Rab10 protein. In some embodiments, the antibody or antigen-binding portion thereof specifically binds to total human Rab10 protein. In some embodiments, the antibody or antigen-binding portion thereof specifically binds to total Rab10 protein (e.g., total human Rab10) is a monoclonal antibody.

In some embodiments, an anti-total Rab10 monoclonal antibody comprises one or more CDRs, heavy chain variable region, and/or light chain variable regions sequences as described herein (e.g., as described in Table 5 below). In some embodiments, an anti-total Rab10 monoclonal antibody comprises one or more CDRs selected from the group consisting of:
  (a) a heavy chain CDR1 having at least 90% sequence identity to the amino acid sequence of SEQ ID NO:132 or having up to two amino acid substitutions relative to the amino acid sequence of SEQ ID NO:132;
  (b) a heavy chain CDR2 having at least 90% sequence identity to the amino acid sequence of SEQ ID NO:133 or having up to two amino acid substitutions relative to the amino acid sequence of SEQ ID NO:133;
  (c) a heavy chain CDR3 having at least 90% sequence identity to the amino acid sequence of SEQ ID NO:134 or having up to two amino acid substitutions relative to the amino acid sequence of SEQ ID NO:134;
  (d) a light chain CDR1 having at least 90% sequence identity to the amino acid sequence of SEQ ID NO:136 or having up to two amino acid substitutions relative to the amino acid sequence of SEQ ID NO:136;
  (e) a light chain CDR2 having at least 90% sequence identity to the amino acid sequence of SEQ ID NO:137 or having up to two amino acid substitutions relative to the amino acid sequence of SEQ ID NO:137; and
  (f) a light chain CDR3 having at least 90% sequence identity to the amino acid sequence of SEQ ID NO:138 or having up to two amino acid substitutions relative to the amino acid sequence of SEQ ID NO:138.

In some embodiments, an anti-total Rab10 monoclonal antibody comprises two, three, four, five, or all six of (a)-(f). In some embodiments, an anti-total Rab10 monoclonal antibody comprises the heavy chain CDR1 of (a), the heavy chain CDR2 of (b), and the heavy chain CDR3 of (c). In some embodiments, an anti-total Rab10 monoclonal antibody comprises the light chain CDR1 of (d), the light chain CDR2 of (e), and the light chain CDR3 of (f). In some embodiments, a CDR having up to two amino acid substitutions has one amino acid substitution relative to the reference sequence. In some embodiments, a CDR having up to two amino acid substitutions has two amino acid substitutions relative to the reference sequence. In some embodiments, the up to two amino acid substitutions are conservative substitutions.

In some embodiments, an anti-total Rab10 monoclonal antibody comprises one or more CDRs selected from the group consisting of:
  (a) a heavy chain CDR1 comprising the amino acid sequence of SEQ ID NO:132;
  (b) a heavy chain CDR2 comprising the amino acid sequence of SEQ ID NO:133;
  (c) a heavy chain CDR3 comprising the amino acid sequence of SEQ ID NO:134;
  (d) a light chain CDR1 comprising the amino acid sequence of SEQ ID NO:136;
  (e) a light chain CDR2 comprising the amino acid sequence of SEQ ID NO:137; and
  (f) a light chain CDR3 comprising the amino acid sequence of SEQ ID NO:138.

In some embodiments, an anti-total Rab10 monoclonal antibody comprises two, three, four, five, or all six of (a)-(f). In some embodiments, an anti-total Rab10 monoclonal antibody comprises the heavy chain CDR1 of (a), the heavy chain CDR2 of (b), and the heavy chain CDR3 of (c). In some embodiments, an anti-total Rab10 monoclonal antibody comprises the light chain CDR1 of (d), the light chain CDR2 of (e), and the light chain CDR3 of (f). In some embodiments, an anti-total Rab10 monoclonal antibody comprises the heavy chain CDR1 of (a), the heavy chain CDR2 of (b), the heavy chain CDR3 of (c), the light chain CDR1 of (d), the light chain CDR2 of (e), and the light chain CDR3 of (f).

In some embodiments, an anti-total Rab10 monoclonal antibody comprises a heavy chain sequence or a portion thereof and/or a light chain sequence or a portion thereof derived from Clone 10-3. The amino acid sequences of the heavy chain variable domain (VH) and light chain variable domain (VL) of the anti-total Rab10 monoclonal antibody Clone 10-3 are set forth in Table 5 below.

In some embodiments, an anti-total Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:131. In some embodiments, an anti-total Rab10 monoclonal antibody comprises a heavy chain variable region comprising the amino acid sequence of SEQ ID NO:131. In some embodiments, a heavy chain variable region having at least 90% sequence identity to a reference sequence (e.g., SEQ ID NO:131) contains one, two, three, four, five, six, seven, eight, nine, ten or more substitutions (e.g., conservative substitutions), insertions, or deletions relative to the reference sequence but retains the ability to specifically bind to phosphorylated and unphosphorylated Rab10 protein. In some embodiments, a heavy chain variable region contains one, two, or three substitutions (e.g., conservative substitutions) in SEQ ID NO:131.

In some embodiments, an anti-total Rab10 monoclonal antibody comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:135. In some embodiments, an anti-total Rab10 monoclonal antibody comprises a light chain variable region comprising the amino acid sequence of SEQ ID NO:135. In some embodiments, a light chain variable region having at least 90% sequence identity to a reference sequence (e.g., SEQ ID NO:135) contains one, two, three, four, five, six, seven, eight, nine, ten or more substitutions (e.g., conservative substitutions), insertions, or deletions relative to the reference sequence but retains the ability to specifically bind to phosphorylated and unphosphorylated Rab10 protein. In some embodiments, a light chain variable region contains one, two, or three substitutions (e.g., conservative substitutions) in SEQ ID NO:135.

In some embodiments, an anti-total Rab10 monoclonal antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:131 and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:135. In some embodiments, an anti-total Rab10 monoclonal antibody comprises a heavy chain variable region comprising the amino acid sequence of SEQ ID NO:131 and further comprises a light chain variable region comprising the amino acid sequence of SEQ ID NO:135.

Methods for the preparation of an anti-total Rab (e.g., Rab10) monoclonal antibody are disclosed herein, e.g., in Section III above and in the Examples section below. In some embodiments, an anti-total Rab (e.g., Rab10) monoclonal antibody as described herein is preparing using recombinant methods. Thus, in some aspects, the present disclosure provides isolated nucleic acids comprising a polynucleotide sequence encoding an anti-total Rab10 antibody as described herein (e.g., any one or more of the CDRs, heavy chain variable regions, and light chain variable regions described herein); vectors comprising such nucleic acids; and host cells into which the nucleic acids are introduced that are used to replicate the antibody-encoding nucleic acids and/or to express the antibodies.

V. Diagnostic Methods Using Anti-Phosphorylated Rab Antibodies

In another aspect, diagnostic methods using an anti-phosphorylated Rab (e.g., Rab10 or Rab8a) monoclonal antibody as described herein are provided. In some embodiments, an anti-phosphorylated Rab10 monoclonal antibody or an anti-phosphorylated Rab8a monoclonal antibody as described in Section III above is used in the practice of the methods described herein.

In some embodiments, a method of diagnosing a subject as having Parkinson's disease is provided. In some embodiments, the form of Parkinson's disease is familial Parkinson's disease or sporadic Parkinson's disease. In some embodiments, the form of Parkinson's disease is LRRK2-associated Parkinson's disease, e.g., LRRK2-associated Parkinson's disease that is characterized by a I1122V, N1437H, R1441C/G/H, R1728H, R1628P, Y1699C, G2019S, I2020T, T2031S or G2385R mutation in LRRK2, or that is characterized by a R1441C, R1441G, Y1699C, G2019S, or I2020T mutation in LRRK2.

In some embodiments, the method comprises:
contacting a sample from the subject with an anti-phosphorylated Rab10 monoclonal antibody (or antigen-binding fragment or pharmaceutical composition) as described herein; and
measuring the amount of phosphorylated Rab10 protein in the sample from the subject;
wherein an amount of phosphorylated Rab10 protein in the sample from the subject that is at least as high as a control value is indicative of the subject having Parkinson's disease.

In some embodiments, the method comprises:
contacting a sample from the subject with an anti-phosphorylated Rab8a monoclonal antibody (or antigen-binding fragment or pharmaceutical composition) as described herein; and
measuring the amount of phosphorylated Rab8a protein in the sample from the subject;
wherein an amount of phosphorylated Rab8a protein in the sample from the subject that is at least as high as a control value is indicative of the subject having Parkinson's disease.

In some embodiments, the amount of phosphorylated Rab10 or phosphorylated Rab8a protein in the sample from the subject is compared to a control value that is determined for a healthy control or population of healthy controls (i.e., not afflicted with Parkinson's disease). In some embodiments, the subject is diagnosed as having Parkinson's disease if the amount of phosphorylated Rab10 or phosphorylated Rab8a protein in the sample from the subject is increased as compared to the control value. In some embodiments, the subject is diagnosed as having Parkinson's disease if the amount of phosphorylated Rab10 or phosphorylated Rab8a protein in the sample from the subject is increased by at least 20%, at least 30%, at least 40%, at least 50%, at least 60%, at least 70%, at least 80%, at least 90% or more as compared to the control value. In some embodiments, the subject is diagnosed as having Parkinson's disease if the amount of phosphorylated Rab10 or phosphorylated Rab8a protein in the sample from the subject is increased by at least 2-fold, 3-fold, 4-fold, 5-fold, 6-fold, 7-fold, 8-fold, 9-fold, 10-fold or more as compared to the control value. In some embodiments, the healthy control value for phosphorylated Rab10 or phosphorylated Rab8a is determined by assessing the level of phosphorylated Rab10 or phosphorylated Rab8a in a subject or population of subjects (e.g., 10, 20, 50, 100, 200, 500, 1000 subjects or more) that all are known not to have Parkinson's disease.

In some embodiments, the amount of phosphorylated Rab10 or phosphorylated Rab8a protein in the sample from the subject is compared to a control value that is determined for a disease control or population of disease controls (i.e., afflicted with Parkinson's disease, e.g., LRRK2-associated Parkinson's disease). In some embodiments, the subject is diagnosed as having Parkinson's disease if the amount of phosphorylated Rab10 or phosphorylated Rab8a protein in the sample from the subject is at least as high as amount of phosphorylated Rab10 or phosphorylated Rab8a, respectively, in the disease control or population of disease controls. In some embodiments, the subject is diagnosed as having Parkinson's disease if the amount of phosphorylated Rab10 or phosphorylated Rab8a protein in the sample from the subject is comparable to (e.g., is within 20%, 10%, 5%, 4%, 3%, 2%, or 1%) of the amount of phosphorylated Rab10 or phosphorylated Rab8a, respectively, in the disease control or population of disease controls. In some embodiments, the disease control value for phosphorylated Rab10 or phosphorylated Rab8a is determined by assessing the level of phosphorylated Rab10 or phosphorylated Rab8a in a subject or population of subjects (e.g., 10, 20, 50, 100, 200, 500, 1000 subjects or more) that all are known to have Parkinson's disease, e.g., LRRK2-associated Parkinson's disease.

In some embodiments, the population of subjects is matched to a test subject according to one or more patient characteristics such as age, sex, ethnicity, or other criteria. In some embodiments, the control value is established using the same type of sample from the population of subjects (e.g., a sample comprising blood or PBMCs) as is used for assessing the level of phosphorylated Rab10 or phosphorylated Rab8a in the test subject.

In some embodiments, the sample comprises a fluid, e.g., blood, plasma, serum, urine, or cerebrospinal fluid. In some embodiments, the sample comprises blood or blood fractions or products (e.g., serum, plasma, platelets, peripheral blood cells, red blood cells, white blood cells, peripheral blood mononuclear cells, or neutrophils). In some embodiments, the sample comprises peripheral blood mononuclear cells (PBMCs). In some embodiments, the sample comprises tissue (e.g., lung, brain, kidney, spleen, nervous tissue, or skeletal muscle) or cells from such tissue. In some embodiments, the sample comprises endogenous fluid, tissue, or cells.

In some embodiments, phosphorylation of Rab10 or Rab8a is detected and/or quantified by immunoassay using an anti-phosphorylated Rab10 antibody or anti-phosphorylated Rab8a antibody as described herein. Immunoassays are known in the art and include, but are not limited to, enzyme immunoassays (EIA) such as enzyme multiplied immunoassay (EMIA), enzyme-linked immunosorbent assay (ELISA), microparticle enzyme immunoassay (MEIA), immunohistochemistry (IHC), immunocytochemistry, capillary electrophoresis immunoassays (CEIA), radioimmunoassays (RIA), immunofluorescence, chemiluminescence immunoassays (CL), and electrochemiluminescence immunoassays (ECL). In some embodiments, phosphorylation of Rab10 or Rab8a is detected and/or quantified by ELISA. In some embodiments, phosphorylation of Rab10 or Rab8a is detected and/or quantified by flow cytometry.

Specific binding of the antibody to a protein (e.g., phosphorylated Rab10 or phosphorylated Rab8a) can be detected directly or indirectly by linking the antibody to a detectable label. The label can be linked directly to the antibody (e.g., by a covalent bond) or the attachment can be indirect (e.g., using a chelator or linker molecule).

Detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, and combinations thereof. In some embodiments, the label can include an optical agent such as a fluorescent agent, phosphorescent agent, or chemiluminescent agent. Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins (e.g., FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye. In some embodiments, a fluorescent agent is a polymer dot or a quantum dot. In some embodiments, the optical agent is an intercalating dye. Intercalating dyes include, but are not limited to, SYBR Green, ethidium bromide, propidium iodide, chromomycin, acridine orange, Hoechst 33258, TOTO-I, YOYO-1, and DAPI (4',6-diamidino-2-phenylindole hydrochloride).

In some embodiments, the label is a radioisotope. Radioisotopes include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y.

In some embodiments, the label is an affinity tag. Examples of suitable affinity tags include, but are not limited to, biotin, peptide tags (e.g., FLAG-tag, HA-tag, His-tag, Myc-tag, S-tag, SBP-tag, Strep-tag), and protein tags (e.g., GST-tag, MBP-tag, GFP-tag).

In some embodiments, the label is an enzyme, and the presence of the label is detected by detecting a product generated by the enzyme. Examples of suitable enzymes include, but are not limited to, a polymerase (e.g., DNA polymerase), urease, alkaline phosphatase, (horseradish) hydrogen peroxidase (HRP), glucose oxidase, β-galactosidase, luciferase, alkaline phosphatase, and an esterase that hydrolyzes fluorescein diacetate. For example, a horseradish-peroxidase detection system can be used with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, which yields a soluble product readily detectable at 405 nm. A β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple.

A detectable label (e.g., a label as described herein) can be detected, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. In some embodiments, the amount of signal can be quantified using an automated high-content imaging system.

In some embodiments, antibodies for use in a detection method as described herein are immobilized on a solid support, such as magnetic or chromatographic matrix particles, the surface of an assay plate (e.g., a multiwall plate, an electrode plate, or ELISA plate), a microarray, chip, bead, column, porous strip, membrane, or nitrocellulose filter. The immobilization can be via covalent or non-covalent binding.

Detection can be carried out using any of a variety of physical formats. In some embodiments, multiwell plates or automation can be used to facilitate the processing of large numbers of test samples.

In some embodiments, such as in an ELISA format, an anti-phosphorylated Rab (e.g., anti-phosphorylated Rab10 or anti-phosphorylated Rab8a) monoclonal antibody as described herein is used in combination with one or more other antibodies. For example, in some embodiments, an anti-phosphorylated Rab10 or an anti-phosphorylated Rab8a monoclonal antibody is used in combination with an antibody against total Rab protein (e.g., total Rab10 or total Rab8a, respectively). In some embodiments, the anti-phosphorylated Rab10 or anti-phosphorylated Rab8a monoclonal antibody and the second antibody are used as a "capture antibody" and "detection antibody" pair. The term "capture antibody," as used herein, refers to an antibody that specifically binds to a target antigen of interest (e.g., Rab10 or Rab8a). In some embodiments, the capture antibody is immobilized to a solid support. The term "detection antibody," as used herein, refers to an antibody comprising a detectable label (e.g., as described above) that specifically binds to a target antigen of interest (e.g., Rab10 or Rab8a). In some embodiments, the capture antibody and the detection antibody bind to the same target antigen of interest (e.g., Rab10 or Rab8a) but at non-overlapping epitopes.

In some embodiments, an anti-phosphorylated Rab (e.g., anti-phosphorylated Rab10 or anti-phosphorylated Rab8a) monoclonal antibody as described herein is used in combination with an anti-total Rab (e.g., anti-total Rab10 or anti-total Rab8a) monoclonal antibody are used to detect phosphorylated Rab protein (e.g., phosphorylated Rab10 or phosphorylated Rab8a) in a sample. In some embodiments, the anti-total Rab antibody (e.g., anti-total Rab10 antibody or anti-total Rab8a antibody) is used as a capture antibody and the anti-phosphorylated Rab antibody (e.g., anti-phosphorylated Rab10 or anti-phosphorylated Rab8a monoclonal antibody) is used as a detection antibody. In some embodiments, the anti-phosphorylated Rab antibody (e.g., anti-phosphorylated Rab10 or anti-phosphorylated Rab8a monoclonal antibody) is used as a capture antibody and the anti-total Rab antibody (e.g., anti-total Rab10 antibody or anti-total Rab8a antibody) is used as a detection antibody.

Antibodies against total Rab10 protein or against total Rab8a protein are commercially available, e.g., from Abcam (Cambridge, Mass.) or Cell Signaling Technology (Danvers, Mass.).

VI. Therapeutic and Prognostic Methods Using Anti-Phosphorylated Rab Antibodies In yet another aspect, therapeutic and prognostic methods using the anti-phosphorylated Rab (e.g., Rab10 or Rab8a) monoclonal antibody as described herein are provided. In some embodiments, an anti-phosphorylated Rab10 monoclonal antibody or an anti-phosphorylated Rab8a monoclonal antibody as described in Section III above, or an anti-total Rab10 monoclonal antibody as described in Section IV above, is used in the practice of the methods described herein.

Treatment with Anti-Phosphorylated Rab Antibodies

In some embodiments, methods of treating a neurodegenerative disease are provided. In some embodiments, the method comprises administering to a subject having a neurodegenerative disease an anti-phosphorylated Rab10 monoclonal antibody, or antigen-binding portion thereof, or a pharmaceutical composition comprising an anti-phosphorylated Rab10 monoclonal antibody, or antigen-binding portion thereof, as described herein. In some embodiments, the method comprises administering to a subject having Parkinson's disease an anti-phosphorylated Rab8a monoclonal antibody, or antigen-binding portion thereof, or a pharmaceutical composition comprising an anti-phosphorylated Rab8a monoclonal antibody, or antigen-binding portion thereof, as described herein.

In some embodiments, the neurodegenerative disease is selected from the group consisting of Parkinson's disease, Parkinson's disease with dementia, dementia with Lewy bodies, Alzheimer's disease, Alzheimer's disease with Lewy bodies, argyrophilic grain dementia, amyotrophic lateral sclerosis, parkinsonism-dementia complex of Guam, corticobasal degeneration, chronic traumatic encephalopathy, Creutzfeldt-Jakob disease, dementia pugilistica, diffuse neurofibrillary tangles with calcification, Down's syndrome, familial British dementia, familial Danish dementia, frontotemporal dementia, frontotemporal dementia with parkinsonism linked to chromosome 17, Gerstmann-Straussler-Scheinker disease, globular glial tauopathy, Guadeloupean parkinsonism with dementia, Guadelopean PSP, Hallevorden-Spatz disease, inclusion-body myositis, multiple system atrophy, myotonic dystrophy, neurofibrillary tangle-predominant dementia, Niemann-Pick disease type C, pallido-ponto-nigral degeneration, Pick's disease, postencephalitic parkinsonism, primary age-related tauopathy, prion protein cerebral amyloid angiopathy, progressive subcortical gliosis, progressive supranuclear palsy (PSP), subacute sclerosing panencephalitis, and tangle only dementia.

In some embodiments, the neurodegenerative disease is Parkinson's disease, e.g., familial Parkinson's disease or sporadic Parkinson's disease. In some embodiments, the neurodegenerative disease is LRRK2-associated Parkinson's disease, e.g., LRRK2-associated Parkinson's disease that is characterized by a I1122V, N1437H, R1441C/G/H, R1728H, R1628P, Y1699C, G2019S, I2020T, T2031S or G2385R mutation in LRRK2, or that is characterized by a R1441C, R1441G, Y1699C, G2019S, or I2020T mutation in LRRK2.

In some embodiments, an anti-phosphorylated Rab10 monoclonal antibody or an anti-phosphorylated Rab8a monoclonal antibody (or antigen-binding fragment or pharmaceutical composition) as described herein is used in treating a neurodegenerative disease, e.g., Parkinson's disease. In some embodiments, the anti-phosphorylated Rab10 monoclonal antibody or anti-phosphorylated Rab8a monoclonal antibody is used in treating familial Parkinson's disease or sporadic Parkinson's disease. In some embodiments, the anti-phosphorylated Rab10 monoclonal antibody or anti-phosphorylated Rab8a monoclonal antibody subject is used in treating LRRK2-associated Parkinson's disease. In some embodiments, the anti-phosphorylated Rab10 monoclonal antibody or anti-phosphorylated Rab8a monoclonal antibody is used in LRRK2-associated Parkinson's disease that is characterized by a I1122V, N1437H, R1441C/G/H, R1728H, R1628P, Y1699C, G2019S, I2020T, T2031S or G2385R mutation in LRRK2, or that is characterized by a R1441C, R1441G, Y1699C, G2019S, or I2020T mutation in LRRK2. In some embodiments, the anti-phosphorylated Rab10 monoclonal antibody or an anti-phosphorylated Rab8a monoclonal antibody is used in treating Parkinson's disease with dementia. In some embodiments, the anti-phosphorylated Rab10 monoclonal antibody or an anti-phosphorylated Rab8a monoclonal antibody is used in treating dementia with Lewy bodies.

In some embodiments, an anti-phosphorylated Rab10 monoclonal antibody or an anti-phosphorylated Rab8a monoclonal antibody (or antigen-binding fragment or pharmaceutical composition) as described herein is used in the preparation of a medicament for treating a neurodegenerative disease, e.g., Parkinson's disease. In some embodiments, the anti-phosphorylated Rab10 monoclonal antibody or anti-phosphorylated Rab8a monoclonal antibody is used in the preparation of a medicament for treating familial Parkinson's disease or sporadic Parkinson's disease. In some embodiments, the anti-phosphorylated Rab10 monoclonal antibody or anti-phosphorylated Rab8a monoclonal antibody subject is used in the preparation of a medicament for treating LRRK2-associated Parkinson's disease, e.g., LRRK2-associated Parkinson's disease that is characterized by a I1122V, N1437H, R1441C/G/H, R1728H, R1628P, Y1699C, G2019S, I2020T, T2031S or G2385R mutation in LRRK2, or that is characterized by a R1441C, R1441G, Y1699C, G2019S, or I2020T mutation in LRRK2. In some embodiments, the anti-phosphorylated Rab10 monoclonal antibody or an anti-phosphorylated Rab8a monoclonal antibody is used in the preparation of a medicament for treating Parkinson's disease with dementia. In some embodiments, the anti-phosphorylated Rab10 monoclonal antibody or an anti-phosphorylated Rab8a monoclonal antibody is used in the preparation of a medicament for treating dementia with Lewy bodies.

In some embodiments, the subject to be treated is a human, e.g., a human adult or a human child.

In some embodiments, an anti-phosphorylated Rab10 or anti-phosphorylated Rab8a monoclonal antibody is administered to a subject at a therapeutically effective amount or dose. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is well within the capability of those skilled in the art.

The route of administration of an anti-phosphorylated Rab10 or anti-phosphorylated Rab8a monoclonal antibody as described herein can be oral, intraperitoneal, transdermal, subcutaneous, intravenous, intramuscular, inhalational, topical, intralesional, rectal, intrabronchial, nasal, transmucosal, intestinal, ocular or otic delivery, or any other methods known in the art. In some embodiments, the antibody is administered orally, intravenously, or intraperitoneally.

In some embodiments, an anti-phosphorylated Rab10 or anti-phosphorylated Rab8a monoclonal antibody is administered in combination with one or more other therapeutic agents. Co-administered agents (e.g., the anti-phosphorylated Rab10 or anti-phosphorylated Rab8a monoclonal antibody and another therapeutic agent) can be administered together or separately, simultaneously or at different times. When administered, the therapeutic agents independently can be administered once, twice, three, four times daily or more or less often, as needed. In some embodiments, the administered therapeutic agents are administered once daily. In some embodiments, the administered therapeutic agents are administered at the same time or times, for instance as an admixture. In some embodiments, one or more of the therapeutic agents is administered in a sustained-release formulation.

In some embodiments, the anti-phosphorylated Rab10 or anti-phosphorylated Rab8a monoclonal antibody and another therapeutic agent are administered concurrently. In some embodiments, the anti-phosphorylated Rab10 or anti-phosphorylated Rab8a monoclonal antibody and another therapeutic agent are administered sequentially. For example, in some embodiments an anti-phosphorylated Rab10 or anti-phosphorylated Rab8a monoclonal antibody is administered first, for example for about 1, 2, 3, 4, 5, 6, 7, 8, 9, 10, 15, 20, 25, 30, 40, 50, 60, 70, 80, 90, 100 days or more prior to administering another therapeutic agent. In some embodiments, the other therapeutic agent is administered first, for example, for about 1, 2, 3, 4, 5, 6, 7, 8, 9, 10, 15, 20, 25, 30, 40, 50, 60, 70, 80, 90, 100 days or more prior to administering an anti-phosphorylated Rab10 or anti-phosphorylated Rab8a monoclonal antibody.

In some embodiments, the anti-phosphorylated Rab10 or anti-phosphorylated Rab8a monoclonal antibody (and optionally another therapeutic agent) is administered to the subject over an extended period of time, e.g., for at least 30, 40, 50, 60, 70, 80, 90, 100, 150, 200, 250, 300, 350 days or longer.

Treatment with LRRK2 Inhibitors

In another aspect, methods are provided for determining the level of Rab protein or phosphorylated Rab protein in a subject, to identify whether the subject is a candidate for LRRK2 inhibitor treatment for treatment of a LRRK-2 associated disease or disorder, for example Parkinson's disease or LRRK2-associated Parkinson's disease. In certain embodiments of the method, the Rab protein is Rab5, Rab8a, Rab12 or Rab29. In certain embodiments, the Rab protein is Rab8a. In certain embodiments, the method further includes administering the LRRK2 inhibitor to the subject. In some embodiments, the method includes administering the LRRK2 inhibitor in an effective amount to treat the disease.

In yet another aspect, methods of diagnosing a subject as having Parkinson's disease (e.g., leucine-rich repeat kinase 2 (LRRK2)-associated Parkinson's disease) are provided. In some embodiments, methods are provided for determining the extent of inhibition of LRRK2 in a subject treated with a LRRK2 inhibitor. In some embodiments, the method comprises:

contacting a sample from the subject with an antibody that specifically binds to a phosphorylated human Rab protein as described herein, and measuring the amount of phosphorylated Rab in the sample from the subject;
wherein an amount of phosphorylated Rab protein in the sample from the subject that is at least as high as a control value identifies the subject as having Parkinson's disease (e.g., LRRK2-associated Parkinson's disease).

In some embodiments, an increased amount of phosphorylated Rab protein in the sample from the subject, as compared to the control value, identifies the subject as having Parkinson's disease (e.g., LRRK2-associated Parkinson's disease). In some embodiments, a comparison of an amount of phosphorylated Rab protein in the sample from the subject to a sample prior to administration determines the extent of inhibition of LRRK2. In some embodiments, an increased amount of phosphorylated Rab protein in the sample from the subject, as compared to the control value, identifies the subject as candidate for LRRK2 inhibitor treatment for treatment of Parkinson's disease (e.g, LRRK2-associated Parkinson's disease). In certain embodiments of the methods, the Rab protein is Rab5, Rab8a, Rab12 or Rab29. In certain embodiments, the Rab protein is Rab8a.

In some embodiments, an anti-phosphorylated Rab10 monoclonal antibody or an anti-phosphorylated Rab8a monoclonal antibody (or antigen-binding fragment or pharmaceutical composition) as described herein is used in identifying suitable candidates for treatment with a LRRK2 inhibitor, determining a suitable dosage of a LRRK2 inhibitor to be administered, monitoring efficacy of treatment with a LRRK2 inhibitor, and/or adjusting a dosage of a LRRK2 inhibitor that is administered to a subject.

In some embodiments, methods of identifying whether a subject is a suitable candidate for treatment with a LRRK2 inhibitor are provided. In some embodiments, the subject has been diagnosed as having a neurodegenerative disease as described herein. In some embodiments, the subject has been diagnosed as having Parkinson's disease. In some embodiments, the subject has been diagnosed as having LRRK2-associated Parkinson's disease, e.g., LRRK2-associated Parkinson's disease that is characterized by a I1122V, N1437H, R1441C/G/H, R1728H, R1628P, Y1699C, G2019S, I2020T, T2031S or G2385R mutation in LRRK2, or that is characterized by a R1441C, R1441G, Y1699C, G2019S, or I2020T mutation in LRRK2.

In some embodiments, the method comprises:
contacting a sample from the subject with an anti-phosphorylated Rab10 monoclonal antibody (or antigen-binding fragment or pharmaceutical composition) as described herein; and
measuring the amount of phosphorylated Rab10 protein in the sample from the subject;

wherein an amount of phosphorylated Rab10 protein in the sample from the subject that is at least as high as a control value identifies the subject as a candidate for treatment with a LRRK2 inhibitor.

In some embodiments, the method comprises:

contacting a sample from the subject with an anti-phosphorylated Rab8a monoclonal antibody (or antigen-binding fragment or pharmaceutical composition) as described herein; and measuring the amount of phosphorylated Rab8a protein in the sample from the subject;

wherein an amount of phosphorylated Rab8a protein in the sample from the subject that is at least as high as a control value identifies the subject as a candidate for treatment with a LRRK2 inhibitor.

The measurement of phosphorylated Rab10 or phosphorylated Rab8a levels can be performed according to any of the detection methods described herein, e.g., as described in Section V above. In some embodiments, the measurement is performed using an immunoassay, e.g., western blot or ELISA or MSD (Meso Scale Discovery) assay.

In some embodiments, for identifying whether a subject is a candidate for treatment with a LRRK2 inhibitor, the amount of phosphorylated Rab10 or phosphorylated Rab8a protein in the sample from the subject is compared to a control value that is determined for a healthy control or population of healthy controls (i.e., not afflicted with Parkinson's disease). In some embodiments, the subject is identified as a candidate for treatment with a LRRK2 inhibitor if the amount of phosphorylated Rab10 or phosphorylated Rab8a protein in the sample from the subject is increased as compared to the control value. In some embodiments, the subject is identified as a candidate for treatment with a LRRK2 inhibitor if the amount of phosphorylated Rab10 or phosphorylated Rab8a protein in the sample from the subject is increased by at least 10%, at least 20%, at least 30%, at least 40%, at least 50%, at least 60%, at least 70%, at least 80%, at least 90% or more as compared to the control value. In some embodiments, the subject is identified as a candidate for treatment with a LRRK2 inhibitor if the amount of phosphorylated Rab10 or phosphorylated Rab8a protein in the sample from the subject is increased by at least 2-fold, 3-fold, 4-fold, 5-fold, 6-fold, 7-fold, 8-fold, 9-fold, 10-fold or more as compared to the control value. In some embodiments, the healthy control value for phosphorylated Rab10 or phosphorylated Rab8a is determined by assessing the level of phosphorylated Rab10 or phosphorylated Rab8a in a subject or population of subjects (e.g., 10, 20, 50, 100, 200, 500, 1000 subjects or more) that all are known not to have a neurodegenerative disease or known not to have Parkinson's disease.

In some embodiments, for identifying whether a subject is a candidate for treatment with a LRRK2 inhibitor, the amount of phosphorylated Rab10 or phosphorylated Rab8a protein in the sample from the subject is compared to a control value that is determined for a disease control or population of disease controls (e.g., a subject who is afflicted with a neurodegenerative disease, e.g., Parkinson's disease or LRRK2-associated Parkinson's disease). In some embodiments, the subject is identified as a candidate for treatment with a LRRK2 inhibitor if the amount of phosphorylated Rab10 or phosphorylated Rab8a protein in the sample from the subject is at least as high as amount of phosphorylated Rab10 or phosphorylated Rab8a, respectively, in the disease control or population of disease controls. In some embodiments, the subject is identified as a candidate for treatment with a LRRK2 inhibitor if the amount of phosphorylated Rab10 or phosphorylated Rab8a protein in the sample from the subject is comparable to (e.g., is within 20%, 10%, 5%, 4%, 3%, 2%, or 1%) of the amount of phosphorylated Rab10 or phosphorylated Rab8a, respectively, in the disease control or population of disease controls. In some embodiments, the disease control value for phosphorylated Rab10 or phosphorylated Rab8a is determined by assessing the level of phosphorylated Rab10 or phosphorylated Rab8a in a subject or population of subjects (e.g., 10, 20, 50, 100, 200, 500, 1000 subjects or more) that all are known to have the neurodegenerative disease, e.g., Parkinson's disease or LRRK2-associated Parkinson's disease.

In some embodiments, after identifying the subject as a candidate for treatment with a LRRK2 inhibitor, the method further comprises administering a LRRK2 inhibitor to the subject, e.g., as described below. In some embodiments, a LRRK2 inhibitor is administered to a subject at a therapeutically effective amount or dose. For example, a daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, or about 10 mg/kg to about 500 mg/kg can be used. The dosages, however, may be varied according to several factors, including the chosen route of administration, the formulation of the composition, patient response, the severity of the condition, the subject's weight, and the judgment of the prescribing physician, and can be increased or decreased over time, as required by an individual patient.

Monitoring Efficacy and Adjusting Dosage of Treatment with LRRK2 Inhibitors

In some embodiments, methods of monitoring the efficacy of treatment with a LRRK2 inhibitor for a subject having a neurodegenerative disease are provided. In some embodiments, the subject being treated has been diagnosed as having a neurodegenerative disease as described herein. In some embodiments, the subject has been diagnosed as having Parkinson's disease. In some embodiments, the subject has been diagnosed as having LRRK2-associated Parkinson's disease, e.g., LRRK2-associated Parkinson's disease that is characterized by a pathogenic mutation in LRRK2, including I1122V, N1437H, R1441C/G/H, R1728H, R1628P, Y1699C, G2019S, I2020T, T2031S or G2385R mutation in LRRK2, or in some embodiments, a R1441C, R1441G, Y1699C, G2019S, or I2020T mutation.

In some embodiments, the method comprises:

measuring the amount of phosphorylated Rab protein (e.g., phosphorylated Rab10 protein or phosphorylated Rab8a protein) in a first sample from a subject taken prior to treatment with a LRRK2 inhibitor;

treating the subject with a LRRK2 inhibitor; and measuring the amount of phosphorylated Rab protein (e.g., phosphorylated Rab10 protein or phosphorylated Rab8a protein) in a second sample from the subject taken subsequent to treatment with the LRRK2 inhibitor;

wherein a decrease in the amount of phosphorylated Rab protein (e.g., phosphorylated Rab10 protein or phosphorylated Rab8a protein) in the second sample from the subject, as compared to the first sample from the subject, indicates that the subject is responding to treatment with the LRRK2 inhibitor.

In some embodiments, the measuring steps comprise using an anti-phosphorylated Rab10 or anti-phosphorylated Rab8a monoclonal antibody (or antigen-binding fragment) as described herein (e.g., as described in Section III above). In some embodiments, the measuring steps comprise detecting the amount of phosphorylated Rab protein using immunoassay, e.g., western blot, ELISA, and MSD assay.

In some embodiments, the sample is a sample as described herein (e.g., as described in Section III above). In some embodiments, the sample comprises a fluid, e.g., blood, plasma, serum, urine, or cerebrospinal fluid. In some embodiments, the sample comprises PBMCs. In some embodiments, the first sample and the second sample are the same type of sample (e.g., each of the first sample and the second sample is a blood sample).

In some embodiments, the subject has been treated with the LRRK2 inhibitor for at least 1 week, at least 2 weeks, at least 3 weeks, at least 4 weeks, at least 5 weeks, at least 6 weeks, at least 7 weeks, at least 8 weeks, at least 9 weeks, at least 10 weeks, or longer. In some embodiments, the subject has been treated with the LRRK2 inhibitor for at least 1 month, at least 2 months, at least 3 months, at least 4 months, at least 5 months, at least 6 months, or longer.

In some embodiments, a decrease of at least at least 20%, at least 30%, at least 40%, at least 50%, at least 60%, at least 70%, at least 80%, or at least 90% in the amount of phosphorylated Rab protein (e.g., phosphorylated Rab10 protein or phosphorylated Rab8a protein) in the second sample from the subject, as compared to the first sample from the subject, indicates that the subject is responding to treatment with the LRRK2 inhibitor.

In some embodiments, depending on the level of decrease that is detected in the second sample as compared to the first sample, the method can further comprise adjusting the dosage of the LRRK2 inhibitor that is administered to the subject (e.g., increasing or decreasing the dosage and/or frequency of administration of the LRRK2 inhibitor). In some embodiments, the method can further comprise adjusting the LRRK2 inhibitor that is administered (e.g., administering an LRRK2 inhibitor of a different class than the initial LRRK2 inhibitor that was administered). In some embodiments, the method can further comprise discontinuing treatment with the LRRK2 inhibitor.

LRRK2 Inhibitors

LRRK2 inhibitors for use in the methods disclosed herein, including methods of making the LRRK2 inhibitors, testing their LRRK2 activity, formulating the LRRK2 inhibitors into pharmaceutical compositions, and methods of administering the LRRK2 inhibitors, are disclosed in WO2013166276, WO2016007540, US20150361038, WO2016042089, WO2013046029, WO2014140235, WO2014170248, WO2014106612, WO2012058193, WO2012118679, WO2014134776, WO2014137719, WO2014137728, WO2014137725, WO2014137723, WO2015026683, WO2015073344, WO2016036586, WO2014134774, WO2014134772, WO2011151360, WO2012062783, WO2013079493, WO2013079495, WO2013079505, WO2013079494, WO2013079496, WO2013164321, WO2013164323, WO2013139882, WO2012038743, WO2012075046, US20140288043, WO2011141756, WO2010106333, WO2012135631, US20120245347, WO2012178015, WO2013166276, WO2009127642, WO2016022902, WO2016022970, WO 2016130920, WO2012162254, WO2014150981, WO2011038572, WO2012028629, U.S. Pat. No. 9,365,551, WO2015113451, WO2015113452, WO2017012576, WO2009030270, WO2012143143, WO2012143144, WO2014060112, WO2014060113, WO2011060295, WO2014160430, WO2014001973, U.S. Pat. No. 9,156,845, WO2015092592, WO2017046675, WO2010085799, WO2015150612, or US 2017/0174694, each of which are incorporated herein by reference in their entirety for all purposes.

In one embodiment, the LRRK2 inhibitor is a compound of Formula (I):

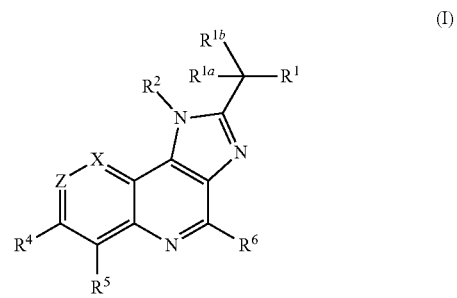

or a pharmaceutically acceptable salt thereof; wherein X is $CR^7$ or N; Z is $CR^3$ or N; $R^1$ is selected from the group consisting of hydrogen, cyano and a 5- to 10-membered heteroaryl which contains 1 to 5 heteroatoms independently selected from N, O and S; wherein the 5- to 10-membered heteroaryl is optionally substituted with 1 to 3 $R^8$; $R^{1a}$ and $R^{1b}$ are each independently hydrogen, halo, hydroxy or $C_1$-$C_3$ alkyl; or $R^{1a}$ and $R^{1b}$ taken together with the carbon to which they are attached are a $C_3$-$C_6$ cycloalkyl or C(O); $R^2$ is a $C_1$-$C_6$ alkyl, $C_3$-$C_7$ cycloalkyl or a 4- to 7-membered heterocycloalkyl which contains 1 to 3 heteroatoms independently selected from NR, 0 and S; wherein the $C_3$-$C_7$ cycloalkyl and 4- to 7-membered heterocycloalkyl are each optionally substituted with 1 to 3 $R^9$; and wherein the $C_1$-$C_6$ alkyl is optionally substituted with 1 to 3 $R^{10}$; R is hydrogen, $C_1$-$C_6$ alkyl or absent; $R^3$, $R^4$, $R^5$, $R^6$ and $R^7$ are each independently selected from the group consisting of hydrogen, deutero, amino, halo, hydroxy, cyano, $C_1$-$C_6$ alkyl, $C_3$-$C_6$ cycloalkyl and $C_1$-$C_6$ alkoxy; wherein the $C_1$-$C_6$ alkyl, $C_3$-$C_6$ cycloalkyl and $C_1$-$C_6$ alkoxy are each optionally substituted with 1 to 3 halo or $C_1$-$C_3$ alkoxy; $R^8$ at each occurrence is independently selected from the group consisting of halo, —C(O)NH$_2$, —C(O)NH($C_1$-$C_3$alkyl), —C(O)N($C_1$-$C_3$alkyl)$_2$, $C_1$-$C_6$alkyl, $C_1$-$C_6$alkoxy and $C_3$-$C_6$cycloalkyl; wherein the $C_1$-$C_6$alkyl, $C_1$-$C_6$alkoxy and $C_3$-$C_6$cycloalkyl are each optionally substituted with 1 to 3 halo, cyano, hydroxy or $C_1$-$C_3$ alkoxy; $R^9$ at each occurrence is independently selected from the group consisting of halo, hydroxy, $C_1$-$C_6$alkyl $C_1$-$C_6$alkoxy, and $C_1$-$C_6$alkoxyC$_1$-$C_6$alkyl, wherein the $C_1$-$C_6$alkyl, $C_1$-$C_6$alkoxy, and $C_1$-$C_6$alkoxyC$_1$-$C_6$alkyl are optionally substituted with one to three halo or a cyano; and $R^{10}$ at each occurrence is independently selected from the group consisting of halo, $C_1$-$C_6$alkoxy, $C_1$-$C_6$thioalkoxy, amino, $C_1$-$C_6$alkylamino and di($C_1$-$C_6$alkyl)amino.

In one embodiment, the LRRK2 inhibitor is a compound of formula (I) or a salt thereof:

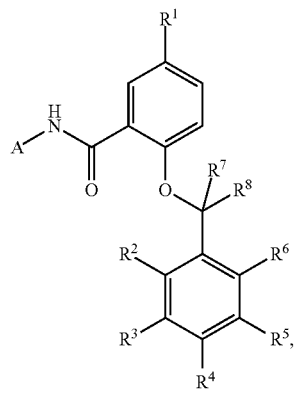

(I)

wherein A represents pyridin-2-yl, pyridin-3-yl, pyridazin-3-yl, pyridazin-4-yl, pyrimidin-5-yl, 1,3-oxazol-2-yl, 1H-pyrazol-4-yl or isoxazol-4-yl or a group of formula (a) wherein * represents the point of attachment:

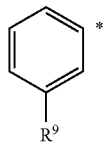

(a)

wherein when A represents pyridin-3-yl, the pyridinyl ring may optionally be substituted at the 2 position by fluoro, methoxy or $CH_2OH$, at the 4 position by methyl or $CH_2OH$, or at the 5 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl; $R^1$ represents halo, halo$C_{1-3}$alkyl, hydroxy, CN, —O($CH_2$)$_2$O ($CH_2$)$_2$NH$_2$, —CNOH, (O)$_n$($CH_2$)$_p$$R^{10}$, —(CO)$R^{10}$, $R^{13}$, —(SO$_2$)$R_{13}$, ($C_{1-3}$alkylene)(CO)$_q$$R^{14}$, (CH=CH)(CO)$R^{14}$, ($C_{1-3}$alkylene)NHCOR$^{14}$, —O-nitrogen containing monoheterocyclic ring with the proviso that the atom directly attached to the oxygen is not nitrogen, or a nitrogen containing heteroaryl ring, wherein the nitrogen containing monoheterocyclic ring is optionally substituted with one, two or three methyl groups and wherein the nitrogen containing heteroaryl ring is optionally substituted by one two or three groups selected from NH$_2$, ($C_{1-3}$alkylene)$R^{13}$, ($C_{1-3}$alkylene)(CO)$_q$$R^{14}$, $C_{1-3}$alkyl and halo; n and q independently represent 0 or 1; p represents 1, 2 or 3; $R^2$, $R^3$, $R^4$, $R^5$ and $R^6$ independently represent hydrogen, halo, CN, $C_{1-3}$alkyl or $C_{1-3}$alkoxy; $R^7$ and $R^8$ independently represent hydrogen or $C_{1-2}$ alkyl; $R^9$ represents halo, $C_{1-2}$alkyl, $C_{1-2}$alkoxy, —$CH_2CO_2H$ or —$CONHCH_3$; $R^{10}$ represents hydrogen, $C_{1-3}$alkyl, —NR$^{11}$R$^{12}$, or a nitrogen containing monoheterocyclic ring which ring is optionally substituted with one, two or three methyl groups; $R^{11}$ and $R^{12}$ are independently selected from hydrogen and $C_{1-3}$ alkyl, wherein said $C_{1-3}$ alkyl group is optionally substituted with one, two or three halo, hydroxy, cyano or $C_{1-2}$alkoxy groups; $R^{13}$ represents —NR$^{11}$R$^{12}$, or a nitrogen containing monoheterocyclic ring which ring is optionally substituted with one, two or three methyl groups and wherein the nitrogen containing mono-heterocyclic ring is attached via a nitrogen atom; and $R^{14}$ represents hydroxy or $C_{1-3}$alkoxy.

In an embodiment, the LRRK2 inhibitor is selected from a compound of formula (I) or a salt thereof, wherein A represents pyridin-3-yl, wherein the pyridinyl ring may optionally be substituted at the 2 position by fluoro, pyridazin-4-yl, 1H-pyrazol-4-yl, wherein the pyrazolyl ring may optionally be substituted at the 1 position by methyl, or isoxazol-4-yl, wherein the isoxazolyl ring may optionally be substituted at the 3 position by methyl or at the 5 position by methyl.

In an embodiment, the LRRK2 inhibitor is selected from a compound of formula (I) or a salt thereof:

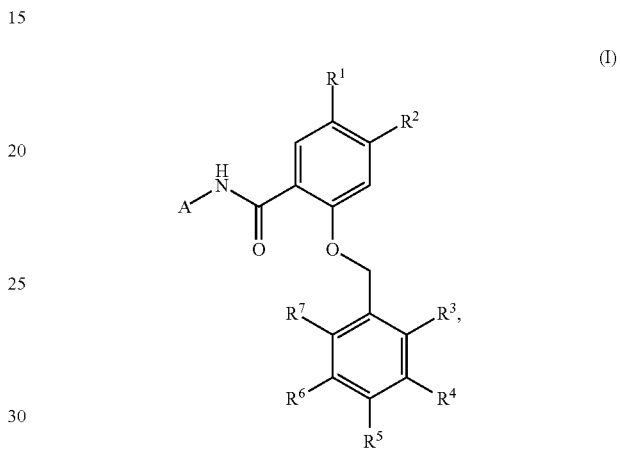

(I)

wherein A represents pyridin-2-yl, pyridin-3-yl, pyridazin-3-yl, pyridazin-4-yl, pyrimidin-5-yl, 1,3-oxazol-2-yl, 1H-pyrazol-4-yl or isoxazol-4-yl or a group of formula (a) wherein * represents the point of attachment:

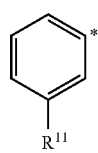

(a)

wherein when A represents pyridin-3-yl, the pyridinyl ring may optionally be substituted at the 2 position by fluoro, methoxy or $CH_2OH$, at the 4 position by methyl or $CH_2OH$, or at the 5 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl; $R^1$ and $R^2$ independently represent halo, $C_{1-3}$haloalkyl, —(CH$_2$) ~$R^8$, —(CO)$R^8$, nitrogen containing heteroaryl ring optionally substituted with one, two or three groups selected from methyl and trifluoromethyl; n represents 1, 2 or 3; $R^3$, $R^4$, $R^5$, $R^6$ and $R^7$ independently represent hydrogen, halo, CN, $C_{1-3}$alkyl or $C_{1-3}$alkoxy; $R^8$ represents hydrogen or —NR$^9$R$^{10}$; $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three groups selected from halo, methyl and trifluoromethyl; and $R^{11}$ represents hydrogen, halo, CN, $C_{1-2}$alkyl, $C_{1-2}$alkoxy, —$CH_2CO_2H$ or —$CONHCH_3$.

In an embodiment, the LRRK2 inhibitor is selected from a compound according to claim 1, wherein $R_1$ represents 4-morpholinylmethyl.

In an embodiment, the LRRK2 inhibitor is a compound of Formula (I) or a pharmaceutically acceptable salt thereof:

Formula (I)

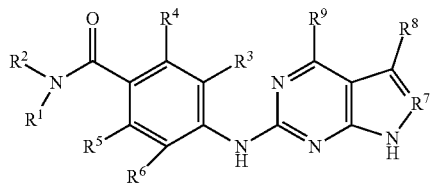

wherein $R^1$ is H; $R^2$ is $C_{1-5}$alkyl optionally substituted with one or more hydroxyl, or $R^1$ and $R^2$, together with the nitrogen to which they are attached, form: (1) a nitrogen containing heterocyclic ring, wherein the heterocyclic ring is optionally substituted with one or more substituents independently selected from the group consisting of $C_{1-3}$alkyl, —$CH_2$—$OCH_3$, halo, and piperazin-1-yl optionally substituted with $C_{1-3}$alkyl on the nitrogen at the 4 position, or (2) a bicyclic ring system selected from the group consisting of

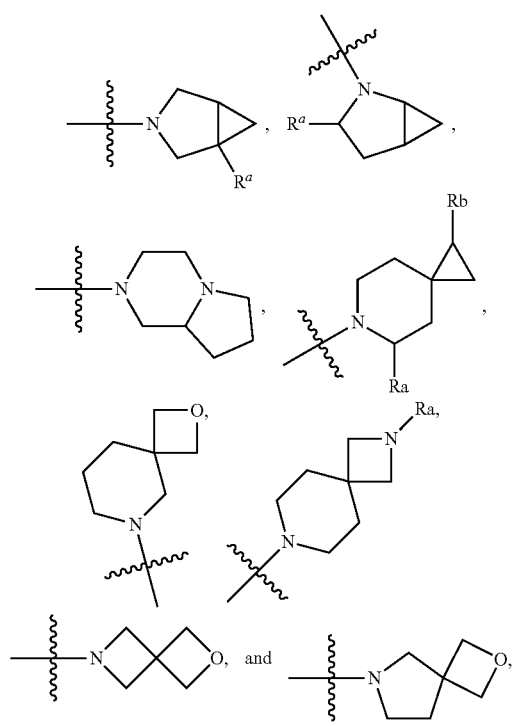

wherein each occurrence of $R^a$ and $R^b$ is independently selected from the group consisting of H, CN, halo, —$CH_2OCH_3$, $C_{1-3}$alkoxyl, and $C_{1-3}$alkyl optionally substituted with one hydroxy group; $R^3$ and $R^6$ are each independently selected from the group consisting of H, $C_{1-3}$alkoxyl, —O—$C_{1-3}$haloalkyl, —O—$CH_2$—$C_{3-6}$cycloalkyl, halo, and —$NR^xR^y$, wherein $R^x$ and $R^y$ are each independently H or $C_{1-3}$alkyl; $R^4$ and $R^5$ are each independently selected from the group consisting of H, halo, $C_{1-3}$alkoxy, and $C_{1-3}$alkyl; $R^7$ is N or CH; $R^8$ is selected from the group consisting of H, CN, $C_{1-3}$haloalkyl and $C_{1-3}$alkyl; and $R^9$ is selected from the group consisting of $C_{1-3}$alkoxyl, $C_{1-3}$haloalkyl, —O—$C_{1-3}$haloalkyl, and —O—$CH_2$—$C_{3-6}$cycloalkyl.

In an embodiment, the LRRK2 inhibitor is a compound of any one of Examples E1 to E66 of U.S. Pat. Pub. No. 2017/0022204 A1, a free base form, a free acid form or a pharmaceutically acceptable salt thereof, which examples are hereby incorporated by reference.

In an embodiment, the LRRK2 inhibitor is a compound of Formula (I) or a pharmaceutically acceptable salt thereof:

(I)

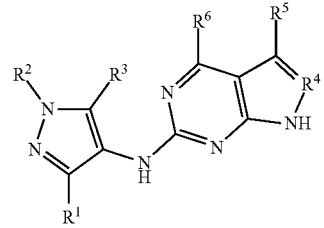

wherein $R^1$ is selected from the group consisting of H, $C_{1-3}$alkoxyl, $C_{1-3}$alkyl, and halo; $R^2$ is $C_{1-5}$alkyl optionally substituted with one or more substituents independently selected from the group consisting of OH, $C_{1-3}$alkoxyl, halo, and CN or $R^2$ is —$(CR_aR_b)_n$—Y, wherein n is 0, 1, or 2; each occurrence of $R_a$ and $R_b$ are independently H or methyl, Y is (1) a four to six-membered heterocyclyl optionally substituted with one or more substituents independently selected from the group consisting of $C_{1-3}$alkyl, halo, OH, oxetanyl, $C_{1-3}$haloalkyl, and morpholinyl; (2) $C_{3-6}$cycloalkyl optionally substituted with one or more substituents independently selected from the group consisting of $C_{1-3}$alkyl, halo, OH, or oxetanyl, $C_{1-3}$haloalkyl, and morpholinyl, or (3)

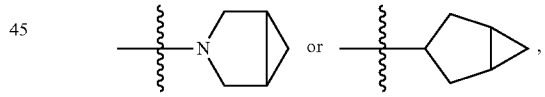

either of which is optionally substituted with one OH group; $R^3$ is selected from the group consisting of H, $C_{1-3}$alkoxyl, $C_{1-3}$alkyl, $C_{3-6}$cycloalkyl, and halo; $R^4$ is CH or N; $R^5$ is H, CN or methyl; and $R^6$ is selected from the group consisting of $C_{1-3}$alkoxy, and —O—$CH_2$—$C_{3-6}$cycloalkyl.

In an embodiment, the LRRK2 inhibitor is a compound of Formula (I) or a salt thereof:

Formula (I)

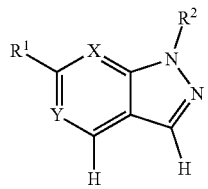

wherein X is selected from CH or N; Y is selected from CH, N or CR₃, wherein R₃ is selected from the group consisting of halo, $C_{1-3}$ alkyl, CN, and $C_{1-3}$ haloalkyl; R¹ is selected from the group consisting of 5 or 6 membered heterocyclyl optionally substituted with one, two, or three substituents independently selected from the group consisting of: $C_{1-3}$ alkyl optionally further substituted with one $C_{1-3}$ alkoxyl, $C_{1-3}$ alkoxyl, halo, hydroxyl, —SO₂CH₃, —COCH₃, oxo group, oxetanyl, —O-4 to 6 membered heterocyclyl optionally substituted with one or two substituents of $C_{1-3}$ alkyl, which may be the same or different, and $C_{1-6}$ alkoxyl; and R² is

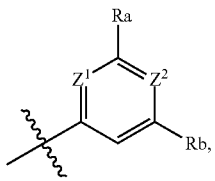

wherein Z¹ and Z² are independently N or CR₇, and wherein R₇ is H or $C_{1-3}$alkoxyl, but Z¹ and Z² cannot both be CR₇, Rᵃ is selected from the group consisting of: H, CN, $C_{1-3}$ alkyl, $C_{1-3}$ alkoxyl, —O—$C_{1-3}$haloalkyl, and $C_{3-6}$cycloalkyl; and R_b is selected from the group consisting of: 2-oxa-6-azaspiro [3.4] octanyl, $C_{3-6}$cycloalkyl, optionally substituted with one hydroxyl, —CONHCH₃, —NHCOCH₃, 4 to 6 membered heterocyclyl optionally substituted with one or two substituents independently selected from the group consisting of hydroxyl, CN, —CONHCH₃, oxetanyl, $C_{1-3}$alkyl, optionally substituted with one hydroxyl, and $C_{1-3}$ alkoxyl, optionally substituted with one hydroxyl.

In an embodiment, the LRRK2 inhibitor is a compound or salt thereof selected from formula (B):

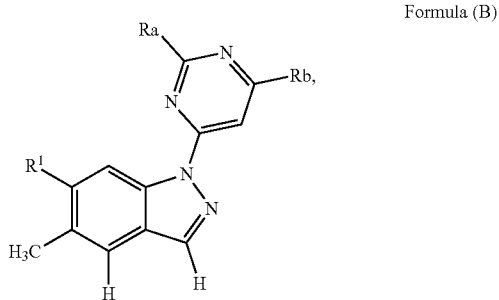

Formula (B)

wherein R¹ is piperidinyl substituted with one or two substituents independently selected from the group consisting of halo, $C_{1-3}$ alkyl and oxetanyl; Rᵃ is $C_{1-3}$ alkyl or $C_{1-3}$ alkoxyl; and R_b is 4 to 6 membered heterocyclyl substituted with one substituent selected from the group consisting of hydroxyl, $C_{1-3}$alkyl optionally substituted with one hydroxyl, and $C_{1-3}$ alkoxyl optionally substituted with one hydroxyl, and the 4 to 6 membered heterocyclyl is selected from the group consisting of morpholinyl, azetinidyl, piperazinyl, and oxetanyl.

In an embodiment, the LRRK2 inhibitor is a compound of Formula I:

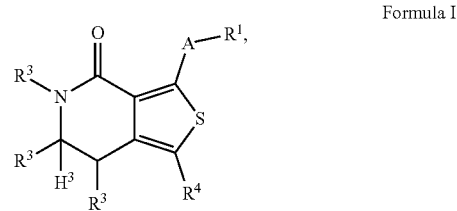

Formula I or a pharmaceutically acceptable salt of Formula I, wherein A is —S—, —SO—, —SO₂—, —O— or —NRᵃ—, wherein Rᵃ is —H, or $C_{1-20}$ alkyl; R¹ is (a) $C_{1-10}$-linear or -branched alkyl optionally substituted with (i) —N=N⁺=N⁻; (ii) $C_{3-6}$-cycloalkyl optionally substituted with a "ring-system substituent", which is independently for each occurrence selected from the group consisting of: alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, R⁶⁰ R⁶⁵ N—, R⁶⁰R⁶⁵N-alkyl-, R⁶⁰R⁶⁵NC(O)— and R⁶⁰R⁶⁵NSO₂—, wherein R⁶⁰ and R⁶⁵ are each independently selected from the group consisting of: hydrogen; alkyl; aryl; and aralkyl; or a $C_{3-7}$-cycloalkyl, wherein optionally 1 or 2 ring carbon atoms are substituted with heteroatoms, and wherein said cycloalkyl is optionally attached to an aryl, heteroaryl, heterocyclyl or heterocyclenyl ring by simultaneously substituting two ring hydrogen atoms on said aryl, heteroaryl, heterocyclyl or heterocyclenyl ring; (iii) —OH; (iv) -carboxylic acid; (v) moiety of formula (—N⁺HRᵃ₂), where Rᵃ is independently for each occurrence —H or $C_{1-10}$alkyl optionally substituted with $C_{1-8}$ alkyl; (vi) a moiety formula (—N(Rᵃ)₂), where Rᵃ is independently —H or $C_{1-10}$ alkyl optionally substituted with $C_{1-7}$ alkyl; (vii) an aryl moiety optionally substituted with a "ring-system substituent", defined above; (viii) a heteroaryl moiety, optionally substituted with a "ring-system substituent", defined above; (ix) an alkoxycarbonyl moiety, optionally substituted with a "ring-system substituent", defined above; and (x) a $C_{1-10}$-alkoxy moiety; (b) $C_{3-7}$-cycloalkyl optionally substituted with: (i) —(C=O)—OH; (ii) $C_{2-10}$-alkoxycarbonyl; or (iii) $C_{1-10}$-alkoxy moiety; (c) heterocyclyl-moiety of up to $C_{10}$ optionally substituted with a "ring-system substituent", defined above; (d) -aryl, optionally substituted with a "ring-system substituent", defined above; (e) -heteroaryl moiety, optionally substituted with a "ring-system substituent", defined above; (f) -alkoxycarbonyl, optionally substituted with a "ring-system substituent", defined above; or (g) $C_{1-10}$-alkoxy moiety; R² and R³are each independently selected from the group consisting of (a) —H; (b) -aryl, optionally substituted with halogen; (c) $C_{1-8}$-alkyl, optionally substituted with (i) halogen; (ii) $C_{1-6}$-alkoxy; (iii) -aryl optionally substituted with 1 to 3 halogen atoms or up to three "ring-system substituents" as defined above; (iv) $C_{3-8}$-cycloalkyl, optionally substituted with one or more "ring-system substituents", as defined above; (d) -heteroaryl, bonded through any ring carbon atom to the substrate lactam ring, wherein said heteroaryl moiety is optionally substituted, independently for each occurrence, with halogen or $C_{1-10}$-alkyl; and (e) an alkoxycarbonyl of Formula AA,

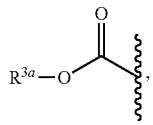

Formula AA where $R^{3a}$ is $C_{1-10}$ alkyl; or $R^3$ is —H, and $R^2$, together with the bonding position occupied by —$H^a$ in Formula I, forms a carbon ring comprising 3 to 7 carbon atoms including the carbon atom incorporated into the lactam ring to which it is bonded, which, together with the lactam ring to which it is bonded, forms a spirocyclic compound, wherein said 3 to 7 carbon atom ring of said spirocycle compound is optionally substituted with an alkoxycarbonyl moiety of Formula AA (defined above); $R^4$ is a substituent of the Formula

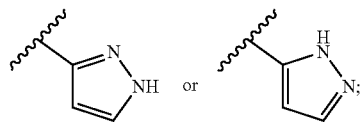 [SMILES: *c1cc[nH]n1 ; "or" ; *c1ccn[nH]1]

and $R^5$ is selected from the group consisting of (I) —H; (II) -aryl, optionally substituted independently for each occurrence with: (a) -alkyl; (b) halogen; or (c) -alkoxy; (III) alkoxycarbonyl of Formula AA (defined above), thereby forming, with the lactam nitrogen to which it is bonded, a carbamate; (IV) $C_{1-6}$-alkyl, optionally substituted with (a) $C_{3-6}$-cycloalkyl; (b) -tetrahydropyranyl bonded to said alkyl moiety through any of $C_2$ to $C_6$ ring carbon atoms; (c) -piperidinyl bonded to said alkyl moiety through the nitrogen atom or any of the ring carbon atoms; (d) aryloxy-, optionally substituted independently for each occurrence with halogen or $C_{1-10}$ alkyl; (e) —(CR'=CR'$_2$) wherein R' is independently for each occurrence: (i) halogen; (ii) —H; or (iii) $C_{1-6}$-alkyl; (f) -aryl, optionally substituted independently for each occurrence with (i) $C_{1-6}$-alkyl; (ii) $C_{1-6}$-alkoxy; or (iii) -halogen; (g) —OH; (h) -pyridinyl, optionally substituted with one or more halogen atoms; (i) —CN; (j) -morpholinyl; (k) -quinolinyl; and (1) -heteroaryl, optionally substituted with one or more "ring-system substituents" as defined above.

In an embodiment, the LRRK2 inhibitor is a compound of the formula:

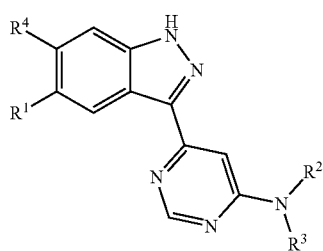

wherein $R^1$ is selected from the group consisting of a) hydrogen, b) halo, c) cyano, d) hydroxyl, e) $C_{2-6}$ alkenyl, which is optionally substituted with one to three substitutents independently selected from the group consisting of halo, cyano and $R^5$; f) $OC_{2-6}$ alkenyl, which is optionally substituted with one to three substituents independently selected from the group consisting of halo, cyano and $R^5$; g) $R^5$, h) $OR^5$, i) $R^7$, j) $S(O)_m R^5$, k) $S(O)_m R^7$, l) (C=O)$R^7$, m) (C=O)$R^5$, n) (C=O)$OR^5$, and o) $NR^cR^d$; $R^2$ is selected from the group consisting of hydrogen and $C_{1-6}$ alkyl, which is optionally substituted with one to three substitutents independently selected from the group consisting of: a) halo, b) cyano, c) $R^5$, d) $R^7$, e) $OR^5$, and f) $NR^cR^d$; $R^3$ is selected from the group consisting of: a) hydrogen, b) $C_{1-6}$ alkyl, which is optionally substituted with one to three substitutents independently selected from the group consisting of halo, cyano, $OR^5$ and $NR^cR^d$, c) $C_{3-8}$ cycloalkyl, which is optionally substituted with one to three substitutents independently selected from the group consisting of halo, cyano, $OR^5$ and $NR^cR^d$, d) heterocyclyl, which is optionally substituted with one to three substitutents independently selected from the group consisting of halo, cyano, oxo, $R^5$, $OR^5$ and $NR^cR^d$, e) heteroaryl, which is optionally substituted with one to three substitutents independently selected from the group consisting of halo, cyano, oxo, $R^5$, $OR^5$ and $NR^cR^d$, f) $C_{4-8}$ cycloalkenyl, which is optionally substituted with one to three substitutents independently selected from the group consisting of halo, cyano, $OR^5$ and $NR^cR^d$, g) (C=O)$R^7$, h) (C=O)$R^5$, i) $S(O)_m R^5$, and j) $S(O)_m R^7$; or $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of: a) halo, b) oxo, c) cyano, d) $OR^5$, e) $NR^cR^d$, f) $SO_3H$, g) $S(O)_m R^5$, h) $S(O)_m R^7$ i) $R^5$, j) $R^6$, k) $R^7$, l) (C=O)$R^5$, m) (C=O)$OR^5$, n) (C=O)$R^7$, and o) (C=O)$NR^cR^d$; $R^4$ is selected from the group consisting of hydrogen, halo, cyano, $OR^5$, aryl, heteroaryl, $C_{3-8}$ cycloalkyl, $C_{4-8}$ cycloalkenyl, $C_{4-8}$ heterocycloalkyl and $C_{1-6}$ alkyl, which is optionally substituted with one to three substitutents independently selected from the group consisting of halo, cyano, $OC_{1-3}$ alkyl, $NR^cR^d$ and hydroxyl; or $R^1$ and $R^4$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of: a) halo, b) oxo, c) cyano, d) $R^5$, and e) $R^7$; $R^5$ is selected from the group consisting of hydrogen and $C_{1-6}$ alkyl, which is optionally substituted with one to three substituents independently selected from the group consisting of: a) halo, b) hydroxyl, c) $OC_{1-6}$ alkyl, d) $NR^cR^d$, e) (C=O)$NR^cR^d$, f) $S(O)_m R^8$, g) $S(O)_m R^7$, h) $R^7$, and i) $OR^7$; $R^6$ is $C_{1-6}$ alkyl, which is optionally substituted with one to three substituents independently selected from the group consisting of halo and hydroxyl; or $R^5$ and $R^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of: a) halo, b) oxo, c) cyano, d) hydroxyl, e) $C_{1-3}$ alkyl, which is optionally substituted with one to three halo, f) $C_{3-8}$ cycloalkyl, g) $OC_{1-3}$ alkyl, which is optionally substituted with one to three halo, and h) $OC_{3-8}$ cycloalkyl; $R^7$ is selected from the group consisting of $C_{4-8}$ heterocyclyl, $C_{3-8}$ cycloalkyl, $C_{4-8}$ cycloalkenyl, aryl or heteroaryl, wherein said heterocyclyl, cycloalkyl, cycloalkenyl, aryl and heteroaryl groups are optionally substituted with one to three substituents independently selected from the group consisting of a) halo, b) cyano, c) hydroxyl, d) oxo, e) $C_{1-3}$ alkyl, which is optionally substituted with one to four substituents independently selected from the group consisting of hydroxyl, halo, cyano, heterocyclyl, $OC_{1-3}$ alkyl and $R^cR^d$, f) $OC_{1-3}$ alkyl, which is optionally substituted with one to four substituents independently selected from the group consisting of hydroxyl, halo, cyano, heterocyclyl, $OC_{1-3}$ alkyl $NR^cR^d$, aryl and heteroaryl, g) $C_{3-8}$ cycloalkyl, which is optionally substituted with one to four substituents independently selected from the group consisting of hydroxyl, halo, cyano, heterocyclyl, $OC_{1-3}$ alkyl and $NR^cR^d$, h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$, i) heteroaryl, which is optionally substituted with one to four substituents independently selected from the group consisting of hydroxyl, halo, cyano, heterocyclyl, $OC_{1-3}$ alkyl, $S(O)_m NR^cR^d$, $C(O)NR^cR^d$ and $NR^cR^d$, j) heterocyclyl, which is optionally substituted with one to four substituents independently selected from the group consisting of hydroxyl, halo, cyano, $OC_{1-3}$ alkyl and $NR^cR^d$, k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$; $R^8$ is hydrogen or $C_{1-6}$ alkyl, which is optionally substituted with one to three substituents independently selected from the group consisting of: a) halo, b) cyano, c) hydroxyl, d) $OC_{1-3}$ alkyl, which is optionally substituted with one to four substituents independently selected from the group consisting of hydroxyl, halo and $NR^cR^d$, and e) $C_{3-8}$ cycloalkyl; $R^c$ is selected from the group consisting of: a) hydrogen, b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl)$_2$, $OC_{1-6}$ alkyl, and $C_{3-8}$ cycloalkyl; $R^d$ is selected from the group consisting of: a) hydrogen, b) $C_{3-8}$ cycloalkyl, c) $C_{3-6}$ heterocyclyl, d) $C_{1-3}$ alkyl, e) (C=O)$C_{1-3}$ alkyl, f) aryl, and g) heteroaryl; wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$ cycloalkyl; or $R^c$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl; m is an integer from zero to two, or a pharmaceutically acceptable salt thereof.

In an embodiment, the LRRK2 inhibitor is a compound of the formula:

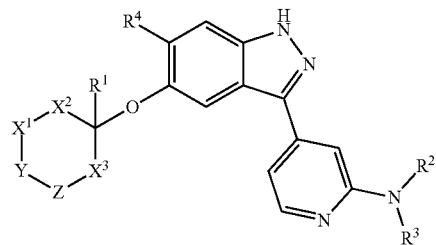

wherein $X^1$, $X^2$ and $X^3$ are each independently selected from the group consisting of a bond or $CR^eR^f$; Y is O, $CR^aR^b$ or NRC; Z is O, $CR^aR^b$ or NRC; $R^1$ is selected from the group consisting of hydrogen and $C_{1-6}$ alkyl, which is optionally substituted with one to three substituents independently selected from the group consisting of halo, cyano, hydroxyl, $NR^cR^d$, $OR^5$ and (C=O)$OR^5$; $R^2$ is selected from the group consisting of hydrogen and $C_{1-6}$ alkyl, which is optionally substituted with one to three substituents independently selected from the group consisting of: a) halo, b) cyano, c) $R^5$, d) $R^7$, e) $OR^5$, and f) $NR^cR^d$; $R^3$ is selected from the group consisting a) hydrogen, b) $C_{1-6}$ alkyl, which is optionally substituted with one to three substituents independently selected from the group consisting of halo, cyano, $OR^5$ and $NR^cR^d$, c) $C_{3-8}$ cycloalkyl, which is optionally substituted with one to three substituents independently selected from the group consisting of halo, cyano, $OR^5$ and $NR^cR^d$, d) heterocyclyl, which is optionally substituted with one to three substituents independently selected from the group consisting of halo, cyano, oxo, $R^5$, $OR^5$ and $NR^cR^d$, e) heteroaryl, which is optionally substituted with one to three substituents independently selected from the group consisting of halo, cyano, oxo, $R^5$, $OR^5$ and $NR^cR^d$; f) $C_{4-8}$ cycloalkenyl, which is optionally substituted with one to three substituents independently selected from the group consisting of halo, cyano, $OR^5$ and $NR^cR^d$, g) (C=O)$R^7$, h) (C=O)$R^5$, i) $S(O)_mR^5$, and j) $S(O)_mR^7$; or $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of: a) halo, b) oxo, c) cyano, d) $OR^5$, e) $NR^cR^d$, f) $SO_3H$, g) $S(O)_mR^5$, h) $S(O)_mR^7$ i) $R^5$, j) $R^6$, k) $R^7$, l) (C=O)$R^5$, m) (C=O)$OR^5$, n) (C=O)$R^7$, and o) (C=O)$NR^cR^d$; $R^4$ is selected from the group consisting of hydrogen, halo, cyano, $OR^5$, aryl, heteroaryl, $C_{3-8}$ cycloalkyl, $C_{4-8}$ cycloalkenyl, $C_{4-8}$ heterocycloalkyl and $C_{1-6}$ alkyl, which is optionally substituted with one to three substituents independently selected from the group consisting of halo, cyano, $OC_{1-3}$ alkyl, $NR^cR^d$ and hydroxyl; $R^5$ is selected from the group consisting of hydrogen and $C_{1-6}$ alkyl, which is optionally substituted with one to three substituents independently selected from the group consisting of: a) halo, b) hydroxyl, c) $OC_{1-6}$ alkyl, d) $NR^cR^d$, e) (C=O)$NR^cR^d$, f) $S(O)_m$, g) $S(O)_mR^8$, h) $S(O)_mR^7$, i) $R^7$, and j) $OR^7$; $R^6$ is $C_{1-6}$ alkyl, which is optionally substituted with one to three substituents independently selected from the group consisting of halo and hydroxyl; or $R^5$ and $R^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of: a) halo, b) oxo, c) cyano, d) hydroxyl, e) $C_{1-3}$ alkyl, which is optionally substituted with one to three halo, f) $C_{3-8}$ cycloalkyl, g) $OC_{1-3}$ alkyl, which is optionally substituted with one to three halo, and h) $OC_{3-8}$ cycloalkyl; $R^7$ is selected from the group consisting of $C_{4-8}$ heterocyclyl, $C_{3-8}$ cycloalkyl, $C_{4-8}$ cycloalkenyl, aryl or heteroaryl, wherein said heterocyclyl, cycloalkyl, cycloalkenyl, aryl and heteroaryl groups are optionally substituted with one to three substituents independently selected from the group consisting of: a) halo, b) cyano, c) hydroxyl, d) oxo, e) $C_{1-3}$ alkyl, which is optionally substituted with one to four substituents independently selected from the group consisting of hydroxyl, halo, cyano, heterocyclyl, $OC_{1-3}$ alkyl and $NR^cR^d$, f) $OC_{1-3}$ alkyl, which is optionally substituted with one to four substituents independently selected from the group consisting of hydroxyl, halo, cyano, heterocyclyl, $OC_{1-3}$ alkyl $NR^cR^d$ and aryl, g) $C_{3-8}$ cycloalkyl, which is optionally substituted with one to four substituents independently selected from the group consisting of hydroxyl, halo, cyano, heterocyclyl, $OC_{1-3}$ alkyl and $NR^cR^d$, h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$, i) heteroaryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$, j) heterocyclyl, which is optionally substituted with one to four substituents independently selected from the group consisting of hydroxyl, halo, cyano, $OC_{1-3}$ alkyl and $NR^cR^d$, k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$; $R^8$ is hydrogen or $C_{1-6}$ alkyl, which is optionally substituted with one to three substituents independently selected from the group consisting of: a) halo, b) cyano, c) hydroxyl, d) $OC_{1-3}$ alkyl, which is optionally substituted with one to four substituents independently selected from the group consisting of hydroxyl, halo and $NR^cR^d$, and e) $C_{3-8}$ cycloalkyl; $R^a$ is selected from the group consisting of hydrogen and $C_{1-6}$ alkyl; $R^b$ is selected from the group consisting of hydrogen and $C_{1-6}$ alkyl; $R^e$ is selected from the group consisting of: a) hydrogen and b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl$)_2$, $OC_{1-6}$ alkyl, and $C_{3-8}$ cycloalkyl; $R^d$ is selected from the group consisting of: a) hydrogen, b) $C_{3-8}$ cycloalkyl, c) $C_{3-6}$ heterocyclyl, d) $C_{1-3}$ alkyl, e) (C=O)$C_{1-3}$ alkyl, f) aryl, and g) heteroaryl; wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$cycloalkyl or $R^e$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl; $R^e$ is selected from the group consisting of hydrogen and $C_{1-3}$ alkyl; $R^1$ is selected from the group consisting of hydrogen and $C_{1-3}$ alkyl; m is an integer from zero to two, or a pharmaceutically acceptable salt thereof.

In an embodiment, the LRRK2 inhibitor is a compound of the formula:

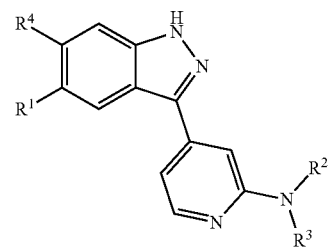

wherein $R^1$ is selected from the group consisting of: a) hydrogen, b) halo, c) cyano, d) hydroxyl, e) $C_{2-6}$ alkenyl, which is optionally substituted with one to three substitutents independently selected from the group consisting of halo, cyano and $R^5$; f) $OC_{2-6}$ alkenyl, which is optionally substituted with one to three substitutents independently selected from the group consisting of halo, cyano and $R^5$; g) $R^5$, h) $OR^5$, i) $R^7$, j) $S(O)_mR^5$, k) $S(O)_mR^7$, 1) (C=O)$R^7$, m) (C=O)$R^5$, n) (C=O)$OR^5$, and o) $NR^cR^d$; $R^2$ is selected from the group consisting of hydrogen and $C_{1-6}$ alkyl, which is optionally substituted with one to three substitutents independently selected from the group consisting of: a) halo, b) cyano, c) $R^5$, d) $R^7$, e) $OR^5$, and f) $NR^cR^d$; selected from the group consisting of: a) hydrogen, b) $C_{1-6}$ alkyl, which is optionally substituted with one to three substitutents independently selected from the group consisting of halo, cyano, $OR^5$ and $NR^cR^d$, c) $C_{3-8}$ cycloalkyl, which is optionally substituted with one to three substitutents independently selected from the group consisting of halo, cyano, $OR^5$ and $NR^cR^d$, d) heterocyclyl, which is optionally substituted with one to three substitutents independently selected from the group consisting of halo, cyano, oxo, $R^5$, $OR^5$ and $NR^cR^d$, e) heteroaryl, which is optionally substituted with one to three substitutents independently selected from the group consisting of halo, cyano, oxo, $R^5$, $OR^5$ and $NR^cR^d$, f) $C_{4-8}$ cycloalkenyl, which is optionally substituted with one to three substitutents independently selected from the group consisting of halo, cyano, $OR^5$ and $NR^cR^d$, g) (C=O)$R^7$, h) (C=O)$R^5$, i) $S(O)_mR^5$ and j) $S(O)_mR^7$; or $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of: a) halo, b) oxo, c) cyano, d) $OR^5$, e) $NR^cR^d$, f) $SO_3H$, g) $S(O)_mR^5$, h) $S(O)_mR^7$ i) $R^5$, j) $R^6$, k) $R^7$, 1) (C=O)$R^5$, m) (C=O)$OR^5$, n) (C=O)$R^7$, and o) (C=O)$NR^cR^d$; $R^4$ is selected from the group consisting of hydrogen, halo, cyano, $OR^5$, aryl, heteroaryl, $C_{3-8}$ cycloalkyl, $C_{4-8}$ cycloalkenyl, $C_{4-8}$ heterocyclyl and $C_{1-6}$ alkyl, which is optionally substituted with one to three substitutents independently selected from the group consisting of halo, cyano, $OC_{1-3}$ alkyl, $NR^cR^d$ and hydroxyl; or $R^1$ and $R^4$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of: a) halo, b) oxo, c) cyano, d) $R^5$, and e) $R^7$; $R^5$ is selected from the group consisting of hydrogen and $C_{1-6}$ alkyl, which is optionally substituted with one to three substituents independently selected from the group consisting of: a) halo, b) hydroxyl, c) $OC_{1-6}$ alkyl, d) $NR^cR^d$, e) $(C=O)NR^cR^d$, f) $S(O)_mR^8$, g) $S(O)_mR^7$, h) $R^7$ and i) $OR^7$; $R^6$ is $C_{1-6}$ alkyl, which is optionally substituted with one to three substituents independently selected from the group consisting of halo and hydroxyl; or $R^5$ and $R^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of: a) halo, b) oxo, c) cyano, d) hydroxyl, e) $C_{1-3}$ alkyl, which is optionally substituted with one to three halo, f) $C_{3-8}$ cycloalkyl, g) $OC_{1-3}$ alkyl, which is optionally substituted with one to three halo, and h) $OC_{3-8}$ cycloalkyl; $R^7$ is selected from the group consisting of $C_{4-8}$ heterocyclyl, $C_{3-8}$ cycloalkyl, $C_{4-8}$ cycloalkenyl, aryl or heteroaryl, wherein said heterocyclyl, cycloalkyl, cycloalkenyl, aryl and heteroaryl groups are optionally substituted with one to three substituents independently selected from the group consisting of: a) halo, b) cyano, c) hydroxyl, d) oxo, e) $C_{1-3}$ alkyl, which is optionally substituted with one to four substituents independently selected from the group consisting of hydroxyl, halo, cyano, heterocyclyl, $OC_{1-3}$ alkyl and $NR^cR^d$, f) $OC_{1-3}$ alkyl, which is optionally substituted with one to four substituents independently selected from the group consisting of hydroxyl, halo, cyano, heterocyclyl, $OC_{1-3}$ alkyl $NR^cR^d$ and aryl, g) $C_{3-8}$ cycloalkyl, which is optionally substituted with one to four substituents independently selected from the group consisting of hydroxyl, halo, cyano, heterocyclyl, $OC_{1-3}$ alkyl and $NR^cR^d$, h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$, i) heteroaryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$, j) heterocyclyl, which is optionally substituted with one to four substituents independently selected from the group consisting of hydroxyl, halo, cyano, $OC_{1-3}$ alkyl and $NR^cR^d$, k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$; $R^8$ is hydrogen or $C_{1-6}$ alkyl, which is optionally substituted with one to three substituents independently selected from the group consisting of: a) halo, b) cyano, c) hydroxyl, d) $OC_{1-3}$ alkyl, which is optionally substituted with one to four substituents independently selected from the group consisting of hydroxyl, halo and $NR^cR^d$, and e) $C_{3-8}$ cycloalkyl; $R^c$ is selected from the group consisting of: a) hydrogen and b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl$)_2$, $OC_{1-6}$ alkyl, and $C_{3-8}$ cycloalkyl; $R^d$ is selected from the group consisting of: a) hydrogen, b) $C_{3-8}$ cycloalkyl, c) $C_{3-6}$ heterocyclyl, d) $C_{1-3}$ alkyl, e) $(C=O)C_{1-3}$ alkyl, f) aryl, and g) heteroaryl; wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$cycloalkyl; or $R^c$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of: halo, cyano, hydroxyl, $C_{1-3}$ alkyl and $OC_{1-3}$ alkyl; m is an integer from zero to two, or a pharmaceutically acceptable salt thereof.

In an embodiment, the LRRK2 inhibitor is a compound of the formula I:

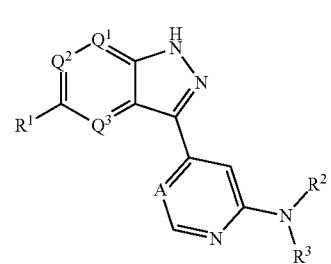

I wherein $R^1$ is selected from the group consisting of: a) hydrogen, b) halo, c) cyano, d) hydroxyl, e) $C_{2-6}$ alkenyl, which is optionally substituted with one to three substitutents independently selected from the group consisting of halo, cyano and $R^5$; f) $OC_{2-6}$ alkenyl, which is optionally substituted with one to three substituents independently selected from the group consisting of halo, cyano and $R^5$; g) $R^5$, h) $OR^5$, i) $R^7$, j) $S(O)_mR^5$, k) $S(O)_mR^7$, l) $(C=O)R^7$, m) $(C=O)R^5$, n) $(C=O)OR^5$, o) $NR^cR^d$ and p)

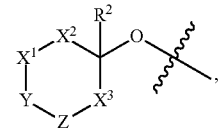

wherein $X^1$, $X^2$ and $X^3$ are each independently selected from the group consisting of a bond or $CR^eR^f$; Y is O, $CR^aR^b$ or $NR^c$; Z is O, $CR^aR^b$ or NRC; $R^z$ is selected from the group consisting of hydrogen and $C_{1-3}$ alkyl, which is optionally substituted with one to three substituents independently selected from the group consisting of halo, hydroxyl, cyano, $NH(C_{1-3}$ alkyl), $N(C_{1-3}$ alkyl$)_2$, $OC_{1-6}$ alkyl and $C_{3-8}$ cycloalkyl; $Q^1$ is CH or N; $Q^2$ is CH or N; $Q^3$ is CH or N; provided that at least one of $Q^1$, $Q^2$ and $Q^3$ must be N; A is CH or N; $R^2$ is selected from the group consisting of hydrogen and $C_{1-6}$ alkyl, which is optionally substituted with one to three substitutents independently selected from the group consisting of: a) halo, b) cyano, c) $R^5$, d) $R^7$, e) $OR^5$ and f) $NR^cR^d$; $R^3$ is selected from the group consisting of: a) hydrogen, b) $C_{1-6}$ alkyl, which is optionally substituted with one to three substitutents independently selected from the group consisting of halo, cyano, $OR^5$ and $NR^cR^d$, c) $C_{3-8}$ cycloalkyl, which is optionally substituted with one to three substitutents independently selected from the group consisting of halo, cyano, $OR^5$ and $NR^cR^d$, d) heterocyclyl, which is optionally substituted with one to three substitutents independently selected from the group consisting of halo, cyano, oxo, $R^5$, $OR^5$ and $NR^cR^d$, e) heteroaryl, which is optionally substituted with one to three substitutents independently selected from the group consisting of halo, cyano, oxo, $R^5$, $OR^5$ and $NR^cR^d$; f) $C_{4-}$ cycloalkenyl, which is optionally substituted with one to three substitutents independently selected from the group consisting of halo, cyano, $OR^5$ and $NR^cR^d$, g) $(C=O)R^7$, h) $(C=O)R^5$, i) $S(O)_mR^5$ and j) $S(O)_mR^7$; or $R^2$ and $R^3$ can be taken together with the atoms to which they are attached to form a 3 to 8 membered heterocyclic or heteroaryl ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of: a) halo, b) oxo, c) cyano, d) $OR^5$, e) $NR^cR^d$, f) $SO_3H$, g) $S(O)_mR^5$, h) $S(O)_mR^7$ i) $R^5$, j) $R^6$, k) $R^7$, l) $(C=O)R^5$, m) $(C=O)OR^5$, n) $(C=O)R^7$ and o) $(C=O)NR^cR^d$; $R^5$ is selected from the group consisting of hydrogen and $C_{1-6}$ alkyl, which is optionally substituted with one to three substituents independently selected from the group consisting of: a) halo, b) hydroxyl, c) $OC_{1-6}$ alkyl, d) $NR^cR^d$, e) $(C=O)NR^cR^d$, f) $S(O)_mR^8$, g) $S(O)_mR^7$, h) $R^7$ and i) $OR^7$; $R^6$ is $C_{1-6}$ alkyl, which is optionally substituted with one to three substituents independently selected from the group consisting of halo and hydroxyl; or $R^5$ and $R^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of: a) halo, b) oxo, c) cyano, d) hydroxyl, e) $C_{1-3}$ alkyl, which is optionally substituted with one to three halo, f) $C_{3-8}$ cycloalkyl, g) $OC_{1-3}$ alkyl, which is optionally substituted with one to three halo, and h) $OC_{3-8}$ cycloalkyl; $R^7$ is selected from the group consisting of $C_{4-8}$ heterocyclyl, $C_{3-8}$ cycloalkyl, $C_{4-8}$ cycloalkenyl, aryl and heteroaryl, wherein said heterocyclyl, cycloalkyl, cycloalkenyl, aryl and heteroaryl groups are optionally substituted with one to three substituents independently selected from the group consisting of: a) halo, b) cyano, c) hydroxyl, d) oxo, e) $C_{1-3}$ alkyl, which is optionally substituted with one to four substituents independently selected from the group consisting of hydroxyl, halo, cyano, heterocyclyl, $OC_{1-3}$ alkyl and $NR^cR^d$, f) $OC_{1-3}$ alkyl, which is optionally substituted with one to four substituents independently selected from the group consisting of hydroxyl, halo, cyano, heterocyclyl, $OC_{1-3}$ alkyl, $NR^cR^d$, aryl and heteroaryl, g) $C_{3-8}$ cycloalkyl, which is optionally substituted with one to four substituents independently selected from the group consisting of hydroxyl, halo, cyano, heterocyclyl, $OC_{1-3}$ alkyl and $NR^cR^d$, h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$, i) heteroaryl, which is optionally substituted with one to four substituents independently selected from the group consisting of hydroxyl, halo, cyano, heterocyclyl, $OC_{1-3}$ alkyl, $S(O)_m NR^cR^d$, $C(O)NR^cR^d$ and $NR^cR^d$, j) heterocyclyl, which is optionally substituted with one to four substituents independently selected from the group consisting of hydroxyl, halo, cyano, $OC_{1-3}$alkyl and $NR^cR^d$, k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$; $R^8$ is hydrogen or $C_{1-6}$ alkyl, which is optionally substituted with one to three substituents independently selected from the group consisting of: a) halo, b) cyano, c) hydroxyl, d) $OC_{1-3}$ alkyl, which is optionally substituted with one to four substituents independently selected from the group consisting of hydroxyl, halo and $NR^cR^d$, and e) $C_{3-8}$ cycloalkyl; $R^a$ is selected from the group consisting of hydrogen and $C_{1-6}$ alkyl; $R^b$ is selected from the group consisting of hydrogen and $C_{1-6}$ alkyl; $R^c$ is selected from the group consisting of: a) hydrogen, b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl)$_2$, $OC_{1-6}$ alkyl and $C_{3-8}$ cycloalkyl; $R^d$ is selected from the group consisting of: a) hydrogen, b) $C_{3-8}$ cycloalkyl, c) $C_{3-6}$ heterocyclyl, d) $C_{1-3}$ alkyl, e) $(C=O)C_{1-3}$alkyl, f) aryl and g) heteroaryl; wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$cycloalkyl; or $R^c$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl; $R^e$ is selected from the group consisting of hydrogen and $C_{1-3}$ alkyl; $R^d$ is selected from the group consisting of hydrogen and $C_{1-3}$ alkyl; m is an integer from zero to two; or a pharmaceutically acceptable salt thereof.

In an embodiment, the LRRK2 inhibitor is a compound of formula I:

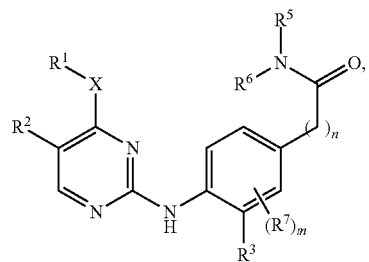

or pharmaceutically acceptable salts thereof, wherein: m is from 0 to 3; X is: —$NR^a$—; —O—; or —$S(O)_r$— wherein r is from 0 to 2 and $R^a$ is hydrogen or $C_{1-6}$alkyl; $R^1$ is: $C_{1-6}$alkyl; $C_{2-6}$alkenyl; $C_{2-6}$alkynyl; halo-$C_{1-6}$alkyl; $C_{1-6}$alkoxy-$C_{1-6}$alkyl; hydroxy-$C_{2-6}$alkenyl; amino-$C_{1-6}$alkyl; $C_{1-6}$alkylsulfonyl-$C_{1-6}$alkyl; $C_{3-6}$cycloalkyl optionally substituted with $C_{1-6}$alkyl; $C_{3-6}$Cycloalkyl-$C_{1-6}$alkyl wherein the $C_3$-6Cycloalkyl portion is optionally substituted with $C_{1-6}$alkyl; tetrahydrofuranyl; tetrahydrofuranyl-$C_{1-6}$alkyl; tetrahydropuranyl; tetrahydropuranyl-$C_{1-6}$alkyl, oxetanyl; or oxetan-$C_{1-6}$alkyl; or $R^1$ and $R^a$ together with the atoms to which they are attached may form a three to six membered ring that may optionally include an additional heteroatom selected from O, N and S, and which is substituted with oxo, halo or $C_{1-6}$alkyl; $R^2$ is: halo; $C_{1-6}$alkoxy; cyano; $C_{2-6}$alkynyl; $C_{2-6}$alkenyl; halo-$C_{1-6}$alkyl; halo-$C_{1-6}$alkoxy; $C_{3-6}$Cycloalkyl wherein the $C_{3-6}$cycloalkyl portion is optionally substituted with $C_{1-6}$alkyl; $C_{3-6}$Cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; acetyl; oxetanyl; or oxetan-$C_{1-6}$alkyl; $R^3$ is: —$OR^4$; halo; cyano; $C_{1-6}$alkyl; halo-$C_{1-6}$alkyl; $C_{3-6}$cycloalkyl optionally substituted with $C_{1-6}$alkyl; $C_{3-6}$Cycloalkyl-$C_{1-6}$alkyl wherein the $C_{3-6}$Cycloalkyl portion is optionally substituted with $C_{1-6}$alkyl; tetrahydrofuranyl; tetrahydrofuranyl-$C_{1-6}$alkyl; oxetanyl; or oxetan-$C_{1-6}$alkyl; $R^4$ is: hydrogen, $C_{1-6}$alkyl; halo-$C_{1-6}$alkyl; $C_{1-6}$alkoxy-$C_{1-6}$alkyl; $C_{3-6}$cycloalkyl optionally substituted with $C_{1-6}$alkyl or halo; $C_{3-6}$cycloalkyl-$C_{1-6}$alkyl wherein the $C_{3-6}$cycloalkyl portion is optionally substituted with $C_{1-6}$alkyl or halo; tetrahydrofuranyl; tetrahydrofuranyl-$C_{1-6}$alkyl; oxetanyl; or oxetan-$C_{1-6}$alkyl; $R^5$ is: hydrogen; or $C_{1-6}$alkyl; n is 0 or 1; $R^6$ is: hydrogen; $C_{1-6}$alkyl; $C_{1-6}$alkyl-$C_{1-6}$alkyl; hydroxy-$C_{1-6}$alkyl; amino-$C_{1-6}$alkyl; $C_{3-6}$Cycloalkyl; $C_{3-6}$Cycloalkyl-$C_{1-6}$alkyl; heterocyclyl; or heterocyclyl-$C_{1-6}$alkyl; wherein the $C_{3-6}$cycloalkyl, $C_{3-6}$Cycloalkyl-$C_{1-6}$alkyl, heterocyclyl and heterocyclyl-$C_{1-6}$alkyl each may be optionally substituted with one, two, three or four groups groups independently selected from: $C_{1-6}$alkyl; halo-$C_{1-6}$alkyl; $C_{1-6}$alkoxy; halo-$C_{1-6}$alkoxy; hydroxy; hydroxy-$C_{1-6}$alkyl; halo; nitrile; $C_{1-6}$alkyl-carbonyl; $C_{1-6}$alkyl-sulfonyl; $C_{3-6}$cycloalkyl; $C_{3-6}$Cycloalkyl-$C_{1-6}$alkyl; $C_{3-6}$cycloalkyl-carbonyl; amino; or heterocyclyl; or two of the groups together with the atoms to which they are attached may form a five or six-membered ring; or $R^5$ and $R^6$ together with the nitrogen atom to which they are attached form a three- to seven-membered ring that optionally includes an additional heteroatom selected from O, N and $S(O)_n$, and which is optionally substituted with one, two, three or four groups independently selected from: $C_{1-6}$alkyl; halo-$C_{1-6}$alkyl; $C_{1-6}$alkoxy; halo-$C_{1-6}$alkoxy; hydroxy; hydroxy-$C_{1-6}$alkyl; halo, nitrile; $C_{1-6}$alkyl-carbonyl; $C_{1-6}$alkyl-sulfonyl; $C_{3-6}$cycloalkyl; $C_{3-6}$Cycloalkyl-$C_{1-6}$alkyl; $C_3$-6Cycloalkyl-carbonyl; amino; $C_{1-6}$alkyl-heterocyclyl, $C_{1-6}$alkoxy-$C_{1-6}$alkyl or heterocyclyl; or two of the groups together with the atoms to which they are attached may form a five or six-membered ring; and $R^7$ is: halo; $C_{1-6}$alkyl; $C_{1-6}$alkoxy; halo-$C_{1-6}$alkyl; or halo-$C_{1-6}$alkoxy.

In an embodiment, the LRRK2 inhibitor is a compound of formula I:

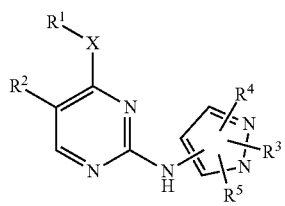

I or a pharmaceutically acceptable salt thereof, wherein: X is: —$NR^a$—; or —O— wherein $R^a$ is hydrogen or $C_{1-6}$alkyl; $R^1$ is: $C_{1-6}$alkyl; $C_{2-6}$alkenyl; $C_{2-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted one or more times with $C_{1-6}$alkyl; $C_{3-6}$cycloalkyl-$C_{1-6}$alkyl wherein the $C_{3-6}$cycloalkyl portion is optionally substituted one or more times with $C_{1-6}$alkyl; heterocyclyl optionally substituted one or more times with $R^7$; or heterocyclyl-$C_{1-6}$alkyl optionally substituted one or more times with $R^7$; or X and $R^1$ together form $C_{1-6}$alkyl; $C_{1-6}$alkoxy-$C_{1-6}$alkyl; $C_{3-6}$cycloalkyl optionally substituted one or more times with $R^6$; or $C_{3-6}$cycloalkyl-$C_{1-6}$alkyl wherein the $C_{3-6}$cycloalkyl portion is optionally substituted one or more times with $R^6$; or $R^1$ and $R^a$ together with the atoms to which they are attached may form a three- to six-membered heterocyclic ring optionally substituted one or more times with $R^7$; $R^2$ is: $C_{1-6}$alkyl; halo; $C_{1-6}$alkoxy; cyano; $C_{2-6}$alkynyl; $C_{2-6}$alkenyl; halo-$C_{1-6}$alkyl; halo-$C_{1-6}$alkoxy; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; —$OR^b$ wherein $R^b$ is $C_{1-6}$alkyl, $C_{3-6}$cycloalkyl optionally substituted one or more times with $R^6$, or $C_{3-6}$cycloalkyl-$C_{1-6}$alkyl wherein the $C_{3-6}$cycloalkyl portion is optionally substituted one or more times with $R^6$; or —C(O)—$R^c$ wherein $R^c$ is $C_{1-6}$alkyl, $C_{1-6}$alkoxy, amino, or heterocyclyl optionally substituted one or more times with $R^7$; $R^3$ is: hydrogen; $C_{1-6}$alkyl; halo-$C_{1-6}$alkyl; $C_{2-6}$alkenyl; $C_{2-6}$alkynyl; hydroxy-$C_{1-6}$alkyl; $C_{1-6}$alkoxy-$C_{1-6}$alkyl; cyano-$C_{1-6}$alkyl; $C_{1-6}$alkylsulfonyl; $C_{1-6}$alkylsulfonyl$C_{1-6}$alkyl; amino-$C_{1-6}$alkyl; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; $C_{3-6}$Cycloalkyl-sulfonyl wherein the $C_{3-6}$cycloalkyl portion is optionally substituted one or more times with $R^6$; heterocyclyl optionally substituted one or more times with $R^7$; heterocyclyl-$C_{1-6}$alkyl wherein the heterocyclyl portion is optionally substituted one or more times with $R^7$; aryl optionally substituted one or more times with $R^8$; aryl-$C_{1-6}$alkyl wherein the aryl portion is optionally substituted one or more times with $R^1$; heteroaryl optionally substituted one or more times with $R^8$; heteroaryl-$C_{1-6}$alkyl wherein the heteroaryl portion is optionally substituted one or more times with $R^8$; or —Y—C(O)—$R^d$; Y is $C_{2-6}$alkylene or a bond; $R^d$ is $C_{1-6}$alkyl, $C_{1-6}$alkoxy, amino, $C_{1-6}$alkyl-amino, di-$C_{1-6}$alkyl-amino, halo-$C_{1-6}$alkyl-amino, di-halo-$C_{1-6}$alkyl-amino, halo-$C_{1-6}$alkyl, hydroxy-$C_{1-6}$alkyl, hydroxy, $C_{1-6}$alkoxy-$C_{1-6}$alkyl, cyano-$C_{1-6}$alkyl, $C_{1-6}$alkylsulfonyl$C_{1-6}$alkyl, amino-$C_{1-6}$alkyl, $C_{3-6}$cycloalkyl optionally substituted one or more times with $R^6$, $C_{3-6}$cycloalkyl-$C_{1-6}$alkyl wherein the $C_{3-6}$cycloalkyl portion is optionally substituted one or more times with $R^6$, heterocyclyl optionally substituted one or more times with $R^7$, or heterocyclyl-$C_{1-6}$alkyl wherein the heterocyclyl portion is optionally substituted one or more times with $R^7$; $R^4$ is: hydrogen; $C_{1-6}$alkyl; halo; cyano; halo-$C_{1-6}$alkyl; $C_{2-6}$alkenyl; $C_{2-6}$alkynyl; $C_{1-6}$alkoxy; $C_{1-6}$alkoxy-$C_{1-6}$alkyl; hydroxy-$C_{1-6}$alkyl; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; or —Y—C(O)—$R^d$; $R^5$ is: hydrogen; or $C_{1-6}$alkyl; each $R^6$ is independently: $C_{1-6}$alkyl; halo-$C_{1-6}$alkyl; $C_{1-6}$alkoxy; oxo; cyano; halo; or Y—C(O)—$R^d$; each $R^7$ is independently: $C_{1-6}$alkyl; halo-$C_{1-6}$alkyl; halo; oxo; $C_{1-6}$alkoxy; $C_{1-6}$alkylsulfonyl; $C_{1-6}$alkoxy-$C_{1-6}$alkyl; cyano; —Y—C(O)—$R^d$; heterocyclyl; heterocyclyl-$C_{1-6}$alkyl; $C_{3-6}$cycloalkyl; $C_{3-6}$cycloalkyl-$C_{1-6}$alkyl; or $C_{3-6}$cycloalkylsulfonyl; and each $R^8$ is independently: oxo; $C_{1-6}$alkyl; halo-$C_{1-6}$alkyl; halo; $C_{1-6}$alkyl-sulfonyl; $C_{1-6}$alkoxy; $C_{1-6}$alkoxy-$C_{1-6}$alkyl; cyano; hetoerycyly; heterocyclyl-$C_{1-6}$alkyl; —Y—C(O)—$R^d$; $C_{3-6}$cycloalkyl, $C_{3-6}$cycloalkyl-$C_{1-6}$alkyl, or $C_{3-6}$cycloalkyl-sulfonyl.

In an embodiment, the LRRK2 inhibitor is a compound of formula L

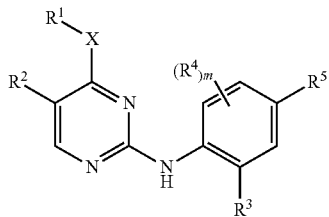

or pharmaceutically acceptable salts thereof, wherein: m is from 0 to 3; X is: —NR$^a$—; —O—; or —S(O)$_r$— wherein r is from 0 to 2 and R$^a$ is hydrogen or C$_{1-6}$alkyl; R$^1$ is: C$_{1-6}$alkyl; C$_{2-6}$alkenyl; C$_{2-6}$alkynyl; halo-C$_{1-6}$alkyl; C$_{1-6}$alkoxy-C$_{1-6}$alkyl; hydroxy-C$_{1-6}$alkyl; amino-C$_{1-6}$alkyl; C$_{1-6}$alkylsulfonyl-C$_{1-6}$alkyl; C$_{3-6}$Cycloalkyl optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; oxetanyl; or oxetan-C$_{1-6}$alkyl; or R$^1$ and R$^a$ together with the atoms to which they are attached may form a three to six membered ring that may optionally include an additional heteroatom selected from O, N and S, and which is substituted with oxo, halo or C$_{1-6}$alkyl; R$^2$ is: halo; C$_{1-6}$alkoxy; cyano; C$_{2-6}$alkynyl; C$_{2-6}$alkenyl; halo-C$_{1-6}$alkyl; halo-C$_{1-6}$alkoxy; C$_{3-6}$Cycloalkyl wherein the C$_{3-6}$Cycloalkyl portion is optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; acetyl; oxetanyl; or oxetan-C$_{1-6}$alkyl; R$^3$ and R$^4$ each independently is: halo; C$_{1-6}$alkyl; C$_{1-6}$alkoxy; C$_{3-6}$Cycloalkyloxy; halo-C$_{1-6}$alkyl; or halo-C$_{1-6}$alkyl; or R$^3$ and R$^4$ together with the atoms to which they are attached may form a five- or six-membered ring that optionally includes one or two heteroatoms each independently selected from O, N and S, the ring being optionally substituted one or more times with R$^6$; R$^5$ is: C$_{1-6}$alkyl-sulfonyl; C$_{3-6}$cycloalkylsulfonyl; C$_{3-6}$cycloalkyl-C$_{1-6}$alkylsulfonyl; cyano; cyano-C$_{1-6}$alkyl; heterocyclyl optionally substituted one or more times with R$^6$; heterocyclyl-C$_{1-6}$alkyl wherein the heterocyclyl moiety is optionally substituted one or more times with R$^6$; halo-C$_{1-6}$alkyl; heterocyclyl-sulfonyl wherein the heterocyclyl moiety is optionally substituted one or more times with R$^6$; or carboxy; and R$^6$ is: C$_{1-6}$alkyl; halo; halo-C$_{1-6}$alkyl; or oxo.

In an embodiment, the LRRK2 inhibitor is a compound of the formula:

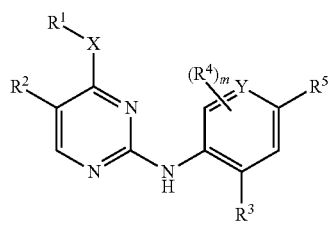

or pharmaceutically acceptable salts thereof, wherein: m is from 0 to 3; X is: —NR$^a$—; —O—; or —S(O)$_r$— wherein r is from 0 to 2 and R$^a$ is hydrogen or C$_{1-6}$ alkyl; Y is C or N; R$^1$ is: C$_{1-6}$alkyl; C$_{2-6}$alkenyl; C$_{2-6}$alkynyl; halo-C$_{1-6}$alkyl; C$_{1-6}$alkoxy-C$_{1-6}$alkyl; hydroxy-C$_{1-6}$alkyl; amino-C$_{1-6}$alkyl; C$_{1-6}$alkylsulfonyl-C$_{1-6}$alkyl; C$_{3-6}$cycloalkyl optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; oxetanyl; or oxetan-C$_{1-6}$alkyl; or R$^1$ and R$^a$ together with the atoms to which they are attached may form a three to six membered ring that may optionally include an additional heteroatom selected from O, N and S, and which is substituted with oxo, halo or C$_{1-6}$alkyl; R$^2$ is: halo; C$_{1-6}$alkoxy; cyano; C$_{2-6}$alkynyl; C$_{2-6}$alkenyl; halo-C$_{1-6}$alkyl; halo-C$_{1-6}$alkoxy; C$_{3-6}$cycloalkyl wherein the C$_{3-6}$cycloalkyl portion is optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; acetyl; oxetanyl; or oxetan-C$_{1-6}$alkyl; R$^3$ and R$^4$ each independently is: halo; C$_{1-6}$alkyl; C$_{1-6}$alkoxy; C$_{3-6}$cycloalkyloxy; halo-C$_{1-6}$alkyl; or halo-C$_{1-6}$alkoxy; and R$^5$ is a 5-membered heteroaryl group optionally substituted one or more times with R$^6$; and R$^6$ is: C$_{1-6}$alkyl; C$_{3-6}$cycloalkyl; C$_{3-6}$cycloalkyl-C$_{1-6}$alkyl; halo; halo-C$_{1-6}$alkyl; C$_{1-6}$alkoxy; heterocyclyl; oxo; or —C(O)—NR$^b$R$^c$ wherein R$^b$ and R$^c$ each independently is hydrogen or —C$_{1-6}$alkyl.

In an embodiment, the LRRK2 inhibitor is a compound of formula I:

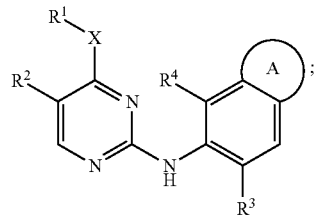

or pharmaceutically acceptable salts thereof, wherein: A is a five- or six-membered saturated or unsaturated ring that includes one or two heteroatoms selected from O, N and S, which is substituted once with R$^5$, and which is optionally substituted one, two or three times with R$^6$; X is: —NR$^a$—; —O—; or —S(O)$_r$— wherein r is from 0 to 2 and R$^a$ is hydrogen or C$_{1-6}$alkyl; R$^1$ is: C$_{1-6}$alkyl; C$_{2-6}$alkenyl; C$_{2-6}$alkynyl; halo-C$_{1-6}$alkyl; C$_{1-6}$alkoxy-C$_{1-6}$alkyl; hydroxy-C$_{1-6}$alkyl; amino-C$_{1-6}$alkyl; C$_{1-6}$alkylsulfonyl-C$_{1-6}$alkyl; C$_{3-6}$Cycloalkyl optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; oxetanyl; or oxetan-C$_{1-6}$alkyl; or R$^1$ and R$^a$ together with the atoms to which they are attached may form a three to six membered ring that may optionally include an additional heteroatom selected from O, N and S, and which is substituted with oxo, halo or C$_{1-6}$alkyl; R$^2$ is: halo; C$_{1-6}$alkoxy; cyano; C$_2$-6alkynyl; C$_{2-6}$alkenyl; halo-C$_{1-6}$alkyl; halo-C$_{1-6}$alkoxy; C$_{3-6}$Cycloalkyl wherein the C$_{3-6}$Cycloalkyl portion is optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; acetyl; oxetanyl; or oxetan-C$_{1-6}$alkyl; one of R$^3$ and R$^4$ is: halo; C$_{1-6}$alkyl; C$_{1-6}$alkoxy; C$_{3-6}$cycloalkyloxy; halo-C$_{1-6}$alkyl; or halo-C$_{1-6}$alkoxy, and the other is hydrogen; R$^5$ is: oxo; C$_{1-6}$alkyl; C$_{3-6}$cycloalkyl; C$_{3-6}$cycloalkyl-C$_{1-6}$alkyl; or —C(O)—NR$^b$R$^c$ wherein R$^b$ and R$^c$ each independently is hydrogen or —C$_{1-6}$alkyl, or R$^b$ and R$^c$ together with the atoms to which they are attached may form a heterocyclyl group that optionally includes an additional heteroatom selected from O, N and S and which is optionally substituted one or more times with R$^6$; and each R$^6$ is independently: C$_{1-6}$alkyl; C$_{3-6}$cycloalkyl; C$_{3-6}$cycloalkyl-C$_{1-6}$alkyl; halo; halo-C$_{1-6}$alkyl; hydroxy-C$_{1-6}$alkyl; C$_{1-6}$alkoxy-C$_{1-6}$alkyl; heterocyclyl; oxo; or —C(O)—NR$^b$R$^c$.

In an embodiment, the LRRK2 inhibitor is a compound of formula I:

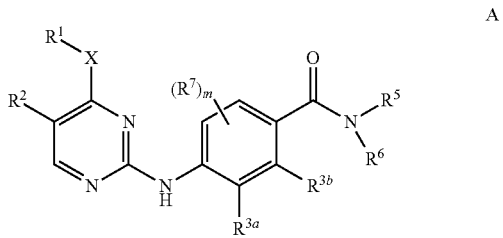

A or pharmaceutically acceptable salts thereof, wherein: m is from 0 to 3; X is: —NR$^a$—; —O—; or —S(O)$_r$— wherein r is from 0 to 2 and R$^a$ is hydrogen or C$_{1-6}$alkyl; R$^1$ is: C$_{1-6}$alkyl; C$_{2-6}$alkenyl; C$_{2-6}$alkynyl; halo-C$_{1-6}$alkyl; C$_{1-6}$alkoxy-C$_{1-6}$alkyl; hydroxy-C$_{1-6}$alkyl; amino-C$_{1-6}$alkyl; C$_{1-6}$alkylsulfonyl-C$_{1-6}$alkyl; C$_{3-6}$cycloalkyl optionally substituted with C$_{1-6}$alkyl or halo; C$_{3-6}$cycloalkyl-C$_{1-6}$alkyl wherein the C$_{3-6}$cycloalkyl portion is optionally substituted with C$_{1-6}$alkyl; tetrahydropyranyl; tetrahydrofuranyl; tetrahydrofuranyl-C$_{1-6}$alkyl; oxetanyl; or oxetan-C$_{1-6}$alkyl; or R$^1$ and R$^a$ together with the atoms to which they are attached may form a three to six membered ring that may optionally include an additional heteroatom selected from O, N and S, and which is substituted with oxo, halo or C$_{1-6}$alkyl; R$^2$ is: halo; C$_{1-6}$alkoxy; cyano; C$_{2-6}$alkynyl; C$_{2-6}$alkenyl; halo-C$_{1-6}$alkyl; halo-C$_{1-6}$alkoxy; C$_{3-6}$cycloalkyl wherein the C$_{3-6}$cycloalkyl portion is optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; acetyl; oxetanyl; or oxetan-C$_{1-6}$alkyl; R$^{3a}$ is: —OR$^4$; halo; cyano; C$_{1-6}$alkyl; halo-C$_{1-6}$alkyl; C$_{3-6}$cycloalkyl optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; oxetanyl; or oxetan-C$_{1-6}$alkyl; R$^{3b}$ is: hydrogen, or R$^{3a}$ and R$^{3b}$ together with the atoms to which they are attached may form a five- or six-membered ring that optionally includes one or two heteroatoms, each independently selected from O, N and S, which ring is optionally substituted one or more times with R$^8$; R$^4$ is: hydrogen; C$_{1-6}$alkyl; halo-C$_{1-6}$alkyl; C$_{1-6}$alkoxy-C$_{1-6}$alkyl; C$_{3-6}$Cycloalkyl optionally substituted with C$_{1-6}$alkyl or halo; C$_{3-6}$Cycloalkyl-C$_{1-6}$alkyl wherein the C$_{3-6}$Cycloalkyl portion is optionally substituted with C$_{1-6}$alkyl or halo; tetrahydrofuranyl; tetrahydrofuranyl-C$_{1-6}$alkyl; oxetanyl; or oxetan-C$_{1-6}$alkyl; R$^5$ is: hydrogen; or C$_{1-6}$alkyl; R$^6$ is: hydrogen; C$_{1-6}$alkyl; C$_{1-6}$alkoxy-C$_{1-6}$alkyl; hydroxy-C$_{1-6}$alkyl; amino-C$_{1-6}$alkyl; C$_{3-6}$Cycloalkyl; C$_{3-6}$Cycloalkyl-C$_{1-6}$alkyl; heteroaryl, heterocyclyl; or heterocyclyl-C$_{1-6}$alkyl; wherein the C$_{3-6}$Cycloalkyl, C$_{3-6}$cycloalkyl-C$_{1-6}$alkyl, heteroaryl, heterocyclyl and heterocyclyl-C$_{1-6}$alkyl each may be optionally substituted with one, two, three or four groups groups independently selected from: C$_{1-6}$alkyl; halo-C$_{1-6}$alkyl; C$_{1-6}$alkoxy; halo-C$_{1-6}$alkoxy; hydroxy; hydroxy-C$_{1-6}$alkyl; halo; nitrile; C$_{1-6}$alkyl-carbonyl; C$_{1-6}$alkyl-sulfonyl; C$_{3-6}$Cycloalkyl; C$_{3-6}$Cycloalkyl-C$_{1-6}$alkyl; C$_{3-6}$Cycloalkyl-carbonyl; amino; or heterocyclyl; or two of the groups together with the atoms to which they are attached may form a five or six-membered ring; or R$^5$ and R$^6$ together with the nitrogen atom to which they are attached form a three- to seven-membered ring that optionally includes an additional heteroatom selected from O, N and S(O)$_n$, and which is optionally substituted with one, two, three or four groups independently selected from: C$_{1-6}$alkyl; halo-C$_{1-6}$alkyl; C$_{1-6}$alkoxy; halo-C$_{1-6}$alkoxy; hydroxy; C$_{1-6}$alkoxy-C$_{1-6}$alkyl; hydroxy-C$_{1-6}$alkyl; halo, nitrile; C$_{1-6}$alkyl-carbonyl; C$_{1-6}$alkyl-sulfonyl; C$_{3-6}$Cycloalkyl; C$_{3-6}$Cycloalkyl-C$_{1-6}$alkyl; C$_3$-6Cycloalkyl-carbonyl; amino; or heterocyclyl; or two of the groups together with the atoms to which they are attached may form a five or six-membered ring; and R$^7$ is: halo; C$_{1-6}$alkyl; C$_{1-6}$alkoxy; halo-C$_{1-6}$alkyl; or halo-C$_{1-6}$alkoxy; and R$^8$ is: halo; C$_{1-6}$alkyl; or oxo.

In one embodiment, the LRRK2 inhibitor is selected from: 8-methoxy-2-[(5-methyl-1,2-oxazol-3-yl)methyl]-1-[(2R,4R)-2-methyltetrahydro-2H-pyran-4-yl]-1H-imidazo[4,5-c]quinoline; 8-methoxy-2-[(5-methyl-1,2-oxazol-3-yl)methyl]-1-[(2S,4S)-2-methyltetrahydro-2H-pyran-4-yl)-1H-imidazo(4,5-c)quinoline; 8-chloro-2-[(5-methoxypyridin-2-yl)methyl)-1-[(2R,4R)-2-methyltetrahydro-2H-pyran-4-yl]-1H-imidazo[4,5-c]quinolone; 2-[(5-methyl-1,2-oxazol-3-yl)methyl)-1-[(2R,4R)-2-methyltetrahydro-2H-pyran-4-yl)-1H-imidazo[4,5-c]quinoline-8-carbonitrile; 8-chloro-2-[(5-methyl-1,2-oxazol-3-yl)methyl]-1-[(2R,4R)-2-methyltetrahydro-2H-pyran-4-yl)-1H-imidazo[4,5-c]quinoline; 8-chloro-2-[(5-methyl-1,2,4-oxadiazol-3-yl)methyl)-1-[(2R,4R)-2-methyltetrahydro-2H-pyran-4-yl)-1H-imidazo[4,5-c]quinoline; 8-bromo-1-[(1S,3R)-3-fluorocyclopentyl)-2-methyl-1H-imidazo[4,5-c]quinoline; 1-[(2R,4R)-2-methyltetrahydro-2H-pyran-4-yl)-2-(1,3-thiazol-4-ylmethyl)-1H-imidazo[4,5-c][1,5]naphthyridine; 1-((2S,4S)-2-methyltetrahydro-2H-pyran-4-yl]-2-(1,3-thiazol-4-ylmethyl)-1H-imidazo(4,5-c)[1,5) naphthyridine; 8-chloro-2-(imidazo[2,1-b][1,3,4]thiadiazol-6-ylmethyl)-1-[(2R,4R)-2-methyltetrahydro-2H-pyran-4-yl]-1H-imidazo[4,5-c]quinoline; {8-chloro-1-((2R,4R)-2-methyltetrahydro-2H-pyran-4-yl]-1H-imidazo[4,5-c]quinolin-2-yl}acetonitrile; 8-chloro-1-[(2R,4R)-2-methyltetrahydro-2H-pyran-4-yl]-2-(1,3-thiazol-4-ylmethyl)(4-$^2$H)-1H-imidazo[4,5-c]quinoline; 8-chloro-1-[(2R,4R)-2-methyltetrahydro-2H-pyran-4-yl]-2-[(4-methyl-1H-1,2,3-triazol-1-yl)methyl)-1H-imidazo[4,5-c]quinoline; 8-bromo-1-[(2R,4R) 2-methyltetrahydro-2H-pyran4-yl]-2-(1,2-oxazol-3-ylmethyl)-1H-imidazo[4,5-c]quinoline; 8-chloro-1-[(2R,4R)-2-methyltetrahydro-2H-pyran-4-yl)-2-(1,2,4-oxadiazol-3-ylmethyl)-1H-imidazo[4,5-c]quinoline; 2-methyl-1-(teahydro-2H-pyran-4-yl)-1H-imidazo[4,5-c]quinolone-8-carbonitrile; 2-methyl-1-(cis-2-methyltetrahdro-2H-pyran-4-yl)-1H-imidazo[4,5-c]quinoline; 1-[(1R,3S)-3-fluorocyclopentyl]-2-(1,2-oxazol-3-ylmethyl)-1H-imidazo[4,5-c]quinoline; 8-chloro-2-methyl-1-(teahdro-2H-pyran-4-yl)-1H-imidazo[4,5-c]quinolone; 2-(1,2-oxazol-3-ylmethyl)-1(tetrahydro-2H-pyran-4-yl)-1H-imidazo[4,5-c]quinoline, 2-methyl-1-(cis-2-methyltetrahydro-2H-pyran-4-yl)-1H-imidazo[4,5-c]quinoline-8-carbonitrile; 1-[(1S,3R)-3-fluorocyclopentyl]-2-methyl-1H-imidazo[4,5-c]quinoline-8-carbonitrile; 1-(cis-2-methyltetrahydro-2H-pyran-4-yl)-2-(1,2-oxazol-3-ylmethyl)-1H-imidazo[4,5-c]quinoline-8-cabonitrile; 1-[(2R-4R)-2-methyltetrahydro-2H-pran-4-yl]-2-(1,2-oxazol-3-ylmethyl)-1H-imidazo[4,5-c]quinoline-8-carbonitrile; 1-(trans-2-methyltetrahydro-2H-pyran-4-yl)-2-(1,2-oxazol- 3-ylmethyl)-1H-imidazo[4,5-c]quinoline-8-carbonitrile; 1-[(2S,4R)-2-methyltetrahydro-2H-pyran-4-yl]-2-(1,2-oxazol-3-ylmethyl)-1H-imidazo[4,5-c]quinoline-8-carbonitrile; 8-bromo-1-[(1S,3R)-3-fluorocyclopentyl]-2-(1,2-oxazol-3-ylmethyl)-1H-imidazo[4,5-c]quinoline; 1-[(1R,3S)-3-fluorocyclopentyl]-2-(1H-1,2,4-triazol-1-ylmethyl)-1H-imidazo[4,5-c]quinoline; 1-[(1R,3S)-3-fluorocyclopentyl]-2-[(4-methyl-1H-1,2,3-triazol-1-yl)methyl]-1H-imidazo[4,5-c]quinoline; 2-(1,3-benzoxazol-2-ylmethyl)-1-[(1R,3S)-3-fluorocyclopentyl]-1H-imidazo[4,5-c]quinoline; 2-(1,2-benzoxazol-3-ylmethyl)-1-(tetrahydro-2H-pyran-4-yl)-1H-imidazo[4,5-c]quinoline; 1-(tetrahydro-2H-pyran-4-yl)-2-(1H-1,2,4-triazol-1-ylmethyl)-1H-imidazo[4,5-c]quinoline; 2-[(2-methylimidazo[2,1-b][1,3]thiazol-6-yl)methyl]-1(tetrahydro-2H-pyran-4-yl)-1H-imidazo[4,5-c]quinoline; 2-[(4-methyl-1H-1,2,3-triazol-1-yl)methyl]-1-(tetrahydro-2H-pyran-4-yl)-1H-imidazo[4,5-c]quinoline; 2-{[4-methoxymethyl)-1H-1,2,3-triazol-1-yl]methyl}-1-(tetrahydro-2H-pyran-4-yl)-1H-imidazo[4,5-c]quinoline; 2-(1,3-benzoxazol-2-ylmethyl)-1-(tetrahydro-2H-pyran-4-yl)-1H-imidazo[4,5-c]quinoline; 1-(tetrahydro-2H-pyran-4-yl)-2-(1H-tetrazol-1-ylmethyl)-1H-imidazo[4,5-c]quinoline; 1-(tetrahydro-2H-pyran-4-yl)-2-(1,3-thiazol-4-ylmethyl)-1H-imidazo[4,5-c]quinoline; 2-[(5-methoxypyridin-2-yl) methyl]-1-(tetrahydro-2H-pyran-4-yl)-1H-imidazo[4,5-c]quinoline; 2-[(2-methylimidazo[2,1-b][1,3]thiazol-6-yl)methyl]-1-(tetrahydro-2H-pyran-4-yl)-1H-imidazo[4,5-c]quinoline; 2-[(5-methyl-1,2-oxazol-3-yl)methyl]-1-(tetrahydro-2H-pyran-4-yl)-1H-imidazo[4,5-c]quinoline; 2-(1-{[tetrahydro-2H-pyran-4-yl)-1H-imidazo[4,5-c]quinoline-2-yl]methyl}-1H-1,2,3-triazol-4-yl)propan-2-ol; 2-(1H-benzotriazol-1-ylmethyl)-1-(tetrahydro-2H-pran-4-yl)-1H-imidazo[4,5-c]quinoline; 2-[(4-cyclopropyl-1H-1,2,3-triazol-1-yl)methyl]-1-(tetrahydro-2H-pyran-4-yl)-1H-imidazo[4,5-c]quinoline; 1-(tetrahydro-2H-pyran-4-yl)-2-{[4-(trifluoromethyl)-1H-pyrazol-1-yl]methyl}-1H-imidazo[4,5-c]quinoline; 2-{[4-(propan-2-yl)-1H-1,2,3-triazol-1-yl]methyl}-1-(tetrahydro-2H-pyran-4-yl)-1H-imidazo[4,5-c]quinoline; 2-(2H-indazol-2-ylmethl)-1-(tetrahydro-2H-pyran-4-yl)-1H-imidazo[4,5-c]quinoline; 1-(2,2-difluorocyclohexyl)-2-(1,2,-oxazol-3-ylmehyl)-1H-imidazo[4,5-c]quinoline; 1-(2,2-dimethyltetrahdro-2H-pyran-4-yl)-2-(1,2,-oxazol-3-ylmehyl)-1H-imidazo[4,5-c]quinoline; 1-(4,4-difluorocyclohexyl)-2-(1,2,-oxazol-3-ylmethyl)-1H-imidazo[4,5-c]quinoline; trans-3-[2-(1,2,-oxazol-3-ylmethyl)-1H-imidazo[4,5-c]quinolin-1-yl]cyclohexanol; 1-cyclohexyl-2-(1,2-oxazol-3-ylmethyl)-1H-imidazo[4,5-c]quinoline; 8-chloro-2-[(5-methyl-1,2,4-oxadiazol-3-yl]-1-[(2S,4S)-2-methyltetrahydro-2H-pyran-4-yl)-1H-imidazo[4,5-c]quinoline; 8-chloro-1-[(2R,4R)-2 methyltetrahydro-2H-pyran-4-yl]-2-(1,2-oxazol-3-ylmethyl-1H-imidazo[4,5-c]quinoline; 8-chloro-1-[(2R,4R)-2 methyltetrahydro-2H-pyran-4-yl]-2-(1,3-thiazol-4-ylmethyl)-1H-imidazo[4,5-c]quinoline; 8-fluoro-1-[(2R,4R)-2 methyltetrahydro-2H-pyran-4-yl]-2-(1,2-oxazol-3-ylmethyl)-1H-imidazo[4,5-c]quinoline; 8-fluoro-1-[(2R,4R)-2 methyltetrahydro-2H-pyran-4-yl]-2-(1,3-thiazol-4-ylmethyl)-1H-imidazo[4,5-c]quinoline; 8-bromo-1-(cis-2-methyltetrahydro-2H-pyran-4-yl]-2-(1,3-thiazol-4-ylmethl)-1H-imidazo[4,5-c]quinoline; 1-[(2R,4R)-2-methyltetrahydro-2H-pyran-4-yl]-2-(1,3-thiazol-4-ylmethl)-1H-imidazo[4,5-c]quinoline-8-carbonitrile; 8-bromo-2-[(5-methyl-1,2-oxazol-3-yl)methyl]-1-(cis-2-methyltetrahydro-2H-pyran-4-yl)-1H-imidazo[4,5-c]quinoline; 8-bromo-1-[(2R,4r,6S)-2,6-dimethyltetrahydro-2H-pyran-4-yl]-2-(1,2-oxazol-3-ylmethyl)-1H-imidazo[4,5-c]quinoline; 8-bromo-1-[(2R,4r,6S)-2,6-dimethyltetrahydro-2H-pyran-4-yl]-2-(1,2-oxazol-3-ylmethyl)-1H-imidazo[4,5-c]quinoline; 8-bromo-1-[(-[2R,4r,6S)-2,6-dimethyltetrahydro-2H-pyran-4-yl]-2-(1,3-thiazol-4-ylmethyl)-1H-imidazo[4,5-c]quinoline; 1-[(2R,4r6S)-2,6-dimethyltetrahydro-2H-pyran-4-yl]-2-(1,3-thiazol-4-ylmethyl)-1H-imidazo [4,5-c]quinoline-8-carbonitrile; 8-methoxy-1-[(2R,4R)-2-methyltetrahydro-2H-pyran-4-yl]-2-(1,2-oxazol-3-ylmethyl)-1H-imidazo[4,5-c]quinoline; 8-chloro-2-(1,2-oxazol-3-ylmethyl)-1-(tetrahydro-2H-pyran-4-yl)-1H-imidazo[4,5-c]quinoline; 8-chloro-2-(imidazo[2,1-b][1,3,4]thiadiazol-6-ylmethyl)-1-[(2S,4S)-2-methyltetrahydro-2H-pyran-4-yl]-1H-imidazo[4,5-c]quinoline; 8-chloro-1-[(2R,4R)-2-methyltetrahydro-2H-pyran-4-yl]-2-(1H-1,2,4-triazol-1-ylmethyl)-1H-imidazo[4,5-c]quinoline; 8-bromo-1-(cis-2-ethyltetrahydro-2H-pyran-4-yl)-2-(1,2-oxazol-3-ylmethyl)-1H-imidazo[4,5-c]quinoline; 1-[(2R,4R)-2-ethyltetrahydro-2H-pyan-4-yl]-2-(1,2-oxazol-3-ylmethyl)-1H-imidazo [4,5-c]quinoline-8-carbonitrile; 1-[(2R,4R)-2-methyltetrahydro-2H-pyran-4-yl]-2-(1,2-oxazol-3-ylmethyl)-1H-imidazo[4,5-c][1,5]naphthyridine; 2-(imidazo[2,1-b][1,3,4]thiadiazol-6-ylmethyl)-1-(tetrahydro-2H-pyran-4-yl)-1H-imidazo[4,5-c]quinoline; 1-(2,2-dimethyltetrahydro-2H-pyran-4-yl)-8-fluoro-2-[(5-methoxypyridin-2-yl)methyl]-1H-imidazo[4,5-c]quinoline; 2-[(2-chloroimidazo[2,1-b][1,3]thiazol-6yl)methyl]-1-tetrahydro-2H-pyran-4-yl)-1H-imidazo[4,5-c]quinoline; 1-(2,2-dimethyltetrahydro-2H-pyran-4-yl)-2-(1,3-thiazol-4-ylmethyl)-1H-imidazo [4,5-c]quinoline; 1-(2,2-dimethyltetrahydro-2H-pyran-4-yl)-2-(imidazo[2,1-b] [1,3,4]thiadiazol-6-ylmethyl)-1H-imidazo[4,5-c]quinoline; 8-fluoro-1-(tetrahydro-2H-pyran-4yl)-2-{[4-(trifluoromethyl)-1H-1,2,3-triazol-1-yl]methyl}-1H-imidazo[4,5-c]quinoline; 8-fluoro-2-(1,2-oxazol-3-ylmrthyl)-1-(tetrahydro-2H-pyran-4-yl)-1H-imidazo[4,5-c]quinoline; 8-fluoro-2-(2H-indazol-2ylmethyl)-1-(tetrahydro-2H-pyran-4-yl)-1H-imidazo[4,5-c]quinoline; 8-fluoro-1-(tetrahydro-2H-pyran-4yl)-2-(1,3-thiazol-4-ylmethyl)-1H-imidazo[4,5-c]quinoline; 8-fluoro-1-(tetrahydro-2H-pyran-4yl)-2-{[4-(trifluoromethyl)-1H-pyrazol-1-yl]methyl}-1H-imidazo[4,5-c]quinoline; 2-[(4-cyclopropyl-1H-1,2,3-triazol-1-yl)-1-(2,2-dimethyltetrahydro-2H-pyran-4-yl)-8-fluoro-1H-imidazo[4,5-c]quinoline; 1-(2,2-dimethyltetrahydro-2H-pyran-4-yl)-8-fluoro-2-(1,3-thiazol-4-ylmethyl)-1H-imidazo[4,5-c]quinoline; 1-(2,2-dimethyltetrahydro-2H-pyran-4-yl)-8-fluoro-2-{[4-(trifluoromethyl)-1H-pyrazol-1-yl]methyl}-1H-imidazo[4,5-c]quinoline; 8-fluoro-2-(imidazo[2,1-b][1,3,4]thiadiazol-6-ylmthl)-1-(terahydro-2H-pyran-4-yl)-1H-imidazo[4,5-c]quinoline; 1-(2,2-dimethyltetrahydro-2H-pyran-4-yl)-8-fluoro-2-[(2-methylimidazo[2,1-b][1,2,3]thiadiazol-6-yl)methyl]-1H-imidazo[4,5-c]quinoline; 1-(2,2-dimethyltetrahydro-2H-pyran-4-yl)-8-fluoro-2-(1,2-oxazol-3-ylmethyl)-1H-imidazo[4,5-c]quinoline; 8-chloro-1-[(2R,4R)-2-methyltetrahydro-2H-pyran-4-yl]-2-(1,3-thiazol-4-ylmethyl)-1H-imidazo[4,5-c]quinolin-4-amine; 8-fluoro-2-(imidazo[2,1-b][1,3,4]thiadiazol-6-ylmethyl)-1-(cis-2-methyltetrahydro-2H-pyran-4-yl)-1H-imidazo[4,5-c]quinoline; 8-methoxy-2-[(5-methyl-1,2,4-oxadiazol-3-yl)methyl]-1-[(2R,4R)-2-methyltetrahydro-2H-pyran-4-yl]-1H-imidazo[4,5-c]quinoline; 8-methoxy-1-[(2R,4R)-2-methyltetrahydro-2H-pyran-4-yl]-2-[(4-methyl-1H-1,2,3-triazol-1-yl)methyl]-1H-imidazo[4,5-c]quinoline; 8-methoxy-1-[(2R,4R)-2-methyltetrahydro-2H-pyran-4-yl]-2-(1,3-thiazol-4-ylmethyl)-1H-imidazo[4,5-c]quinoline; 2-(imidazo[2,1-b][1,3,4]thiadiazol-6-ylmethyl)-8-methoxy-1-[(2R,4R)-2-methyltetrahydro-2H-pyran-4-yl]-1H-imidazo[4,5-c]quinoline; [cis-4-(2-methyl-1H-imidazo[4,5-c]quinoline-1-yl)tetrahydro-2H-pyran-2-yl]acetonitrile; and 8-chloro-2-[(5-methyl-1,3-oxazol-2-yl)methyl]-1-[(2R,4R)-2-methyltetrahydro-2H-pyran-4-yl]-1H-imidazo[4,5-c]quinoline; or a pharmaceutically acceptable salt thereof.

In an embodiment, the LRRK2 inhibitor is a compound selected from: N2-(2-chloro-4-(2H-tetrazol-5-yl)phenyl)-N4-methyl-5-(trifluoromethyl)pyrimidine-2,4-diamine, N2-(2-chloro-4-(1-methyl-1H-tetrazol-5-yl)phenyl)-N4-methyl-5-(trifluoromethyl)pyrimidine-2,4-diamine, N2-(2-chloro-4-(2-methyl-2H-tetrazol-5-yl)phenyl)-N4-methyl-5-(trifluoromethyl)pyrimidine-2,4-diamine, N2-(2-methoxy-4-(1H-1,2,4-triazol-1-yl)phenyl)-N4-methyl-5-(trifluoromethyl)pyrimidine-2,4-diamine, N2-(2-methoxy-4-(1-methyl-1H-pyrazol-4-yl)phenyl)-N4-methyl-5-(trifluoromethyl)pyrimidine-2,4-diamine, N2-(5-fluoro-2-methoxy-4-(3-methyl-1,2,4-oxadiazol-5-yl)phenyl)-N4-methyl-5-trifluoromethyl)pyrimidine-2,4-diamine, N2-(2-chloro-5-methoxy-4-(5-methyl-1,3,4-oxadiazol-2-yl)phenyl)-N4-methyl-5-(trifluoromethyl)pyrimidine-2,4-diamine, N2-(2-methoxy-4-(1-methyl-1H-imidazol-5-yl)phenyl)-N4-methyl-5-(trifluoromethyl)pyrimidine-2,4-diamine, N2-(4-methoxy-6-(thiazol-5-yl)pyridin-3-yl)-N4-methyl-5-(trifluoromethyl)pyrimidine-2,4-diamine, 5-chloro-N2-(2-methoxy-4-(1-methyl-1H-tetrazol-5-yl)phenyl)-N4-methylpyrimidine-2,4-diamine, N2-(2-chloro-5-methoxy-4-(1-methyl-1H-1,2,3-triazol-5-yl)phenyl)-N4-methyl-5-(trifluoromethyl)pyrimidine-2,4-diamine, N2-(4-methoxy-6-(thiazol-4-yl)pyridin-3-yl)-N4-methyl-5-(trifluoromethyl)pyrimidine-2,4-diamine, N2-(4-methoxy-6-(oxazol-2-yl)pyridin-3-yl)-N4-methyl-5-(trifluoromethyl)pyrimidine-2,4-diamine, 5-chloro-N2-(4-(isoxazol-4-yl)-2-methoxyphenyl)-N4-methylpyrimidine-2,4-diamine, 5-chloro-N2-(2-methoxy-4-(1-methyl-1H-imidazol-2-yl)phenyl)-N4-methylpyrimidine-2,4-diamine, 5-chloro-N2-(2-methoxy-4-(1-methyl-1H-imidazol-5-yl)phenyl)-N4-methylpyrimidine-2,4-diamine, N2-(2-methoxy-4-(1-methyl-1H-1,2,3-triazol-5-yl)phenyl)-N4-methyl-5-(trifluoromethyl)pyrimidine-2,4-diamine, N2-(2-methoxy-4-(2-methyl-2H-tetrazol-5-yl)phenyl)-N4-methyl-5-(trifluoromethyl)pyrimidine-2,4-diamine, N2-(2-chloro-5-methoxy-4-(1-methyl-1H-imidazol-2-yl)phenyl)-N4-methyl-5-(trifluoromethyl)pyrimidine-2,4-diamine, N2-(2-methoxy-4-(1-methyl-1H-tetrazol-5-yl)phenyl)-N4-methyl-5-(trifluoromethyl)pyrimidine-2,4-diamine, N2-(2-chloro-5-methoxy-4-(1-methyl-1H-imidazol-5-yl)phenyl)-N4-methyl-5-(trifluoromethyl)pyrimidine-2,4-diamine, N2-(5-fluoro-2-methoxy-4-(1-methyl-1H-tetrazol-5-yl)phenyl)-N4-methyl-5-(trifluoromethyl)pyrimidine-2,4-diamine, 5-chloro-N2-(2-methoxy-4-(1-methyl-1H-1,2,3-triazol-5-yl)phenyl)-N4-methylpyrimidine-2,4-diamine, N2-(2-chloro-5-methoxy-4-(1,3,5-trimethyl-1H-pyrazol-4-yl)phenyl)-N4-methyl-5-(trifluoromethyl)pyrimidine-2,4-diamine, N2-(2-methoxy-4-(1-methyl-1H-pyrazol-5-yl)phenyl)-N4-methyl-5-(trifluoromethyl)pyrimidine-2,4-diamine, N2-(4-(3,5-dimethylisoxazol-4-yl)-2-methoxyphenyl)-N4-methyl-5-(trifluoromethyl)pyrimidine-2,4-diamine, N2-(2-methoxy-4-(1H-tetrazol-1-yl)phenyl)-N4-methyl-5-(trifluoromethyl)pyrimidine-2,4-diamine, N2-(2-chloro-5-methoxy-4-(1-methyl-1H-pyrazol-5-yl)phenyl)-N4-methyl-5-(trifluoromethyl)pyrimidine-2,4-diamine, N4-ethyl-N2-(5-fluoro-2-methoxy-4-(5-methyl-1,3,4-oxadiazol-2-yl)phenyl)-5-(trifluoromethyl)pyrimidine-2,4-diamine, N2-(5-fluoro-2-methoxy-4-(5-methyl-1,3,4-oxadiazol-2-yl)phenyl)-N4-methyl-5-(trifluoromethyl)pyrimidine-2,4-diamine, N2-(2-chloro-5-methoxy-4-(3-methyl-1,2,4-oxadiazol-5-yl)phenyl)-N4-methyl-5-(trifluoromethyl)pyrimidine-2,4-diamine, N2-(2-chloro-5-methoxy-4-(1-methyl-1H-pyrazol-4-yl)phenyl)-N4-methyl-5-(trifluoromethyl)pyrimidine-2,4-diamine, 5-chloro-N2-(2-chloro-4-(5-methyl-1,3,4-oxadiazol-2-yl)phenyl)-N4-methylpyrimidine-2,4-diamine, 5-chloro-N2-(2-chloro-4-(3-methyl-1,2,4-oxadiazol-5-yl)phenyl)-N4-methylpyrimidine-2,4-diamine, 5-chloro-N2-(2-methoxy-4-(1-methyl-1H-pyrazol-4-yl)phenyl)-N4-methylpyrimidine-2,4-diamine, 5-chloro-N2-(2-chloro-5-methoxy-4-(3-methyl-1,2,4-oxadiazol-5-yl)phenyl)-N4-methylpyrimidine-2,4-diamine, 5-chloro-N2-(2-chloro-5-methoxy-4-(5-methyl-1,3,4-oxadiazol-2-yl)phenyl)-N4-methylpyrimidine-2,4-diamine, N2-(4-(1,3-dimethyl-1H-pyrazol-4-yl)-2-methoxyphenyl)-N4-methyl-5-(trifluoromethyl)pyrimidine-2,4-diamine, N2-(4-(1,5-dimethyl-1H-pyrazol-4-yl)-2-methoxyphenyl)-N4-methyl-5-(trifluoromethyl)pyrimidine-2,4-diamine, N2-(2-methoxy-4-(4-methyl-4H-1,2,4-triazol-3-yl)phenyl)-N4-methyl-5-(trifluoromethyl)pyrimidine-2,4-diamine, 4-(2-fluoro-5-methoxy-4-(4-(methylamino)-5-(trifluoromethyl)pyrimidin-2-ylamino)phenyl)-N,N,1-trimethyl-1H-pyrazole-5-carboxamide, N2-(5-fluoro-2-methoxy-4-(5-methyl-1H-tetrazol-1-yl)phenyl)-N4-methyl-5-(trifluoromethyl)pyrimidine-2,4-diamine, N2-(5-fluoro-2-methoxy-4-(1-methyl-1H-1,2,3-triazol-5-yl)phenyl)-N4-methyl-5-(trifluoromethyl)pyrimidine-2,4-diamine, N2-(5-fluoro-2-methoxy-4-(1-(oxetan-3-yl)-1H-pyrazol-4-yl)phenyl)-N4-methyl-5-(trifluoromethyl)pyrimidine-2,4-diamine, N2-(2-methoxy-5-methyl-4-(5-methyl-1H-tetrazol-1-yl)phenyl)-N4-methyl-5-(trifluoromethyl)pyrimidine-2,4-diamine, N2-(2-methoxy-4-(5-(methoxymethyl)-1H-tetrazol-1-yl)-5-methylphenyl)-N4-methyl-5-(trifluoromethyl)pyrimidine-2,4-diamine, N2-(5-fluoro-2-methoxy-4-(5-(methoxymethyl)-3-methyl-1H-pyrazol-1-yl)phenyl)-N4-methyl-5-(trifluoromethyl)pyrimidine-2,4-diamine, N2-(2-methoxy-4-(5-(methoxymethyl)-3-methyl-1H-pyrazol-1-yl)phenyl)-N4-methyl-5-(trifluoromethyl)pyrimidine-2,4-diamine, and N2-(5-fluoro-2-methoxy-4-(5-(methoxymethyl)-1-tetrazol-1-yl)phenyl)2,4-diamine; or a pharmaceutically acceptable salt thereof.

In one embodiment, the LRRK2 inhibitor is 5-(1-methyl-1H-pyrazol-4-yl)-4-(morpholin-4-yl)-7H-pyrrolo[2,3-d]pyrimidine; 6-[4-(morpholin-4-yl)-7H-pyrrolo[2,3-d]pyrimidin-5-yl]pyridine-2-carbonitrile; 3-[4-(morpholin-4-yl)-7H-pyrrolo[2,3-d]pyrimidin-5-yl]benzonitrile; 3-[4-(dimethylamino)-7H-pyrrolo[2,3-d]pyrimidin-5-yl]benzonitrile; 3-{4-[(2S)-2-methylmorpholin-4-yl]-7H-pyrrolo[2,3-d]pyrimidin-5-yl}benzonitrile; 3-[4-(piperidin-1-yl)-7H-pyrrolo[2,3-d]pyrimidin-5-yl]benzonitrile; 3-[4-(dimethylamino)-7H-pyrrolo[2,3-d]pyrimidin-5-yl]-2-fluorobenzonitrile; 3-[4-(pyrrolidin-1-yl)-7H-pyrrolo[2,3-d]pyrimidin-5-yl]benzonitrile; 2-fluoro-3-[4-(morpholin-4-yl)-7H-pyrrolo[2,3-d]pyrimidin-5-yl]benzonitrile; 5-(3-chlorophenyl)-4-(morpholin-4-yl)-7H-pyrrolo[2,3-d]pyrimidine; 5-(5-fluoro-2-methoxyphenyl)-4-(morpholin-4-yl)-7H-pyrrolo[2,3-d]pyrimidine; 5-(5-bromopyridin-3-yl)-4-(morpholin-4-yl)-7H-pyrrolo[2,3-d]pyrimidine; 5-(imidazo[1,2-b]pyridazin-3-yl)-4-(morpholin-4-yl)-7H-pyrrolo[2,3-d]pyrimidine; or 1-methyl-4-[4-(morpholin-4-yl)-7H-pyrrolo[2,3-d]pyrimidin-5-yl]-1H-pyrrole-2-carbonitrile; or a pharmaceutically acceptable salt thereof. In one embodiment, the LRRK2 inhibitor is 5-(1-methyl-1H-pyrazol-4-yl)-4-(morpholin-4-yl)-7H-pyrrolo[2,3-d]pyrimidine; or a pharmaceutically acceptable salt thereof. In one embodiment, the LRRK2 inhibitor is 6-[4-(morpholin-4-yl)-7H-pyrrolo[2,3-d]pyrimidin-5-yl]pyridine-2-carbonitrile; or a pharmaceutically acceptable salt thereof. In one embodiment, the LRRK2 inhibitor is 3-[4-(morpholin-4-yl)-7H- pyrrolo[2,3-d]pyrimidin-5-yl]benzonitrile; or a pharmaceutically acceptable salt thereof. In one embodiment, the LRRK2 inhibitor is 3-{4-[(2S)-2-methylmorpholin-4-yl]-7H-pyrrolo[2,3-d]pyrimidin-5-yl}benzonitrile; or a pharmaceutically acceptable salt thereof.

In an embodiment, the LRRK2 inhibitor is a compound of the formula:

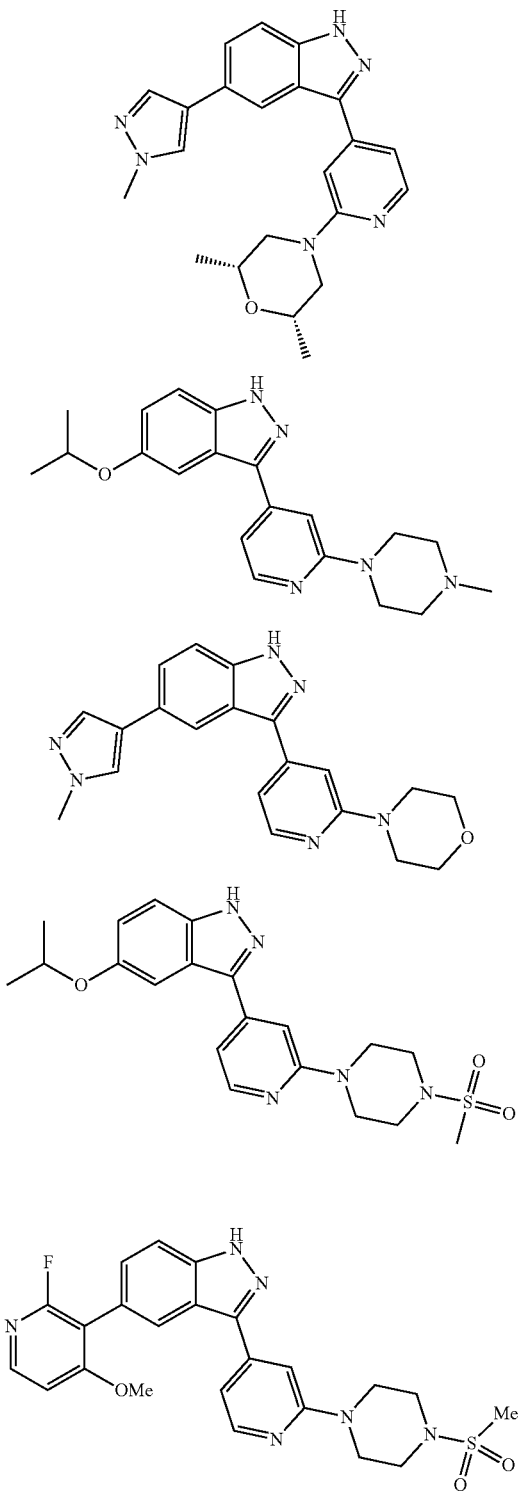

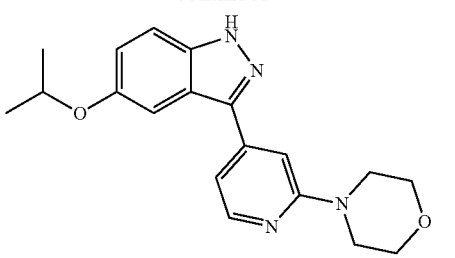 [SMILES: CC1(Oc2cc3c(-c4cc(N5CCOCC5)ncn4)n[nH]c3cc2F)CC1]

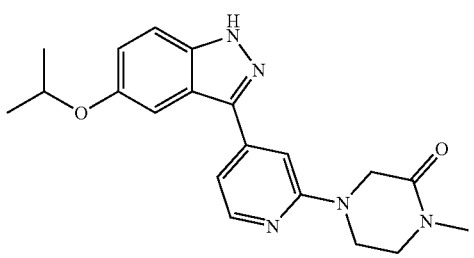

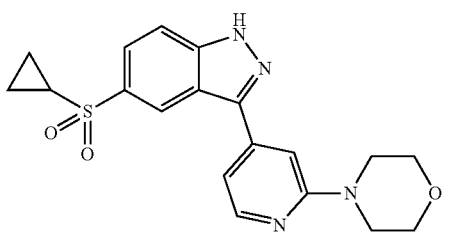

or a pharmaceutically acceptable salt thereof.

In an embodiment, the LRRK2 inhibitor is a compound selected from:

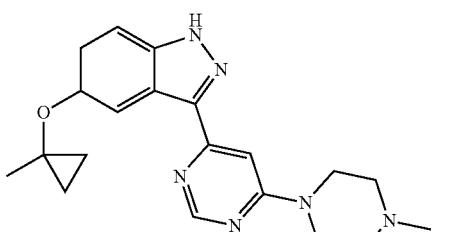

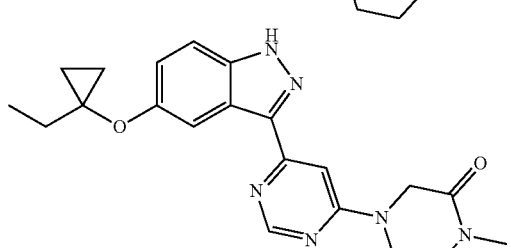

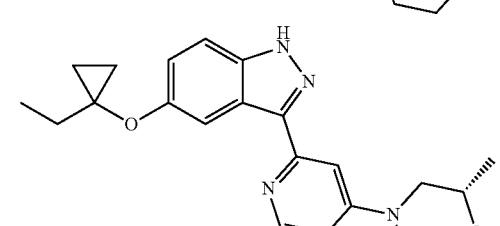

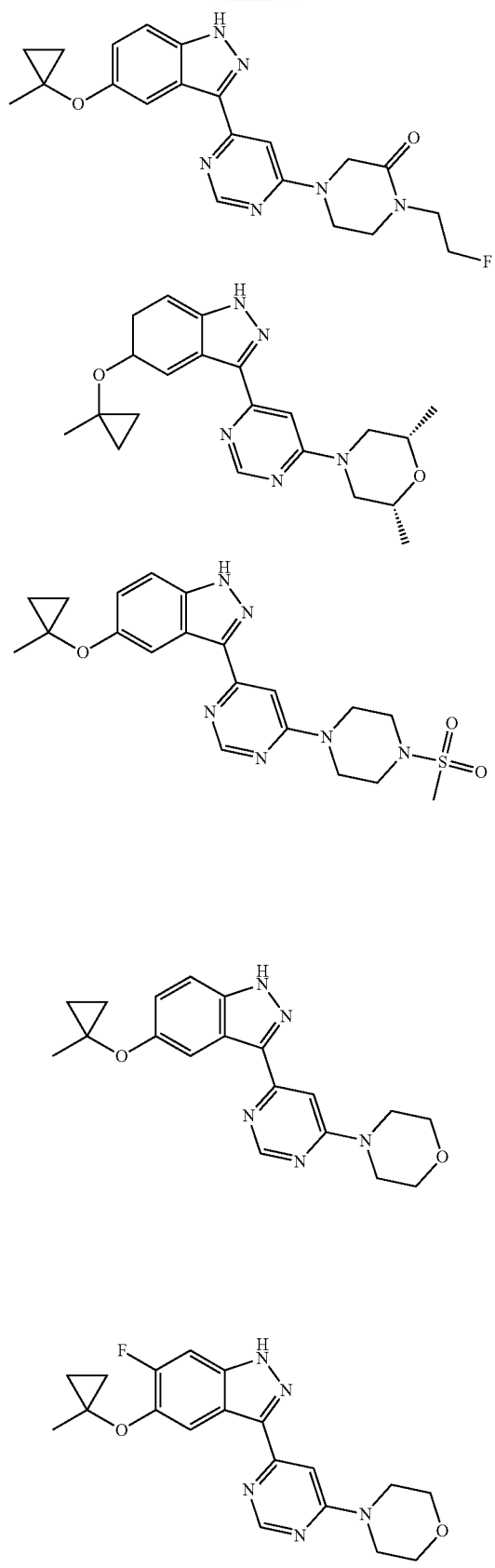
or a pharmaceutically acceptable salt thereof.
In an embodiment, the LRRK2 inhibitor is a compound selected from:
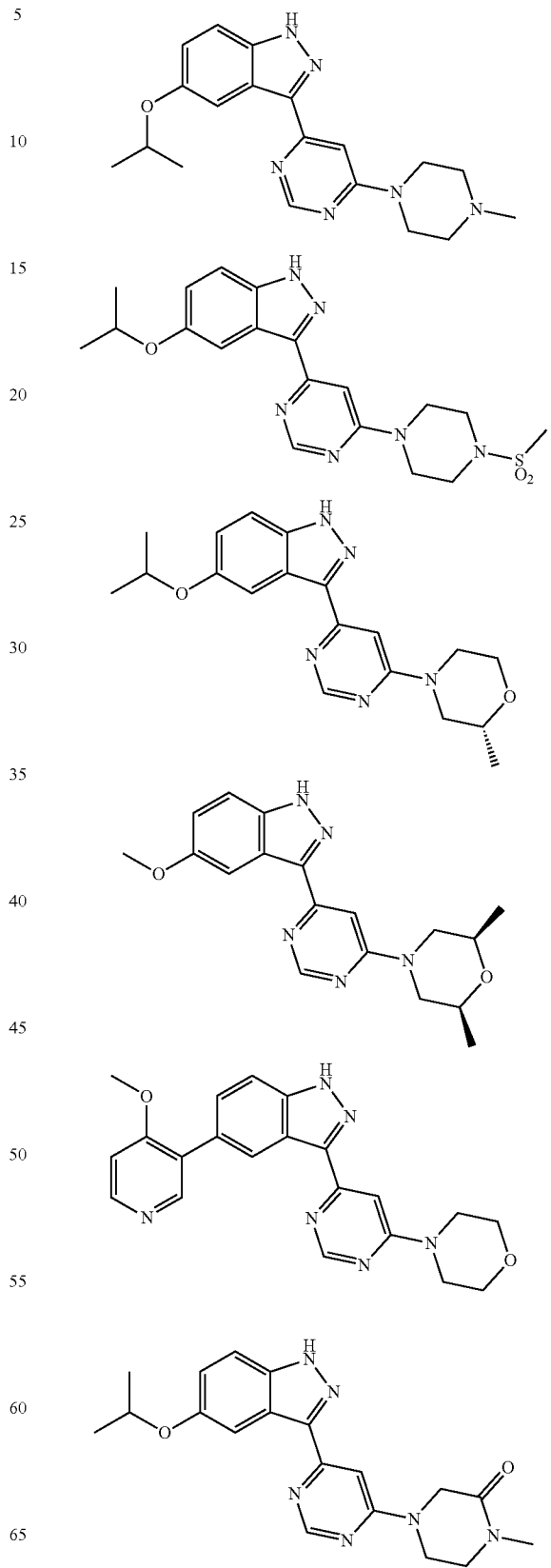

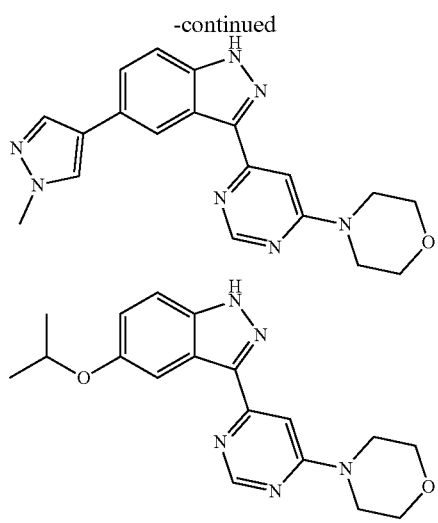
or a pharmaceutically acceptable salt thereof.
In an embodiment, the LRRK2 inhibitor is a compound or salt thereof selected from:
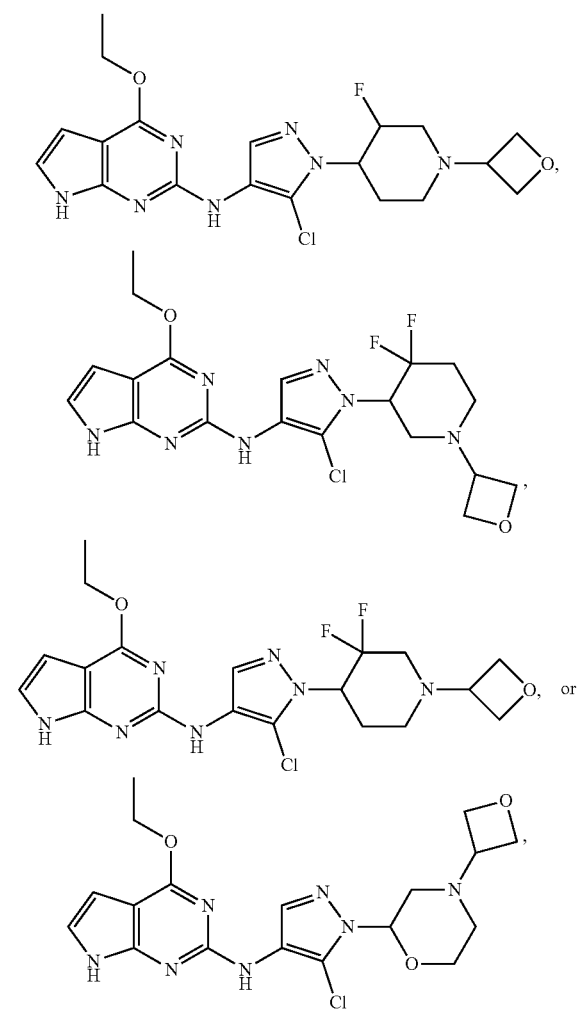
or a pharmaceutically acceptable salt thereof.
In an embodiment, the LRRK2 inhibitor is selected from:
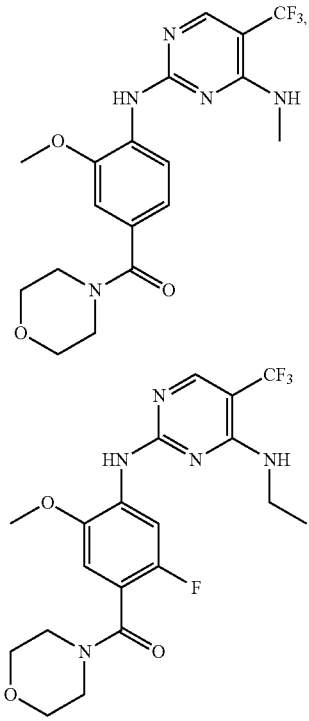
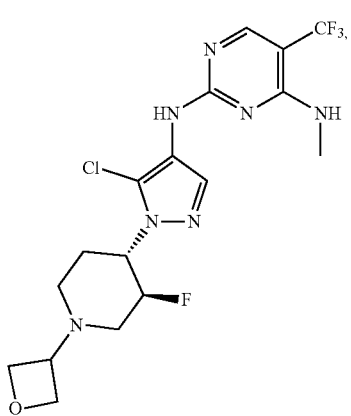

101
-continued
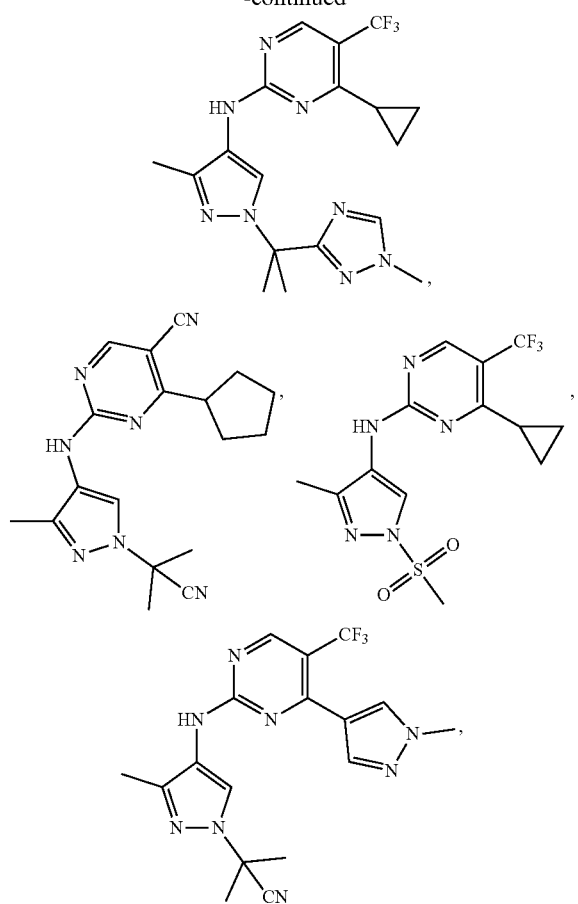
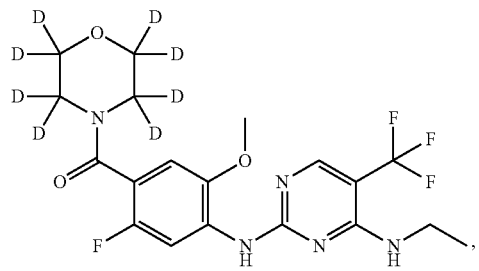
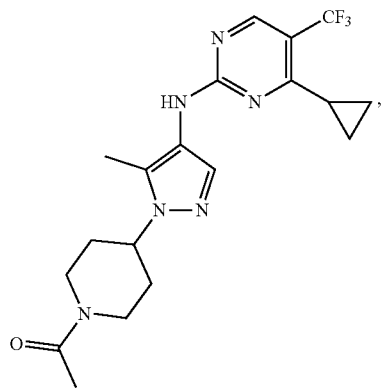
102
-continued
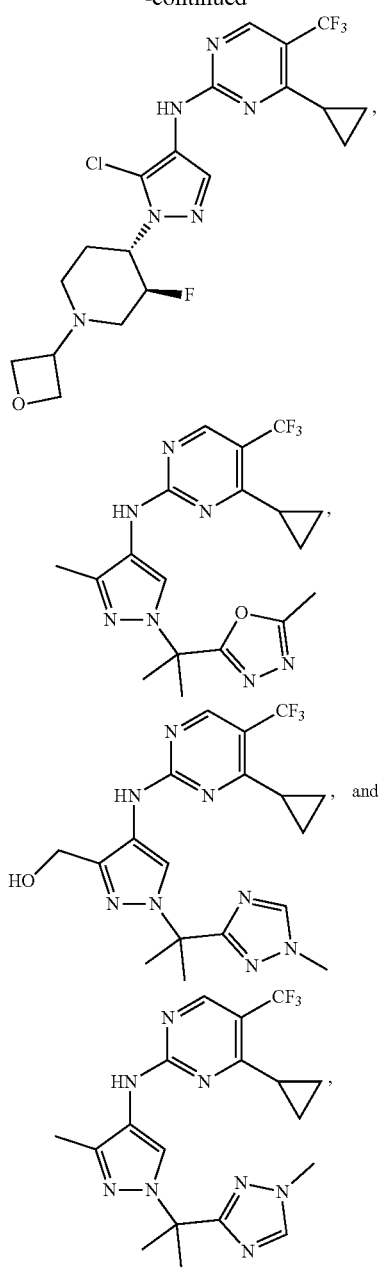
or a pharmaceutically acceptable salt thereof.
In an embodiment, the LRRK2 inhibitor is:
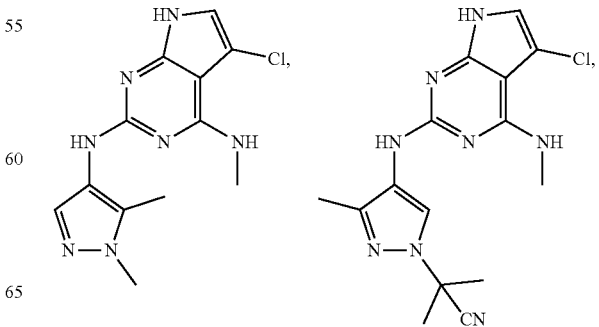

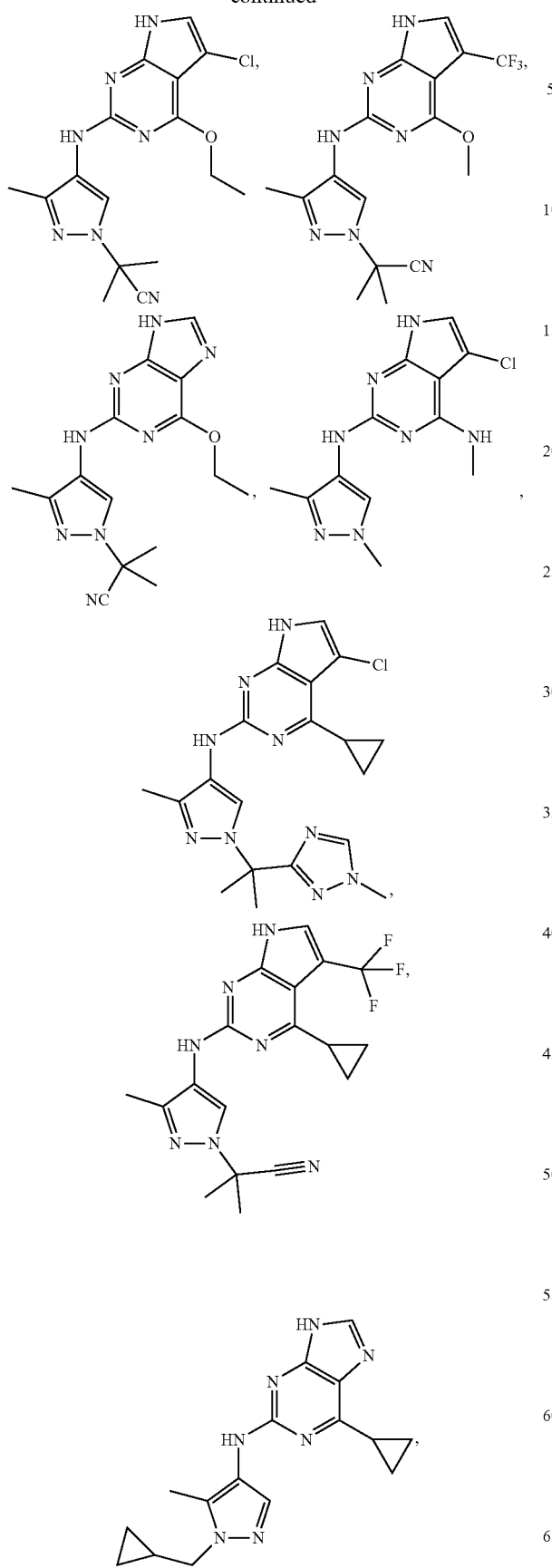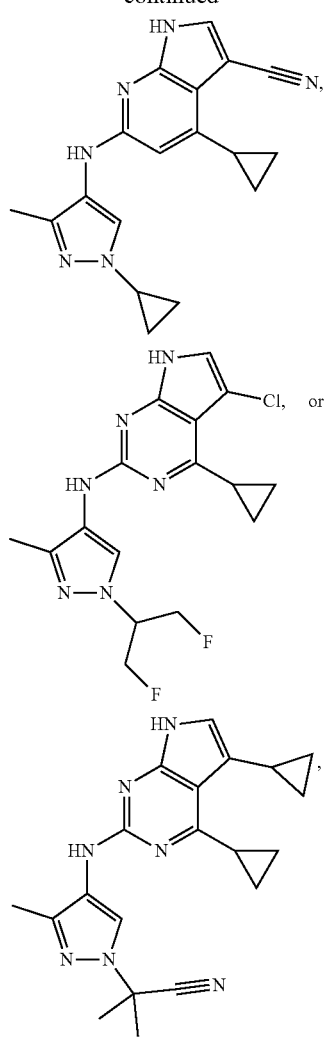
pharmaceutically acceptable salt thereof.
In an embodiment, the LRRK2 inhibitor is a compound or salt thereof selected from:
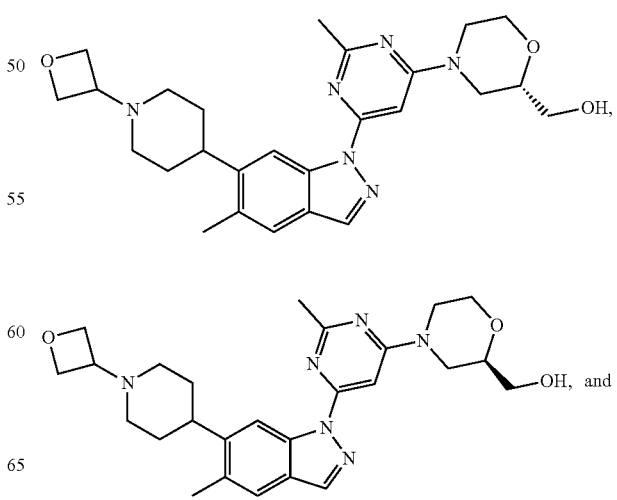

-continued

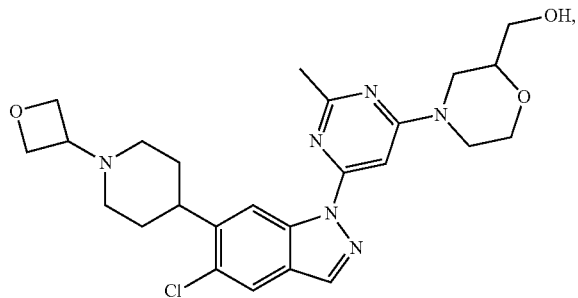

or a pharmaceutically acceptable salt thereof.

In one embodiment, the LRRK2 inhibitor is 3-[4-(morpholin-4-yl)-1H-pyrrolo[2,3-b]pyridin-3-yl]benzonitrile; 1-methyl-4-[4-(morpholin-4-yl)-1H-pyrrolo[2,3-b]pyridin-3-yl]-1H-pyrrole-2-carbonitrile; or 3-(1-methyl-1H-pyrazol-4-yl)-4-(morpholin-4-yl)-1H-pyrrolo[2,3-b]pyridine; or a pharmaceutically acceptable salt thereof.

In one embodiments, the LRRK2 inhibitor is a compound of the formula:

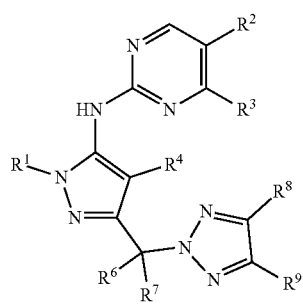

or a pharmaceutically acceptable salt, deuterated analog, prodrug, stereoisomer, or a mixture of stereoisomers thereof, wherein: $R^1$ is optionally substituted cycloalkyl or $C_{1-6}$ alkyl optionally substituted with halo; $R^2$ is halo, cyano, optionally substituted $C_{1-6}$ alkyl, optionally substituted $C_{2-6}$ alkenyl, optionally substituted $C_{2-6}$ alkynyl, optionally substituted cycloalkyl, optionally substituted $C_{1-6}$ alkoxy, optionally substituted cycloalkoxy, optionally substituted $C_{1-6}$ alkylthio, optionally substituted $C_{1-6}$ alkylsulfonyl, —C(O)$R^{10}$, or —C(O)N($R^{11}$)($R^{12}$); $R^3$ is optionally substituted $C_{1-6}$ alkoxy, optionally substituted cycloalkyl, optionally substituted cycloalkoxy, optionally substituted $C_{1-6}$ alkylthio, optionally substituted $C_{1-6}$ alkylsulfonyl, or —N($R^{11}$)($R^{12}$); $R^4$ is hydrogen or halo; $R^6$ and $R^7$ are each independently hydrogen or $C_{1-6}$ alkyl optionally substituted with halo; $R^8$ and $R^9$ are each independently hydrogen, cyano, halo, optionally substituted $C_{1-6}$ alkyl, optionally substituted $C_{1-6}$ alkoxy, or optionally substituted heteroaryl; $R^{10}$ is optionally substituted $C_{1-6}$ alkyl or optionally substituted $C_{1-6}$ alkoxy; and $R^{11}$ and $R^{12}$ are each independently hydrogen, optionally substituted $C_{1-6}$ alkyl, or optionally substituted cycloalkyl.

In an embodiment, the LRRK2 inhibitor is:

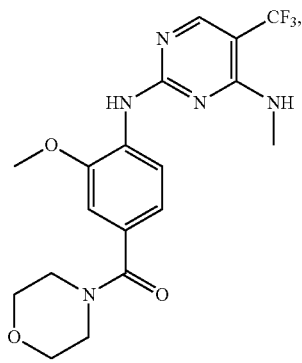 [SMILES: CNc1nc(Nc2ccc(C(=O)N3CCOCC3)cc2OC)ncc1C(F)(F)F]

or a pharmaceutically acceptable salt thereof.

In an embodiment, the LRRK2 inhibitor is:

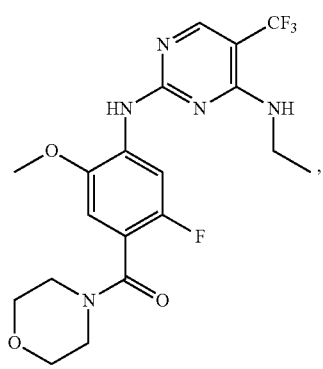 [SMILES: CCNc1nc(Nc2cc(F)c(C(=O)N3CCOCC3)cc2OC)ncc1C(F)(F)F]

or a pharmaceutically acceptable salt thereof.

In an embodiment, the LRRK2 inhibitor is:

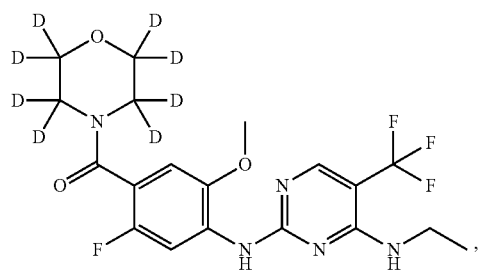 [SMILES: [2H]C1([2H])OC([2H])([2H])C([2H])([2H])N(C(=O)c2cc(OC)c(Nc3ncc(C(F)(F)F)c(NCC)n3)cc2F)C1([2H])[2H]]

or a pharmaceutically acceptable salt thereof.

107

In an embodiment, the LRRK2 inhibitor is:

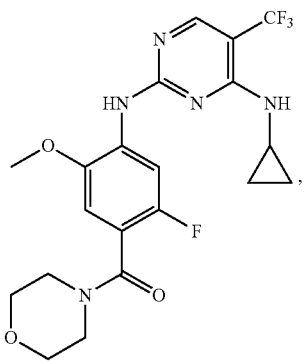 [SMILES: COc1cc(C(=O)N2CCOCC2)c(F)cc1Nc1ncc(C(F)(F)F)c(NC2CC2)n1]

or a pharmaceutically acceptable salt thereof.

In an embodiment, the LRRK2 inhibitor is:

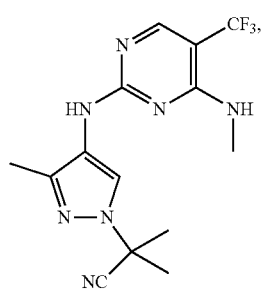 [SMILES: CNc1nc(Nc2cn(C(C)(C)C#N)nc2C)ncc1C(F)(F)F]

or a pharmaceutically acceptable salt thereof.

In an embodiment, the LRRK2 inhibitor is:

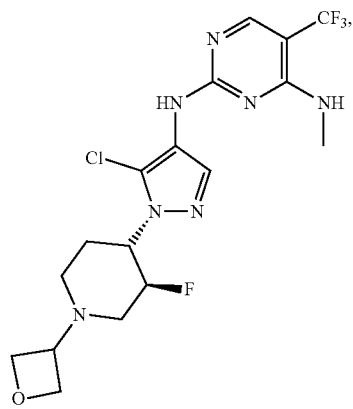

or a pharmaceutically acceptable salt thereof.

108

In an embodiment, the LRRK2 inhibitor is:

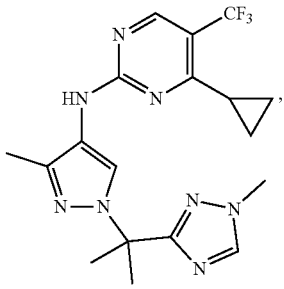 [SMILES: Cc1nn(C(C)(C)c2ncn(C)n2)cc1Nc1ncc(C(F)(F)F)c(C2CC2)n1]

or a pharmaceutically acceptable salt thereof.

In an embodiment, the LRRK2 inhibitor is:

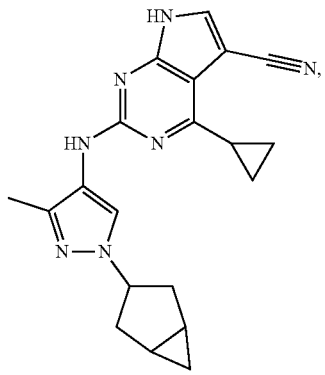 [SMILES: Cc1nn(C2CC3CC3C2)cc1Nc1nc(C2CC2)c2c(C#N)c[nH]c2n1]

or a pharmaceutically acceptable salt thereof.

In an embodiment, the LRRK2 inhibitor is:

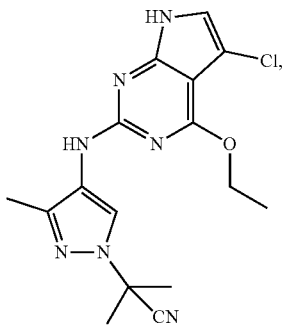 [SMILES: CCOc1nc(Nc2cn(C(C)(C)C#N)nc2C)nc2[nH]cc(Cl)c12]

or a pharmaceutically acceptable salt thereof.

In an embodiment, the LRRK2 inhibitor is:

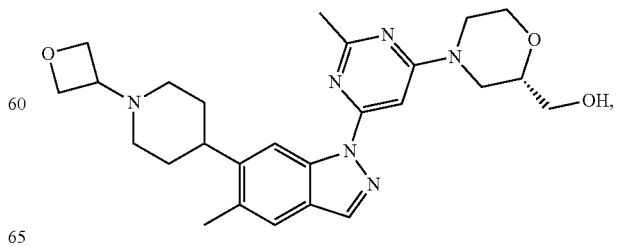

or a pharmaceutically acceptable salt thereof.

In an embodiment, the LRRK2 inhibitor is MLi-2, GNE-7915, GNE-0877, GNE-0965, CZC 25146, CZC 54252 hydrochloride, GSK2578215A, LRRK2-IN-1, PF 06447475, URMC-099, or TAE684.

In an embodiment, the LRRK2 inhibitor is 2-methyl-2-(3-methyl-4-(4-(methylamino)-5-(trifluoromethyl)pyrimidin-2-ylamino)-1H-pyrazol-1-yl)propanenitrile (LRRK2 Inhibitor B).

In an embodiments, the LRRK2 inhibitor (4-cyclopropyl-N-(3-methyl-1-(2-(1-methyl-1H-1,2,4-triazol-3-yl)propan-2-yl)-1H-pyrazol-4-yl)-5-(trifluoromethyl)pyrimidin-2-amine) (LRRK2 Inhibitor C).

In an embodiment, the LRRK2 inhibitor is cis-2,6-dimethyl-4-(6-(5-(1-methylcyclopropoxy)-1H-indazol-3-yl)pyrimidin-4-yl)morpholine or a pharmaceutically acceptable salt thereof.

In an embodiment, the LRRK2 inhibitor is (R)-N-(5-chloro-1-(3,3-difluoro-1-(oxetan-3-yl)piperidin-4-yl)-1H-pyrazol-4-yl)-4-ethoxy-7H-pyrrolo [2,3-d]pyrimidin-2-amine or a pharmaceutically acceptable salt thereof.

In an embodiment, the LRRK2 inhibitor is 2-(1,2-oxazol-3-ylmethyl)-1(tetrahydro-2H-pyran-4-yl)-1H-imidazo[4,5-c]quinolone or a pharmaceutically acceptable salt thereof.

In an embodiment, the LRRK2 inhibitor is 2-methyl-1-(cis-2-methyltetrahydro-2H-pyran-4-yl)-1H-imidazo[4,5-c]quinoline-8-carbonitrile or a pharmaceutically acceptable salt thereof.

In an embodiment, the LRRK2 inhibitor is 1-(2,2-dimethyltetrahydro-2H-pyran-4-yl)-8-fluoro-2-[(2-methylimidazo[2,1-b][1,2,3]thiadiazol-6-yl)methyl]-1H-imidazo[4,5-c]quinoline or a pharmaceutically acceptable salt thereof.

In an embodiment, the LRRK2 inhibitor is 1-(2,2-dimethyltetrahydro-2H-pyran-4-yl)-8-fluoro-2-(1,2-oxazol-3-ylmethyl)-1H-imidazo[4,5-c]quinoline or a pharmaceutically acceptable salt thereof.

In an embodiment, the LRRK2 inhibitor is 8-chloro-1-[(2R,4R)-2-methyltetrahydro-2H-pyran-4-yl]-2-(1,3-thiazol-4-ylmethyl)-1H-imidazo[4,5-c]quinolin-4-amine or a pharmaceutically acceptable salt thereof.

In an embodiment, the LRRK2 inhibitor is 8-fluoro-2-(imidazo[2,1-b][1,3,4]thiadiazol-6-ylmethyl]-1-(cis-2-methyltetrahydro-2H-pyran-4-yl)-1H-imidazo[4,5-c]quinoline or a pharmaceutically acceptable salt thereof.

In an embodiment, the LRRK2 inhibitor is N4-ethyl-N2-[1-(3-isocyanocyclobutyl)-5-methyl-pyrazol-4-yl]-5-(trifluoromethyl)pyrimidine-2,4-diamine or a pharmaceutically acceptable salt thereof.

In an embodiment, the LRRK2 inhibitor is [9]N4-ethyl-N2-[1-(2H$_3$))methyl-3-[2-(2H-1,2,3-triazol-2-yl)propan-2-yl]-1H-pyrazol-5-yl]-5-(trifluoromethyl)pyrimidine-2,4-diamine or a pharmaceutically acceptable salt thereof.

In an embodiment, the LRRK2 inhibitor is N2-[2-cyclopropyl-5-[1-methyl-1-(triazol-2-yl)ethyl]pyrazol-3-yl]-N4-ethyl-5-(trifluoromethyl)pyrimidine-2,4-diamine or a pharmaceutically acceptable salt thereof.

In an embodiment, the LRRK2 inhibitor is (3S)-3-[1-cyclopropyl-5-[[4-(ethylamino)-5-(trifluoromethyl)pyrimidin-2-yl]amino]pyrazol-3-yl]-3-methyl-tetrahydrofuran-2-one or a pharmaceutically acceptable salt thereof.

In an embodiment, the LRRK2 inhibitor is (3R)-3-[1-cyclopropyl-5-[[4-(ethylamino)-5-(trifluoromethyl)pyrimidin-2-yl]amino]pyrazol-3-yl]-3-methyl-tetrahydrofuran-2-one or a pharmaceutically acceptable salt thereof.

In an embodiment, the LRRK2 inhibitor is 1-(1-cyclopropyl-5-((4-(ethylamino)-5-(trifluoromethyl)pyrimidin-2-yl)amino)-1H-pyrazol-3-yl)pyrrolidin-2-one or a pharmaceutically acceptable salt thereof.

In an embodiment, the LRRK2 inhibitor is N2-(1-((1r,3r)-3-(2H-1,2,3-triazol-2-yl)cyclobutyl)-1H-pyrazol-5-yl)-N4-ethyl-5-(trifluoromethyl)pyrimidine-2,4-diamine or a pharmaceutically acceptable salt thereof.

VII. Pharmaceutical Compositions and Kits

In another aspect, pharmaceutical compositions and kits comprising an antibody that specifically binds to a phosphorylated Rab protein (e.g., Rab10 or Rab8a) are provided. In some embodiments, the pharmaceutical compositions and kits are for use in diagnosing Parkinson's disease, such as familial Parkinson's disease, sporadic Parkinson's disease, or LRRK2-associated Parkinson's disease, e.g., LRRK2-associated Parkinson's disease that is characterized by a I1122V, N1437H, R1441C/G/H, R1728H, R1628P, Y1699C, G2019S, I2020T, T2031S or G2385R mutation in LRRK2, or in some embodiments, a R1441C, R1441G, Y1699C, G2019S, or I2020T mutation. In some embodiments, the pharmaceutical compositions and kits are for use in treating a neurodegenerative disease, e.g., Parkinson's disease. In some embodiments, the pharmaceutical compositions and kits are for use in identifying whether a subject having a neurodegenerative disease is a suitable candidate for treatment with a LRRK2 inhibitor. In some embodiments, the pharmaceutical compositions and kits are for use in monitoring the efficacy of LRRK2 treatment in a subject having a neurodegenerative disease.

In another aspect, pharmaceutical compositions and kits comprising a LRRK2 inhibitor or a pharmaceutically acceptable salt thereof described herein are provided. In some embodiments, the pharmaceutical compositions and kits are for use in treating a neurodegenerative disease, e.g., Parkinson's disease.

Pharmaceutical Compositions

In some embodiments, pharmaceutical compositions comprising an anti-phosphorylated Rab (e.g., anti-phosphorylated Rab10 or anti-phosphorylated Rab8a) monoclonal antibody are provided. In some embodiments, the anti-phosphorylated Rab (e.g., anti-phosphorylated Rab10 or anti-phosphorylated Rab8a) monoclonal antibody is an antibody or antigen-binding fragment thereof as described in Section III above.

In some embodiments, a pharmaceutical composition comprises an anti-phosphorylated Rab (e.g., anti-phosphorylated Rab10 or anti-phosphorylated Rab8a) monoclonal antibody as described herein and further comprises one or more pharmaceutically acceptable carriers and/or excipients. A pharmaceutically acceptable carrier includes any solvents, dispersion media, or coatings that are physiologically compatible and that preferably does not interfere with or otherwise inhibit the activity of the active agent. Various pharmaceutically acceptable excipients are well-known in the art.

In some embodiments, pharmaceutical compositions and kits comprising a LRRK2 inhibitor or a pharmaceutically acceptable salt thereof further comprises one or more pharmaceutically acceptable carriers and/or excipients. A pharmaceutically acceptable carrier includes any solvents, dispersion media, or coatings that are physiologically compatible and that preferably does not interfere with or otherwise inhibit the activity of the active agent. Various pharmaceutically acceptable excipients are well-known in the art.

In some embodiments, the carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known in the art.

The pharmaceutical compositions described herein can be manufactured in a manner that is known to those of skill in the art, e.g., by means of conventional mixing, dissolving, granulating, dragee-making, emulsifying, encapsulating, entrapping or lyophilizing processes. The following methods and excipients are merely exemplary and are in no way limiting.

For oral administration, an anti-phosphorylated Rab monoclonal antibody can be formulated by combining it with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

For oral administration, a LRRK2 inhibitor or a pharmaceutically acceptable salt thereof can be formulated by combining it with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

An anti-phosphorylated Rab monoclonal antibody can be formulated for parenteral administration by injection, e.g., by bolus injection or continuous infusion. For injection, the compound or compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, compounds can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

In some embodiments, an anti-phosphorylated Rab monoclonal antibody is prepared for delivery in a sustained-release, controlled release, extended-release, timed-release or delayed-release formulation, for example, in semi-permeable matrices of solid hydrophobic polymers containing the active agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients. Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

Typically, a pharmaceutical composition for use in in vivo administration is sterile. Sterilization can be accomplished according to methods known in the art, e.g., heat sterilization, steam sterilization, sterile filtration, or irradiation.

Dosages and desired drug concentration of pharmaceutical compositions of the disclosure may vary depending on the particular use envisioned. The determination of the appropriate dosage or route of administration is well within the skill of one in the art. Suitable dosages are also described in Section VI above.

Kits

In some embodiments, kits comprising an anti-phosphorylated Rab monoclonal antibody, e.g., an anti-phosphorylated Rab10 monoclonal antibody or an anti-phosphorylated Rab8a monoclonal antibody, or an antigen-binding fragment thereof (e.g., as described in Section III above), or an anti-total Rab10 monoclonal antibody or an antigen-binding fragment thereof (e.g., as described in Section IV above), are provided. In some embodiments, the kits are for use in diagnosing neurodegenerative diseases, for example Parkinson's disease. In some embodiments, the kits are for use in identifying whether a subject having a neurodegenerative disease, for example Parkinson's disease, is a suitable candidate for treatment with a LRRK2 inhibitor. In some embodiments, the kits are for use in monitoring the efficacy of LRRK2 treatment in a subject having a neurodegenerative disease, for example Parkinson's disease. In some embodiments, the kits comprising the antibody therapeutics are for use in treating a neurodegenerative disease, for example Parkinson's disease.

In some embodiments, the kit comprises a pharmaceutical composition comprising an anti-phosphorylated Rab10 or anti-phosphorylated Rab8a monoclonal antibody as described herein. In some embodiments, the kit is for use in treating a neurodegenerative disease, e.g., Parkinson's disease. In some embodiments, the kit comprises one or more additional therapeutic agents for treating a neurodegenerative disease, e.g., Parkinson's disease. In some embodiments, the therapeutic agent is an agent for use in treating a cognitive or behavioral symptom of a neurodegenerative disease (e.g., an antidepressant, a dopamine agonist, or an anti-psychotic). In some embodiments, the therapeutic agent is a neuroprotective agent (e.g., carbidopa/levodopa, an anticholinergic agent, a dopaminergic agent, a monoamine oxidase B (MAO-B) inhibitor, a catechol-O-methyl transferase (COMT) inhibitor, a glutamatergic agent, a histone deacetylase (HDAC) inhibitor, a cannabinoid, a caspase inhibitor, melatonin, an anti-inflammatory agent, a hormone (e.g., estrogen or progesterone), or a vitamin).

In some embodiments, the kit comprises an anti-phosphorylated Rab10 or anti-phosphorylated Rab8a monoclonal antibody that is modified with a detectable label. In some embodiments, the kit is for use in diagnosing a neurodegenerative disease, for example Parkinson's disease, identifying whether a subject having a neurodegenerative disease is a suitable candidate for treatment with a LRRK2 inhibitor, or monitoring the efficacy of LRRK2 treatment. In some embodiments, the kit further comprises one or more other antibodies against Rab protein, e.g., against total Rab protein (e.g., an anti-total Rab10 antibody or an anti-total Rab8 antibody).

In some embodiments, the kit further comprises instructional materials containing directions (i.e., protocols) for the practice of the methods described herein (e.g., instructions for using the kit for a diagnostic, prognostic, or therapeutic method as described in Section V or Section VI above). While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD-ROM), and the like. Such media may include addresses to internet sites that provide such instructional materials.

VIII. Examples

The present invention will be described in greater detail by way of specific examples. The following examples are offered for illustrative purposes only, and are not intended to limit the invention in any manner.

Example 1. Anti-Phosphorylated Rab Antibody Generation and Screening

Antibody Generation
Immunizations and Antisera Screening

To achieve high antigen recognition and generate antibody diversity for use in different applications, rabbits were used for the phospho-Rab protein immunizations (Zhu, W, "Rabbit Monoclonal Antibody: a New Technology for Diagnostics," *IVD Technology,* Spring 2013: 22-25). Based on structural analysis around the phosphorylation site (T72 for Rab8a and T73 for Rab10), to maximize the immunogenicity, specific peptide lengths were designed and synthesized. To generate antibodies against phospho-T72-Rab8a, peptide C-QERFR(pT)ITTAY (SEQ ID NO:125; conjugated with either -KLH (keyhole limpet hemocyanin) or -OVA (ovalbumin)) was used to inject 4 rabbits (New Zealand White rabbits). For phospho-T73-Rab10, peptide C-AGQERFH(pT)ITTSYYR (SEQ ID NO: 123; conjugated with either -KLH or -OVA) was used to inject 4 rabbits. In each case, the rabbits were immunized subcutaneously with Freund's complete adjuvant for the initial injection of 0.5 mg peptide, and by another 4 injections every 2 weeks with Freund's incomplete adjuvant at 0.25 mg peptide/injection. Rabbit bleeds/antisera were collected before the first injection (as a blank control) and after the fourth and fifth injections. The antisera contained a mixture of antibodies and other components. Two assays were used to screen for the desired antibodies in antisera. Peptide ELISAs were used as a primary screen to test if the antisera bound to the immunogen peptides (see Peptide ELISA screening assay below for details). As a secondary screen, antisera were tested using western blots to select antibodies that specifically bound to denatured full-length, phosphorylated Rab protein from cell lysate (see western screening assay below for detail). The antisera that performed the best in the two assays were selected. For anti-phosphorylated T72-Rab8a antibody, antisera from two rabbits (E8118, E8119) were selected for affinity purification to generate purified polyclonal antibodies. For anti-phosphorylated T73-Rab10 antibody, antisera from two rabbits (E8121, E8124) were selected to generate purified polyclonal antibodies (used in FIGS. 1C-1D).

Monoclonal Antibody Generation

Monoclonal antibodies were developed with high specific binding to phosphorylated Rab proteins and consistent reproducibility and performance. Lymphocytes were isolated from rabbit spleen, and fused with a myeloma cell line 240E-W2 cells (Abcam) by PEG (Polyethylene glycol)-mediated cell fusion to generate immortal hybridomas that secrete antibodies. The hybridoma cells were plated into 96-well plates, and each well could contain multiple cell types or multiclones. The supernatants from multiclone hybridomas were screened by peptide ELISA, western blot and sandwich ELISA with cell lysate. The sandwich ELISA assay was established to select antibodies that specifically bind to native, non-denatured full-length phosphorylated Rab protein from cell lysate to identify potential antibodies for use in ELISA or MSD applications (see "Sandwich ELISA with cell lysate" section below for details). To generate an antibody pool with a wide range of application diversity, the best multiclones from either peptide ELISA, western blot screening, or sandwich ELISA screening were selected. For each case, 6-9 multiclones were selected. The multiclones were then diluted and replated to isolate single cell lines or subclones. The same screening and selection strategy was used for screening subclone supernatants, and the 18 best monoclonal antibodies were selected based on the results of peptide ELISA, western blot, and sandwich ELISA assays. For each case, 8 monoclonal antibodies were sequenced. Anti-phosphorylated Rab protein monoclonal antibodies were affinity purified from supernatants of hybridoma cells or supernatants from cells transiently transfected with recombinant antibody.

Antibody Screening
Peptide ELISA Screening Assay 96-well ELISA plates were coated with 1 ug/ml BSA (bovine serum albumin) conjugated peptide in PBS overnight at 4° C. For anti-pT72-Rab8a antibody screening, the phosphorylated peptide QERFR(pT)ITTAY (SEQ ID NO:125; the immunogen peptide) was used, and the non-phosphorylated peptide QERFRTITTAY (SEQ ID NO:127) was used as a negative control. For anti-pT73-Rab10 antibody screening, the phosphorylated peptide AGQERFH(pT)

ITTSYYR (SEQ ID NO:123; the immunogen peptide) was used, and the non-phosphorylated peptide AGQERFHTITTSYYR (SEQ ID NO:126) was used as a negative control. Plates were washed with PBS and blocked with 1% BSA at room temperature for 1 hour. Samples (antisera or hybridoma supernatants) were added and incubated at room temperature for 1 hour. AP (Alkaline phosphatase)-conjugated or HRP (Horseradish Peroxidase)-conjugated anti-rabbit IgG secondary antibody was added at room temperature for 1 hour. Substrate solution was added and developed for 15 minutes at room temperature. Absorbance (OD) was measured at 405 nm with a plate reader. For antisera screening, the antisera were added in serial dilutions from 1/250 to 1/256000. The antisera bound to phospho-peptide with the highest OD value at 1/64000 (with minimal binding to non-phospho-peptide) were selected. For hybridoma screening, the supernatants were added without dilutions. The difference between phosphorylated peptide binding and non-phosphorylated peptide binding were calculated and ranked. The best clones were selected based on ranking. For clones selected based on peptide ELISA, they were determined to have a ratio of binding phospho-peptide to non-phospho-peptide of greater than 10.

Western Blot Screening Assay

For anti-phospho-Rab8a antibody screening, HEK293T cells were transiently transfected with N-terminal HA (hemagglutinin)-tagged full-length Rab8a plasmid together with N-terminal FLAG-tagged full-length wild-type LRRK2 plasmid or FLAG-LRRK2-R1441C plasmid using Lipofectamine 3000. Because expression of LRRK2-R1441C mutant resulted in ~3 folds higher signals of phospho-Rab compared to that of wild-type LRRK2 expression (see FIGS. 1C-1D), cell lysates with wild-type LRRK2 (low basal phosphorylated Rab signal) or LRRK2-R1441C (high basal phosphorylated Rab signal) were used to differentiate the binding affinity for hybridoma clones. Because the reference polyclonal antibodies A and B only detected weak signal in LRRK2-WT overexpression cells by western blot, we aimed to select antibodies with stronger signals from LRRK2-WT expression. For anti-phospho-Rab10 antibody screening, HEK293T cells were transiently transfected with HA-Rab10 plasmid together with FLAG-LRRK2 or FLAG-LRRK2-R1441C plasmid using Lipofectamine 3000. In both cases, cells were treated with DMSO or LRRK2 inhibitor A (500 nM) for 1 hour, and then were lysed in lysis buffer (including 1% Triton X-100) supplemented with cOmplete phosphatase and PhosStop protease inhibitor cocktails (Roche) and Benzonase nuclease (Sigma, E1014). Cell lysates were cleared via centrifugation at 14,000 rpm for 10 min at 4° C. Protein concentrations were measured using DC Protein Assay (Bio-Rad), and were normalized for equal protein loading. Cell lysates were prepared by incubating with Laemmli Sample Buffer (Bio-Rad) containing 0-mercaptoethanol for 10 min at 70° C. to denature samples. Lysates were loaded onto NuPAGE 4-12% Bis-Tris gels (Invitrogen) and transferred to nitrocellulose membranes for 7 min (Trans-Blot Turbo Transfer System, Bio-Rad). Membranes were blocked with Rockland blocking buffer, incubated with primary antibody overnight at 4° C., and then incubated with secondary antibodies (1:20,000, LI-COR) for 1 hr at room temperature. LI-COR Odyssey system was used for Western blot detection and quantitation. For rabbit bleed testing, the antisera (1:1000, or 1:10000 dilusion) were used as primary antibodies. For hybridoma clone screening, the supernatants (1:2-1:20 dilution) were used as primary antibodies. The hybridoma clones that gave strong signals with wild-type LRRK2 expression, and low background signals with LRRK2 inhibitor A treatment were selected. Anti-Rab8a antibody (1:1000, Abcam, ab188574) or anti-Rab10 antibody (1:1000, Abcam, ab104859) was used for Rab protein expression control. Anti-actin antibody (Sigma, A2228) was used for protein loading control.

Sandwich ELISA with Cell Lysate 96-well ELISA plates were coated with 10 µg/ml anti-rabbit IgG (Millipore) overnight at 4° C. Plates were washed with TBST (Tris Buffered Saline with Tween 20), and blocked with 2% BSA. Hybridoma supernatants were added in different dilutions, and incubated at room temperature for 2 hours. After TBST wash, cell lysates were then added at different protein concentration (0.08 mg/ml or 0.8 mg/ml). For anti-pRab8a antibody screening, cell lysates were from HEK293T cells overexpressing HA-Rab8a and FLAG-LRRK2 (or FLAG-LRRK2-R1441C), treated with or without LRRK2 inhibitor A. For anti-pRab10 antibody screening, lysates were from HEK293T cells overexpressing HA-Rab10 and FLAG-LRRK2 (or FLAG-LRRK2-R1441C), treated with or without LRRK2 inhibitor A. Cell lysates from wild-type LRRK2 expression (low basal phosphorylated Rab signal) and LRRK2-R1441C mutant (high basal phosphorylated Rab signal) were used to differentiate the binding affinity of hybridoma clones. HRP conjugated anti-HA antibody (1:5000, CST #2999) was used for detection. TMB substrate was added and developed. Absorbance (OD) was measured at 650 nm using a plate reader. For hybridoma clones, the difference between OD value with DMSO treatment and OD value with LRRK2 inhibitor A treatment were calculated and ranked, and the best clones were selected based on this ranking.

Sandwich ELISA (Diagnostic) with Anti-Phospho-Rab10 Antibody as the Capture Antibody:

ELISA plates were prepared by coating white Nunc MaxiSorp 384 well plates (Thermo Fisher #460372/Sigma #P6491) with capture antibody for 1 hour at room temperature on a shaking platform. The capture antibody was purified anti-phospho-Rab10 clone 19-4 diluted to 1 ug/mL in carbonate-bicarbonate buffer, and 15 uL/well of coating solution was added to the plate before incubation. Plates were then washed 3× with TBST on a BioTek plate washer. For all subsequent blocking/incubation steps, Pierce Starting Block T20 (TBS) was used (Thermo Fisher #37543). Plates were blocked for at room temperature in this solution using 80 uL/well and washed 3× as before. Afterwards samples of cell lysates were added (neat with no dilution) using 30 uL/well and incubated 1 hour at room temperature on a shaking platform. After another 3× wash detection antibody (Creative Diagnostics DCABH 13141, or Abcam, ab104859, 2 ug/mL) was added using 30 uL/well. After 60 minute incubation at room temperature and washing 3×, the secondary anti-species conjugate was added (anti-rabbit HRP antibody (Jackson ImmunoResearch 111-035-144) diluted 1:20000 in assay diluent) at 30 uL/well. After a 60 minute incubation, plates were washed 3× as before. The HRP substrate (Supersignal ELISA Femto HRP substrate—Thermo Fisher #37075) was prepared during this time by mixing both components and equilibrating to room temperature. 50 uL/well of substrate was added to plates, which then were covered and briefly incubated for 1-2 minutes on a shaker platform. Afterwards plates were read on the Synergy plate reader to measure relative light units (RLU).

Sandwich ELISA (Diagnostic) with Anti-Rab10 (Total) Antibody as the Capture Antibody:

ELISA plates were prepared by coating white Nunc MaxiSorp 384 well plates (Thermo Fisher #460372/Sigma # P6491) with capture antibody overnight at 4° C. on a shaking platform. The capture antibodies (anti-Rab10 antibody from either Creative Diagnostics, DCABH-13141, or Abcam, ab104859) were diluted to 10 ug/L (or 1:100 if the concentration not known) in carbonate-bicarbonate buffer, and 15 uL/well of coating solution was added to the plate before incubation. After this plates were washed 3× with TBST on a BioTek plate washer. For all subsequent blocking/incubation steps, Pierce Starting Block (TBS) (no Tween added) was used (Thermo Fisher #37542). Plates were blocked for 1 hour at room temperature in this solution using 80 uL/well and washed 3× as before. Afterwards samples were added (with lysates being diluted 1:20 in the assay diluent) using 30 uL/well and incubated 2 hours at room temperature on a shaking platform. After another 3× wash detection antibodies were added (diluted to 1 ug/mL for purified antibodies or 1:2 for supernatants) using 30 uL/well. After 90 minute incubation at room temperature and washing 3× the secondary anti-species conjugate was added (anti-rabbit HRP antibody (Jackson ImmunoResearch 111-035-144) diluted 1:20000 in assay diluent) at 30 uL/well. After a 45 minute incubation plates were washed 3× as before. The HRP substrate (Supersignal ELISA Femto HRP substrate—Thermo Fisher #37075) was prepared during this time by mixing both components and equilibrating to room temperature. 50 uL/well of substrate was added to plates, which then were covered and briefly incubated for 1-2 minutes on a shaker platform. Afterwards plates were read on the Synergy plate reader to measure relative light units (RLU).

Table 1 and Table 2 above demonstrate that both anti-phospho-Rab10 and anti-phospho-Rab8 antibodies of the present invention specifically bind to phosphorylated Rab10 protein or phosphorylated Rab8a protein, respectively, that is endogenously expressed in a human biological sample, such as human peripheral blood mononuclear cells. Given the above ratios are greater than 2, the antibodies of the present invention can be useful as diagnostic antibodies as described herein. In contrast, reference polyclonal antibodies against phosphorylated Rab10 or phosphorylated Rab8a do not exhibit a significant decrease in detectable phosphorylated Rab10 or phosphorylated Rab8a, respectively, in response to treatment with a LRRK2 inhibitor (given the undetectable ratio above), and therefore, could not be used in a diagnostic assay (e.g., for determining levels of endogenously expressed phospho-Rab8a or phospho-Rb10 protein in a human sample).

Example 2. Phospho-Rab10 and Phospho-Rab8a as Biomarkers for LRRK2 Kinase Activity Parkinson's-Associated LRRK2 Mutations Increase Phosphorylation of Rab10

Mutations in the LRRK2 gene have been found in both familial and sporadic forms of Parkinson's disease (PD) (Li et al., Mol. Neurodegen., 2014, 9:47). LRRK encodes a

TABLE 1

Characteristics of Anti-pT73-Rab10 Antibody Clones

| Clone ID | Sandwich ELISA screening assay HEK cells overexpressing LRRK2[1] | | | Western blot Human PBMC | Sandwich ELISA (diagnostic) HEK cells overexpressing LRRK2 | | |
|---|---|---|---|---|---|---|---|
| | DMSO (OD A$_{650}$) | LRRK2 inhibitor A (OD A$_{650}$) | Ratio | Ratio of DMSO/LRRK2 inhibitor A (mean ± SEM)[2] | DMSO (RLU mean ± SD) | LRRK2 inhibitor A (RLU mean ± SD) | Ratio |
| Reference antibody A | N.A. | N.A. | N.A. | Non-detectable | N.A. | N.A. | N.A. |
| 5 | 2.703 | 0.255 | 10.60 | 3.45 ± 0.53 | 85175 ± 16412 | 3604 ± 1165 | 23.63 |
| 19 | 2.735 | 0.234 | 11.69 | 3.39 ± 0.89 | | | |
| 19-4 | 2.810 | 0.307 | 9.150 | 2.95 ± 0.68 | 80524 ± 7835 | 2153 ± 774 | 37.40 |
| 81-11 | 2.159 | 0.076 | 28.41 | 2.48 ± 0.31 | 473585 ± 44210 | 14037 ± 1627 | 33.74 |
| 133-2 | 1.859 | 0.081 | 22.95 | N.A. | 18605 ± 4874 | 8265 ± 1428 | 2.25 |
| 153-2 | 0.637 | 0.093 | 6.850 | N.A. | 596606 ± 80346 | 4223 ± 293 | 141.26 |
| 247-8 | 0.779 | 0.030 | 25.97 | N.A. | 13096 ± 1715 | 1820 ± 276 | 7.20 |
| 256-6 | 1.893 | 0.282 | 6.710 | N.A. | 212085 ± 27432 | 2741 ± 309 | 77.37 |

[1]Cell lysates from HEK293T cells overexpressing LRRK2-R1441C and Rab10
[2]As measured by band intensity normalized with Actin control for each of DMSO and LRRK2 inhibitor A

TABLE 2

Characteristics of Anti-pT72-Rab8a Antibody Clones

| Clone ID | Sandwich ELISA screening assay HEK cells overexpressing LRRK2[1] | | | Western blot Human PBMC |
|---|---|---|---|---|
| | DMSO (ODA$_{650}$) | LRRK2 inhibitor A (ODA$_{650}$) | Ratio | Ratio of DMSO/LRRK2 inhibitor A (mean ± SEM)[2] |
| Reference antibody B | N.A | N.A | N.A | Non-detectable |
| 20 | 0.827 | 0.099 | 8.35 | 3.50 ± 0.52 |
| 71-3 | 1.561 | 0.339 | 4.60 | 2.61 ± 0.42 |
| 86-9 | 1.443 | 0.247 | 5.84 | 2.26 ± 0.12 |
| 24-3 | 1.484 | 0.286 | 5.19 | N.A. |
| 165-4 | 0.768 | 0.159 | 4.83 | N.A. |
| 170-1 | 1.043 | 0.173 | 6.03 | N.A. |
| 170-3 | 1.183 | 0.178 | 6.65 | N.A. |
| 184-1 | 1.582 | 0.205 | 7.72 | N.A. |

Figure 1A:
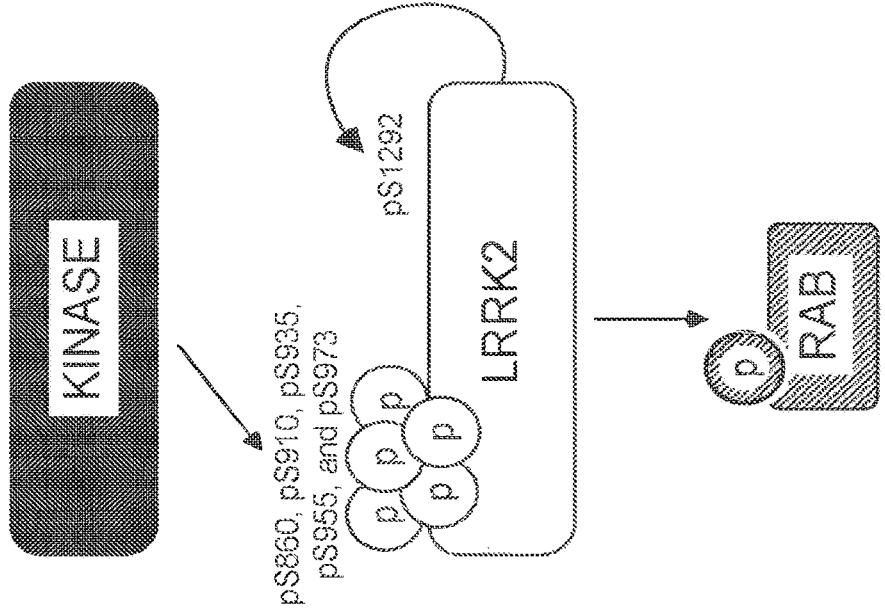

[1]Cell lysates from HEK293T cells overexpressing LRRK2-R1441C and Rab8a
[2]As measured by band intensity normalized with Actin control for each of DMSO and LRRK2 inhibitor A large protein containing a ROC-COR (GTPase) domain, a kinase domain, and several potential protein-protein interaction domains. The majority of identified familial mutations are located within its central catalytic domains, including the most common PD-associated mutation associated with LRRK2 (G2019S). The G2385R variant of LRRK2 lies in its C-terminal WD-40 domain and acts as a risk factor for PD (FIG. 1B). While the LRRK2 G2019S mutation consistently leads to increased LRRK2 kinase activity, the effects of other pathogenic mutations in LRRK2 on kinase activity have been inconsisitent largely due to the lack of reliable cellular readouts for LRRK2 kinase activity. Phosphorylation of a series of LRRK2 residues upstream of the LRR repeats (including S935) has been used to show dose-dependent dephosphorylation in response to LRRK2 inhibitors. However, these residues are not sites of LRRK2 autophosporylation and their phosphorylation is not consistently altered with mutations shown to increase or ablate LRRK2 kinase activity in vitro. Residue S1292 of LRRK2 (Sheng, Z. et al., *Sci. Transl. Med.*, 2012, 4:164ra161) was identified as an autophosphorylation site in cells and in mouse models overexpressing LRRK2 (FIG. 1A). However, S1292 appears to show very low levels of phosphorylation with endogenous LRRK2 expression.

Using phosphorylated Rab10 as a readout for LRRK2 kinase activity, the effects of different PD-associated LRRK2 mutations were tested in HEK293T cells. HEK 293T cells were transiently transfected with HA-Rab10 plasmid together with either wild-type or PD-associated LRRK2 variants (R1441C, R1441G, Y1699C, G2019S, I2020T and G2385R). Cell lysates were analyzed by western blot for pS935-LRRK2, total LRRK2, and pT73-Rab10, total Rab10 and actin. Briefly, cells were lysed in RIPA (Radioimmunoprecipitation assay) buffer supplemented with cOmplete phosphatase and PhosStop protease inhibitor cocktails (Roche) and Benzonase nuclease (Sigma, E1014). Lysates were normalized with sample buffer and reducing reagent, and were heated for 10 min at 70° C. NuPAGE 4-12% Bis-Tris gels were used for Rab10 analysis. NuPAGE™ 3-8% Tris-Acetate gels were used for LRRK2 analysis. The primary antibodies used were anti-pS935-LRRK2 (1:500, Abcam, ab133450), anti-LRRK2 (1:500, Abcam, ab133475), anti-LRRK2 (1:500, N241A/34, NeuroMab), anti-vinculin (1:500, Abcam, ab129002), anti-pT73-Rab10 (1 ug/ml, polyclonal antibody, E8124 described above), anti-Rab10 (1:1000, Abcam, ab104859) and anti-actin (1:5000, Sigma, A2228). LI-COR Odyssey system was used for western blot detection and quantitation. The pT73-Rab10 signals were quantified and normalized to total Rab10 levels. Signals from different LRRK2 mutant groups were normalized to wild-type LRRK2 group. Data were presented from 3 independent experiments, as mean with SEM (standard error of the mean).

Figures 1C, 1D:
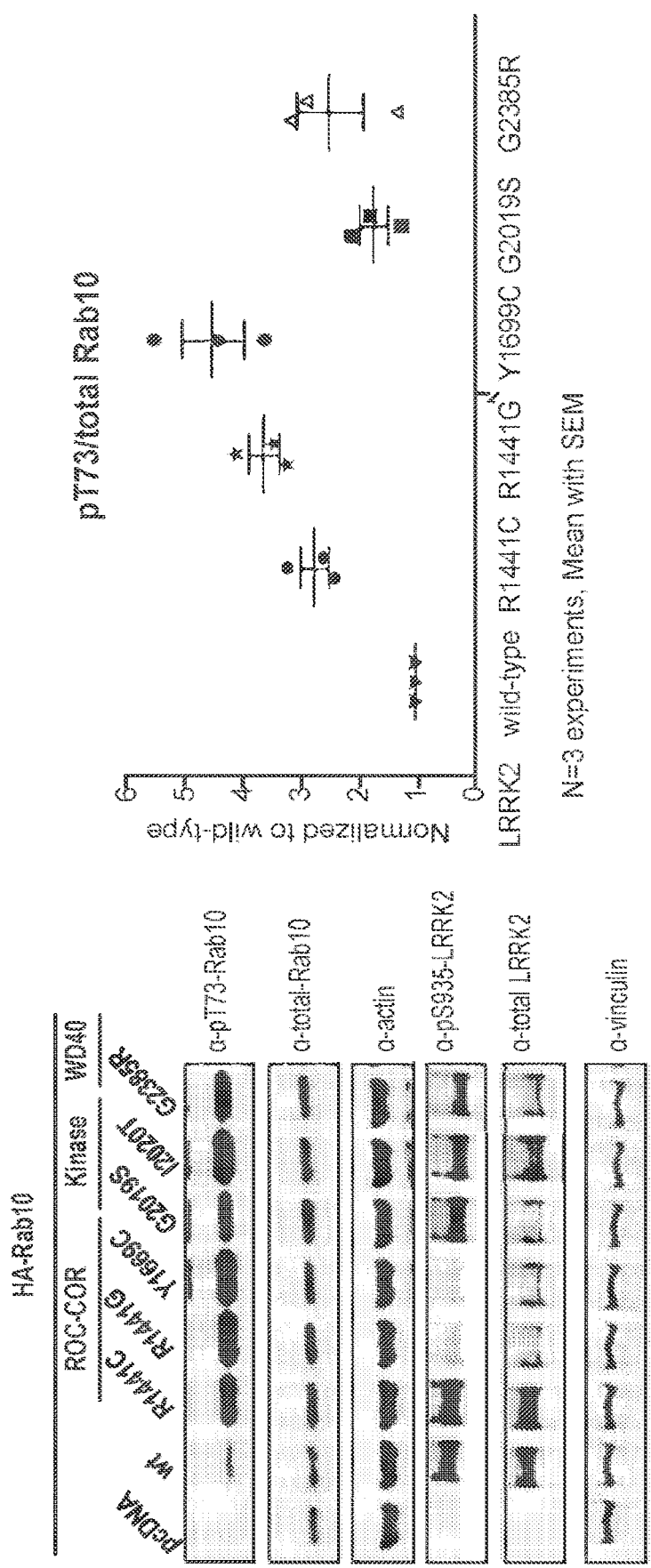

FIGS. 1C-1D show that, compared with wild-type LRRK2, all the LRRK2 mutations tested (R1441C, R1441G, Y1699C, G2019S, I2020T and G2385R) demonstrated significantly increased phosphorylation levels of Rab10 (approximately 2- to 4-fold, depending on the mutation).

These results suggested that in addition to G2019S, other PD-associated LRRK2 mutations lead to increased kinase activity and result in elevated pT73 Rab10 level in cells. The results also indicated that increased T73-Rab10 phosphorylation is a common feature of PD-associated LRRK2 mutations and may serve as a readout of LRRK2's kinase activity. Further, these studies highlight the potential of pT73-Rab10 as a biomarker to identify idiopathic PD patients with increased LRRK2 kinase activity that may benefit from therapeutic strategies to inhibit LRRK2's kinase activity.

Detection of Phosphorylated Rab10 in Human PBMCs Using Anti-Phosphorylated Rab10 Monoclonal Antibodies Strong endogenous phosphorylated Rab10 or phosphorylated Rab8a in human PBMC (peripheral blood mononuclear cell) samples were detected by anti-phosphorylated Rab10 and anti-phosphorylated Rab8a monoclonal antibodies in western blot. Human PBMCs were either isolated from whole blood, or were purchased as cryopreserved vials (AllCell). Samples from different donors (n>3) were tested, and the results were consistent among donors. PBMCs are commonly used pheripheral samples for biomarker analysis. The detection of LRRK2 kinase-dependent phosphorylation of T73-Rab10 and T72-Rab8a in endogenous system provides further support for phosphorylated Rab proteins as a LRRK2 kinase activity readout. The strong basal levels of phosphorylated Rab proteins in human PBMC promise phosphorylation of Rabs as a pheripheral biomarker.

Figure 2A:
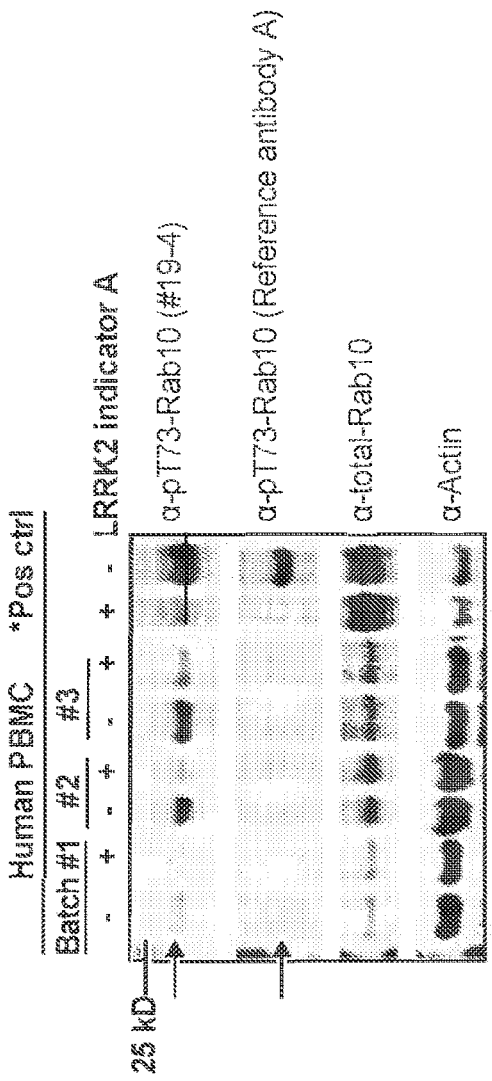
FIG. 2A-2B. Detection of phospho-Rabs in human PBMCs. (A) Detection of phosphorylated Rab10 in human peripheral blood mononuclear cells (PBMCs) with the anti-phosphorylated T73-Rab10 monoclonal antibody clone 19-4, and loss of phosphorylated Rab10 signal in response to treatment with LRRK2 inhibitor A (cis-2,6-Dimethyl-4-(6-(5-(1-methylcyclopropoxy)-1H-indazol-3-yl)pyrimidin-4-yl)morpholine). A polyclonal antibody ("Reference Antibody A") described in Steger et al. (*eLife*, 2016, 5:e12813) failed to detect pRab10 signals in human PBMC. HEK293T cells overexpressing LRRK2-R1441C and Rab10 are included as a positive control. (B) Phosphorylated Rab8a is detected in human PBMCs with the anti-phosphorylated T72-Rab8a monoclonal antibody (clone 20), while LRRK2 inhibitor A treatment causes loss of phosphorylated Rab8a signals. Another reference polyclonal antibody ("Reference Antibody B") described in Steger et al. (*eLife*, 2016, 5:e12813) failed to detect pRab8a signals in PBMC. HEK293T cells overexpressing LRRK2-R1441C and Rab8a are included as a positive control.
Figure 2B:
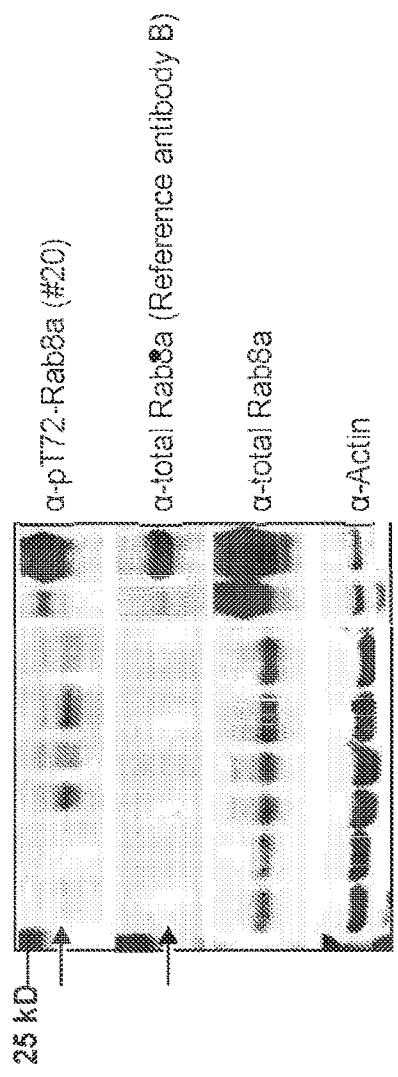

The anti-pT73-Rab10 monoclonal antibody clones 5, 19, 19-4, and 81-11 and the anti-pT72-Rab8a monoclonal antibody clones 20, 71-3 and 86-9 as described herein were tested for detecting phosphorylation of Rab10 or Rab8a in the absence or presence of LRRK2 inhibitor in human PBMC by western blot. All the primary antibodies were used at 1 ug/ml. All of the monoclonal anti-pT73-Rab10 and anti-pT72-Rab8a antibodies that were tested detected endogenous phosphorylated Rab signals in human PBMC. These phosphorylated Rab signals were significantly reduced following treatment with a LRRK2 inhibitor (LRRK2 inhibitor A). FIGS. 2A-B show examples of western blot results with anti-pT73-Rab10 antibody (clone 19-4) and anti-pT72-Rab8a antibody (clone 20).

In contrast, the polyclonal anti-phospho-Rab antibodies failed to detect endogenous phosphorylated Rab signals in human PBMC samples. See, FIGS. 2A-2B. The antibodies tested included anti-pT73-Rab10 polyclonal antibody (reference antibody A, S873D) and anti-pT72-Rab8a polyclonal antibody (reference antibody B, S874D). Antibodies were used at final concentrations of 1 ug/ml in the presence of 10 ug/ml of non-phosphorylated peptide (AGQERFRTIT-TAYYR (SEQ ID NO:128)) for Rab8a, AGQERFHTITT-SYYR (SEQ ID NO:126) for Rab10. As a positive control, the polyclonal antibodies detected pRab signals in cell lysates from HEK293T overexpressing the LRRK2 mutant R1441C and Rab protein. Thus, the monoclonal anti-pT73-Rab10 and anti-pT72-Rab8a antibodies disclosed herein are unique in their ability to detect endogenous phosphorylated Rab10 or phosphorylated Rab8a, and loss of phosphorylation in response to LRRK2 inhibitor treatment, in a human biological sample.

Figure 3:
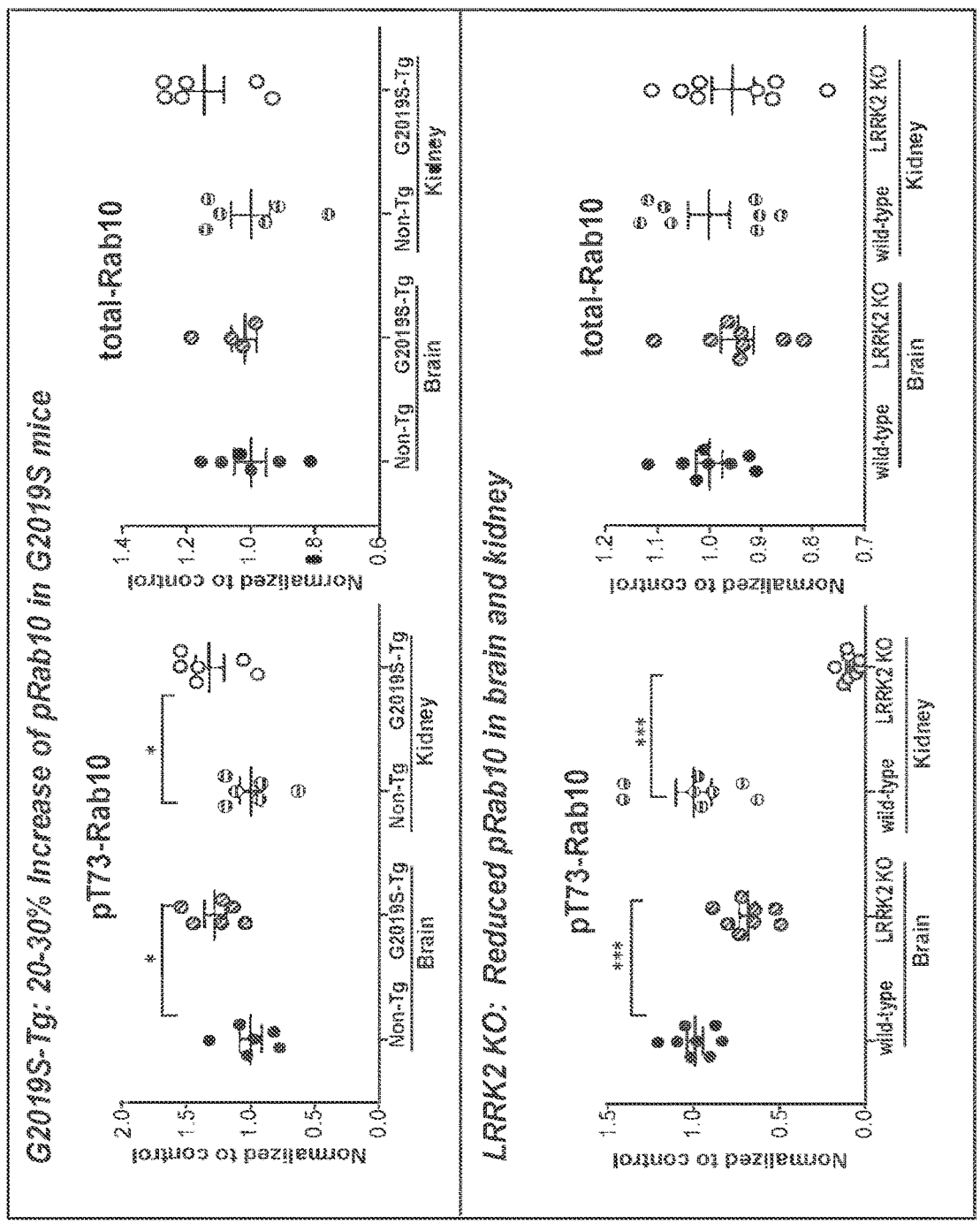
FIG. 3. Analysis of phosphorylated Rab10 levels in LRRK2 mouse models. Upper panel: pRab10 expression was analyzed using the anti-phosphorylated Rab10 monoclonal antibody (clone 19-4) for brain and kidney samples from a G2019S-LRRK2 transgenic (Tg) mouse models (Jackson lab, #018785). The study included 6 G2019S-LRRK2-Tg mice and 6 non-transgenic littermate controls. Lower panel: pRab10 expression was analyzed using the anti-phosphorylated Rab10 monoclonal antibody clone 19-4 for brain and kidney samples from a LRRK2 knockout (KO) mouse model (Jackson Lab, #016121). The study included 8 LRRK2 KO mice and 8 wild-type littermate controls.

Phosphorylated Rab10 Analysis in LRRK2-G2019S Transgenic Mouse Model and LRRK2 Knockout Mouse Model G2019S is the most common LRRK2 mutation associated with Parkinson's disease and has been shown to cause increased LRRK2 kinase activity. To assess if the G2019S mutation increases pT73-Rab10 level in vivo, a G2019S-LRRK2 BAC transgenic (G2019S-Tg) mouse model was used (Jackson Laboratories, #018785). The study included 6 of G2019S-LRRK2-Tg mice and 6 of non-transgenic littermate controls (non-Tg). Tissues (brain and kidney) were harvested, and homogenized in lysis buffer (CST #9803) supplemented with cOmplete phosphatase and PhosStop protease inhibitor cocktails (Roche), using the tissue homogenizer (Qiagen Tissue Lyser II) at 4° C. (3 min at a frequency of 30/s, homogenize twice). Tissue lysates were cleared via centrifugation at 14,000 rpm for 30 min at 4° C. Protein concentration was measured with BCA assay (Pierce). As described previously, tissue lysates were prepared for western blot. pT73-Rab10 levels were analyzed using anti-pT73-Rab10 monoclonal antibody (clone 19-4, 1 ug/ml). Other primary antibodies include anti-actin antibody and anti-Rab10 antibody (as described before). The pT73-Rab10 signals were quantified and normalized to actin as a protein loading control. Signals from G2019S-Tg group were normalized to control group (non-Tg). Data were presented as mean with SEM. As shown in FIG. 3 (upper panel), both brain and kidney samples from G2019S transgenic mice showed a 20-30% increase in pT73-Rab10 level, providing a strong support that the LRRK2 G2019S mutation causes increased pRab10 level in vivo, and the pRab antibodies disclosed herein can be used as a diagnostic for measuring levels of pRab proteins in vivo. As a control, total Rab10 levels were comparable in G2019S-Tg compared with non-Tg controls.

Published research (Ito et al., Biochem. J., 2016, 473: 2671-2685) showed that primary fibroblasts from LRRK2 knock-out (KO) mice displayed a loss of pRab10 signals by a challenging and laborious assay using the Phos-tag gel system that utilizes antibodies against total Rab10. However, no studies have showed that Rab10 is phosphorylated by LRRK2 in vivo using anti-phospho-specific antibodies. This study included 8 LRRK2 KO mice (Jackson Lab, #016121) and 8 wild-type littermate controls (wild-type, wt). pT73-Rab10 levels were analyzed by western blot using anti-pT73Rab10 monoclonal antibody (clone 19-4, 1 ug/ml). The pT73-Rab10 signals were quantified and normalized to actin. Signals from LRRK2-KO group were normalized to wild-type control group. Data were presented as mean with SEM. As shown in FIG. 3 (lower panel), brain samples from LRRK2 KO mice showed a 30-40% reduction for pT73-Rab10 level, and LRRK2 KO kidney samples showed more than 90% reduction of pRab10 level. No change in total Rab10 levels were observed in LRRK2 KO brain and kidney. These results indicate that pT73-Rab10 is phosphorylated by LRRK2 in vivo.

Analysis of Rab10 Phosphorylation in Dosed Animal Study

These studies evaluated the effects on Rab10 phosphorylation using the anti-phosphorylated Rab10 monoclonal antibody as described herein on samples obtained from rats or cynomolgus monkeys dosed with the LRRK2 Inhibitor B.

Dose-dependent inhibition of pT73-Rab10 was tested in a 10-day oral dosing study in rats. Rats were dosed daily with the LRRK2 Inhibitor B at a dose of 10 mg/kg, 30 mg/kg, or 45 mg/kg. Tissues (brain and lung) were harvested, homogenized and analyzed by western blot. NuPAGE 4-12% Bis-Tris gels were used for Rab10 analysis, 3-8% Tris-acetate gels were used for LRRK2 analysis. pT73-Rab10 signals were detected using anti-pT73-Rab10 monoclonal antibody (clone 19-4, 1 ug/ml) and normalized to actin as a loading control. pS935-LRRK2 signals were normalized to vinculin as a loading control. Signals from dosed groups were normalized to vehicle control group. Data were presented as mean with SEM. As shown in Table 3 below, pS935-LRRK2 and pT73-Rab10 showed a comparable dose-dependent dephosphorylation with LRRK2 inhibitor treatment in both brain and lung.

TABLE 3 pT73-Rab10 analysis in rats dosed with LRRK2 Inhibitor B

|  | Vehicle (no inhibitor) (N = 4) | Low dose LRRK2 Inhibitor B (N = 6) | Medium dose LRRK2 Inhibitor B (N = 6) | High dose LRRK2 Inhibitor B (N = 5) |
|---|---|---|---|---|
| pT73-Rab10 | | | | |
| Brain | 1 ± 0.318 | 0.676 ± 0.102 | 0.268 ± 0.0745 | 0.225 ± 0.0394 |
| Lung | 1 ± 0.0463 | 0.25 ± 0.0126 | 0.133 ± 0.0137 | 0.109 ± 0.0126 |
| pS935-LRRK2 | | | | |
| Brain | 1 ± 0.174 | 0.693 ± 0.164 | 0.086 ± 0.021 | 0.04 ± 0.016 |
| Lung | 1 ± 0.133 | 0.295 ± 0.026 | 0.094 ± 0.012 | 0.076 ± 0.022 |

Phosphorylated Rab10 was also tested in cynomolgus monkey lung and kidney tissue following 7 days of dosing with a LRRK2 inhibitor. Cynomolgus monkeys were dosed daily with the LRRK2 Inhibitor C at a dose of 45 mg/kg. Tissues were harvested, homogenized and analyzed by western blot, as described previously. pT73-Rab10 signals were detected using the anti-pT73-Rab10 monoclonal antibody (clone 19-4) and was normalized to actin as a loading control. pS935-LRRK2 signals were normalized to vinculin as a loading control. Signals from dosed groups were normalized to vehicle control group. Data were presented as mean with SEM. As shown in Table 4 below, both pT73-Rab10 and pS935-LRRK2 showed significant dephosphorylation with LRRK2 inhibitor treatment.

TABLE 4 pT73-Rab10 analysis in cynomolgus monkeys dosed with LRRK2 Inhibitor C

|  | Vehicle (N = 4) | LRRK2 Inhibitor C (N = 4) |
|---|---|---|
| pT73-Rab10 | | |
| Lung | 1 ± 0.341 | 0.189 ± 0.0562 |
| Kidney | 1 ± 0.119 | 0.547 ± 0.125 |
| pS935-LRRK2 | | |
| Lung | 1 ± 0.589 | 0.102 ± 0.0215 |
| Kidney | 1 ± 0.288 | 0.0563 ± 0.0147 |

Example 3. Development of Highly Sensitive Plate-Based Immunoassay to Quantify Phospho-Rab Signals and Total Rab Signals The anti-phosphorylated Rab10 monoclonal antibody and anti-phosphorylated Rab8a monoclonal antibodies as described can be used to develop a plate-based assay with high sensitivity that is suitable for clinical sample testing. Suitable assay formats can include ELISA or MSD (Meso Scale Discovery) assay.

For a phospho-Rab10 ELISA assay, a total Rab10 antibody (such as a total Rab10 antibody as disclosed herein or a commercially available total Rab10 antibody from Abcam or Creative Diagnostics) is paired with an anti-phosphorylated Rab10 monoclonal antibody as described herein to quantify pRab10 level in clinical samples (e.g., human PBMC, urine, whole blood, CSF) and/or preclinical animal samples (e.g., rats, mice and cynomolgus monkeys). The ELISA format can use either (1) total Rab10 antibody for capture and pRab10 antibody for detection, or (2) pRab10 antibody for capture and total Rab10 antibody for detection.

Figures 4A, 4B:
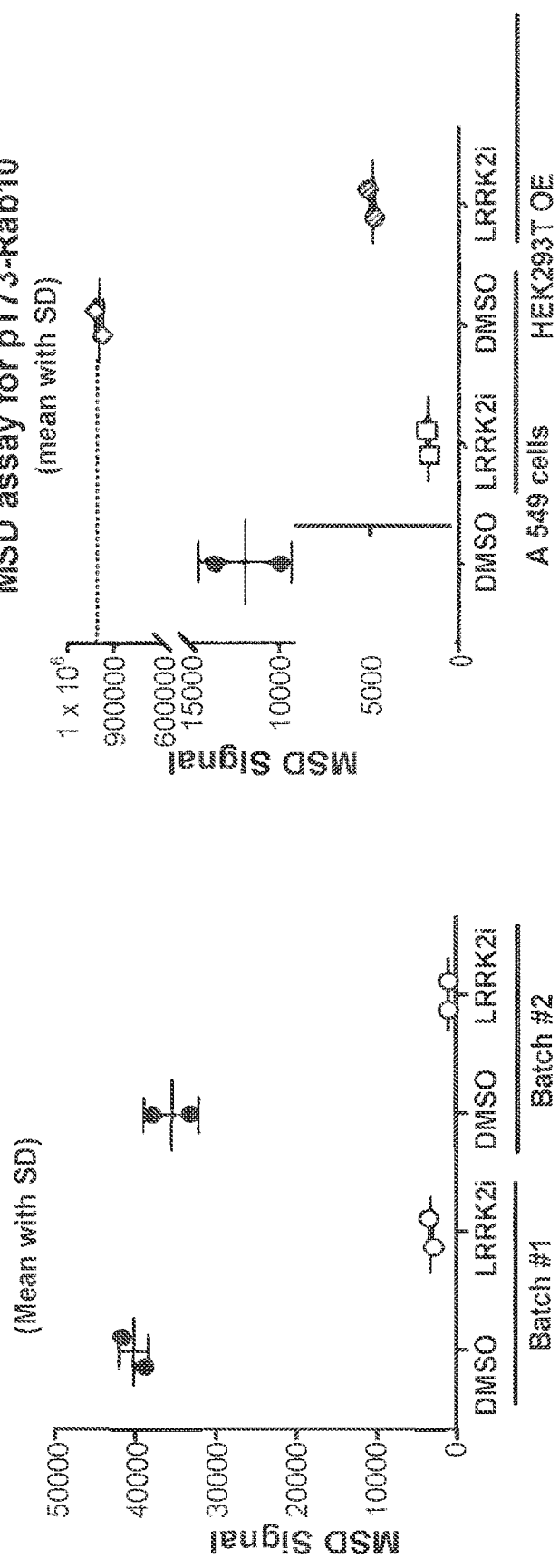
FIG. 4A-4B. Detection of phospho-Rab10 in human cells using Meso Scale Discovery (MSD) assay. MSD assay is developed using anti-pT73-Rab10 monoclonal antibody clone 19-4 as the capture antibody and anti-total Rab10 antibody as the detection antibody. (A) The phospho-Rab10 MSD assay showed pRab10 signals in human PBMCs and loss of the signals with LRRK2 inhibitor A ("LRRK2i") treatment. (B) The phospho-Rab10 MSD assay showed pRab10 signals in human A549 cells (a human lung epithelial cell line) and loss of the signals with LRRK2 inhibitor A ("LRRK2i") treatment. HEK293T cells overexpressing LRRK2-R1441C and Rab10 ("HEK293T OE") were included as a positive control, showing much higher signals.

An MSD assay was developed as shown in FIGS. 4A-4B using anti-pT73-Rab10 monoclonal antibody (clone 19-4) as the capture antibody, and anti-total Rab10 antibody as the detection antibody. Briefly, anti-pT73-Rab10 antibody (clone 19-4) was biotinylated using EZ-Link NHS LC-LC Biotin (Thermo Fisher, #21343). 96-well MSD GOLD small spot streptavidin plates (MSD, Cat# L45SA) are coated with 40 ul of 1 ug/ml biotinylated anti-pT73-Rab10 antibody each well for 1 hour at room temperature. Plates were washed with TBST and blocked with 150 ul MSD blocker A (MSD, R93BA) for 1 hour at room temperature. After wash, cell lysates (25 ul/well) are transferred to the plate and incubated for 2 hours at room temperature. After wash, anti-Rab10 antibody (Creative Diagnostics, DCABH-13141, 25 ul/well) is diluted to 1 ug/ml in Diluent 100 (MSD, R50AA), and added as a detection antibody for 1 hour at room temperature. After wash, SULFO-tag goat anti-mouse secondary antibody (MSD, R32AC, 25 ul/well) is diluted to 1 ug/ml in Diluent 100 (MSD, R50AA), added and incubated 1 hour at room temperature. After wash, MSD read buffer (MSD, R92TC) is added to the plates, and plates are read on the MSD Sector S 600 for electrochemiluminescence. As shown in FIG. 4B, the phospho-Rab10 MSD assay showed a strong detection of pT73-Rab10 signals in A549 cells (a human lung epithelial cell line) and loss of the signals with LRRK2 inhibitor A treatment. HEK293T cells overexpressing LRRK2-R1441C and Rab10 were included as a positive control, showing a much higher signal.

For a phospho-Rab8a ELISA assay, a total Rab8a antibody is paired with an anti-phosphorylated Rab8a monoclonal antibody as described herein to quantify pRab8a level in clinical samples (e.g., human PBMC, urine, whole blood, CSF) and/or preclinical animal samples (e.g., rats, mice and cynomolgus monkeys). The ELISA format can use either (1) total Rab8a antibody for capture and pRab8a antibody for detection, or (2) pRab8a antibody for capture and total Rab8a antibody for detection.

Example 4. Total Rab10 Antibody Generation and Screening

Antibody Generation
Immunizations and Antisera Screening

Rabbits were used for the Rab10 protein immunizations. Two peptides were designed to target specific sequence against Rab10 among the whole Rab8 family, with good antigenicity, and to avoid T73 region. "Peptide A" (PVKEPNSENVDISSGGGVTGWK-C (SEQ ID NO: 129), from the C-terminus region of Rab10, residues 175-196) and "Peptide B" (DKRVVPKGKGEQIAR-C(SEQ ID NO:130), from the middle region of Rab10, residues 128-142), conjugated with either -KLH or -OVA, were used to immunize 2 rabbits each (New Zealand White rabbits). In each case, the rabbits were immunized subcutaneously with Freund's complete adjuvant for the initial injection of 0.5 mg peptide, and by another 4 injections every 2 weeks with Freund's incomplete adjuvant at 0.25 mg peptide/injection. Rabbit bleeds/antisera were collected before the first injection (as a blank control) and after the fourth and fifth injections. The antisera contained a mixture of antibodies.

Three assays were used to screen for the desired antibodies in antisera. Peptide ELISA was used as a primary screen to test the titer of the bleed, using a procedure as described in Example 1. The peptides PVKEPNSENVDISSGGGVTGWK (SEQ ID NO:129) and DKRVVPKGKGEQIAR (SEQ ID NO:130) (the immunogens) were used. Peptide AGQERFHTITTSYYR (SEQ ID NO:126), a peptide from the phospho-T73 region, was used as a negative control to avoid binding competition with anti-pT73-Rab10 antibody. Rabbit E8473 bleed showed better titers against peptide A immunization, and rabbit E8476 bleed showed better titers against peptide B immunization. For the secondary assay, antisera were tested using sandwich ELISA with recombinant Rab10 protein. A sandwich ELISA assay was developed (see, "Sandwich ELISA" section below) to select antibodies that are suitable for specific detection of Rab10 in ELISA format. The bleed E8473 gave the strongest signal for binding to recombinant Rab10 protein. Western blot with cell lysates was used as the tertiary assay to select antibodies that specifically bound to endogenously expressed denatured full length Rab10 protein. Cell lysates were from HEK293T cells overexpressing HA-Rab10 or HA-Rab8a. In addition, lysates were prepared from A549 cells (wild-type), Rab8a KO A549 cells, and Rab10 KO A549 cells. All of the four rabbit bleeds showed very strong signals with the lysates from HEK293T cells overexpressing Rab10 protein, but not with lysates from HEK293T cells overexpressing Rab8a protein. All of the four rabbit bleeds showed strong signals with lysates from wild-type A549 cells, and Rab8a KO A549 cells, but no signals in Rab10 KO A549 cells. The results indicated that all of the four rabbit bleeds detected highly specific endogenously-expressed Rab10 signals in western blot. Based on the screen results, the rabbit E8473 was selected to move for the monoclonal antibody generation. The E8473 antisera was purified to generate polyclonal antibodies.

Monoclonal Antibody Generation

Monoclonal antibodies were developed to obtain highly specific antibodies with consistent reproducibility and performance. Lymphocytes were isolated from rabbit spleen, and fused with a myeloma cell line 240E-W2 cells (Abcam) by PEG (Polyethylene glycol)-mediated cell fusion to generate immortal hybridomas that secrete antibodies. The hybridoma cells were plated into 96-well plates, and each well could contain multiple cell types or multiclones. The supernatants from multiclone hybridomas were screened by peptide ELISA, sandwich ELISA with recombinant Rab proteins and cell lysates. Multiclones were selected if (a) in the sandwich ELISA assay, they showed strong signals with recombinant Rab10 protein, but not with recombinant Rab8a protein, and (b) in the sandwich ELISA assay they showed strong signals binding to cell lysates from HEK293T cells overexpressing Rab10 protein but not with overexpressed Rab8a protein. Based on the screening results, 3 multiclones were selected to be diluted and replated to isolate single cell lines or subclones. The same screening and selection strategy was used for screening subclone supernatants. In addition, to further select antibodies that specifically detect endogenously-expressed Rab10 protein from cell lysates, a quaternary assay was performed using sandwich ELISA with cell lysates from wild-type A549 cells, using cell lysates from Rab10 KO A549 cells as negative controls. The best 9 clones were selected to be frozen down, and 2 clones were selected for sequencing. The sequencing results indicated that the 2 clones shared the same sequence. These sequences are the sequences of Clone 10-3: a heavy chain variable region having the sequence of SEQ ID NO:131 and a light chain variable region having the sequence of SEQ ID NO:135.

Sandwich ELISA

ELISA plates were prepared by coating white Nunc MaxiSorp 384 well plates (Thermo Fisher #460372/Sigma

P6491) with capture antibody for 1 hour at room temperature or overnight at 4° C. on a shaking platform. The capture antibody was purified anti-Rab10 antibody (Creative Diagnostics DCABH 13141, or Abcam, ab104859, 2 ug/mL). Plates were then washed 3× with TBST on a BioTek plate washer. For all subsequent blocking/incubation steps, Pierce Starting Block T20 (TBS) was used (Thermo Fisher #37543). Plates were blocked for 1 hour at room temperature using 100 uL/well and washed 3× as before. Afterwards samples were added using 30 uL/well and incubated 1 hour at room temperature on a shaking platform. For ELISA with recombinant Rab proteins, the samples were recombinant Rab10 protein (Abnova, H00010890-P01) or Rab8a protein (Abnova, H00004218-Q01). For ELISA with cell lysates with overexpressed Rab10 protein, lysates were from HEK293T cells overexpressing HA-Rab10, and lysates from HEK293T cells overexpressing HA-Rab8a were used as negative controls. For ELISA with cell lysates with endogenously-expressed Rab10 protein, lysates were from A549 cells (wild-type), and lysates from Rab10 KO A549 cells were used as negative controls. After another 3× wash, bleeds/antisera or hybridoma supernatants were added as detection antibody with different dilutions at 30 ul/well, and were incubated at room temperature for 1 hour. After wash 3 times, the secondary anti-rabbit HRP antibody (Jackson ImmunoResearch 111-035-144) diluted 1:20000 in assay diluent) were added at 30 uL/well. After 1 hour incubation, plates were washed 3× as before. The HRP substrate (Supersignal ELISA Femto HRP substrate—Thermo Fisher #37075) was prepared during this time by mixing both components and equilibrating to room temperature. 50 uL/well of substrate was added to plates, which then were covered and briefly incubated for 1-2 minutes on a shaker platform. Afterwards plates were read on the Synergy plate reader to measure relative light units (RLU).

Example 5. LRRK2 and pT73 Rab from Exosomes

Cerebrospinal (CSF) or urine from healthy donors was quick-thawed and placed on ice after thawing. A minimum of 12.5 mL of CSF was placed in 14×95 mm ultra-clear centrifuge tubes (Beckman Coulter; cat. no. 344060) and centrifuged at 1000×g for 10 minutes at 4° C. to remove any potential cell contamination. The supernatant was centrifuged at 10,000×g for 30 minutes at 4° C., then the resulting supernatant collected and spun at 200,000×g for 2 hours at 4° C. The supernatant was carefully aspirated, and the exosome-enriched pellet was resuspended into 40 μL lysis buffer (Cell Lysis Buffer (Cell Signaling Technology; cat. no. 9803S) diluted 1:10 in water) with protease and phosphatase inhibitors (Protease/phosphatase inhibitor cocktail from Cell Signaling Technology; cat. no. 5872S)). To the resuspended samples, 6 μL of 10×NuPAGE sample reducing agent (Invitrogen; NP0009) and 14 μL of 4×NuPAGE LDS sample buffer (Invitrogen; cat. no. NP0007) were added, and samples were heated for 5 minutes at 70° C. Samples were loaded onto a 4-12% Bis-Tris gradient gel (Invitrogen) using MES SDS running buffer (Invitrogen). The gels were then transferred to PVDF using the Trans-blot Turbo transfer system (BioRad) using the mixed molecular weight fast transfer protocol (Mixed MW mode: 2.5 amps, 25 volts, 7 minutes). The PVDF membranes were then blocked for 1 hour at room temperature using blocking buffer (Rockland; cat. no. MB-070-010TF) and primary antibodies were applied and incubated overnight rocking at 4° C. Rabbit anti-LRRK2 (clone N21A/34; NeuroMab), mouse anti-pSer935 LRRK2 (Abcam; cat. no. ab133450), mouse anti-Rab10 (Abcam; cat. no. ab104859), and rabbit anti-pT73 Rab10 antibodies disclosed herein were used at a dilution of 1:500 in blocking buffer to detect total LRRK2 and pSer935 LRRK2, respectively. Exosome enrichment was detected using the following antibodies: mouse anti-Alix (Cell Signaling Technology; cat. no. 2171S); rabbit anti-flotillin (Cell Signaling Technology; cat. no. 18634S) and rabbit anti-TSG101 (Abcam; cat. no. ab125011) used at a dilution of 1:1000 in blocking buffer. The membranes were washed three times for five minutes each using TBS-T (Teknova; cat. no. T9501A), and secondary antibodies (LI-COR anti-rabbit 680 and LiCor anti-mouse 800) were diluted 1:20,000 in blocking buffer and rocked for one hour at room temperature. The membranes were washed with TBS-T three times for five minutes at room temperature and scanned using Odyssey CLx imaging system (LI-COR). Resulting protein band intensities were analyzed using Image Studio software (version 5.2.5; LI-COR). Target protein enrichment was quantified by normalizing fluorescence intensity to exosome marker fluorescence intensity after background subtraction.

Total LRRK2, pSer935 LRRK2, and pT73 Rab were successfully detected according to the above procedure from 10-32 mL of urine from healthy donors. Total LRRK2 and pSer935 LRRK2 were successfully detected according to the above procedure from 12-32 mL of CSF from healthy donors.

Example 6. Quantification of Total LRRK2 and pS935 LRRK2

Immunoassay analysis reagents: 10× cell lysis buffer (Cell Signaling Technologies 9803), PhosSTOP phosphatase inhibitor (Roche 04906837001); Complete protease inhibitor (Roche 04693159001); Benzonase (Sigma E8263), Streptavidin small-spot 96-well plates (MSD L45SSA-1); Blocker A (MSD R93AA-1); Read Buffer (MSD R92TC-1); EZ-Link™ NHS-LC-Biotin (ThermoFisher SB242443); Sulfo-Tag kit (MSD R31AA-1); 10×TBS with 0.5% Tween 20 (Teknova T9501).

Antibodies for immunoassay: Anti-LRRK2 (phospho S935) [UDD2 10(12)](Abcam ab133450) tagged with biotin using EZ-Link kit; anti-LRRK2 clone MC.028(Biolegend 808201) tagged with Sulfo-tag using Sulfo-tag kit; anti-LRRK2 clone 8G10 (Biolegend 844401) tagged with biotin using EZ-Link kit.

Streptavidin small spot 96-well plates were coated with 40 μL biotinylated LRRK2 pS935 antibody (1 μg/mL) (pS935 LRRK2 assay) or 8G10 antibody (for total LRRK2 assay) for 1 hour at room temperature, followed by blocking with blocker A for 1 hour at room temperature. 25 μL lysate from each PBMC lysate well was then pipetted onto these plates and incubated overnight at 4° C. Plates were washed and then 40 μL detection antibody (anti-LRRK2 clone MC.028 with Sulfo-Tag, 1 μg/ml) diluted in 25% blocker A and 75% 1× TBST was added to each well. Following 1 hour room temperature incubation, 150 μL 2× read buffer (diluted from 4× with water) was added to each well and the plate was read on an MSD (Meso Scale Discovery) imager.

Figure 5:
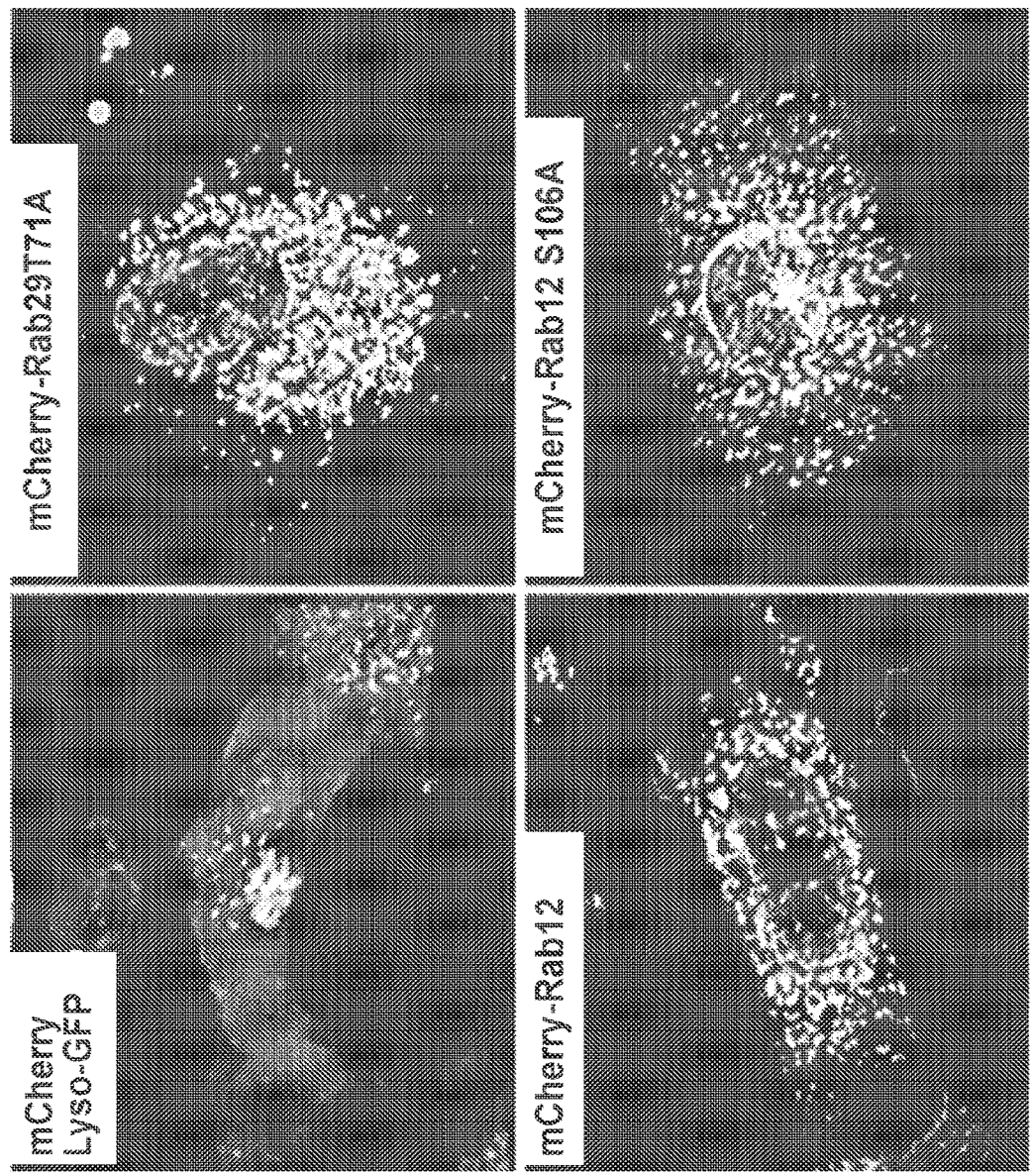
FIG. 5. LRRK2 G2019S-expressing H4 cells showed reduced lysosomal number as a phenotype of lysosomal dysfunction. Lysosomes were labelled by Cell Light lysosome-GFP.

Example 7. Introduction of Wild-Type and Phospho-Mutant Rabs to Identify Rabs that Rescue LRRK2-Mediated Effects on Lysosomal Capacity To investigate the mechanisms by which increased LRRK2 kinase activity induces lysosomal dysfunction, a group of 14 Rab GTPases were identified as potential LRRK2 substrates, including Rab3a, Rab3b, Rab3c, Rab3d, Rab5a, Rab5b, Rab5c, Rab8a, Rab8b, Rab10, Rab12, Rab29, Rab35, and Rab43. Lysosomal number as a phenotype of lysosomal dysfunction was measured in LRRK2 G2019S-expressing H4 cells, whereby LRRK2 G2019S-expressing H4 cells showed reduced lysosomal number. To identify which Rabs mediate LRRK2-induced lysosomal dysfunction, wild-type and phospho-mutant versions of the above 14 Rabs were transfected into LRRK2 G2019S-expressing H4 cells to measure which Rabs rescued the G2019S phenotype of reduced lysosome number. Lysosomes were labeled by Cell Light lysosome-GFP (lyso-GFP, FIG. 5).

Figure 6:
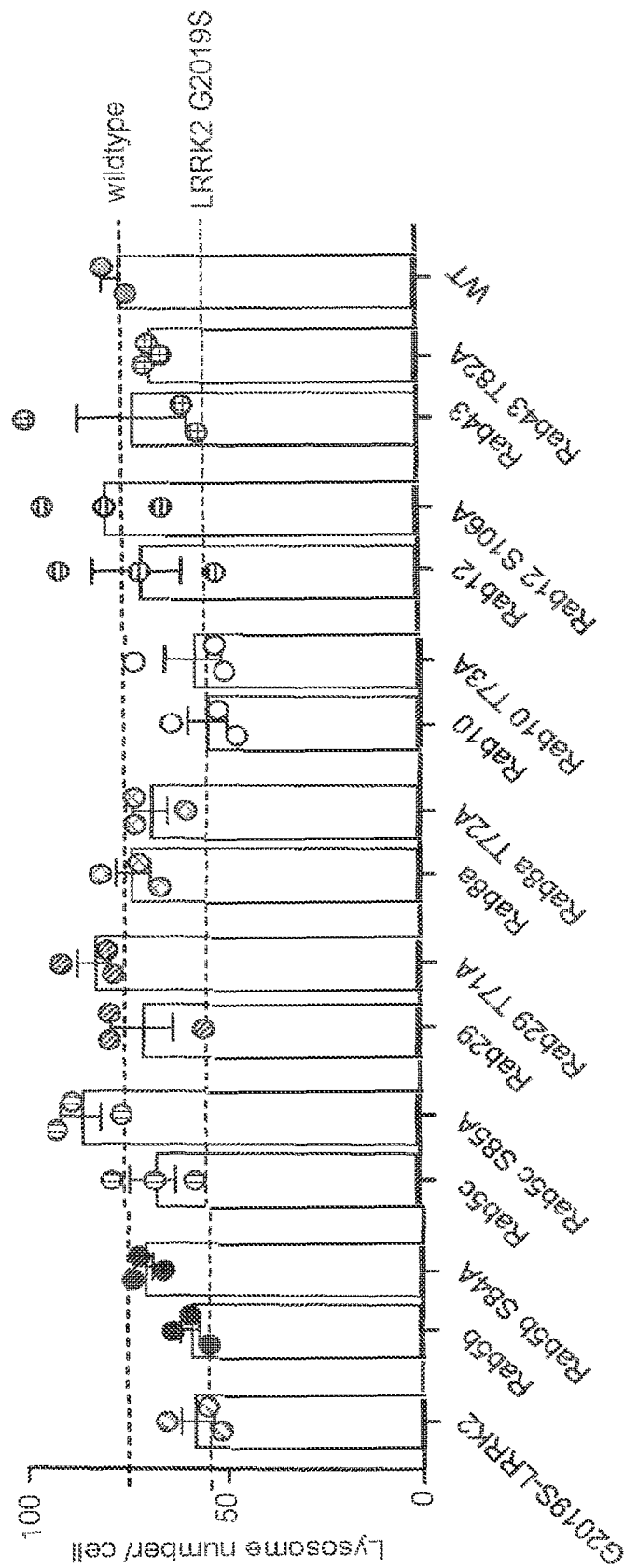
FIG. 6. Wild-type and phospho-mutant Rabs corrected reduced lysosomal number in LRRK2 G2019S-expresssing H4 cells (n=3 experiments, data presented as mean with SEM).

Data for wild-type and phospho-mutant Rabs are shown in FIG. 6, indicating that a subset of Rabs corrected reduced lysosomal number in LRRK2 G2019S-express sing H4 cells (n=3 experiments, data presented as mean with SEM). In this experiment, Rab10 (wt and T73A mutant) failed to reverse the reduced lysosomal number, suggesting it failed to correct the observed lysosomal phenotype. Out of 14 Rabs analyzed, Rab5, Rab8a, Rab12 and Rab29 showed data suggesting they reverse the reduced lysosomal number, suggesting they correct LRRK2-mediated lysosomal alterations.

It is understood that the examples and embodiments described herein are for illustrative purposes only and that various modifications or changes in light thereof will be suggested to persons skilled in the art and are to be included within the spirit and purview of this application and scope of the appended claims.

TABLE 5

Informal Sequence Listing

| SEQ ID NO | Sequence | Description |
|---|---|---|
| 1 | *METGLRWLLLVAVLKGVQC*QSVEESGGRLVTPGTPLTLTCTVS<u>GFSLSSYAMV</u>WVRQAPGKGLEYIG<u>LISRSGVTYYATWAKG</u>RFTISKASTTVDLKIASPTTGDTATYFC<u>VRDYDINGWSGFTI</u>WGPGTLVTVSA | VH for anti-phospho Rab10 clone 5 (signal peptide italicized; CDRs underlined) |
| 2 | GFSLSSYAMV | CDR-H1 for anti-phospho Rab10 clones 5, 19, and 19-4 |
| 3 | LISRSGVTYYATWAKG | CDR-H2 for anti-phospho Rab10 clones 5, 19, 19-4, and 256-6 |
| 4 | VRDYDINGWSGFTI | CDR-H3 for anti-phospho Rab10 clone 5 |
| 5 | *MDTRAPTQLLGLLLWLPGAI*CDPVMTQTPSSTSAAVGGTVTINC<u>QSSQSVYGNNYFS</u>WYQQKPGQPPKLLIY<u>KASTLA</u>SGVPSRFKGSGSGTQFTLTISDLECDDAATYYC<u>AGAASDTRF</u>FGGGTELVVN | VL for anti-phospho Rab10 clone 5 (signal peptide italicized; CDRs underlined) |
| 6 | QSSQSVYGNNYFS | CDR-L1 for anti-phospho Rab10 clone 5 |
| 7 | KASTLAS | CDR-L2 for anti-phospho Rab10 clones 5, 19, 19-4, 247-8, and 256-6 and for anti-phospho Rab8a clones 86-9 and 24-3 |
| 8 | AGAASDTRF | CDR-L3 for anti-phospho Rab 10 clones 5, 19, 19-4, and 256-6 |
| 9 | ATGGAGACTGGGCTGCGCTGGCTTCTCCTGGTCGCTGTGCTCAAAGGTGTCCAGTGTCAGTCGGTGGAGGAGTCCGGGGGTCGCCTGGTCACGCCTGGGACACCCCTGACACTCACCTGCACCGTCTCTGGATTCTCCCTCAGTAGCTATGCAATGGTCTGGGTCCGCCAGGCTCCAGGGAAGGGGCTGGAATACATCGGACTCATTAGTAGGAGTGGTGTGACATACTACGCGACCTGGGCGAAAGGCCGATTCACCATCTCCAAAGCCTCGACCACAGTGGATCTGAAAATCGCCAGTCCGACAACCGGGGACACGGCCACCTATTTTTGTGTCAGAGATTACGATATTAATGGCTGGAGTGGGTTTACCATCTGGGGCCCAGGCACCCTGGTCACCGTCTCCGCA | Nucleotide sequence for anti-phospho Rab10 clone 5 VH |
| 10 | ATGGACACGAGGGCCCCCACTCAGCTGCTGGGGCTCCTGCTCTGGCTCCCAGGTGCCATATGTGACCCTGTGATGACCCAGACTCCATCTTCCACGTCTGCGGCTGTGGGAGGCACAGTCACCATCAACTGCCAGTCCAGTCAGAGTGTTTATGGTAACAACTACTTTTCCTGGTATCAGCAGAAACCAGGGCAGCCTCCCAAGCTCCTGATCTACAAGGCTTCCACTCTGGCATCTGGGGTCCCATCGCGATTCAAAGGCAGTGGATCTGGGACACAGTTCACTCTCACCATCAGCGACCTGGAGTGTGACGATGCTGCCACTTACTACTGTGCAGGCGCTGCTAGTGATACTAGATTTTCGGCGGAGGGACCGAACTGGTGGTCAAT | Nucleotide sequence for anti-phospho Rab10 clone 5 VL |

TABLE 5-continued

Informal Sequence Listing

| SEQ ID NO | Sequence | Description |
|---|---|---|
| 11 | *METGLRWLLLVAVLKGVQ*CQSVEESGGRLVTPGTPLTLT CTVSG<u>FSLSSYAMV</u>WVRQAPGKGLEYIG<u>LISRSGVTYYA TWAKG</u>RFTISKASTTVDLKIASPTTGDTATYFC<u>VRDYDS AGWSGFTI</u>WGPGTLVTVSA | VH for anti-phospho Rab10 clone 19 (signal peptide italicized; CDRs underlined) |
| 12 | VRDYDSAGWSGFTI | CDR-H3 for anti-phospho Rab10 clones 19 and 19-4 |
| 13 | *MDTRAPTQLLGLLLLWLPGAIC*DPVMTQTPSSTSAAVGG TVTINC<u>QSSQSVYGNNYLS</u>WYQQKPGQPPKLLIY<u>KASTL ASG</u>VPSRSVGSGSGTQFTLTISDLECDDAATYYC<u>AGAAS DTRF</u>FGGGIELVVN | VL for anti-phospho Rab10 clone 19 (signal peptide italicized; CDRs underlined) |
| 14 | QSSQSVYGNNYLS | CDR-L1 for anti-phospho Rab10 clones 19, 19-4, 247-8, and 256-6 |
| 15 | ATGGAGACTGGGCTGCGCTGGCTTCTCCTGGTCGCTGTG CTCAAAGGTGTCCAGTGTCAGTCGGTGGAGGAGTCCGGG GGTCGCCTGGTCACGCCTGGGACACCCCTGACACTCACC TGCACCGTCTCTGGGTTCTCCCTCAGTAGCTATGCAATG GTCTGGGTCCGCCAGGCTCCAGGGAAGGGGCTGGAATAC ATCGGACTCATTAGTAGGAGTGGTGTGACATACTACGCG ACCTGGGCGAAAGGCCGATTCACCATCTCCAAAGCCTCG ACCACAGTGGATCTGAAAATCGCCAGTCCGACAACCGGG GACACGGCCACCTATTTTTGTGTCAGAGATTACGATAGT GCTGGCTGGAGTGGGTTTACCATCTGGGGCCCAGGCACC CTGGTCACCGTCTCCGCA | Nucleotide sequence for anti-phospho Rab10 clone 19 VH |
| 16 | ATGGACACGAGGGCCCCCACTCAGCTGCTGGGGCTCCTG CTGCTCTGGCTCCCAGGTGCCATATGTGACCCTGTGATG ACCCAGACTCCATCTTCCACGTCTGCGGCTGTGGGAGGC ACAGTCACCATCAACTGCCAGTCCAGTCAGAGTGTTTAT GGTAACAACTACTTGTCCTGGTATCAGCAGAAACCAGGG CAGCCTCCCAAGCTCCTGATCTACAAGGCTTCCACTCTG GCATCTGGGGTCCCATCGCGGTCCGTAGGCAGTGGATCT GGGACACAGTTCACTCTCACCATCAGCGACCTGGAGTGT GACGATGCTGCCACTTACTACTGTGCAGGCGCTGCTAGT GATACTAGATTTTTCGGCGGAGGGACCGAACTGGTGGTC AAT | Nucleotide sequence for anti-phospho Rab 10 clone 19 VL |
| 17 | *METGLRWLLLVAVLKGVQ*CQSVEESGGRLVTPGTPLTLT CTVSG<u>FSLSSYAMV</u>WVRQAPGKGLEYIG<u>LISRSGVTYYA TWAKG</u>RFTISKASTTVDLKIASPTTGDTATYFC<u>VRDYDS AGWSGFTI</u>WGPGTLVTVSA | VH for anti-phospho Rab10 clone 19-4 (signal peptide italicized; CDRs underlined) |
| 18 | *MDTRAPTQLLGLLLLWLPGAIC*DPVMTQTPSSTSAAVGG TVTINC<u>QSSQSVYGNNYLS</u>WYQQKPGQPPKLLIY<u>KASTL ASG</u>VPSRFVGSGSGTQFTLTISDLECDDAATYYC<u>AGAAS DTRF</u>FGGGIELVVN | VL for anti-phospho Rab10 clone 19-4 (signal peptide italicized; CDRs underlined) |
| 19 | ATGGAGACTGGGCTGCGCTGGCTTCTCCTGGTCGCTGTG CTCAAAGGTGTCCAGTGTCAGTCGGTGGAGGAGTCCGGG GGTCGCCTGGTCACGCCTGGGACACCCCTGACACTCACC TGCACCGTCTCTGGGTTCTCCCTCAGTAGCTATGCAATG GTCTGGGTCCGCCAGGCTCCAGGGAAGGGGCTGGAATAC ATCGGACTCATTAGTAGGAGTGGTGTGACATACTACGCG ACCTGGGCGAAAGGCCGATTCACCATCTCCAAAGCCTCG ACCACAGTGGATCTGAAAATCGCCAGTCCGACAACCGGG GACACGGCCACCTATTTTTGTGTCAGAGATTACGATAGT GCTGGCTGGAGTGGGTTTACCATCTGGGGCCCAGGCACC CTGGTCACCGTCTCCGCA | Nucleotide sequence for anti-phospho Rab 10 clone 19-4 VH |
| 20 | ATGGACACGAGGGCCCCCACTCAGCTGCTGGGGCTCCTG CTGCTCTGGCTCCCAGGTGCCATATGTGACCCTGTGATG ACCCAGACTCCATCTTCCACGTCTGCGGCTGTGGGAGGC ACAGTCACCATCAACTGCCAGTCCAGTCAGAGTGTTTAT GGTAACAACTACTTGTCCTGGTATCAGCAGAAACCAGGG CAGCCTCCCAAGCTCCTGATCTACAAGGCTTCCACTCTG GCATCTGGGGTCCCATCGCGGTTCGTAGGCAGTGGATCT GGGACACAGTTCACTCTCACCATCAGCGACCTGGAGTGT GACGATGCTGCCACTTACTACTGTGCAGGCGCTGCTAGT GATACTAGATTTTTCGGCGGAGGGACCGAACTGGTGGTC AAT | Nucleotide sequence for anti-phospho Rab 10 clone 19-4 VL |

TABLE 5-continued

Informal Sequence Listing

| SEQ ID NO | Sequence | Description |
|---|---|---|
| 21 | METGLRWLLLVAVLKGVQCQSVEESGGRLVTPGTPLTLT CTVSGFSLSSYAMSWVRQAPGKGLEYIGLFNDVGIAYYA NWAKGRFTFSKTSTTVDLKITSPTTEDTATYFCARVGGT TRVYGMDLWGPGTLVTSS | VH for anti-phospho Rab10 clone 81-11 (signal peptide italicized; CDRs underlined) |
| 22 | GFSLSSYAMS | CDR-H1 for anti-phospho Rab10 clone 81-11 |
| 23 | LFNDVGIAYYANWAKG | CDR-H2 for anti-phospho Rab10 clone 81-11 |
| 24 | ARVGGTTRVYGMDL | CDR-H3 for anti-phospho Rab10 clone 81-11 |
| 25 | MDTRAPTQLLGLLLLWLPGATFAAVLTQTPSPVSAAVGG TVSISCQSSKSVRHNNYLSWYQQKPGQRPKLLIYGASTL ASGVPSRFSGSGSGTEFTLTISDVQCDDAATYYCAGGYS GGGDDAFGGGTEVVVE | VL for anti-phospho Rab10 clone 81-11 (signal peptide italicized; CDRs underlined) |
| 26 | QSSKSVRHNNYLS | CDR-L1 for anti-phospho Rab10 clone 81-11 |
| 27 | GASTLAS | CDR-L2 for anti-phospho Rab10 clone 81-11 and for anti-phospho Rab8a clone 20 |
| 28 | AGGYSGGGDDA | CDR-L3 for anti-phospho Rab10 clone 81-11 |
| 29 | ATGGAGACTGGGCTGCGCTGGCTTCTCCTGGTCGCTGTG CTCAAAGGTGTCCAGTGTCAGTCGGTGGAGGAGTCCGGG GGTCGCCTGGTCACGCCTGGGACACCCCTGACACTCACC TGCACAGTCTCTGGATTCTCCCTCAGTAGTTATGCAATG AGCTGGGTCCGCCAGGCTCCAGGGAAGGGGCTGGAATAC ATCGGATTATTTAATGATGTTGGTATCGCATACTACGCG AACTGGGCGAAAGGCCGATTCACCTTCTCCAAAACCTCG ACCACGGTGGATCTGAAAATCACCAGTCCGACAACCGAG GACACGGCCACCTATTTCTGTGCCAGAGTGGGTGGTACT ACTCGTGTCTACGGCATGGACCTCTGGGGCCCAGGGACC CTCGTCACCGTCTCTTCA | Nucleotide sequence for anti-phospho Rab10 clone 81-11 VH |
| 30 | ATGGACACGAGGGCCCCCACTCAGCTGCTGGGGCTCCTG CTGCTCTGGCTCCCAGGTGCCACATTTGCCGCCGTGCTG ACCCAGACTCCATCTCCCGTGTCTGCAGCTGTGGGAGGC ACAGTCAGCATCAGTTGCCAGTCCAGTAAGAGTGTTAGG CATAACAACTACTTATCCTGGTATCAGCAGAAACCAGGG CAGCGTCCCAAGCTCCTGATCTATGGTGCATCCACTCTG GCATCTGGGGTCCCATCGCGGTTCAGCGGCAGTGGATCT GGGACAGAGTTCACTCTCACCATCAGCGACGTGCAGTGT GACGATGCTGCCACTTACTACTGTGCAGGCGGTTATAGT GGTGGTGGTGACGATGCGTTCGGCGGAGGGACCGAGGTG GTGGTCGAA | Nucleotide sequence for anti-phospho Rab10 clone 81-11 VL |
| 31 | METGLRWLLLVAVLKGVQCQEQLVESGGGLVQPEGSLTL TCKASGFDLSSHYYMCWVRQAPGKGLEWIVCISNGSGNT YYASWAKGRFTISKTSSTTVTLHMTSLTVADTATYFCAR NFGSNYGDAFDPWGPGTLVTVSS | VH for anti-phospho Rab10 clone 133-2 (signal peptide italicized; CDRs underlined) |
| 32 | GFDLSSHYYMC | CDR-H1 for anti-phospho Rab10 clone 133-2 |
| 33 | CISNGSGNTYYASWAKG | CDR-H2 for anti-phospho Rab10 clone 133-2 |
| 34 | ARNFGSNYGDAFDP | CDR-H3 for anti-phospho Rab10 clone 133-2 |
| 35 | MDTRAPTQLLGLLLLWLPGATFAQVLTQTPSPVSAAVGG TVTISCQSSKSVYSNNYLSWYQQKPGQPPKLLIYSASIL ASGVPSRFSGSGSGTQFTLTISGVQCDDAATYYCQGSYA GSGWYIGFGGGTEVVVK | VL for anti-phospho Rab10 clone 133-2 (signal peptide italicized; CDRs underlined) |
| 36 | QSSKSVYSNNYLS | CDR-L1 for anti-phospho Rab10 clone 133-2 |

TABLE 5-continued

Informal Sequence Listing

| SEQ ID NO | Sequence | Description |
|---|---|---|
| 37 | SASILAS | CDR-L2 for anti-phospho Rab10 clone 133-2 |
| 38 | QGSYAGSGWYIG | CDR-L3 for anti-phospho Rab10 clone 133-2 |
| 39 | *METGLRWLLLVAVLKGVQCQSVEESGGRLVTPGTPLTLT CTAS*<u>GFSLSTYYMS</u>*WVRQAPGKGLEWIGI*<u>IINTGGIVHYA NWVRG</u>*RFTISKTSTTVDLRITSPTAEDTATYFC*<u>ARAYSA DRLDL</u>*WGQGTLVTVSS* | VH for anti-phospho Rab10 clone 153-2 (signal peptide italicized; CDRs underlined) |
| 40 | GFSLSTYYMS | CDR-H1 for anti-phospho Rab10 clone 153-2 |
| 41 | IINTGGIVHYANWVRG | CDR-H2 for anti-phospho Rab10 clone 153-2 |
| 42 | ARAYSADRLDL | CDR-H3 for anti-phospho Rab10 clone 153-2 |
| 43 | *MDTRAPTQLLGLLLLWLPGATFAAVLTQTPSPVSAAVGG TVTISC*<u>QSSESVYGNNRLS</u>*WYQQKPGQPPKLLMY*<u>YASTL AS</u>*GVPSRFRGSGSGTQFTLTISDVQCDDAASYYC*<u>LGGYK RDSNNA</u>*FGGGTEVVVK* | VL for anti-phospho Rab10 clone 153-2 (signal peptide italicized; CDRs underlined) |
| 44 | QSSESVYGNNRLS | CDR-L1 for anti-phospho Rab10 clone 153-2 |
| 45 | YASTLAS | CDR-L2 for anti-phospho Rab10 clone 153-2 |
| 46 | LGGYKRDSNNA | CDR-L3 for anti-phospho Rab10 clone 153-2 |
| 47 | METGLRWLLLVAVLKGVQCQSVEESGGRLVTPGTPLTLT CTVS<u>GFSLSSYAMG</u>WVRQAPGKGLEYIGI<u>IISRSGITYYA TWAKG</u>RFTISKASTTVDLRIASPTTEDTATFFC<u>VRDYDS SGWSGFNI</u>WGPGTLVTVSL | VH for anti-phospho Rab10 clone 247-8 (signal peptide italicized; CDRs underlined) |
| 48 | GFSLSSYAMG | CDR-H1 for anti-phospho Rab10 clone 247-8 and anti-phospho Rab8a clone 20 |
| 49 | IISRSGITYYATWAKG | CDR-H2 for anti-phospho Rab10 clone 247-8 |
| 50 | VRDYDSSGWSGFNI | CDR-H3 for anti-phospho Rab10 clone 247-8 |
| 51 | *MDTRAPTQLLGLLLLWLPGAIC*DPVMTQTPSSTSAAVGG TVTINC<u>QSSQSVYGNNYLS</u>WFQQKPGQPPKLLIY<u>KASTL AS</u>GVPSRFKGSGSGTQFTLTISGVQCDDAATYYC<u>AGAYS DNRV</u>FGGGTEVVVK | VL for anti-phospho Rab10 clone 247-8 (signal peptide italicized; CDRs underlined) |
| 52 | AGAYSDNRV | CDR-L3 for anti-phospho Rab10 clone 247-8 |
| 53 | *METGLRWLLLVAVLKGVQCQSVEESGGRLVTPGTPLTLT CTVS*<u>GFSLSNYAMV</u>*WVRQAPGKGLEYIG*<u>LISRSGVTYYA TWAKG</u>*RFTISKASTTVDLKIASPTTGDTATYFC*<u>VRDYDA NGWSGFTI</u>*WGPGTLVTVSA* | VH for anti-phospho Rab10 clone 256-6 (signal peptide italicized; CDRs underlined) |
| 54 | GFSLSNYAMV | CDR-H1 for anti-phospho Rab10 clone 256-6 |
| 55 | VRDYDANGWSGFTI | CDR-H3 for anti-phospho Rab10 clone 256-6 |
| 56 | *MDTRAPTQLLGLLLLWLPGAIC*DPVMTQTPSSTSAAVGG TVTINC<u>QSSQSVYGNNYLS</u>WYQQKPGQPPKLLIY<u>KASTL AS</u>GVPSRFKGSGSGTQFTLTISDLDCDDAATYYC<u>AGAAS DTRF</u>FGGGTEVVVK | VL for anti-phospho Rab 10 clone 256-6 (signal peptide italicized; CDRs underlined) |

TABLE 5-continued

Informal Sequence Listing

| SEQ ID NO | Sequence | Description |
|---|---|---|
| 57 | GFSLSxYxMx | Anti-phospho Rab 10 CDR-H1 consensus sequence |
| 58 | xxxxxGxxYYAxWAKG | Anti-phospho Rab 10 CDR-H2 consensus sequence |
| 59 | VRDYDxxGWSGFxI | Anti-phospho Rab 10 CDR-H3 consensus sequence |
| 60 | QSSxSVxxNNxxS | Anti-phospho Rab 10 CDR-L1 consensus sequence |
| 61 | xASxLAS | Anti-phospho Rab 10 CDR-L2 consensus sequence |
| 62 | AGAxSThax | Anti-phospho Rab10 CDR-L3 consensus sequence |
| 63 | *METGLRWLLLVAVLKGVQCQ*SVEESGGRLVTPGTPLTLT CTVSGFSLSSYAMGWVRQAPGEGLEYFGIINTGGSAYYT NWAKGRFTISRTSTTVHLKITSPTTEDTATYFCARIAGD TRYYGMDPWGPGTLVTVSS | VH for anti-phospho Rab8a clone 20 (signal peptide italicized; CDRs underlined) |
| 64 | IINTGGSAYYTNWAKG | CDR-H2 for anti-phospho Rab8a clone 20 |
| 65 | ARIAGDTRYYGMDP | CDR-H3 for anti-phospho Rab8a clone 20 |
| 66 | *MDTRAPTQLLGLLLLWLPGATF*AAVLTQTPSPVSAAVGG TVSISCQSSKSVRNNNYLAWYQQKPGQPPKLLIYGASTL ASGVPSRFKGSGSGTQFTLTISDVQCDDAATYYCAGGYD GGSDDAFGGGTEVVVK | VL for anti-phospho Rab8a clone 20 (signal peptide italicized; CDRs underlined) |
| 67 | QSSKSVRNNNYLA | CDR-L1 for anti-phospho Rab8a clone 20 |
| 68 | AGGYDGGSDDA | CDR-L3 for anti-phospho Rab8a clone 20 |
| 69 | ATGGAGACTGGGCTGCGCTGGCTTCTCCTGGTCGCTGTG CTCAAGGGTGTCCAGTGTCAGTCGGTGGAGGAGTCCGGG GGTCGCCTGGTCACGCCTGGGACACCCCTGACACTCACC TGCACAGTCTCTGGATTCTCCCTCAGTAGCTATGCAATG GGCTGGGTCCGCCAGGCTCCAGGGGAGGGGCTGGAATAC TTCGGAATCATTAATACTGGTGGTAGCGCATACTACACG AACTGGGCAAAAGGCCGATTCACCATCTCCAGAACCTCG ACCACGGTGCATCTGAAAATCACCAGTCCGACAACCGAG GACACGGCCACCTATTTCTGTGCCAGGATTGCTGGTGAT ACTAGATACTACGGCATGGACCCCTGGGGCCCAGGGACC CTCGTCACCGTCTCTTCA | Nucleotide sequence for anti-phospho Rab8a clone 20 VH |
| 70 | ATGGACACGAGGGCCCCCACTCAGCTGCTGGGGCTCCTG CTGCTCTGGCTCCCAGGTGCCACATTTGCCGCCGTGCTG ACCCAGACTCCATCTCCCGTGTCTGCAGCTGTGGGAGGC ACAGTCAGCATCAGTTGCCAGTCCAGTAAGAGTGTTCGT AATAACAACTACTTAGCCTGGTATCAGCAGAAACCTGGG CAGCCTCCCAAACTCCTGATCTATGGTGCATCCACTCTG GCATCTGGGGTCCCATCGCGGTTCAAAGGCAGTGGATCT GGGACACAGTTCACTCTCACCATCAGCGACGTGCAGTGT GACGATGCTGCCACTTACTACTGTGCAGGCGGTTATGAT GGTGGTAGTGATGATGCTTTCGGCGGAGGGACCGAGGT GGTGGTCAAA | Nucleotide sequence for anti-phospho Rab8a clone 20 VL |
| 71 | *METGLRWLLLVAVLKGVQCQ*SVEESGGRLVTPGTPLTLT CTASGFSLNVYYMTWVRQAPGKGLDWIGIINTDITVHYA NWARGRFTISKTSTTVDLKITSPTTEDTATYFCARARNS AWMDIWGPGTLVTVSL | VH for anti-phospho Rab8a clone 71-3 (signal peptide italicized; CDRs underlined) |
| 72 | GFSLNVYYMT | CDR-H1 for anti-phospho Rab8a clone 71-3 |
| 73 | IINTDITVHYANWARG | CDR-H2 for anti-phospho Rab8a clone 71-3 |

TABLE 5-continued

Informal Sequence Listing

| SEQ ID NO | Sequence | Description |
|---|---|---|
| 74 | ARARNSAWMDI | CDR-H3 for anti-phospho Rab8a clone 71-3 |
| 75 | *MDTRAPTQLLGLLLLWLPGATF*AAVLTQTPSPVSAAVGG TVTINC<u>QSDWSVYNNNLA</u>WYQHKPGQPPKLLIY<u>KTSTLA</u> <u>S</u>GVPSRFRGSGSGTQFTLTISDVQCDDTATYYC<u>AGGYYR</u> <u>DSDTA</u>FGGGTEVVVK | VL for anti-phospho Rab8a clone 71-3 (signal peptide italicized; CDRs underlined) |
| 76 | QSDWSVYNNNLA | CDR-L1 for anti-phospho Rab8a clone 71-3 |
| 77 | KTSTLAS | CDR-L2 for anti-phospho Rab8a clone 71-3 |
| 78 | AGGYYRDSDTA | CDR-L3 for anti-phospho Rab8a clone 71-3 |
| 79 | ATGGAGACTGGGCTGCGCTGGCTTCTCCTGGTCGCTGTG CTCAAAGGTGTCCAGTGTCAGTCAGTGGAGGAGTCCGGG GGTCGCCTGGTCACGCCTGGGACACCCCTGACACTCACC TGCACAGCCTCTGGATTCTCCCTCAATGTCTACTACATG ACCTGGGTCCGCCAGGCTCCAGGGAAGGGGCTGGATTGG ATCGGAATCATTAATACAGATATTACCGTGCACTACGCG AACTGGGCGAGAGGCCGATTCACCATCTCCAAAACCTCG ACCACGGTGGATCTGAAAATCACCAGTCCGACAACCGAG GACACGGCCACCTATTTCTGTGCCAGAGCTCGTAATAGT GCTTGGATGGACATCTGGGGCCCAGGCACCCTGGTCACC GTCTCGTTG | Nucleotide sequence for anti-phospho Rab8a clone 71-3 VH |
| 80 | ATGGACACGAGGGCCCCCACTCAGCTGCTGGGGCTCCTG CTGCTCTGGCTCCCAGGTGCCACATTTGCCGCCGTGCTG ACCCAGACTCCATCCCCCGTGTCTGCAGCTGTGGGAGGC ACAGTCACCATCAATTGCCAGTCCGATTGGAGTGTTTAT AATAACAACTTAGCCTGGTATCAGCACAAGCCAGGGCAG CCTCCCAAGCTCCTGATCTACAAGACTTCCACTCTGGCA TCTGGGGTCCCATCGCGGTTCAGAGGCAGTGGATCTGGG ACACAGTTCACTCTCACCATCAGCGACGTTCAGTGTGAC GATACTGCCACTTATTACTGTGCAGGCGGTTATTATCGC GACAGTGATACGGCTTTCGGCGGAGGGACCGAGGTGGTG GTCAAA | Nucleotide sequence for anti-phospho Rab8a clone 71-3 VL |
| 81 | *METGLRWLLLVAVLKGVQ*CQSVEESGGRLVTPGTPLTLT CTVS<u>GFSLSSYYIT</u>WVRQAPGKGLEWLG<u>IMNAGTTVHYA</u> <u>NWVKG</u>RFAISKTSTTVDLKITSPTTEDTATYFC<u>ARARNS</u> <u>VWMDI</u>WGPGTLVTVSL | VH for anti-phospho Rab8a clone 86-9 (signal peptide italicized; CDRs underlined) |
| 82 | GFSLSSYYIT | CDR-H1 for anti-phospho Rab8a clones 86-9 and 24-3 |
| 83 | IMNAGTTVHYANWVKG | CDR-H2 for anti-phospho Rab8a clones 86-9 and 24-3 |
| 84 | ARARNSVWMDI | CDR-H3 for anti-phospho Rab8a clones 86-9 and 24-3 |
| 85 | *MDTRAPTQLLGLLLLWLPGATL*AAVLTQTPSPVSGAVGG SVTVNC<u>QSDKSVYRDNLA</u>WYQQKPGQPPKLLIY<u>KASTLA</u> <u>S</u>GVPSRFRGSGAGTQFTLTISDVQCDDAATYFC<u>AGGYSS</u> <u>DSDTA</u>FGGGTEVVVK | VL for anti-phospho Rab8a clones 86-9 and 24-3 (signal peptide italicized; CDRs underlined) |
| 86 | QSDKSVYRDNLA | CDR-L1 for anti-phospho Rab8a clones 86-9 and 24-3 |
| 87 | AGGYSSDSDTA | CDR-L3 for anti-phospho Rab8a clones 86-9, 24-3, and 184-1 |
| 88 | ATGGAGACTGGGCTGCGCTGGCTTCTCCTGGTCGCTGTG CTCAAAGGTGTCCAGTGTCAGTCGGTGGAGGAGTCCGGG GGTCGCCTGGTCACGCCTGGGACACCCCTGACACTCACC TGCACAGTCTCTGGATTCTCCCTCAGTAGCTACTACATA ACCTGGGTCCGCCAGGCTCCAGGGAAGGGGCTGGAGTGG CTCGGAATCATGAATGCTGGTACTACCGTACATTATGCG AACTGGGTGAAAGGCCGATTCGCCATCTCCAAAACCTCG ACCACGGTGGATCTGAAAATCACCAGTCCGACAACCGAG | Nucleotide sequence for anti-phospho Rab8a clone 86-9 VH |

TABLE 5-continued

Informal Sequence Listing

| SEQ ID NO | Sequence | Description |
|---|---|---|
| | GACACGGCCACCTATTTCTGTGCCAGAGCTCGTAATAGT GTTTGGATGGACATCTGGGGCCCAGGCACCCTGGTCACC GTCTCCTTA | |
| 89 | ATGGACACGAGGGCCCCCACTCAGCTGCTGGGGCTCCTG CTGCTCTGGCTCCCAGGTGCCACGCTTGCCGCCGTTCTG ACCCAGACTCCATCCCCCGTGTCTGGAGCTGTGGGAGGC TCAGTCACCGTCAATTGCCAGTCCGATAAGAGTGTTTAT AGGGACAACTTAGCCTGGTATCAGCAGAAACCAGGGCAG CCTCCCAAGCTCCTGATCTACAAGGCTTCCACTCTGGCA TCTGGGGTCCCATCGCGTTTCAGAGGCAGTGGAGCTGGG ACACAGTTCACTCTCACCATCAGCGACGTGCAGTGTGAC GATGCTGCCACTTACTTCTGTGCAGGCGGTTATAGTAGC GACAGTGATACGGCTTTCGGCGGAGGGACCGAGGTGGTG GTCAAA | Nucleotide sequence for anti-phospho Rab8a clone 86-9 VL |
| 90 | *METGLRWLLLVAVLKGVQ*CQSVEESGGRLVTPGTPLTLT CTVSGFSLSSYYITWVRQAPGKGREWLGIMNAGTTVHYA NWVKGRFAISKTSTTVDLKITSPTTEDTATYFCARARNS VWMDIWGPGTLVTVSL | VH for anti-phospho Rab8a clone 24-3 (signal peptide italicized; CDRs underlined) |
| 91 | *METGLRWLLLVAVLKGVQ*CQSLEESGGRLVTPGTPLTLT CTVSGFSLSTYVMSWVRQAPGKGLEWIGVLSSSGRTDYA SWAKGRFAISKTSTTVDLRITSPT1EDTATYFCVRAPIY SNGGYYLDIWGPGTLVTVSL | VH for anti-phospho Rab8a clone 165-4 (signal peptide italicized; CDRs underlined) |
| 92 | GFSLSTYVMS | CDR-H1 for anti-phospho Rab8a clone 165-4 |
| 93 | VLSSSGRTDYASWAKG | CDR-H2 for anti-phospho Rab8a clone 165-4 |
| 94 | VRAPIYSNGGYYLDI | CDR-H3 for anti-phospho Rab8a clone 165-4 |
| 95 | *MDTRAPTQLLGLLLLWLPGAR*CAVVMTQTASPVSAAVGG TVTINCQASRSLLSLTYLSWYQQKPGQPPKLLIYRASTL ASGVPSRFKGSGSGTQFTLTISGVECADAATYYCLYGYY SRGSGDTAFGGGTEVVVK | VL for anti-phospho Rab8a clone 165-4 (signal peptide italicized; CDRs underlined) |
| 96 | QASRSLLSLTYLS | CDR-L1 for anti-phospho Rab8a clone 165-4 |
| 97 | RASTLAS | CDR-L2 for anti-phospho Rab8a clone 165-4 |
| 98 | LYGYYSRGSGDTA | CDR-L3 for anti-phospho Rab8a clone 165-4 |
| 99 | *METGLRWLLLVAVLKGVQ*CQSLEESGGDLVKPEGSPTLT CTASGFSFSSSYWICWVRQAPGKGLEWIACIYGGSSGTI YYASWAKGRFTISKTSSTTVTLQMTSLTAADTATYFCAR RAAGGYGGRLDLWGQGTLVTVSS | VH for anti-phospho Rab8a clone 170-1 (signal peptide italicized; CDRs underlined) |
| 100 | GFSFSSSYWIC | CDR-H1 for anti-phospho Rab8a clone 170-1 |
| 101 | CIYGGSSGTIYYASWAKG | CDR-H2 for anti-phospho Rab8a clones 170-1 and 170-3 |
| 102 | ARRAAGGYGGRLDL | CDR-H3 for anti-phospho Rab8a clones 170-1 and 170-3 |
| 103 | *MDTRAPTQLLGLLLLWLPGATFA*QVMTQTPASVSAAVGG TVTINCQSSESVLNNNYLAWYQQKSGQPPKLLIWTASSL ASGVPSRFSGSGSGTQFTLTISDVQCDDAATYYCAGGYY IGSDIFAFGGGTEVVVR | VL for anti-phospho Rab8a clones 170-1 and 170-3 (signal peptide italicized; CDRs underlined) |
| 104 | QSSESVLNNNYLA | CDR-L1 for anti-phospho Rab8a clones 170-1 and 170-3 |
| 105 | TASSLAS | CDR-L2 for anti-phospho Rab8a clones 170-1 and 170-3 |

TABLE 5-continued

Informal Sequence Listing

| SEQ ID NO | Sequence | Description |
|---|---|---|
| 106 | AGGYYIGSDIFA | CDR-L3 for anti-phospho Rab8a clones 170-1 and 170-3 |
| 107 | *METGLRWLLLVAVLKGVQCQ*EQLEESGGDLVKPEGSPTL TCTAS<u>GFSFSSSYGIC</u>WVRQAPGKGREWIA<u>CIYGGSSGT IYYASWAK</u>GRFTISKTSSTTVTLQMTSLTAADTATYFCA <u>RRAAGGYGGRLDL</u>WGQGTLVTVSS | VH for anti-phospho Rab8a clone 170-3 (signal peptide italicized; CDRs underlined) |
| 108 | GFSFSSSYGIC | CDR-H1 for anti-phospho Rab8a clone 170-1 |
| 109 | *METGLRWLLLVAVLKGVQCQ*SVEESGGRLVTPGTPLTLT CTAS<u>GFSLSSYYMT</u>WVRQAPGKGLEWIGI<u>INTGVTVHYA NWARG</u>RFTISKSSTTVDLRITSPT1EDTATYFC<u>ARARNS AWMDL</u>WGPGTLVTVSL | VH for anti-phospho Rab8a clone 184-1 (signal peptide italicized; CDRs underlined) |
| 110 | GFSLSSYYMT | CDR-H1 for anti-phospho Rab8a clone 184-1 |
| 111 | IINTGVTVHYANWARG | CDR-H2 for anti-phospho Rab8a clone 184-1 |
| 112 | ARARNSAWMDL | CDR-H3 for anti-phospho Rab8a clone 184-1 |
| 113 | *MDTRAPTQLLGLLLLWLPGATF*AAVLTQTPSSVSAAVGG TVTINC<u>QSDWSVVNNNLA</u>WYQQKPGQPPKLLIY<u>KTSSLP S</u>GVPSRFRGSGSGTQFTLTISDVQCDDAATYYC<u>AGGYSS DSDTA</u>FGGGTEVVVK | VL for anti-phospho Rab8a clone 184-1 (signal peptide italicized; CDRs underlined) |
| 114 | QSDWSVVNNNLA | CDR-L1 for anti-phospho Rab8a clone 184-1 |
| 115 | KTSSLPS | CDR-L2 for anti-phospho Rab8a clone 184-1 |
| 116 | GFSLxxYxxx | Anti-phospho Rab8a CDR-H1 consensus sequence |
| 117 | IxNxxxxxxxYxNWxxG | Anti-phospho Rab8a CDR-H2 consensus sequence |
| 118 | ARARNSxWMDx | Anti-phospho Rab8a CDR-H3 consensus sequence |
| 119 | QSxxSVxxxNxLA | Anti-phospho Rab8a CDR-L1 consensus sequence |
| 120 | xxSxLxS | Anti-phospho Rab8a CDR-L2 consensus sequence |
| 121 | AGGYxxxSDxxA | Anti-phospho Rab8a CDR-L3 consensus sequence |
| 122 | MAKKTYDLLFKLLLIGDSGVGKTCVLFRFSDDAFNTTFI STIGIDFKIKTVELQGKKIKLQIWDTAGQERFTHTITTS YYRGAMGIMLVYDITNGKSFENISKWLRNIDEHANEDVE RMLLGNKCDMDDKRVVPKGKGEQIAREHGIRFFETSAKA NINIEKAFLTLAEDILRKTPVKEPNSENVDISSGGGVTG WKSKCC | Human Rab 10 protein sequence |
| 123 | AGQERFH(pT)ITTSYYR | phospho-Rab10 epitope (amino acid residues 66-80 of full-length Rab 10 protein) |
| 124 | MAKTYDYLFKLLLIGDSGVGKTCVLFRFSEDAFNSTFIS TIGIDFKIRTIELDGKRIKLQIWDTAGQERFRTITTAYY RGAMGIMLVYDITNEKSFDNIRNWIRNIEEHASADVEKM ILGNKCDVNDKRQVSKERGEKLALDYGIKFMETSAKANI NVENAFFTLARDIKAKMDKKLEGNSPQGSNQGVKITPDQ QKRSSFFRCVLL | Human Rab8a protein sequence |

TABLE 5-continued

Informal Sequence Listing

| SEQ ID NO | Sequence | Description |
|---|---|---|
| 125 | QERFR(pT)ITTAY | phospho-Rab8a epitope (amino acid residues 67-77 of full-length Rab8a protein) |
| 126 | AGQEREHTITTSYYR | non-phosphorylated Rab 10 peptide |
| 127 | QERFRTITTAY | non-phosphorylated Rab8a peptide |
| 128 | AGQERFRTITTAYYR | non-phosphorylated Rab8a peptide |
| 129 | PVKEPNSENVDISSGGGVTGWK | Rab10 peptide |
| 130 | DKRVVPKGKGEQIAR | Rab10 peptide |
| 131 | *METGLRWLLLLVAVLKGVQCQ*SVEESGGRLVTPGTPLTLT CTASGFSLSSYYMNWVRQAPGKGLEWIGFISSGGRTYYA NWAKGRFTISKTSTTVDLKITSPT*f*EDMATYFCARAIYS SGNSAMAIWGPGTLVTVSL | VH for anti-total Rab10 clone 10-3 (signal peptide italicized) |
| 132 | GFSLSSYYMN | CDR-H1 for anti-total Rab10 clone 10-3 |
| 133 | FISSGGRTYYANWAKG | CDR-H2 for anti-total Rab10 clone 10-3 |
| 134 | ARAIYSSGNSAMAI | CDR-H3 for anti-total Rab10 clone 10-3 |
| 135 | *MDTRAPTQLLGLLLLWLPGATFA*QVLTQTPSSVSAAVGG TVTISCQASQSVYDNSNLAWYQQKPGQPPELLIYYTSTL ASGVPSRFSGSGSGTQFTLTISGVQCDDAAIYYCLGAFT CSSGDCNVFGGGTEVVVK | VL for anti-total Rab10 clone 10-3 (signal peptide italicized) |
| 136 | QASQSVYDNSNLA | CDR-L1 for anti-total Rab10 clone 10-3 |
| 137 | YTSTLAS | CDR-L2 for anti-total Rab10 clone 10-3 |
| 138 | LGAFTCSSGD | CDR-L3 for anti-total Rab10 clone 10-3 |

---

What is claimed is:

1. An isolated monoclonal antibody or antigen-binding portion thereof that specifically binds to a phosphorylated human Rab10 protein and recognizes an epitope within or comprising the sequence AGQERFH(pT)ITTSYYR (SEQ ID NO:123), wherein said antibody or antigen-binding portion thereof comprises the following complementarity determining regions (CDRs):
   (i) a heavy chain CDR1 comprising the amino acid sequence of SEQ ID NO:2, a heavy chain CDR2 comprising the amino acid sequence of SEQ ID NO:3, a heavy chain CDR3 comprising the amino acid sequence of SEQ ID NO:4, a light chain CDR1 comprising the amino acid sequence of SEQ ID NO:6, a light chain CDR2 comprising the amino acid sequence of SEQ ID NO:7, and a light chain CDR3 comprising the amino acid sequence of SEQ ID NO:8;
   ii) a heavy chain CDR1 comprising the amino acid sequence of SEQ ID NO:2, a heavy chain CDR2 comprising the amino acid sequence of SEQ ID NO:3, a heavy chain CDR3 comprising the amino acid sequence of SEQ ID NO:12, a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:8; or
   (iii) a heavy chain CDR1 comprising the amino acid sequence of SEQ ID NO:54, a heavy chain CDR2 comprising the amino acid sequence of SEQ ID NO:3, a heavy chain CDR3 comprising the amino acid sequence of SEQ ID NO:55, a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:8.

2. The isolated monoclonal antibody of claim 1, comprising a heavy chain CDR1 comprising the amino acid sequence of SEQ ID NO:2, a heavy chain CDR2 comprising the amino acid sequence of SEQ ID NO:3, a heavy chain CDR3 comprising the amino acid sequence of SEQ ID NO:4, a light chain CDR1 comprising the amino acid sequence of SEQ ID NO:6, a light chain CDR2 comprising the amino acid sequence of SEQ ID NO:7, and a light chain CDR3 comprising the amino acid sequence of SEQ ID NO:8.

3. The isolated monoclonal antibody of claim 1, comprising a heavy chain CDR1 comprising the amino acid sequence of SEQ ID NO:2, a heavy chain CDR2 comprising the amino acid sequence of SEQ ID NO:3, a heavy chain CDR3 comprising the amino acid sequence of SEQ ID NO:12, a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:8.

4. The isolated monoclonal antibody of claim 1, comprising a heavy chain CDR1 comprising the amino acid sequence of SEQ ID NO:54, a heavy chain CDR2 comprising the amino acid sequence of SEQ ID NO:3, a heavy chain CDR3 comprising the amino acid sequence of SEQ ID NO:55, a light chain CDR1 comprising the amino acid sequence of SEQ ID NO:14, a light chain CDR2 comprising the amino acid sequence of SEQ ID NO:7, and a light chain CDR3 comprising the amino acid sequence of SEQ ID NO:8.

5. The isolated monoclonal antibody of claim 1, comprising a heavy chain variable region comprising the amino acid sequence of SEQ ID NO:1 and a light chain variable region comprising the amino acid sequence of SEQ ID NO:5.

6. The isolated monoclonal antibody of claim 1, comprising a heavy chain variable region comprising the amino acid sequence of SEQ ID NO:17 and a light chain variable region comprising the amino acid sequence of SEQ ID NO:18.

7. The isolated monoclonal antibody of claim 1, comprising a heavy chain variable region comprising the amino acid sequence of SEQ ID NO:53 and a light chain variable region comprising the amino acid sequence of SEQ ID NO:56.

8. A pharmaceutical composition comprising the isolated monoclonal antibody of claim 1 and a pharmaceutically acceptable carrier.

9. An isolated polynucleotide comprising a nucleotide sequence encoding the isolated monoclonal antibody of claim 1.

10. A vector comprising the polynucleotide of claim 9.

11. A host cell comprising the polynucleotide of claim 9.

12. A kit for diagnostic, prognostic, or therapeutic use, the kit comprising:
 the pharmaceutical composition of claim 8; and
 instructions for use thereof for diagnosis, prognosis or therapy.

13. A method of identifying a subject having Parkinson's disease as a candidate for treatment with a LRRK2 inhibitor, the method comprising: contacting a sample from the subject with an isolated monoclonal antibody of claim 1, and measuring the amount of phosphorylated Rab10 protein in the sample from the subject wherein an amount of phosphorylated Rab10 protein in the sample from the subject that is at least as high as a control value identifies the subject as a candidate for treatment with a LRRK2 inhibitor.

* * * * *